US009198420B2

(12) United States Patent
Hopkins et al.

(10) Patent No.: US 9,198,420 B2
(45) Date of Patent: Dec. 1, 2015

(54) RODENTICIDAL NORBORMIDE ANALOGUES

(71) Applicant: Landcare Research New Zealand Limited, Lincoln (NZ)

(72) Inventors: Brian Hopkins, Lincoln (NZ); Margaret Anne Brimble, Auckland (NZ); David Rennison, Auckland (NZ); Sergio Bova, Padua (IT); Maurizio Cavalli, Chioggia (IT); Olivia Laita, Auckland (NZ)

(73) Assignee: Landcare Research New Zealand Limited, Lincoln (NZ)

( * ) Notice: Subject to any disclaimer, the term of this patent is extended or adjusted under 35 U.S.C. 154(b) by 0 days.

(21) Appl. No.: 14/383,718

(22) PCT Filed: Mar. 11, 2013

(86) PCT No.: PCT/NZ2013/000034
§ 371 (c)(1),
(2) Date: Sep. 8, 2014

(87) PCT Pub. No.: WO2013/133726
PCT Pub. Date: Sep. 12, 2013

(65) Prior Publication Data
US 2015/0025113 A1 Jan. 22, 2015

(30) Foreign Application Priority Data

Mar. 9, 2012 (NZ) ....................................... 598698

(51) Int. Cl.
*A01N 43/40* (2006.01)
*C07D 401/14* (2006.01)

(52) U.S. Cl.
CPC .............. *A01N 43/40* (2013.01); *C07D 401/14* (2013.01)

(58) Field of Classification Search
None
See application file for complete search history.

(56) References Cited

U.S. PATENT DOCUMENTS

| | | | |
|---|---|---|---|
| 3,297,706 A | 1/1967 | Hopkins et al. | |
| 3,378,566 A | 4/1968 | Mohrbacher et al. | |
| 3,471,619 A | 10/1969 | Mohrbacher et al. | |
| 3,506,675 A * | 4/1970 | Takacs et al. ................. | 546/256 |
| 4,622,339 A | 11/1986 | Lieb et al. | |
| 4,927,934 A | 5/1990 | Abou-Gharbia et al. | |
| 4,937,347 A | 6/1990 | Abou-Gharbia et al. | |

FOREIGN PATENT DOCUMENTS

| | | |
|---|---|---|
| EP | 613886 | 9/1994 |
| GB | 1059405 | 2/1967 |
| GB | 1105181 | 3/1968 |
| GB | 1164124 | 9/1969 |
| GB | 1400660 | 7/1975 |

OTHER PUBLICATIONS

Poos, G.I. et al., Structure-Activity Studies with the Selective Rat Toxicant Norbormide, Journal Medicinal Chemistry, 1966, vol. 9, Issue 4, pp. 537-540.
Chemical Abstracts Accession No. 1972:59465 and CAS Registry File RN 34941-70-3.
Rennison, D. et al., Design and Synthesis of Prodrugs of the Rat Selective Toxicant Norbormide, Bioorganic & Medicinal Chemistry, May 2012, vol. 20, pp. 3997-4011.
Roszkowski, A.P. et al., Selective Rat Toxicant, Science 1964, 144, pp. 412-413.
Bova, S. et al., Norbormide: A Calcium Entry Blocker with Selective Vasoconstrictor Activity in Rat Peripheral Arteries, Cardiovasc. Drug Rev. 2001, 19, pp. 226-233.
Brimble, M.A. et al., Synthesis and Evaluation of Vasoconstrictor and Vasorelaxant Activity of Norbormide Isomers, Arkivoc 2004, pp. 1-11.
Bova, S. et al., Signaling Mechanisms for the Selective Vasoconstrictor Effect of Norbormide on the Rat Small Arteries, J. Pharm. Exp. Ther. 2001, 296, pp. 458-463.
Fusi, F. et al., Ca2+ Entry Blocking and Contractility Promoting Actions of Norbormide in Single Rat Caudal Artery Myocytes, British J. Pharmacol. 2002, 137, pp. 323-328.
Kusano, T.J., Physiological and Psychological Analysis of the Acceptability of Acute Rodenticides by Rats, Fac. Agri. Tottori Univ. 1975, 5, pp. 15-26.
Greaves, J.H., Some Laboratory Observations on the Toxicity and Acceptability of Norbormide to Wild Rattus Norvegicus and on Feeding Behaviour Associated with Sublethal Dosing, J. Hygiene, 1966, 64, pp. 275-285.
Ogushi, K. et al, Studies on Rodenticides (II): Fedding Preference of Norway Rat on Poison Baits with Acute Rodenticides and Their Killing Effects, Eisei Dobutsu (in Japanese), 1970, 21, pp. 181-185.
Rennison, B.D. et al., A Comparative Trial of Norbormide and Zinc Phosphide Against Rattus Norvegicus on Farms, J. Hygiene, 1968, 66, pp. 147-158.
Greaves, J.H. et al., Microencapsulation of Rodenticides, Nature 1968, 219, pp. 402-403.
Nadian, A. et al., Studies on the Development of a Microencapsulated Delivery System for Norbormide, A Species-Specific Acute Rodenticide, Int. J. Pharm. 2002, 22, pp. 63-68.
Iyer, R.P. et al., Synthesis of Iodoalkylacylates and Their Use in the Preparation of S-Alkyl Phosphorothiolates, Synth. Commun. 1995, 25, pp. 2739-2749.
Harada, N. et al., A Simple Preparation of Chloromethyl Esters of the Blocked Amino Acids, Synth. Commun. 1994, 24, pp. 767-772.
Lu, M.C. et al., Molecular Modification of Anticholinergics as Probes for Muscarinic Receptors. 1. Amino Esters of a-Substituted Phenylacetic Acid and Related Analogues, J. Med. Chem. 1987, 30, pp. 273-278.
Mohrbacher, R.J. et al., Reaction of Aryl Ketones with Cyclopentadienyl Sodium. Syntheses of Fulvenylmethanols, J. Org. Chem. 1966, 31, pp. 2149-2159.

(Continued)

*Primary Examiner* — Timothy R Rozof
(74) *Attorney, Agent, or Firm* — Honigman Miller Schwartz and Cohn LLP; Thomas A. Wootton; Jonathan P. O'Brien

(57) ABSTRACT

The present invention relates to norbormide analogs having rodenticidal activity; rodenticidal compositions comprising the analogs; uses of the analogs as rodenticides; uses of the analogs in the manufacture of rodenticidal compositions; and methods for controlling rodents using the compositions.

20 Claims, No Drawings

(56) References Cited

OTHER PUBLICATIONS

Mohrbacher, R.J. et al., Stereoisomerism of 5-(a-Hydroxy-a-2-pyridylbenzyl)-7-(a-2-pyridylbenzylidene)-5-norbornene-2,3-dicarboximide, a Selective Rat Toxicant, J. Org. Chem. 1966, 31, pp. 2141-2148.

Gasanov, R.A. et al., A Procedure for Preparing N-Hydroxyethyl-Substituted Succinimde and Phthalimide, Russian J. Appl. Chem. 2004, 77, pp. 2034-2035.

Van Vliet, L.D. et al., Molecular Recognition of DNA by Rigid [n]-Polynorbornane-Derived Bifunctional Intercalators: Synthesis and Evaluation of Their Binding Properties, J. Med. Chem. 2007, 50, 2326-2340.

Hursthouse, M.B. et al., Tin (IV)-Mediated Steroselective Synthesis of Epoxides with Concomitant Alkyl Peroxide Formation, Tetrahedron Lett. 1995, 36, 33, pp. 5979-5982.

Nitsche, B. et al., A New Synthesis and Nmr-Spectroscopy of [15N-, 5,4-13C]-Aminolevulinic Acid, J. Labelled Compd. Radiopharm. 1987, 24, 6, pp. 623-630.

Binderup, E. et al., Chlorosulfates as Reagents in the Synthesis of Carboxylic Acid Esters Under Phase-Transfer Conditions, Synth. Commun. 1984, 14, pp. 857-864.

Bodor, N., et al., A Convenient Synthesis of (Acyloxy)alkyl a-Ethers of Phenols, J. Org. Chem. 1983, 48, pp. 5280-5284.

Nagao, Y. et al., New Chiral Recognition of Chiral Tin (II) Enolates Toward Cyclic Acyl Iminium Species, Asymmetric Total Synthesis of (−)-Supinidine, Tetrahedron Lett. 1988, 29, pp. 6133-6136.

Bartalucci, G. et al., Naturalised Dyes: A Simple Straightforward Synthetic Route to a New Class of Dyes—Glycoazodyes (GADs), Eur. J. Org. Chem. 2007, pp. 588-595.

Schwartz E., et al., Synthesis and Postpolymerization Functionalization of Poly(5-iodo-1,2,3-triazole)s, Macromolecules 2011, 4, pp. 4735-4741.

Kalgutkar, A.S. et al., Ester and Amide Derivatives of the NonSteroidal Antiinflammaotry Drug, Indomethacin, as Selective Cyclooxygenase-2 Inhibitors, J. Med. Chem. 2000, 43, pp. 2860-2870.

Miki T. et al., Synthesis of Novel 4,1-Benzoxazepine Derivatives as Squalene Synthase Inhibitors and Their Inhibition of Choleterol Synthesis, J. Med. Chem. 2002, 45, pp. 4571-4580.

Di, L. et al., Development and Application of High Throughput Plasma Stability Assay for Drug Discovery, Int. J. Pharm. 2005, 297, pp. 110-119.

Abrahamsson, S. et al., Stereochemistry of the Most Active Racemate of Norbormide, A Selective Rate Toxicant, J. Org. Chem 1966, 31(11), pp. 3631-3634.

Roszkowski, A.P. et al., The Pharmacological Properties of Norbormide, A Selective Rat Toxicant, J. Pharmacol Exp Ther. 1965, 149(2), pp. 288-299.

Rennison, D. et al., Synthesis and Activity Studies of Analogues of the Rat Selective Toxicant Norbormide, Bloorganic & Medicinal Chemistry, vol. 15, Issue 8, 2007, pp. 2963-2974.

Laita, O.S., Prodrug Studies on the Rat Selective Toxicant Norbormide, Thesis (Ph.D. Chemistry), Univ. of Auckland, 2009.

Steele, P.J. et al., Two Steroisomers of the Rat Toxicant Norbormide, Intl. Union of Crystallography, 2004, C60, pp. 374-376.

Shimizu, T., Poison-Based Shyness of Albion Rats by Norbormide Rodenticide, Appl. Ent. Zool. 1983, 18(2), pp. 243-251.

Nilsson, B., Stereochemistry of an Inactive Racemate of Norbormide a Selective Rat Toxicant, ACTA Chemica Scandinavica 22, 1968, pp. 518-530.

\* cited by examiner

RODENTICIDAL NORBORMIDE ANALOGUES

REFERENCE TO RELATED APPLICATIONS

This application claims priority from PCT application PCT/NZ2013/000034, filed Mar. 11, 2013, which claims the benefit of earlier filed New Zealand Application 598698, filed on Mar. 9, 2012, the entire contents of which are incorporated herein by reference.

TECHNICAL FIELD

The present invention relates to rodenticidal compounds; rodenticidal compositions comprising the compounds; uses of the compounds; and methods for controlling rodent populations using the compositions.

BACKGROUND ART

Rats cause substantial damage each year to agricultural interests worldwide. The World Health Organization estimates that 20% of all human food is destroyed or contaminated by rodents each year (Chow, C. Y. *The Biology and Control of the Norway Rat, Roof Rat and House Mouse*, World Health. Organization, 1971). A recent US government report claims that each rat damages up to $10 worth of food and stored grains annually and contaminates five to 10 times that amount (Committee on Urban Pest Management, *Urban Pest Management*, National Academy Press: Washington D.C., 1980). With an estimated birth rate of 3.5 million per day globally, the estimated damage is valued at hundreds of millions of dollars per annum (Danoff, J. R. B. *Introduced species summary reports*, Centre of Research and Conservation, Columbia University, 2002).

In addition to this vast economic loss, rats are responsible for a number of health problems. By acting as vectors for both viral and bacterial diseases, rats transmit more than 35 types of disease to humans including leptospirosis, cholera, *salmonella* and the bubonic plague. Furthermore, rats are known to be one of the most invasive species responsible for a loss of biodiversity and native habitats, second only to humans. Rats threaten both plant and animal species by predation and habitat destruction.

Currently, a number of available toxicants are effective in controlling rats. Almost all are non-specific broad-spectrum rodenticides. To date, rodent control has been achieved through the use of sub-chronic poisons (e.g., cholecalciferol, bromethalin), acute poisons (e.g., zinc phosphide), first-generation anticoagulants (e.g., warfarin, coumatetralyl, diphacinone, chlorophacinone), and second-generation anticoagulants (e.g., brodifacoum, bromadiolone, bromethalin, difethialone, difenacoum), with varying degrees of success (Pelfrene, A. F. et al. *Handbook of Pesticide Toxicology (Second Edition)*; Academic Press: San Diego, 2001, p 1793-1836). Annually, more than $500 million is spent on rodent control products. Second-generation anticoagulants are the most preferred products. However, most of these share a common disadvantage in that they associated with secondary non-target poisoning risks and are dangerous not only to children, but also to domestic pets, wildlife, and livestock.

Rodenticides rank second in the number of pesticide related poisonings recorded each year. A recent study revealed that just under 15,000 people were exposed to rodenticides in the US in 2008 alone, 86% being children under the age of six (Bronstein, A. C. et al. *Clin. Toxicol.* 2008, 46, 927-1057). In addition, rodenticides pose increasing risks to the environment and through the accumulation of residues in food chains. These poisons also suffer from a general lack of humaneness.

Norbormide (NRB) is a vasoactive also known under the trade names Shoxin® and Raticate® that was first introduced to the market as a rodenticide over thirty years ago. NRB was discovered in the 1960s and was found to be uniquely toxic to rats, but relatively harmless to other rodents and mammals (Roszkowski, A. P. et al. *Science* 1964, 144, 412-413). NRB displays unique species-specific constrictor activity that is restricted to the peripheral arteries of the rat. In arteries from all other species tested, as well as in rat aorta and extravascular smooth muscle tissue, NRB exhibits vasorelaxant properties at concentrations that induce vasoconstriction in the rat peripheral arteries (Bova, S. et al. *Cardiovasc. Drug Rev.* 2001, 19, 226-233).

Detailed studies conducted on the individual stereoisomers of NRB, isolated from the endo rich stereoisomeric mixture, found the parent compound's physiological effects to be strongly stereospecific. In rat peripheral arteries only the endo isomers of NRB retained the contractile activity elicited by the stereoisomeric mixture. Both the endo and exo isomers exhibit vasodilatory activity in rat aorta (Brimble, M. A. et al. *Arkivoc* 2004, 1-11). In vivo evaluation established that only the endo isomers of NRB were toxic in rats (Poos, G. I. et al. *J. Med. Chem.* 1966, 9, 537-540).

The mechanisms involved in the physiological divergent effects of NRB have not yet been clarified. Available evidence suggests that the vasoconstrictor effect may be mediated by the stimulation of a number of signal transduction pathways that lead to modulation of calcium influx, which is presumably mediated by phospholipase C (PLC)-coupled receptors expressed in rat peripheral artery myocytes (Bova, S. et al. *J. Pharm. Exp. Ther.* 2001, 296, 458-463). The relaxant effect may be the result of a reduction of $Ca^{2+}$ entry through L-type $Ca^{2+}$ channels (Fusi, F. et al. *Br. J. Pharmacol.* 2002, 137, 323-328).

To date, efforts to establish NRB as a commercially viable rodenticide have been largely unsuccessful. Over time, rats as a species have developed an evolutionary trait relating to how they sample food, particularly novel food, which reduces the risk of ingesting a potentially toxic dose. This survival strategy is most likely a consequence of their lack of an emetic centre and, therefore, their incapacity to vomit. As an acute poison, NRB has a rapid onset of action. Toxic symptoms appear almost immediately. Rats appear to develop a learnt aversion to this poison following the consumption of sub-lethal doses during sampling, a phenomenon referred to as bait-shyness (Kusano, T. J. *Fac. Agri. Tottori Univ.* 1975, 5, 15-26). In addition, NRB is also known to be relatively unpalatable to rats (Greaves, J. H. *J. Hygiene,* 1966, 64, 275-285; Ogushi, K. and Iwao, T. *Eisei Dobutsu (in Japanese)*, 1970, 21, 181-185; Rennison, B. D. et al. *J. Hygiene,* 1968, 66, 147-158).

While a pre-requisite for lethality in rats, this intrinsic vasoconstrictory activity is believed to be the most significant shortcoming of NRB as a rodenticide. The sub-lethal dosing due to the unpleasant 'taste' of NRB is believed to be a consequence of NRB-induced vasoconstriction of the blood vessels of the buccal cavity, a primary culprit leading to bait-shyness. Efforts to address this palatability problem using microencapsulation technologies have been made, but the rapid release of the toxicant in vivo led to bait shyness (Greaves, J. H. et al. *Nature* 1968, 219, 402-403; Nadian, A. and Lindblom, L. *Int. J. Pharm.* 2002, 242, 63-68).

There remains a need for rodenticides that avoid one or more of the aforementioned disadvantages.

It is an object of the present invention to go some way towards meeting this need; and/or to at least provide the public with a useful choice.

Other objects of the invention may become apparent from the following description which is given by way of example only.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date.

SUMMARY OF THE INVENTION

In one aspect the present invention provides a compound of the formula (I):

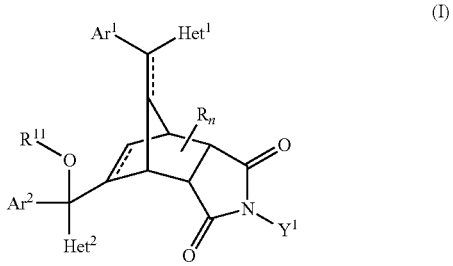

wherein:

$Ar^1$ and $Ar^2$ are each independently a 6 to 10 membered monocyclic or bicyclic aryl ring, wherein the ring is optionally substituted with one or more $R^8$;

$Het^1$ and $Het^2$ are each independently a 5 to 10 membered monocyclic or bicyclic heteroaryl ring comprising 1 to 4 ring nitrogen atoms, wherein the ring is optionally substituted with one or more $R^8$;

each dashed line and solid line together represent a double bond or a single bond;

$Y^1$ is

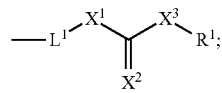

$X^1$ and $X^3$ are each independently selected from the group consisting of O, S, $NR^5$, and a bond, provided that $X^1$ and $X^3$ do not both represent a bond;

$X^2$ is selected from the group consisting of O, S, and $NR^5$;

$L^1$ is selected from the group consisting of $C_{1-6}$alkylene, $C_{3-6}$cycloalkylene, arylene, heteroarylene, heterocyclylene, $C_{1-6}$alkyl$C_{3-6}$cycloalkylene, $C_{1-6}$alkylarylene, $C_{1-6}$alkylheteroarylene, $C_{1-6}$alkylheterocyclylene, $C_{3-6}$cycloalkyl$C_{1-6}$alkylene, aryl$C_{1-6}$alkylene, heteroaryl$C_{1-6}$alkylene, heterocyclyl$C_{1-6}$alkylene, $C_{1-6}$alkoxy$C_{1-6}$alkylene, $C_{3-6}$cycloalkyloxy$C_{1-6}$alkylene, aryloxy$C_{1-6}$alkylene, heteroaryloxy$C_{1-6}$alkylene, heterocyclyloxy$C_{1-6}$alkylene, $C_{1-6}$alkoxy$C_{3-6}$cycloalkylene, $C_{1-6}$alkoxyarylene, $C_{1-6}$alkoxyheteroalkylene, $C_{1-6}$alkoxyheterocyclylalkylene, $C_{1-6}$alkylthio$C_{1-6}$alkylene, $C_{3-6}$cycloalkylthio$C_{1-6}$alkylene, arylthio$C_{1-6}$alkylene, heteroarylthio$C_{1-6}$alkylene, heterocyclylthio$C_{1-6}$alkylene, $C_{1-6}$alkylthio$C_{3-6}$cycloalkylene, $C_{1-6}$alkylthioarylene, $C_{1-6}$alkylthioheteroalkylene, $C_{1-6}$alkylthioheterocyclylalkylene, $C_{1-6}$alkylamino$C_{1-6}$alkylene, $C_{3-6}$cycloalkylamino$C_{1-6}$alkylene, arylamino$C_{1-6}$alkylene, heteroarylamino$C_{1-6}$alkylene, heterocyclylamino$C_{1-6}$alkylene, $C_{1-6}$alkylamino$C_{3-6}$cycloalkylene, $C_{1-6}$alkylaminoarylene, $C_{1-6}$alkylaminoheteroalkylene, and $C_{1-6}$alkylaminoheterocyclylalkylene each of which is optionally substituted with one or more $R^6$;

$R^1$ is selected from the group consisting of $C_{3-18}$alkyl, $C_{3-8}$cycloalkyl, aryl, heterocyclyl, heteroaryl, $C_{3-8}$cycloalkyl$C_{1-6}$alkyl, aryl$C_{1-6}$alkyl, heterocyclyl$C_{1-6}$alkyl, heteroaryl$C_{1-6}$alkyl, $C_{3-18}$alkyloxy$C_{1-6}$alkyl, $C_{3-8}$cycloalkyloxy$C_{1-6}$alkyl, aryloxy$C_{1-6}$alkyl, heterocyclyloxy$C_{1-6}$alkyl, heteroaryloxy$C_{1-6}$alkyl, $C_{3-18}$alkylcarbonyloxy$C_{1-6}$alkyl, $C_{3-8}$cycloalkylcarbonyloxy$C_{1-6}$alkyl, arylcarbonyloxy$C_{1-6}$alkyl, heterocyclylcarbonyloxy$C_{1-6}$alkyl, heteroarylcarbonyloxy$C_{1-6}$alkyl, $C_{3-18}$alkyloxycarbonyl$C_{1-6}$alkyl, $C_{3-8}$cycloalkyloxycarbonyl$C_{1-6}$alkyl, aryloxycarbonyl$C_{1-6}$alkyl, heterocyclyloxycarbonyl$C_{1-6}$alkyl, heteroaryloxycarbonyl$C_{1-6}$alkyl, each of which is optionally substituted with one or more $R^7$;

$R^5$ at each instance is independently selected from the group consisting of hydrogen, $C_{1-6}$alkyl, $C_{3-6}$cycloalkyl, aryl, heterocyclyl, and heteroaryl;

$R^6$ at each instance is independently selected from the group consisting of hydroxyl, thiol, amino, cyano, nitro, halo, $C_{1-6}$alkyl, $C_{1-6}$haloalkyl, $C_{1-6}$alkoxy, and $C_{1-6}$haloalkoxy;

$R^7$ at each instance is independently selected from the group consisting of hydroxyl, thiol, amino, amido, acylamino, cyano, nitro, nitroso, azide, halo, cyanate, thiocyanate, isocyanate, isothiocyanate, oxo, imino, acyl, $C_{1-6}$alkyl, $C_{1-6}$haloalkyl, $C_{3-6}$cycloalkyl, aryl, heterocyclyl, heteroaryl, $C_{1-6}$alkoxy, $C_{1-6}$haloalkoxy, $C_{3-6}$cycloalkoxy, aryloxy, heterocyclyloxy, heteroaryloxy, $C_{1-6}$alkylcarbonyloxy, $C_{3-6}$cycloalkylcarbonyloxy, arylcarbonyloxy, heterocyclylcarbonyloxy, heteroarylcarbonyloxy, $C_{1-6}$alkyloxycarbonyl, $C_{3-6}$cycloalkyloxycarbonyl, aryloxycarbonyl, heterocyclyloxycarbonyl, heteroaryloxycarbonyl, sulfenyl, sulfonyl, sulfoxide, sulfate, sulfonate, sulfonamide, phosphate, phosphonate, phosphinate, phosphine, phosphite, carbonate, carbamate, and urea;

$R^8$ at each instance is selected from the group consisting of hydroxyl, thiol, amino, cyano, nitro, halo, $C_{1-6}$alkyl, $C_{1-6}$haloalkyl, $C_{1-6}$alkoxyl, and $C_{1-6}$haloalkoxy;

$R^{11}$ is selected from the group consisting of hydrogen, $C_{1-6}$alkyl, and $C_{1-6}$haloalkyl;

R at each instance is selected from the group consisting of halo, $C_{1-6}$alkyl, carboxyl, carboxyl$C_{1-6}$alkyl, amido$C_{1-6}$alkyl, acyloxy, sulfenyl, sulfoxide, sulfonyl, and aryl, wherein each $C_{1-6}$alkyl and aryl is optionally substituted with one or more $R^8$; and n is an integer selected from 0 to 3; or a salt or solvate thereof.

In another aspect the present invention provides a compound of the formula (I):

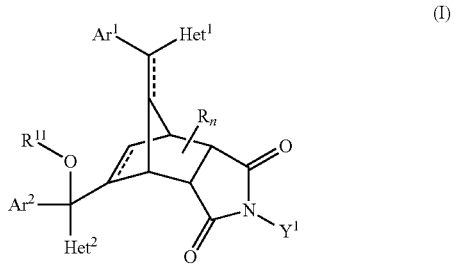

wherein:

Ar$^1$ and Ar$^2$ are each independently a 6 to 10 membered monocyclic or bicyclic aryl ring, wherein the ring is optionally substituted with one or more R$^8$;

Het$^1$ and Het$^2$ are each independently a 5 to 10 membered monocyclic or bicyclic heteroaryl ring comprising 1 to 4 ring nitrogen atoms, wherein the ring is optionally substituted with one or more R$^8$;

each dashed line and solid line together represent a double bond or a single bond;

Y$^1$ is

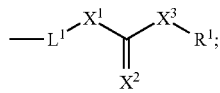

X$^1$ and X$^3$ are each independently selected from the group consisting of O, S, NR$^5$, and a bond, provided that X$^1$ and X$^3$ do not both represent a bond;

X$^2$ is selected from the group consisting of O, S, and NR$^5$;

L$^1$ is selected from the group consisting of C$_{1-6}$alkylene, C$_{3-6}$cycloalkylene, arylene, heteroarylene, heterocyclylene, C$_{1-6}$alkylC$_{3-6}$cycloalkylene, C$_{1-6}$alkylarylene, C$_{1-6}$alkylheteroarylene, C$_{1-6}$alkylheterocyclylene, C$_{3-6}$cycloalkylC$_{1-6}$alkylene, arylC$_{1-6}$alkylene, heteroarylC$_{1-6}$alkylene, heterocyclylC$_{1-6}$alkylene, C$_{1-6}$alkoxyC$_{1-6}$alkylene, C$_{3-6}$cycloalkyloxyC$_{1-6}$alkylene, aryloxyC$_{1-6}$alkylene, heteroaryloxyC$_{1-6}$alkylene, heterocyclyloxyC$_{1-6}$alkylene, C$_{1-6}$alkoxyC$_{3-6}$cycloalkylene, C$_{1-6}$alkoxyarylene, C$_{1-6}$alkoxyheteroalkylene, C$_{1-6}$alkoxyheterocyclylalkylene, C$_{1-6}$alkylthioC$_{1-6}$alkylene, C$_{3-6}$cycloalkylthioC$_{1-6}$alkylene, arylthioC$_{1-6}$alkylene, heteroarylthioC$_{1-6}$alkylene, heterocyclylthioC$_{1-6}$alkylene, C$_{1-6}$alkylthioC$_{3-6}$cycloalkylene, C$_{1-6}$alkylthioarylene, C$_{1-6}$alkylthioheteroalkylene, C$_{1-6}$alkylthioheterocyclylalkylene, C$_{1-6}$alkylaminoC$_{1-6}$alkylene, C$_{3-6}$cycloalkylaminoC$_{1-6}$alkylene, arylaminoC$_{1-6}$alkylene, heteroarylaminoC$_{1-6}$alkylene, heterocyclylaminoC$_{1-6}$alkylene, C$_{1-6}$alkylaminoC$_{3-6}$cycloalkylene, C$_{1-6}$alkylaminoarylene, C$_{1-6}$alkylaminoheteroalkylene, and C$_{1-6}$alkylaminoheterocyclylalkylene each of which is optionally substituted with one or more R$^6$;

R$^1$ is selected from the group consisting of C$_{1-6}$alkyl C$_{3-8}$cycloalkyl, C$_{1-6}$alkylaryl, C$_{1-6}$alkylheterocyclyl, C$_{1-6}$alkylheteroaryl, C$_{1-6}$alkylC$_{3-8}$cycloalkylC$_{1-6}$alkyl, C$_{1-6}$alkylheterocyclylC$_{1-6}$alkyl, C$_{1-6}$alkylheteroaryl C$_{1-6}$alkyl, C$_{1-18}$alkylcarbonyloxyC$_{1-6}$alkyl, C$_{1-18}$alkyloxycarbonylC$_{1-6}$alkyl, each of which is optionally substituted with one or more R$^7$; or R$^1$ is C$_{1-6}$alkylarylC$_{1-6}$alkyl substituted with one or more R$^7$;

R$^5$ at each instance is independently selected from the group consisting of hydrogen, C$_{1-6}$alkyl, C$_{3-6}$cycloalkyl, aryl, heterocyclyl, and heteroaryl;

R$^6$ at each instance is independently selected from the group consisting of hydroxyl, thiol, amino, cyano, nitro, halo, C$_{1-6}$alkyl, C$_{1-6}$haloalkyl, C$_{1-6}$alkoxy, and C$_{1-6}$haloalkoxy;

R$^7$ at each instance is independently selected from the group consisting of hydroxyl, thiol, amino, amido, acylamino, cyano, nitro, nitroso, azide, halo, cyanate, thiocyanate, isocyanate, isothiocyanate, oxo, imino, acyl, C$_{1-6}$alkyl, C$_{1-6}$haloalkyl, C$_{3-6}$cycloalkyl, aryl, heterocyclyl, heteroaryl, C$_{1-6}$alkoxy, C$_{1-6}$haloalkoxy, C$_{3-6}$cycloalkoxy, aryloxy, heterocyclyloxy, heteroaryloxy, C$_{1-6}$alkylcarbonyloxy, C$_{3-6}$cycloalkylcarbonyloxy, arylcarbonyloxy, heterocyclylcarbonyloxy, heteroarylcarbonyloxy, C$_{1-6}$alkyloxycarbonyl, C$_{3-6}$cycloalkyloxycarbonyl, aryloxycarbonyl, heterocyclyloxycarbonyl, heteroaryloxycarbonyl, sulfenyl, sulfonyl, sulfoxide, sulfate, sulfonate, sulfonamide, phosphate, phosphonate, phosphinate, phosphine, phosphite, carbonate, carbamate, and urea;

R$^8$ at each instance is selected from the group consisting of hydroxyl, thiol, amino, cyano, nitro, halo, C$_{1-6}$alkyl, C$_{1-6}$haloalkyl, C$_{1-6}$alkoxyl, and C$_{1-6}$haloalkoxy;

R$^{11}$ is selected from the group consisting of hydrogen, C$_{1-6}$alkyl, and C$_{1-6}$haloalkyl;

R at each instance is selected from the group consisting of halo, C$_{1-6}$alkyl, carboxyl, carboxylC$_{1-6}$alkyl, amidoC$_{1-6}$alkyl, acyloxy, sulfenyl, sulfoxide, sulfonyl, and aryl, wherein each C$_{1-6}$alkyl and aryl is optionally substituted with one or more R$^8$; and n is an integer selected from 0 to 3; or a salt or solvate thereof.

In another aspect, the present invention provides a compound of formula (III):

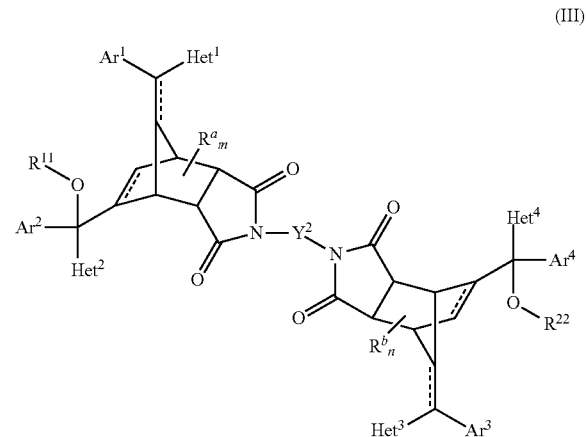

wherein:

Ar$^1$, Ar$^2$, Ar$^3$, and Ar$^4$ at each instance are independently a 6 to 10 membered monocyclic or bicyclic aryl ring, wherein the ring is optionally substituted with one or more R$^8$;

Het$^1$, Het$^2$, Het$^3$, and Het$^4$ at each instance are independently a 5 to 10 membered monocyclic or bicyclic heteroaryl ring comprising 1 to 4 ring nitrogen atoms, wherein the ring is optionally substituted with one or more R$^8$;

each dashed line and solid line together represent a double bond or a single bond;

Y$^2$ is

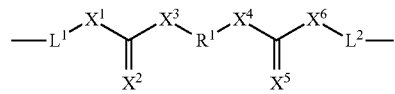

L$^1$ and L$^2$ are each independently selected from the group consisting of C$_{1-6}$alkylene, C$_{3-6}$cycloalkylene, arylene, heteroarylene, heterocyclylene, C$_{1-6}$alkylC$_{3-6}$cycloalkylene, C$_{1-6}$alkylarylene, C$_{1-6}$alkylheteroarylene, C$_{1-6}$alkylheterocyclylene, C$_{3-6}$cycloalkylC$_{1-6}$alkylene, arylC$_{1-6}$alkylene, heteroarylC$_{1-6}$alkylene, heterocyclylC$_{1-6}$alkylene, C$_{1-6}$alkoxyC$_{1-6}$alkylene, C$_{3-6}$cycloalkyloxyC$_{1-6}$alkylene, aryloxyC$_{1-6}$alkylene, heteroaryloxyC$_{1-6}$alkylene, heterocyclyloxyC$_{1-6}$alkylene, C$_{1-6}$alkoxyC$_{3-6}$cycloalkylene, C$_{1-6}$alkoxyarylene, C$_{1-6}$alkoxyheteroalkylene, C$_{1-6}$alkoxyheterocyclylalkylene, C$_{1-6}$alkylthioC$_{1-6}$alkylene, C$_{3-6}$cycloalkylthioC$_{1-6}$alkylene, arylthioC$_{1-6}$alkylene, heteroarylthioC$_{1-6}$alkylene, heterocyclylthioC$_{1-6}$alkylene, C$_{1-6}$alkylthioC$_{3-6}$cycloalkylene, C$_{1-6}$alkylthioarylene, C$_{1-6}$alkylthioheteroalkylene, C$_{1-6}$alkylthioheterocyclylalkylene, C$_{1-6}$alkylaminoC$_{1-6}$alkylene, C$_{3-6}$cycloalkylaminoC$_{1-6}$alkylene, arylaminoC$_{1-6}$alkylene, heteroarylaminoC$_{1-6}$alkylene, heterocyclylaminoC$_{1-6}$alkylene, C$_{1-6}$alkylaminoC$_{3-6}$cycloalkylene, C$_{1-6}$alkylaminoarylene, C$_{1-6}$alkylaminoheteroalkylene, and C$_{1-6}$alkylaminoheterocyclylalkylene each of which is optionally substituted with one or more R$^6$;

R$^1$ is —(R$^2$—Z)$_q$—R$^3$—;

R$^2$ at each instance and R$^3$ are independently selected from the group consisting of C$_{2-12}$alkylene, C$_{3-8}$cycloalkylene, arylene, heterocyclylene, and heteroarylene, each of which is optionally substituted with one or more R$^7$;

Z at each instance is independently selected from the group consisting of X$^7$—C(=X$^8$)—X$^9$ and X$^{10}$;

X$^1$, X$^3$, X$^4$, and X$^6$ and X$^7$, X$^9$, and X$^{10}$ at each instance are independently selected from the group consisting of O, S, NR$^5$, and a bond, provided that X$^1$ and X$^3$ do not both represent a bond, X$^4$ and X$^6$ do not both represent a bond, and X$^7$ and X$^9$ do not both represent a bond;

X$^2$, X$^5$, and X$^8$ at each instance are independently selected from the group consisting of O, S, and NR$^5$;

q is an integer selected from 0 to 10;

R$^5$ at each instance is independently selected from the group consisting of hydrogen, C$_{1-6}$alkyl, C$_{3-6}$cycloalkyl, aryl, heterocyclyl, and heteroaryl;

R$^6$ at each instance is independently selected from the group consisting of hydroxyl, thiol, amino, cyano, nitro, halo, C$_{1-6}$alkyl, C$_{1-6}$haloalkyl, C$_{1-6}$alkoxy, and C$_{1-6}$haloalkoxy;

R$^7$ at each instance is independently selected from the group consisting of hydroxyl, thiol, amino, amido, acylamino, cyano, nitro, nitroso, azide, halo, cyanate, thiocyanate, isocyanate, isothiocyanate, oxo, imino, acyl, C$_{1-6}$alkyl, C$_{1-6}$haloalkyl, C$_{3-6}$cycloalkyl, aryl, heterocyclyl, heteroaryl, C$_{1-6}$alkoxy, C$_{1-6}$haloalkoxy, C$_{3-6}$cycloalkoxy, aryloxy, heterocyclyloxy, heteroaryloxy, C$_{1-6}$alkylcarbonyloxy, C$_{3-6}$cycloalkylcarbonyloxy, arylcarbonyloxy, heterocyclylcarbonyloxy, heteroarylcarbonyloxy, C$_{1-6}$alkyloxycarbonyl, C$_{3-6}$cycloalkyloxycarbonyl, aryloxycarbonyl, heterocyclyloxycarbonyl, heteroaryloxycarbonyl, sulfenyl, sulfonyl, sulfoxide, sulfate, sulfonate, sulfonamide, phosphate, phosphonate, phosphinate, phosphine, phosphite, carbonate, carbamate, and urea;

R$^8$ at each instance is selected from the group consisting of hydroxyl, thiol, amino, cyano, nitro, halo, C$_{1-6}$alkyl, C$_{1-6}$haloalkyl, C$_{1-6}$alkoxy, and C$_{1-6}$haloalkoxy;

R$^{11}$ and R$^{22}$ are each independently selected from the group consisting of hydrogen, C$_{1-6}$alkyl, and C$_{1-6}$haloalkyl;

R$^a$ and R$^b$ at each instance are each independently selected from the group consisting of halo, C$_{1-6}$alkyl, carboxyl, carboxylC$_{1-6}$alkyl, amidoC$_{1-6}$alkyl, acyloxy, sulfenyl, sulfoxide, sulfonyl, and aryl, wherein each C$_{1-6}$alkyl and aryl is optionally substituted with one or more R$^8$; and m and n are each an integer independently selected from 0 to 3; or a salt or solvate thereof.

In another aspect the present invention provides a compound of formula (V):

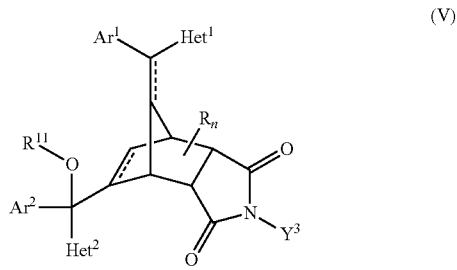

wherein
Ar$^1$ and Ar$^2$ at each instance are independently a 6 to 10 membered monocyclic or bicyclic aryl ring, wherein the ring is optionally substituted with one or more R$^8$;

Het$^1$ and Het$^2$ at each instance are each independently a 5 to 10 membered monocyclic or bicyclic heteroaryl ring comprising 1 to 4 ring nitrogen atoms, wherein the ring is optionally substituted with one or more R$^8$;

each dashed line and solid line together represent a double bond or a single bond;

Y$^3$ is

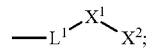

L$^1$ is selected from the group consisting of C$_{1-6}$alkylene, C$_{3-6}$cycloalkylene, arylene, heteroarylene, heterocyclylene, C$_{1-6}$alkylC$_{3-6}$cycloalkylene, C$_{1-6}$alkylarylene, C$_{1-6}$alkylheteroarylene, C$_{1-6}$alkylheterocyclylene, C$_{3-6}$cycloalkylC$_{1-6}$alkylene, arylC$_{1-6}$alkylene, heteroarylC$_{1-6}$alkylene, and heterocyclylC$_{1-6}$alkylene, each of which is optionally substituted with one or more R$^6$;

X$^1$ is selected from the group consisting of C(=O), C(=S), C(=NR$^5$), and a bond;

X$^2$ is selected from the group consisting of OH, SH, and NHR$^5$;

R$^5$ at each instance is independently selected from the group consisting of hydrogen, C$_{1-6}$alkyl, C$_{3-6}$cycloalkyl, aryl, heterocyclyl, and heteroaryl;

R$^6$ at each instance is independently selected from the group consisting of hydroxyl, thiol, amino, cyano, nitro, halo, C$_{1-6}$alkyl, C$_{1-6}$haloalkyl, C$_{1-6}$alkoxy, and C$_{1-6}$haloalkoxy;

R$^8$ at each instance is selected from the group consisting of hydroxyl, thiol, amino, cyano, nitro, halo, C$_{1-6}$alkyl, C$_{1-6}$haloalkyl, C$_{1-6}$alkoxy, and C$_{1-6}$haloalkoxy;

R$^{11}$ is selected from the group consisting of hydrogen, C$_{1-6}$alkyl, and C$_{1-6}$haloalkyl;

R at each instance is selected from the group consisting of halo, C$_{1-6}$alkyl, carboxyl, carboxylC$_{1-6}$alkyl, amidoC$_{1-6}$alkyl, acyloxy, sulfenyl, sulfoxide, sulfonyl, and aryl, wherein each C$_{1-6}$alkyl and aryl is optionally substituted with one or more R$^8$; and n is an integer selected from 0 to 3; or
a salt or solvate thereof.

In one aspect the present invention provides a use of a compound of the present invention as a rodenticide.

In another aspect the present invention provides a rodenticidal composition comprising an effective amount of a compound of the invention; and one or more edible diluent or carrier materials.

In another aspect the present invention provides a use of a compound of the invention in the manufacture of a rodenticidal composition.

In another aspect the present invention provides a method of controlling rodents comprising making a rodenticidal composition of the invention available for consumption by the rodents.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

Although the present invention is broadly as defined above, those persons skilled in the art will appreciate that the invention is not limited thereto and that the invention also includes embodiments of which the following description gives examples.

DETAILED DESCRIPTION OF THE INVENTION

The present invention relates to compounds with rodenticidal activity and rodenticidal compositions comprising the compounds. The present invention also relates to methods for reducing rodent populations that comprise using these compositions.

The term "alkyl" employed alone or in combination with other terms means, unless otherwise stated, a saturated or unsaturated monovalent straight chain or branched chain hydrocarbon group. Examples of saturated hydrocarbon groups include methyl, ethyl, n-propyl, isopropyl, n-butyl, t-butyl, isobutyl, sec-butyl, and the like. Unsaturated alkyl groups have one or more carbon-carbon double bonds or triple bonds. Examples of unsaturated alkyl groups include vinyl, prop-2-enyl, crotyl, isopent-2-enyl, 2-butadienyl, penta-2,4-dienyl, penta-1,4-dienyl, ethynyl, prop-3-ynyl, but-3-ynyl, and the like. In some embodiments alkyl is $C_{1-18}$alkyl, $C_{3-18}$alkyl, $C_{1-12}$alkyl, $C_{3-12}$alkyl, $C_{1-6}$alkyl, $C_{1-4}$alkyl, $C_{2-6}$alkyl, or $C_{2-4}$alkyl. In other embodiments alkyl is $C_{1-6}$alkyl. In certain embodiments alkyl is saturated or alkenyl.

The term "cycloalkyl" employed alone or in combination with other terms means, unless otherwise stated, a saturated or unsaturated monovalent cyclic hydrocarbon group. Examples of cycloalkyl groups include cyclopentyl, cyclohexyl, cyclohex-1-enyl, cyclohex-3-enyl, cycloheptyl, and the like. In some embodiments cycloalkyl is $C_{3-8}$cycloalkyl or $C_{3-6}$cycloalkyl. In other embodiments the cycloalkyl is $C_{3-6}$cycloalkyl.

The term "aryl" employed alone or in combination with other terms means, unless otherwise stated, a phenyl ring or a monovalent bicyclic or tricyclic aromatic ring system comprising only carbon and hydrogen atoms. Monovalent bicyclic aromatic ring systems include naphthyl groups and phenyl rings fused to cycloalkyl rings. Monovalent bicyclic aromatic ring systems are attached to the parent molecular moiety through any available carbon atom within a phenyl ring. Examples of monovalent bicyclic aromatic ring systems include, but are not limited to, dihydroindenyl, indenyl, naphthyl, dihydronaphthalenyl, and tetrahydronaphthalenyl. Monovalent tricyclic aromatic ring systems include anthracenyl groups, phenanthrenyl groups, and monovalent bicyclic aromatic rings system fused to cycloalkyl or phenyl rings. Monovalent tricyclic aromatic ring systems are attached to the parent molecular moiety through any available carbon atom within a phenyl ring. Examples of monovalent tricyclic aromatic ring systems include, but are not limited to, azulenyl, dihydroanthracenyl, fluorenyl, and tetrahydrophenanthrenyl. In some embodiments aryl is monocyclic or bicyclic. In other embodiments aryl is phenyl or naphyl. In certain embodiments aryl is phenyl.

The term "heteroaryl" employed alone or in combination with other terms means, unless otherwise stated, a monocyclic heteroaryl group or bicyclic heteroaryl group. Monocyclic heteroaryl groups include monovalent 5- or 6-membered aromatic rings containing at least one heteroatom independently selected from the group consisting of nitrogen, oxygen, and sulfur in the ring. Monocyclic heteroaryl groups are connected to the parent molecular moiety through any available carbon atom or nitrogen atom within the ring. Examples of 5- and 6-membered heteroaryl rings include, but are not limited to, furyl, imidazolyl, isoxazolyl, isothiazolyl, oxazolyl, pyrazinyl, pyrazolyl, pyridazinyl, pyridinyl, pyrimidinyl, pyrrolyl, tetrazolyl, thiadiazolyl, thiadiazolonyl, thiadiazinonyl, oxadiazolyl, oxadiazolonyl, oxadiazinonyl, thiazolyl, thienyl, triazinyl, triazolyl, triazolyl, pyridazinonyl, pyridinyl, and pyrimidinonyl. Bicyclic heteroaryl groups include monovalent 8-, 9-, 10-, 11-, or 12-membered bicyclic aromatic rings containing one or more heteroatoms independently selected from the group consisting of oxygen, sulfur, and nitrogen in the ring. Bicyclic heteroaryl groups are attached to the parent molecular moiety through any available carbon atom or nitrogen atom within the rings. Examples of bicyclic heteroaryl rings include, but are not limited to, indolyl, benzothienyl, benzofuranyl, indazolyl, benzimidazolyl, benzothiazolyl, benzoxazolyl, benzoisothiazolyl, benzoisoxazolyl, quinolinyl, isoquinolinyl, quinazolinyl, quinoxalinyl, phthalazinyl, pteridinyl, purinyl, naphthyridinyl, and pyrrolopyrimidinyl. In some embodiments the heteroaryl is monocyclic.

The term "heterocyclyl" employed alone or in combination with other terms means, unless otherwise stated, a saturated or unsaturated non-aromatic monocyclic heterocyclyl ring or a bicyclic heterocyclyl ring. Monocyclic heterocyclyl rings include monovalent 3-, 4-, 5-, 6-, or 7-membered rings containing one or more heteroatoms independently selected from the group consisting of oxygen, nitrogen, and sulfur in the ring. Monocyclic heterocyclyl groups are connected to the parent molecular moiety through any available carbon atom or nitrogen atom within the ring. Examples of monocyclic heterocyclyl groups include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiopyranyl, and trithianyl. Bicyclic heterocyclyl rings include monovalent monocyclic heterocyclyl rings fused to phenyl rings, cycloalkyl rings, or other monocyclic heterocyclyl rings. Bicyclic heterocyclyl groups are connected to the parent molecular moiety through any available carbon atom or nitrogen atom within the rings. Examples of bicyclic heterocyclyl groups include, but are not limited to, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl. In some embodiments the heterocyclyl is monocyclic.

The term "acyl" employed alone or in combination with other terms means, unless otherwise stated, a —C(O)R group, wherein R is hydrogen, alkyl or aryl. In some embodiments, alkyl is $C_{1-6}$alkyl. In other embodiments, aryl is phenyl. In certain embodiments, alkyl is $C_{1-6}$alkyl and aryl is phenyl.

The term "amino" employed alone or in combination with other terms means, unless otherwise stated, a —NR$^1$R$^2$ group wherein R$^1$ and R$^2$ are each independently selected from the group consisting of hydrogen, alkyl, and aryl. In some embodiments, alkyl is C$_{1-6}$alkyl. In other embodiments, aryl is phenyl. In certain embodiments, alkyl is C$_{1-6}$alkyl and aryl is phenyl.

The term "amido" employed alone or in combination with other terms means, unless otherwise stated, an amino-C(O)— group. In some embodiments, alkyl is C$_{1-6}$alkyl. In other embodiments, aryl is phenyl. In certain embodiments, alkyl is C$_{1-6}$alkyl and aryl is phenyl.

The term "acylamino" employed alone or in combination with other terms means, unless otherwise stated, an acyl-NR— group, wherein R is independently selected from the group consisting of hydrogen, alkyl, and aryl. In some embodiments, alkyl is C$_{1-6}$alkyl. In other embodiments, aryl is phenyl. In certain embodiments, alkyl is C$_{1-6}$alkyl and aryl is phenyl.

The term "carbamate" employed alone or in combination with other terms means, unless otherwise stated, an amino-C(O)O— or a R$^1$OC(O)NR$^2$—, wherein R$^1$ and R$^2$ are each independently selected from the group consisting of hydrogen, alkyl, and aryl. In some embodiments, alkyl is C$_{1-6}$alkyl. In other embodiments, aryl is phenyl. In certain embodiments, alkyl is C$_{1-6}$alkyl and aryl is phenyl.

The term "carbonate" employed alone or in combination with other terms means, unless otherwise stated, a R$^1$OC(O)O— group, wherein R$^1$ is selected from the group consisting of hydrogen, alkyl, and aryl. In some embodiments, alkyl is C$_{1-6}$alkyl. In other embodiments, aryl is phenyl. In certain embodiments, alkyl is C$_{1-6}$alkyl and aryl is phenyl.

The term "carboxyl" employed alone or in combination with other terms means, unless otherwise stated, a RO(O)C— group, wherein R is selected from the group consisting of hydrogen, alkyl, aryl, and a metal cation. In some embodiments, alkyl is C$_{1-6}$alkyl. In other embodiments, aryl is phenyl. In certain embodiments, alkyl is C$_{1-6}$alkyl and aryl is phenyl.

The term "imino" employed alone or in combination with other terms means, unless otherwise stated, a =NR group, wherein R is selected from the group consisting of hydrogen, alkyl, and aryl. In some embodiments, alkyl is C$_{1-6}$alkyl. In other embodiments, aryl is phenyl. In certain embodiments, alkyl is C$_{1-6}$alkyl and aryl is phenyl.

The term "oxo" employed alone or in combination with other terms means, unless otherwise stated, a =O group.

The term "urea" employed alone or in combination with other terms means, unless otherwise stated, an amino-C(O)NR— group, wherein R is independently selected from the group consisting of hydrogen, alkyl, and aryl. In some embodiments, alkyl is C$_{1-6}$alkyl. In other embodiments, aryl is phenyl. In certain embodiments, alkyl is C$_{1-6}$alkyl and aryl is phenyl.

The term "phosphate" employed alone or in combination with other terms means, unless otherwise stated, a —OP(O)(OR$^1$)(OR$^2$) group, wherein R$^1$ and R$^2$ are each independently selected from the group consisting of hydrogen, alkyl, aryl, and a metal cation. In some embodiments, alkyl is C$_{1-6}$alkyl. In other embodiments, aryl is phenyl. In certain embodiments, alkyl is C$_{1-6}$alkyl and aryl is phenyl.

The term "phosphinate" employed alone or in combination with other terms means, unless otherwise stated, an —OP(O)R$^1$R$^2$ or —P(O)(OR$^3$)R$^4$ group, wherein R$^1$, R$^2$, and R$^3$ are each independently selected from the group consisting of hydrogen, alkyl, aryl, and a metal cation and R$^4$ is independently selected from the group consisting of hydrogen, alkyl, and aryl. In some embodiments, alkyl is C$_{1-6}$alkyl. In other embodiments, aryl is phenyl. In certain embodiments, alkyl is C$_{1-6}$alkyl and aryl is phenyl.

The term "phosphine" employed alone or in combination with other terms means, unless otherwise stated, a —PR$^1$R$^2$ group, wherein R$^1$ and R$^2$ are each independently selected from the group consisting of hydrogen, alkyl, and aryl. In some embodiments, alkyl is C$_{1-6}$alkyl. In other embodiments, aryl is phenyl. In certain embodiments, alkyl is C$_{1-6}$alkyl and aryl is phenyl.

The term "phosphite" employed alone or in combination with other terms means, unless otherwise stated, a —OP(OR$^1$)(OR$^2$) group, wherein R$^1$ and R$^2$ are each independently selected from the group consisting of hydrogen, alkyl, aryl, and a metal cation. In some embodiments, alkyl is C$_{1-6}$alkyl. In other embodiments, aryl is phenyl. In certain embodiments, alkyl is C$_{1-6}$alkyl and aryl is phenyl.

The term "phosphonate" employed alone or in combination with other terms means, unless otherwise stated, a —P(O)(OR$^1$)(OR$^2$) or —OP(O)(OR$^3$)R$^4$ group, wherein R$^1$, R$^2$, and R$^3$ are each independently selected from the group consisting of hydrogen, alkyl, aryl, and a metal cation and R$^4$ is independently selected from the group consisting of hydrogen, alkyl, and aryl. In some embodiments, alkyl is C$_{1-6}$alkyl. In other embodiments, aryl is phenyl. In certain embodiments, alkyl is C$_{1-6}$alkyl and aryl is phenyl.

The term "phosphine oxide" employed alone or in combination with other terms means, unless otherwise stated, a —P(O)R$^1$R$^2$ group, wherein R$^1$ and R$^2$ are each independently selected from the group consisting of hydrogen, alkyl, and aryl. In some embodiments, alkyl is C$_{1-6}$alkyl. In other embodiments, aryl is phenyl. In certain embodiments, alkyl is C$_{1-6}$alkyl and aryl is phenyl.

The term "sulfate" employed alone or in combination with other terms means, unless otherwise stated, a —OS(O)$_2$OR group, wherein. R is selected from the group consisting of hydrogen, alkyl, aryl, and a metal cation. In some embodiments, alkyl is C$_{1-6}$alkyl. In other embodiments, aryl is phenyl. In certain embodiments, alkyl is C$_{1-6}$alkyl and aryl is phenyl.

The term "sulfenyl" employed alone or in combination with other terms means, unless otherwise stated, a —SR group, wherein R is alkyl or aryl. In some embodiments, alkyl is C$_{1-6}$alkyl. In other embodiments, aryl is phenyl. In certain embodiments, alkyl is C$_{1-6}$alkyl and aryl is phenyl.

The term "sulfonyl" employed alone or in combination with other terms means, unless otherwise stated, a —S(O)$_2$R group, wherein R is alkyl or aryl. In some embodiments, alkyl is C$_{1-6}$alkyl. In other embodiments, aryl is phenyl. In certain embodiments, alkyl is C$_{1-6}$alkyl and aryl is phenyl.

The term "sulfonamide" employed alone or in combination with other terms means, unless otherwise stated, an amino-S(O)$_2$— or sulfonyl-NR— group, wherein R is independently selected from the group consisting of hydrogen, alkyl, and aryl. In some embodiments, alkyl is C$_{1-6}$alkyl. In other embodiments, aryl is phenyl. In certain embodiments, alkyl is C$_{1-6}$alkyl and aryl is phenyl.

The term "sulfonate" employed alone or in combination with other terms means, unless otherwise stated, a —S(O)$_2$OR group, wherein R is selected from the group consisting of hydrogen, alkyl, aryl, and a metal cation. In some embodiments, alkyl is C$_{1-6}$alkyl. In other embodiments, aryl is phenyl. In certain embodiments, alkyl is C$_{1-6}$alkyl and aryl is phenyl.

The term "sulfoxide" employed alone or in combination with other terms means, unless otherwise stated, a —S(O)R group, wherein R is alkyl or aryl. In some embodiments, alkyl is $C_{1-6}$alkyl. In other embodiments, aryl is phenyl. In certain embodiments, alkyl is $C_{1-6}$alkyl and aryl is phenyl.

As used herein, the term "substituted" is intended to mean that one or more hydrogen atoms in the group indicated is replaced with one or more independently selected suitable substituents, provided that the normal valency of each atom to which the substituents are attached is not exceeded, and that the substitution results in a stable compound.

The suffix "-ene" as used herein, in combination with other terms, designates a divalent group.

The other general chemical terms used in the formulae herein have their usual meanings.

Asymmetric centers exist in the compounds of the invention. The asymmetric centers may be designated by the symbols "R" or "S", depending on the configuration of substituents in three dimensional space at the chiral carbon atom. All stereochemical isomeric forms of the compounds of the present invention, including diastereomeric, enantiomeric, and epimeric forms, as well as d-isomers and l-isomers, erythro and threo isomers, syn and anti isomers, and endo and exo isomers, and mixtures thereof are within the scope of the present invention.

A particularly preferred stereochemical conformation of the compounds of the invention at the bridgehead of the dicarboximide ring is endo.

Individual enantiomers of the compounds may be prepared synthetically from commercially available enantiopure starting materials or by preparing enantiomeric mixtures of the compounds and resolving the mixture into individual enantiomers. Resolution methods include conversion of the enantiomeric mixture into a mixture of diastereomers and separation of the diastereomers by, for example, recrystallization or chromatography; direct separation of the enantiomers on chiral chromatographic columns; and any other appropriate method known in the art. Starting materials of defined stereochemistry may be commercially available or made and resolved by techniques well known in the art.

The compounds of the invention may exist as geometric isomers. All cis, trans, syn, anti, entgegen (E), and zusammen (Z) isomers, as well as mixtures thereof of the compounds of the invention are within the scope of the present invention.

The compounds of the invention may also exist as tautomeric isomers, such as, keto/enol, imine/enamine, amide/imino alcohol, nitroso/oxime, thioketone/enethiol, and nitro/aci-nitro tautomers. All tautomeric isomers of the compounds of the invention are within the scope of the present invention.

Salts of the compounds of the invention are also within the scope of the present invention. The salts include, for example, acid addition salts, base addition salts, and quaternary salts of basic nitrogen-containing groups.

Acid addition salts can be prepared by reacting compounds, in free base form, with inorganic or organic acids. Examples of acid addition salts include: sulfates; methanesulfonates; acetates; hydrochlorides; hydrobromides; phosphates; toluenesulfonates; citrates; maleates; succinates; tartrates; lactates; and fumarates. Base addition salts can be prepared by reacting compounds, in free acid form, with inorganic or organic bases. Examples of base addition salts include: ammonium salts; alkali metal salts such as sodium salts and potassium salts; and alkaline earth metal salts such as calcium salts and magnesium salts. Other salts will be apparent to those skilled in the art.

Quaternary salts of basic nitrogen-containing groups can be prepared by reacting compounds containing basic nitrogen-containing groups with, for example, alkyl halides such as methyl, ethyl, propyl, and butyl chlorides, bromides, and iodides; dialkyl sulfates such as dimethyl, diethyl, dibutyl, and diamyl sulfates; arylalkyl halides such as benzyl and phenylethyl bromides; and the like. Other reagents suitable for preparing quaternary salts of basic nitrogen-containing groups will be apparent to those skilled in the art.

N-Oxides of the compounds of the invention are also within the scope of the present invention.

The compounds of the invention may form or exist as solvates with various solvents. If the solvent is water, the solvate may be referred to as a hydrate, for example, a monohydrate, a di-hydrate, or a tri-hydrate. All solvated forms and unsolvated forms of the compounds of the invention are within the scope of the present invention.

Isotopologues and isotopomers of the compounds of the invention, wherein one or more atoms in the compounds are replaced with different isotopes are also within the scope of the present invention. Suitable isotopes include, for example, $^{1}H$, $^{2}H$ (D), $^{3}H$ (T), $^{12}C$, $^{13}C$, $^{14}C$, $^{16}O$, and $^{18}O$.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

In one aspect the present invention provides a compound of the formula (I):

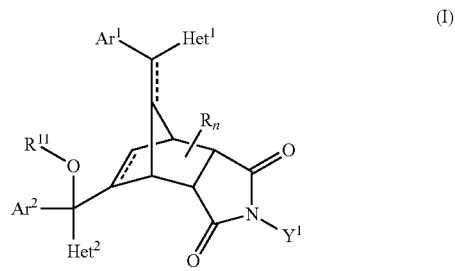

wherein:

$Ar^1$ and $Ar^2$ are each independently a 6 to 10 membered monocyclic or bicyclic aryl ring, wherein the ring is optionally substituted with one or more $R^8$;

$Het^1$ and $Het^2$ are each independently a 5 to 10 membered monocyclic or bicyclic heteroaryl ring comprising 1 to 4 ring nitrogen atoms, wherein the ring is optionally substituted with one or more $R^8$;

each dashed line and solid line together represent a double bond or a single bond;

$Y^1$ is

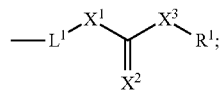

$X^1$ and $X^3$ are each independently selected from the group consisting of O, S, $NR^5$, and a bond, provided that $X^1$ and $X^3$ do not both represent a bond;

$X^2$ is selected from the group consisting of O, S, and $NR^5$;

$L^1$ is selected from the group consisting of $C_{1-6}$alkylene, $C_{3-6}$cycloalkylene, arylene, heteroarylene, heterocyclylene, $C_{1-6}$alkyl$C_{3-6}$cycloalkylene, $C_{1-6}$alkylarylene, $C_{1-6}$alkylheteroarylene, $C_{1-6}$alkylheterocyclylene, $C_{3-6}$cycloalkyl$C_{1-6}$alkylene, aryl$C_{1-6}$alkylene, heteroaryl$C_{1-6}$alkylene, heterocyclyl$C_{1-6}$alkylene, $C_{1-6}$alkoxy$C_{1-6}$alkylene, $C_{3-6}$cycloalkyloxy$C_{1-6}$alkylene, aryloxy$C_{1-6}$alkylene, heteroaryloxy$C_{1-6}$alkylene, heterocyclyloxy$C_{1-6}$alkylene, $C_{1-6}$alkoxy$C_{3-6}$cycloalkylene, $C_{1-6}$alkoxyarylene, $C_{1-6}$alkoxyheteroalkylene, $C_{1-6}$alkoxyheterocyclylalkylene, $C_{1-6}$alkylthio$C_{1-6}$alkylene, $C_{3-6}$cycloalkylthio$C_{1-6}$alkylene, arylthio$C_{1-6}$alkylene, heteroarylthio$C_{1-6}$alkylene, heterocyclylthio$C_{1-6}$alkylene, $C_{1-6}$alkylthio$C_{3-6}$cycloalkylene, $C_{1-6}$alkylthioarylene, $C_{1-6}$alkylthioheteroalkylene, $C_{1-6}$alkylthioheterocyclylalkylene, $C_{1-6}$alkylamino$C_{1-6}$alkylene, $C_{3-6}$cycloalkylamino$C_{1-6}$alkylene, arylamino$C_{1-6}$alkylene, heteroarylamino$C_{1-6}$alkylene, heterocyclylamino$C_{1-6}$alkylene, $C_{1-6}$alkylamino$C_{3-6}$cycloalkylene, $C_{1-6}$alkylaminoarylene, $C_{1-6}$alkylaminoheteroalkylene, and $C_{1-6}$alkylaminoheterocyclylalkylene each of which is optionally substituted with one or more $R^6$;

$R^1$ is selected from the group consisting of $C_{3-18}$alkyl, $C_{3-8}$cycloalkyl, aryl, heterocyclyl, heteroaryl, $C_{3-8}$cycloalkyl$C_{1-6}$alkyl, aryl$C_{1-6}$alkyl, heterocyclyl$C_{1-6}$alkyl, heteroaryl$C_{1-6}$alkyl, $C_{3-18}$alkyloxy$C_{1-6}$alkyl, $C_{3-8}$cycloalkyloxy$C_{1-6}$alkyl, aryloxy$C_{1-6}$alkyl, heterocyclyloxy$C_{1-6}$alkyl, heteroaryloxy$C_{1-6}$alkyl, $C_{3-18}$alkylcarbonyloxy$C_{1-6}$alkyl, $C_{3-8}$cycloalkylcarbonyloxy$C_{1-6}$alkyl, arylcarbonyloxy$C_{1-6}$alkyl, heterocyclylcarbonyloxy$C_{1-6}$alkyl, heteroarylcarbonyloxy$C_{1-6}$alkyl, $C_{3-18}$alkyloxycarbonyl$C_{1-6}$alkyl, $C_{3-8}$cycloalkyloxycarbonyl$C_{1-6}$alkyl, aryloxycarbonyl$C_{1-6}$alkyl, heterocyclyloxycarbonyl$C_{1-6}$alkyl, heteroaryloxycarbonyl$C_{1-6}$alkyl, each of which is optionally substituted with one or more $R^7$;

$R^5$ at each instance is independently selected from the group consisting of hydrogen, $C_{1-6}$alkyl, $C_{3-6}$cycloalkyl, aryl, heterocyclyl, and heteroaryl;

$R^6$ at each instance is independently selected from the group consisting of hydroxyl, thiol, amino, cyano, nitro, halo, $C_{1-6}$alkyl, $C_{1-6}$haloalkyl, $C_{1-6}$alkoxy, and $C_{1-6}$haloalkoxy;

$R^7$ at each instance is independently selected from the group consisting of hydroxyl, thiol, amino, amido, acylamino, cyano, nitro, nitroso, azide, halo, cyanate, thiocyanate, isocyanate, isothiocyanate, oxo, imino, acyl, $C_{1-6}$alkyl, $C_{1-6}$haloalkyl, $C_{3-6}$cycloalkyl, aryl, heterocyclyl, heteroaryl, $C_{1-6}$alkoxy, $C_{1-6}$haloalkoxy, $C_{3-6}$cycloalkoxy, aryloxy, heterocyclyloxy, heteroaryloxy, $C_{1-6}$alkylcarbonyloxy, $C_{3-6}$cycloalkylcarbonyloxy, arylcarbonyloxy, heterocyclylcarbonyloxy, heteroarylcarbonyloxy, $C_{1-6}$alkyloxycarbonyl, $C_{3-6}$cycloalkyloxycarbonyl, aryloxycarbonyl, heterocyclyloxycarbonyl, heteroaryloxycarbonyl, sulfenyl, sulfonyl, sulfoxide, sulfate, sulfonate, sulfonamide, phosphate, phosphonate, phosphinate, phosphine, phosphite, carbonate, carbamate, and urea;

$R^8$ at each instance is selected from the group consisting of hydroxyl, thiol, amino, cyano, nitro, halo, $C_{1-6}$alkyl, $C_{1-6}$haloalkyl, $C_{1-6}$alkoxyl, and $C_{1-6}$haloalkoxy;

$R^{11}$ is selected from the group consisting of hydrogen, $C_{1-6}$alkyl, and $C_{1-6}$haloalkyl;

R at each instance is selected from the group consisting of halo, $C_{1-6}$alkyl, carboxyl, carboxyl$C_{1-6}$alkyl, amido, $C_{1-6}$alkyl, acyloxy, sulfenyl, sulfoxide, sulfonyl, and aryl, wherein each $C_{1-6}$alkyl and aryl is optionally substituted with one or more $R^8$; and n is an integer selected from 0 to 3; or a salt or solvate thereof.

In another aspect the present invention provides a compound of the formula (I), wherein $Ar^1$, $Ar^2$, $Het^1$, $Het^2$, each dashed line and solid line together, $Y^1$, R, and n are as defined in the aspect above.

In another aspect the present invention provides a compound of the formula (I):

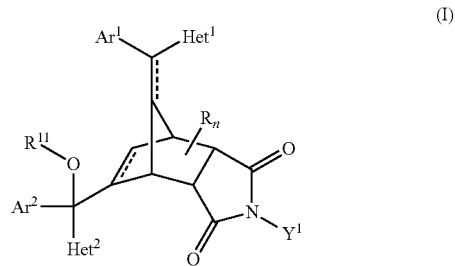

wherein:

$Ar^1$ and $Ar^2$ are each independently a 6 to 10 membered monocyclic or bicyclic aryl ring, wherein the ring is optionally substituted with one or more $R^8$;

$Het^1$ and $Het^2$ are each independently a 5 to 10 membered monocyclic or bicyclic heteroaryl ring comprising 1 to 4 ring nitrogen atoms, wherein the ring is optionally substituted with one or more $R^8$;

each dashed line and solid line together represent a double bond or a single bond;

$Y^1$ is

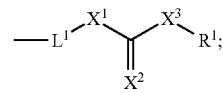

$X^1$ and $X^3$ are each independently selected from the group consisting of O, S, $NR^5$, and a bond, provided that $X^1$ and $X^3$ do not both represent a bond;

$X^2$ is selected from the group consisting of O, S, and $NR^5$;

$L^1$ is selected from the group consisting of $C_{1-6}$alkylene, $C_{3-6}$cycloalkylene, arylene, heteroarylene, heterocyclylene, $C_{1-6}$alkyl$C_{3-6}$cycloalkylene, $C_{1-6}$alkylarylene, $C_{1-6}$alkylheteroarylene, $C_{1-6}$alkylheterocyclylene, $C_{3-6}$cycloalkyl$C_{1-6}$alkylene, aryl$C_{1-6}$alkylene, heteroaryl$C_{1-6}$alkylene, heterocyclyl$C_{1-6}$alkylene, $C_{1-6}$alkoxy$C_{1-6}$alkylene, $C_{3-6}$cycloalkyloxy$C_{1-6}$alkylene, aryloxy$C_{1-6}$alkylene, heteroaryloxy$C_{1-6}$alkylene, heterocyclyloxy$C_{1-6}$alkylene, $C_{1-6}$alkoxy$C_{3-6}$cycloalkylene, $C_{1-6}$alkoxyarylene, $C_{1-6}$alkoxyheteroalkylene, $C_{1-6}$alkoxyheterocyclylalkylene, $C_{1-6}$alkylthio$C_{1-6}$alkylene, $C_{3-6}$cycloalkylthio$C_{1-6}$alkylene, arylthio$C_{1-6}$alkylene, heteroarylthio$C_{1-6}$alkylene, heterocyclylthio$C_{1-6}$alkylene, $C_{1-6}$alkylthio$C_{3-6}$cycloalkylene, $C_{1-6}$alkylthioarylene, $C_{1-6}$alkylthioheteroalkylene, $C_{1-6}$alkylthioheterocyclylalkylene, $C_{1-6}$alkylamino$C_{1-6}$alkylene, $C_{3-6}$cycloalkylamino$C_{1-6}$alkylene, arylamino$C_{1-6}$alkylene, heteroarylamino$C_{1-6}$alkylene, heterocyclylamino$C_{1-6}$alkylene, $C_{1-6}$alkylamino$C_{3-6}$cycloalkylene, $C_{1-6}$alkylaminoarylene, $C_{1-6}$alkylaminoheteroalkylene, and $C_{1-6}$alkylaminoheterocyclylalkylene each of which is optionally substituted with one or more $R^6$;

$R^1$ is selected from the group consisting of $C_{1-6}$alkyl $C_{3-8}$cycloalkyl, $C_{1-6}$alkylaryl, $C_{1-6}$alkylheterocyclyl, $C_{1-6}$alkylheteroaryl, $C_{1-6}$alkyl$C_{3-8}$cycloalkyl$C_{1-6}$alkyl, $C_{1-6}$alkylheterocyclyl$C_{1-6}$alkyl, $C_{1-6}$alkylheteroaryl $C_{1-6}$alkyl, $C_{1-18}$alkylcarbonyloxy$C_{1-6}$alkyl, and $C_{1-18}$alkyloxycarbonyl$C_{1-6}$alkyl, each of which is optionally substituted with one or more $R^7$; or $R^1$ is $C_{1-6}$alkylaryl$C_{1-6}$alkyl substituted with one or more $R^7$;

$R^5$ at each instance is independently selected from the group consisting of hydrogen, $C_{1-6}$alkyl, $C_{3-6}$cycloalkyl, aryl, heterocyclyl, and heteroaryl;

$R^6$ at each instance is independently selected from the group consisting of hydroxyl, thiol, amino, cyano, nitro, halo, $C_{1-6}$alkyl, $C_{1-6}$haloalkyl, $C_{1-6}$alkoxy, and $C_{1-6}$haloalkoxy;

$R^7$ at each instance is independently selected from the group consisting of hydroxyl, thiol, amino, amido, acylamino, cyano, nitro, nitroso, azide, halo, cyanate, thiocyanate, isocyanate, isothiocyanate, oxo, imino, acyl, $C_{1-6}$alkyl, $C_{1-6}$haloalkyl, $C_{3-6}$cycloalkyl, aryl, heterocyclyl, heteroaryl, $C_{1-6}$alkoxy, $C_{1-6}$haloalkoxy, $C_{3-6}$cycloalkoxy, aryloxy, heterocyclyloxy, heteroaryloxy, $C_{1-6}$alkylcarbonyloxy, $C_{3-6}$cycloalkylcarbonyloxy, arylcarbonyloxy, heterocyclylcarbonyloxy, heteroarylcarbonyloxy, $C_{1-6}$alkyloxycarbonyl, $C_{3-6}$cycloalkyloxycarbonyl, aryloxycarbonyl, heterocyclyloxycarbonyl, heteroaryloxycarbonyl, sulfenyl, sulfonyl, sulfoxide, sulfate, sulfonate, sulfonamide, phosphate, phosphonate, phosphinate, phosphine, phosphite, carbonate, carbamate, and urea;

$R^8$ at each instance is selected from the group consisting of hydroxyl, thiol, amino, cyano, nitro, halo, $C_{1-6}$alkyl, $C_{1-6}$haloalkyl, $C_{1-6}$alkoxyl, and $C_{1-6}$haloalkoxy;

$R^{11}$ is selected from the group consisting of hydrogen, $C_{1-6}$alkyl, and $C_{1-6}$haloalkyl;

R at each instance is selected from the group consisting of halo, $C_{1-6}$alkyl, carboxyl, carboxyl$C_{1-6}$alkyl, amido $C_{1-6}$alkyl, acyloxy, sulfenyl, sulfoxide, sulfonyl, and aryl, wherein each $C_{1-6}$alkyl and aryl is optionally substituted with one or more $R^8$; and n is an integer selected from 0 to 3; or a salt or solvate thereof.

The following embodiments relate to the compound of formula (I).

In one embodiment $Ar^1$ and $Ar^2$ are each independently a phenyl ring optionally substituted with one or more $R^8$.

In one embodiment $Het^1$ and $Het^2$ are each independently a 5 or 6 membered monocyclic heteroaryl ring comprising 1 to 3 ring nitrogen atoms, wherein the ring is optionally substituted with one or more $R^8$. Preferably, $Het^1$ and $Het^2$ are each independently a 6 membered monocyclic heteroaryl ring comprising 1 to 3 ring nitrogen atoms, wherein the ring is optionally substituted with one or more $R^8$. More preferably, $Het^1$ and $Het^2$ are each independently pyridyl optionally substituted with one or more $R^8$.

In one embodiment each dashed line and solid line together represent a double bond.

In one embodiment n is 0 or 1. Preferably, n is 0.

In one embodiment $R^{11}$ is selected from the group consisting of hydrogen and $C_{1-6}$alkyl. Preferably, $R^{11}$ is selected from the group consisting of hydrogen and methyl. More preferably, $R^{11}$ is hydrogen.

In one embodiment, $R^7$ at each instance is independently selected from the group consisting of hydroxyl, thiol, amino, amido, acylamino, cyano, nitro, nitroso, azide, halo, cyanate, thiocyanate, isocyanate, isothiocyanate, oxo, imino, acyl, $C_{1-6}$alkyl, $C_{1-6}$haloalkyl, $C_{3-6}$cycloalkyl, aryl, heterocyclyl, heteroaryl, $C_{1-6}$alkoxy, $C_{1-6}$haloalkoxy, $C_{3-6}$cycloalkoxy, aryloxy, heterocyclyloxy, heteroaryloxy, $C_{1-6}$alkylcarbonyloxy, $C_{3-6}$cycloalkylcarbonyloxy, arylcarbonyloxy, heterocyclylcarbonyloxy, heteroarylcarbonyloxy, $C_{1-6}$alkyloxycarbonyl, $C_{3-6}$cycloalkyloxycarbonyl, aryloxycarbonyl, heterocyclyloxycarbonyl, heteroaryloxycarbonyl, sulfenyl, sulfonyl, sulfoxide, sulfate, sulfonate, sulfonamide, phosphate, phosphonate, phosphinate, phosphine, phosphite, carbonate, carbamate, and urea.

In another embodiment $R^7$ at each instance is independently selected from the group consisting of hydroxyl, thiol, amino, cyano, nitro, nitroso, azide, halo, cyanate, thiocyanate, isocyanate, isothiocyanate, oxo, $C_{1-6}$alkyl, $C_{1-6}$haloalkyl, $C_{3-6}$cycloalkyl, aryl, heterocyclyl, heteroaryl, $C_{1-6}$alkoxy, $C_{1-6}$haloalkoxy, $C_{3-6}$cycloalkoxy, aryloxy, heterocyclyloxy, and heteroaryloxy. In another embodiment $R^7$ at each instance is independently selected from the group consisting of hydroxyl, thiol, amino, cyano, nitro, halo, oxo, $C_{1-6}$alkyl, $C_{1-6}$haloalkyl, aryl, $C_{1-6}$alkoxy, $C_{1-6}$haloalkoxy, and aryloxy.

In another embodiment $R^7$ at each instance is independently selected from the group consisting of hydroxyl, thiol, amino, amido, acylamino, cyano, nitro, nitroso, azide, halo, cyanate, thiocyanate, isocyanate, isothiocyanate, oxo, acyl, $C_{1-6}$alkyl, $C_{1-6}$haloalkyl, aryl, $C_{1-6}$alkoxy, $C_{1-6}$haloalkoxy, aryloxy, $C_{1-6}$alkylcarbonyloxy, arylcarbonyloxy, $C_{1-6}$alkyloxycarbonyl, aryloxycarbonyl, sulfenyl, sulfonyl, sulfoxide, sulfate, sulfonate, sulfonamide, phosphate, phosphonate, carbonate, carbamate, and urea.

In yet another embodiment $R^7$ at each instance is independently selected from the group consisting of hydroxyl, thiol, amino, amido, acylamino, cyano, nitro, nitroso, azide, halo, cyanate, thiocyanate, isocyanate, isothiocyanate, oxo, acyl, $C_{1-6}$alkyl, $C_{1-6}$haloalkyl, aryl, $C_{1-6}$alkoxy, $C_{1-6}$haloalkoxy, aryloxy, $C_{1-6}$alkylcarbonyloxy, arylcarbonyloxy, $C_{1-6}$alkyloxycarbonyl, aryloxycarbonyl, sulfenyl, sulfonyl, sulfoxide, sulfate, sulfonate, sulfonamide, phosphate, and phosphonate.

In yet another embodiment, $R^7$ at each instance is independently selected from the group consisting of hydroxyl, thiol, amino, amido, acylamino, cyano, nitro, halo, oxo, acyl, $C_{1-6}$alkyl, $C_{1-6}$haloalkyl, aryl, $C_{1-6}$alkoxy, $C_{1-6}$haloalkoxy, aryloxy, $C_{1-6}$alkylcarbonyloxy, arylcarbonyloxy, $C_{1-6}$alkyloxycarbonyl, aryloxycarbonyl, sulfenyl, sulfonyl, sulfoxide, sulfate, sulfonate, sulfonamide, and phosphate.

In one embodiment $R^5$ at each instance is independently selected from the group consisting of hydrogen, $C_{1-6}$alkyl, and aryl. In one embodiment, $R^5$ at each instance is independently selected from the group consisting of hydrogen and $C_{1-6}$alkyl. In another embodiment, $R^5$ at each instance is hydrogen.

In one embodiment $Ar^1$ and $Ar^2$ are each independently a phenyl ring optionally substituted with one or more $R^8$; $Het^1$ and $Het^2$ are each independently pyridyl optionally substituted with one or more $R^8$; and each dashed line and solid line together represent a double bond; and n is 0.

In one embodiment the stereochemical configuration at the bridgehead of the dicarboximide ring is endo.

In one embodiment the compound of formula (I) is a compound of formula (II):

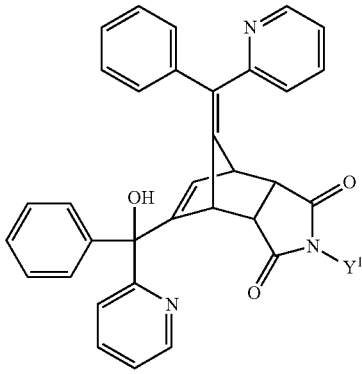

(II)

wherein $Y^1$, $L^1$, $X^1$, $X^2$, $X^3$, and $R^1$ are as defined in any of the embodiments relating to the compound of formula (I). The following embodiments relate to the compound of formula (I) and the compound of formula (II).

In one embodiment $L^1$ is selected from the group consisting of $C_{1-6}$alkylene, $C_{3-6}$cycloalkylene, arylene, heteroarylene, heterocyclylene, $C_{1-6}$alkyl$C_{3-6}$cycloalkylene, $C_{1-6}$alkylarylene, $C_{1-6}$alkylheteroarylene, $C_{1-6}$alkylheterocyclylene, $C_{3-6}$cycloalkyl$C_{1-6}$alkylene, aryl$C_{1-6}$alkylene, heteroaryl$C_{1-6}$alkylene, heterocyclyl$C_{1-6}$alkylene, $C_{1-6}$alkoxy$C_{1-6}$alkylene, $C_{3-6}$cycloalkyloxy$C_{1-6}$alkylene, aryloxy$C_{1-6}$alkylene, heteroaryloxy$C_{1-6}$alkylene, heterocyclyloxy$C_{1-6}$alkylene, $C_{1-6}$alkylthio$C_{1-6}$alkylene, $C_{3-6}$cycloalkylthio$C_{1-6}$alkylene, arylthio$C_{1-6}$alkylene, heteroarylthio$C_{1-6}$alkylene, heterocyclylthio$C_{1-6}$alkylene, $C_{1-6}$alkylamino$C_{1-6}$alkylene, $C_{3-6}$cycloalkylamino$C_{1-6}$alkylene, arylamino$C_{1-6}$alkylene, heteroarylamino$C_{1-6}$alkylene, and heterocyclylamino$C_{1-6}$alkylene, each of which is optionally substituted with one or more $R^6$.

In one embodiment $L^1$ is selected from the group consisting of $C_{1-6}$alkylene, $C_{3-6}$cycloalkylene, arylene, heteroarylene, heterocyclylene, $C_{1-6}$alkyl$C_{3-6}$cycloalkylene, $C_{1-6}$alkylarylene, $C_{1-6}$alkylheteroarylene, $C_{1-6}$alkylheterocyclylene, $C_{3-6}$cycloalkyl$C_{1-6}$alkylene, aryl$C_{1-6}$alkylene, heteroaryl$C_{1-6}$alkylene, heterocyclyl$C_{1-6}$alkylene, $C_{1-6}$alkoxy$C_{1-6}$alkylene, $C_{3-6}$cycloalkyloxy$C_{1-6}$alkylene, aryloxy$C_{1-6}$alkylene, heteroaryloxy$C_{1-6}$alkylene, and heterocyclyloxy$C_{1-6}$alkylene, each of which is optionally substituted with one or more $R^6$.

In one embodiment $L^1$ is selected from the group consisting of $C_{1-6}$alkylene, $C_{1-6}$alkyl$C_{3-6}$cycloalkylene, $C_{1-6}$alkylarylene, $C_{3-6}$cycloalkyl$C_{1-6}$alkylene, aryl$C_{1-6}$alkylene, $C_{1-6}$alkoxy$C_{1-6}$alkylene, each of which is optionally substituted with one or more $R^6$.

In another embodiment $L^1$ is selected from the group consisting of $C_{1-6}$alkylene, $C_{1-6}$alkyl$C_{3-6}$cycloalkylene, $C_{1-6}$alkylarylene, $C_{3-6}$cycloalkyl$C_{1-6}$alkylene, aryl$C_{1-6}$alkylene, $C_{1-6}$alkoxy$C_1$alkylene, each of which is optionally substituted with one or more $R^6$.

Preferably, $L^1$ is selected from the group consisting of $C_{1-6}$alkylene and $C_{1-6}$alkyloxy$C_1$alkylene, each of which is optionally substituted with one or more $R^6$. In one embodiment $L^1$ is $C_{1-6}$alkylene optionally substituted with one or more $R^6$.

In another embodiment, $L^1$ is selected from the group consisting of $C_{1-4}$alkylene and $C_{1-4}$alkoxy$C_1$alkylene, each of which is optionally substituted with one or more $R^6$. In one embodiment $L^1$ is $C_{1-4}$alkylene optionally substituted with one or more $R^6$. In another embodiment $L^1$ is saturated $C_{1-4}$alkylene.

In one embodiment $X^1$ and $X^3$ are each independently selected from the group consisting of O, $NR^5$, and a bond. In one embodiment, one of $X^1$ and $X^3$ is a bond.

In one embodiment, $X^1$ is selected from the group consisting of O and $NR^5$ and $X^3$ is selected from the group consisting of O, $NR^5$, and a bond. In another embodiment, $X^1$ is selected from the group consisting of O, $NR^5$, and a bond and $X^3$ is selected from the group consisting of 0 and $NR^5$.

In another embodiment, $X^1$ is O and $X^3$ is selected from the group consisting of O, $NR^5$, and a bond. In another embodiment, $X^1$ is selected from the group consisting of O, $NR^5$, and a bond and $X^3$ is O. In another embodiment, $X^1$ is $NR^5$ and $X^3$ is selected from the group consisting of O, $NR^5$, and a bond.

In another embodiment, $X^1$ is O and $X^3$ is selected from the group consisting of O and a bond.

In one specific embodiment, $X^1$ is O and $X^3$ is a bond. In another specific embodiment, $X^1$ is a bond and $X^3$ is O. In another specific embodiment, $X^1$ is $NR^5$ and $X^3$ is a bond.

In one embodiment $X^2$ is O or $NR^5$. Preferably, $X^2$ is O.

In one embodiment $X^1$ is selected from the group consisting of O and $NR^5$, $X^2$ is O, and $X^3$ is a bond; or $X^1$ is a bond, $X^2$ is O, and $X^3$ is selected from the group consisting of O and $NR^5$.

In one embodiment, $X^1$ and $X^2$ are each O and $X^3$ is a bond; $X^1$ is $NR^5$, $X^2$ is O, and $X^3$ is a bond; or $X^1$ is a bond, $X^2$ is O, and $X^3$ is O. In another embodiment, $X^1$ and $X^2$ are each O and $X^3$ is a bond; or $X^1$ is a bond, $X^2$ is O, and $X^3$ is O. In another embodiment, $X^1$ and $X^2$ are each O and $X^3$ is a bond.

In one embodiment $X^1$ and $X^2$ are each O and $X^3$ is a bond. In another embodiment, $X^1$ is $NR^5$, $X^2$ is O, and $X^3$ is a bond. In another embodiment, $X^1$ is a bond, $X^2$ is O, and $X^3$ is O.

In one embodiment, $R^1$ is selected from the group consisting of $C_{3-18}$alkyl, $C_{3-8}$cycloalkyl, aryl, heterocyclyl, heteroaryl, $C_{3-8}$cycloalkyl$C_{1-6}$alkyl, aryl$C_{1-6}$alkyl, heterocyclyl$C_{1-6}$alkyl, heteroaryl$C_{1-6}$alkyl, $C_{3-18}$alkyloxy$C_{1-6}$alkyl, $C_{3-8}$cycloalkyloxy$C_{1-6}$alkyl, aryloxy$C_{1-6}$alkyl, heterocyclyloxy$C_{1-6}$alkyl, heteroaryloxy$C_{1-6}$alkyl, $C_{3-18}$alkylcarbonyloxy$C_{1-6}$alkyl, $C_{3-8}$cycloalkylcarbonyloxy$C_{1-6}$alkyl, arylcarbonyloxy$C_{1-6}$alkyl, heterocyclylcarbonyloxy$C_{1-6}$alkyl, heteroarylcarbonyloxy$C_{1-6}$alkyl, $C_{3-18}$alkyloxycarbonyl$C_{1-6}$alkyl, $C_{3-8}$cycloalkyloxycarbonyl$C_{1-6}$alkyl, aryloxycarbonyl$C_{1-6}$alkyl, heterocyclyloxycarbonyl$C_{1-6}$alkyl, heteroaryloxycarbonyl$C_{1-6}$alkyl, each of which is optionally substituted with one or more $R^7$.

In one embodiment $R^1$ is selected from the group consisting of $C_{3-18}$alkyl, $C_{3-8}$cycloalkyl, aryl, $C_{3-8}$cycloalkyl$C_{1-6}$alkyl, aryl$C_{1-6}$alkyl, $C_{3-8}$cycloalkyloxy$C_{1-6}$alkyl, aryloxy$C_{1-6}$alkyl, $C_{3-8}$cycloalkylcarbonyloxy$C_{1-6}$alkyl, arylcarbonyloxy$C_{1-6}$alkyl, $C_{3-8}$cycloalkyloxycarbonyl$C_{1-6}$alkyl, aryloxycarbonyl$C_{1-6}$alkyl, each of which is optionally substituted with one or more $R^7$.

Preferably, $R^1$ is selected from the group consisting of $C_{3-18}$alkyl, aryl, aryl$C_{1-6}$alkyl, aryloxy$C_{1-6}$alkyl, arylcarbonyloxy$C_{1-6}$alkyl, and aryloxycarbonyl$C_{1-6}$alkyl, each of which is optionally substituted with one or more $R^7$. Preferably, $R^1$ is selected from the group consisting of $C_{3-12}$alkyl, aryl, aryl$C_{1-6}$alkyl, arylcarbonyloxy$C_{1-6}$alkyl, and aryloxycarbonyl$C_{1-6}$alkyl, each of which is optionally substituted with one or more $R^7$.

In one embodiment $R^1$ is selected from the group consisting of $C_{3-18}$alkyl, $C_{3-8}$cycloalkyl, aryl, $C_{3-8}$cycloalkyl$C_{1-6}$alkyl, aryl$C_{1-6}$alkyl, $C_{3-8}$cycloalkyloxy$C_{1-6}$alkyl, aryloxy$C_{1-6}$alkyl, $C_{3-8}$cycloalkylcarbonyloxy$C_{1-6}$alkyl, arylcarbonyloxyC$_{1-6}$alkyl, C$_{3-8}$cycloalkyloxycarbonylC$_{1-6}$alkyl, aryloxycarbonylC$_{1-6}$alkyl, each of which is optionally substituted with one or more R$^7$.

In another embodiment, R$^1$ is selected from the group consisting of C$_{1-6}$alkylC$_{3-8}$cycloalkyl, C$_{1-6}$alkylaryl, C$_{1-6}$alkylC$_{3-8}$cycloalkylC$_{1-6}$alkyl, and C$_{1-18}$alkylcarbonyloxyC$_{1-6}$alkyl, C$_{1-18}$alkyloxycarbonylC$_{1-6}$alkyl, each of which is optionally substituted with one or more R$^7$; or R$^1$ is C$_{1-6}$alkylarylC$_{1-6}$alkyl substituted with one or more R$^7$.

In one embodiment, R$^1$ is selected from the group consisting of C$_{3-18}$alkyl, aryl, arylC$_{1-6}$alkyl, aryloxyC$_{1-6}$alkyl, arylcarbonyloxyC$_{1-6}$alkyl, and aryloxycarbonylC$_{1-6}$alkyl, each of which is optionally substituted with one or more R$^7$.

In another embodiment, R$^1$ is selected from the group consisting of C$_{1-6}$alkylaryl, C$_{1-18}$alkylcarbonyloxyC$_{1-6}$alkyl, and C$_{1-18}$alkyloxycarbonylC$_{1-6}$alkyl, each of which is optionally substituted with one or more R$^7$; or R$^1$ is C$_{1-6}$alkylarylC$_{1-6}$alkyl substituted with one or more R$^7$.

In one embodiment R$^1$ is selected from the group consisting of C$_{3-12}$alkyl, aryl, arylC$_{1-6}$alkyl, arylcarbonyloxyC$_{1-6}$alkyl, and aryloxycarbonylC$_{1-6}$alkyl, each of which is optionally substituted with one or more R$^7$.

In another embodiment, R$^1$ is selected from the group consisting of C$_{1-6}$alkylaryl, C$_{1-12}$alkylcarbonyloxyC$_{1-6}$alkyl, and C$_{1-12}$alkyloxycarbonylC$_{1-6}$alkyl, each of which is optionally substituted with one or more R$^7$; or R$^1$ is C$_{1-6}$alkylarylC$_{1-6}$alkyl substituted with one or more R$^7$.

In another embodiment, R$^1$ is selected from the group consisting of C$_{1-6}$alkylaryl, C$_{1-6}$alkylcarbonyloxyC$_{1-6}$alkyl, and C$_{1-6}$alkyloxycarbonylC$_{1-6}$alkyl, each of which is optionally substituted with one or more R$^7$; or R$^1$ is C$_{1-6}$alkylaryl C$_{1-6}$alkyl substituted with one or more R$^7$.

In one embodiment R$^1$ is selected from the group consisting of C$_{3-12}$alkyl, aryl, arylC$_{1-6}$alkyl, each of which is optionally substituted with one or more R$^7$. In one embodiment R$^1$ is selected from the group consisting of C$_{3-12}$alkyl, aryl, arylC$_{1-6}$saturated alkyl, arylC$_{1-6}$alkenyl, each of which is optionally substituted with one or more R$^7$.

In one embodiment R$^1$ is selected from the group consisting of C$_{1-6}$alkylaryl optionally substituted with one or more R$^7$ and C$_{1-6}$alkylarylC$_{1-6}$alkyl substituted with one or more R$^7$. In another embodiment, R$^1$ is selected from the group consisting of C$_{1-6}$alkylaryl optionally substituted with one or more R$^7$, C$_{1-6}$alkylarylC$_{1-6}$saturated alkyl substituted with one or more R$^7$, C$_{1-6}$alkylarylC$_{1-6}$alkenyl substituted with one or more R$^7$.

In one embodiment R$^1$ is selected from the group consisting of aryl and arylC$_{1-6}$alkyl, each of which is optionally substituted with one or more R$^7$. In another embodiment R$^1$ is selected from the group consisting of aryl, arylC$_{1-6}$saturated alkyl, and arylC$_{1-6}$alkenyl, each of which is optionally substituted with one or more. R$^7$.

In one embodiment R$^1$ is selected from the group consisting of arylC$_{1-6}$alkyl optionally substituted with one or more R$^7$. In one embodiment R$^1$ is selected from the group consisting of arylC$_{1-6}$alkenyl optionally substituted with one or more R$^7$. In one embodiment R$^1$ is selected from the group consisting of phenylC$_{1-4}$alkenyl, wherein the phenyl is optionally substituted with one or more R$^7$.

In one embodiment, L$^1$ is selected from the group consisting of C$_{1-6}$alkylene, C$_{1-6}$alkylC$_{3-6}$cycloalkylene, C$_{1-6}$alkylarylene, C$_{3-6}$cycloalkylC$_{1-6}$alkylene, arylC$_{1-6}$alkylene, and C$_{1-6}$alkoxyC$_{1-6}$alkylene, each of which is optionally substituted with one or more R$^6$; X$^1$ and X$^3$ are each independently selected from the group consisting of O, NR$^5$, and a bond; X$^2$ is O or NR$^5$; and R$^1$ is selected from the group consisting of C$_{3-18}$alkyl, C$_{3-8}$cycloalkyl, aryl, C$_{3-8}$cycloalkylC$_{1-6}$alkyl, arylC$_{1-6}$alkyl, C$_{3-8}$cycloalkyloxyC$_{1-6}$alkyl, aryloxyC$_{1-6}$alkyl, C$_{3-8}$cycloalkylcarbonyloxyC$_{1-6}$alkyl, arylcarbonyloxyC$_{1-6}$alkyl, C$_{3-8}$cycloalkyloxycarbonylC$_{1-6}$alkyl, aryloxycarbonylC$_{1-6}$alkyl, each of which is optionally substituted with one or more R$^7$.

In another embodiment L$^1$ is selected from the group consisting of C$_{1-6}$alkylene, C$_{1-6}$alkylC$_{3-6}$cycloalkylene, C$_{1-6}$alkylarylene, C$_{3-6}$cycloalkylC$_{1-6}$alkylene, arylC$_{1-6}$alkylene, and C$_{1-6}$alkoxyC$_1$alkylene, each of which is optionally substituted with one or more R$^6$; X$^1$ and X$^3$ are each independently selected from the group consisting of O, NR$^5$, and a bond; X$^2$ is O or NR$^5$; and R$^1$ is selected from the group consisting of C$_{3-18}$alkyl, C$_{3-8}$cycloalkyl, aryl, C$_{3-8}$cycloalkylC$_{1-6}$alkyl, arylC$_{1-6}$alkyl, C$_{3-8}$cycloalkyloxy C$_{1-6}$alkyl, aryloxyC$_{1-6}$alkyl, C$_{3-8}$cycloalkylcarbonyloxy C$_{1-6}$alkyl, arylcarbonyloxyC$_{1-6}$alkyl, C$_{3-8}$cycloalkyloxycarbonylC$_{1-6}$alkyl, aryloxycarbonylC$_{1-6}$alkyl, each of which is optionally substituted with one or more R$^7$.

In another embodiment L$^1$ is selected from the group consisting of C$_{1-6}$alkylene and C$_{1-6}$alkyloxyC$_1$alkylene, each of which is optionally substituted with one or more R$^6$; X$^1$ is selected from the group consisting of O and NR$^5$; X$^3$ is selected from the group consisting of O, NR$^5$, and a bond; X$^2$ is O or NR$^5$; and R$^1$ is selected from the group consisting of C$_{3-18}$alkyl, aryl, arylC$_{1-6}$alkyl, aryloxyC$_{1-6}$alkyl, arylcarbonyloxyC$_{1-6}$alkyl, and aryloxycarbonylC$_{1-6}$alkyl, each of which is optionally substituted with one or more R$^7$.

In another embodiment L$^1$ is selected from the group consisting of C$_{1-6}$alkylene and C$_{1-6}$alkyloxyC$_1$alkylene, each of which is optionally substituted with one or more R$^6$; X$^1$ is O; X$^3$ is selected from the group consisting of O, NR$^5$, and a bond; X$^2$ is O or NR$^5$; and R$^1$ is selected from the group consisting of C$_{3-18}$alkyl, aryl, arylC$_{1-6}$alkyl, aryloxy C$_{1-6}$alkyl, arylcarbonyloxyC$_{1-6}$alkyl, and aryloxycarbonylC$_{1-6}$alkyl, each of which is optionally substituted with one or more R$^7$.

In another embodiment L$^1$ is selected from the group consisting of C$_{1-6}$alkylene and C$_{1-6}$alkyloxyC$_1$alkylene, each of which is optionally substituted with one or more R$^6$; X$^1$ is O; X$^3$ is selected from the group consisting of O, NR$^5$, and a bond; X$^2$ is O; and R$^1$ is selected from the group consisting of C$_{3-12}$alkyl, aryl, arylC$_{1-6}$alkyl, arylcarbonyloxyC$_{1-6}$alkyl, and aryloxycarbonylC$_{1-6}$alkyl, each of which is optionally substituted with one or more R$^7$.

In another embodiment L$^1$ is selected from the group consisting of C$_{1-6}$alkylene and C$_{1-6}$alkoxyC$_1$alkylene, each of which is optionally substituted with one or more R$^6$; X$^1$ is O; X$^3$ is a bond; X$^2$ is O; and R$^1$ is selected from the group consisting of C$_{3-12}$alkyl, aryl, arylC$_{1-6}$alkyl, arylcarbonyloxyC$_{1-6}$alkyl, and aryloxycarbonylC$_{1-6}$alkyl, each of which is optionally substituted with one or more R$^7$.

In another embodiment L$^1$ is selected from the group consisting of C$_{1-4}$alkylene and C$_{1-4}$alkoxyC$_1$alkylene, each of which is optionally substituted with one or more R$^6$; X$^1$ is O; X$^3$ is a bond; X$^2$ is O; and R$^1$ is selected from the group consisting of C$_{3-12}$alkyl, aryl, arylC$_{1-6}$alkyl, arylcarbonyloxyC$_{1-6}$alkyl, and aryloxycarbonylC$_{1-6}$alkyl, each of which is optionally substituted with one or more R$^7$.

In another embodiment L$^1$ is C$_{1-4}$alkylene optionally substituted with one or more R$^6$; X$^1$ is O; X$^3$ is a bond; X$^2$ is O; and R$^1$ is selected from the group consisting of C$_{3-12}$alkyl, aryl, and arylC$_{1-6}$alkyl, each of which is optionally substituted with one or more R$^7$.

In another embodiment L$^1$ is C$_{1-4}$alkylene optionally substituted with one or more R$^6$; X$^1$ is O; X$^3$ is a bond; X$^2$ is O; and R$^1$ is selected from the group consisting of C$_{3-12}$alkyl optionally substituted with one or more $R^7$. Preferably, $R^1$ is $C_{4-12}$alkyl optionally substituted with one or more $R^7$.

In another embodiment $L^1$ is $C_{1-4}$alkylene optionally substituted with one or more $R^6$; $X^1$ is O; $X^3$ is a bond; $X^2$ is O; and $R^1$ is selected from the group consisting of aryl optionally substituted with one or more $R^7$. Preferably, $R^1$ is phenyl or naphthyl optionally substituted with one or more $R^7$.

In another embodiment $L^1$ is $C_{1-4}$alkylene optionally substituted with one or more $R^6$; $X^1$ is O; $X^3$ is a bond; $X^2$ is O; and $R^1$ is selected from the group consisting of aryl$C_{1-6}$alkyl optionally substituted with one or more $R^7$. In a preferred embodiment $L^1$ is $C_{1-4}$alkylene optionally substituted with one or more $R^6$; $X^1$ is O; $X^3$ is a bond; $X^2$ is O; and $R^1$ is aryl$C_{2-6}$alkenyl optionally substituted with one or more $R^7$.

In one embodiment $L^1$ is saturated $C_{1-4}$alkylene; $X^1$ is O; $X^3$ is a bond; $X^2$ is O; and $R^1$ is selected from the group consisting of phenyl$C_2$alkenyl, phenyl$C_2$alkynyl, and 2-naphthyl, wherein each phenyl $C_2$alkenyl is optionally substituted with one or more halo or methoxy.

In another embodiment $L^1$ is $C_{1-4}$alkylene optionally substituted with one or more $R^6$; $X^1$ is O; $X^3$ is a bond; $X^2$ is O; and $R^1$ is selected from the group consisting of $C_{3-12}$alkyl optionally substituted with one or more $R^7$. Preferably, $R^1$ is $C_{4-12}$alkyl optionally substituted with one or more $R^7$.

In another embodiment $L^1$ is $C_{1-4}$alkylene optionally substituted with one or more $R^6$; $X^1$ is O; $X^3$ is a bond; $X^2$ is O; and $R^1$ is selected from the group consisting of aryl optionally substituted with one or more $R^7$. Preferably, $R^1$ is phenyl or naphthyl optionally substituted with one or more $R^7$.

In another embodiment $L^1$ is $C_{1-4}$alkylene optionally substituted with one or more $R^6$; $X^1$ is O; $X^3$ is a bond; $X^2$ is O; and $R^1$ is selected from the group consisting of aryl$C_{1-6}$alkyl optionally substituted with one or more $R^7$. In a preferred embodiment $L^1$ is $C_{1-4}$alkylene optionally substituted with one or more $R^6$; $X^1$ is O; $X^3$ is a bond; $X^2$ is O; and $R^1$ is aryl$C_{2-6}$alkenyl optionally substituted with one or more $R^7$.

In one embodiment $L^1$ is saturated $C_{1-4}$alkylene; $X^1$ is O; $X^3$ is a bond; $X^2$ is O; and $R^1$ is selected from the group consisting of phenyl$C_2$alkenyl, phenyl$C_2$alkynyl, and 2-naphthyl, wherein each phenyl $C_2$alkenyl is optionally substituted with one or more halo or methoxy.

In one embodiment $L^1$ is selected from the group consisting of $C_{1-6}$alkylene, $C_{1-6}$alkyl$C_{3-6}$cycloalkylene, $C_{1-6}$alkylarylene, $C_{3-6}$cycloalkyl$C_{1-6}$alkylene, aryl$C_{1-6}$alkylene, and $C_{1-6}$alkoxy$C_{1-6}$alkylene, each of which is optionally substituted with one or more $R^6$; $X^1$ and $X^3$ are each independently selected from the group consisting of O, $NR^5$, and a bond; $X^2$ is O or $NR^5$; and $R^1$ is selected from the group consisting of $C_{3-18}$alkyl, $C_{3-8}$cycloalkyl, aryl, $C_{3-8}$cycloalkyl$C_{1-6}$alkyl, aryl$C_{1-6}$alkyl, $C_{3-18}$alkoxy$C_{1-6}$alkyl, $C_{3-8}$cycloalkyloxy $C_{1-6}$alkyl, aryloxy$C_{1-6}$alkyl, $C_{3-18}$alkylcarbonyloxy $C_{1-6}$alkyl, $C_{3-8}$cycloalkylcarbonyloxy$C_{1-6}$alkyl, arylcarbonyloxy$C_{1-6}$alkyl, $C_{3-18}$alkyloxycarbonyl$C_{1-6}$alkyl, $C_{3-8}$cycloalkyloxycarbonyl$C_{1-6}$alkyl, aryloxycarbonyl$C_{1-6}$alkyl, each of which is optionally substituted with one or more $R^7$.

In one embodiment $L^1$ is selected from the group consisting of $C_{1-6}$alkylene, $C_{1-6}$alkyl$C_{3-6}$cycloalkylene, $C_{1-6}$alkylarylene, $C_{3-6}$cycloalkyl$C_{1-6}$alkylene, aryl$C_{1-6}$alkylene, and $C_{1-6}$alkoxy$C_{1-6}$alkylene, each of which is optionally substituted with one or more $R^6$; $X^1$ and $X^3$ are each independently selected from the group consisting of O, $NR^5$, and a bond; $X^2$ is O or $NR^5$; $R^1$ is selected from the group consisting of $C_{1-6}$alkyl$C_{3-8}$cycloalkyl, $C_{1-6}$alkylaryl, $C_{1-6}$alkylheterocyclyl, $C_{1-6}$alkylheteroaryl, $C_{1-6}$alkyl$C_{3-8}$cycloalkyl$C_{1-6}$alkyl, $C_{1-6}$alkylheterocyclyl$C_{1-6}$alkyl, $C_{1-6}$alkylheteroaryl $C_{1-6}$alkyl, $C_{1-18}$alkylcarbonyloxy$C_{1-6}$alkyl, and $C_{1-18}$alkyloxycarbonyl$C_{1-6}$alkyl, each of which is optionally substituted with one or more $R^7$; or $R^1$ is $C_{1-6}$alkylaryl$C_{1-6}$alkyl substituted with one or more $R^7$.

In one embodiment $L^1$ is selected from the group consisting of $C_{1-6}$alkylene, $C_{1-6}$alkyl$C_{3-6}$cycloalkylene, $C_{1-6}$alkylarylene, $C_{3-6}$cycloalkyl$C_{1-6}$alkylene, aryl$C_{1-6}$alkylene, and $C_{1-6}$alkoxy$C_{1-6}$alkylene, each of which is optionally substituted with one or more $R^6$; $X^1$ and $X^3$ are each independently selected from the group consisting of O, $NR^5$, and a bond; $X^2$ is O or $NR^5$; and $R^1$ is selected from the group consisting of $C_{3-18}$alkyl, $C_{3-8}$cycloalkyl, aryl, $C_{3-8}$cycloalkyl$C_{1-6}$alkyl, aryl$C_{1-6}$alkyl, $C_{3-18}$alkoxy$C_{1-6}$alkyl, $C_{3-8}$cycloalkyloxy $C_{1-6}$alkyl, aryloxy$C_{1-6}$alkyl, $C_{3-18}$alkylcarbonyloxy $C_{1-6}$alkyl, $C_{3-8}$cycloalkylcarbonyloxy$C_{1-6}$alkyl, arylcarbonyloxy$C_{1-6}$alkyl, $C_{3-18}$alkyloxycarbonyl$C_{1-6}$alkyl, $C_{3-8}$cycloalkyloxycarbonyl$C_{1-6}$alkyl, aryloxycarbonyl$C_{1-6}$alkyl, each of which is optionally substituted with one or more $R^7$.

In another embodiment $L^1$ is selected from the group consisting of $C_{1-6}$alkylene and $C_{1-6}$alkyloxy$C_{1-6}$alkylene, each of which is optionally substituted with one or more $R^6$; $X^1$ is selected from the group consisting of O and $NR^5$, $X^2$ is O, and $X^3$ is a bond; or $X^1$ is a bond, $X^2$ is O, and $X^3$ is selected from the group consisting of O and $NR^5$; and $R^1$ is selected from the group consisting of $C_{3-18}$alkyl, aryl, aryl$C_{1-6}$alkyl, aryloxy$C_{1-6}$alkyl, $C_{3-18}$alkylcarbonyloxy$C_{1-6}$alkyl, arylcarbonyloxy$C_{1-6}$alkyl, $C_{3-18}$alkyloxycarbonyl$C_{1-6}$alkyl, and aryloxycarbonyl$C_{1-6}$alkyl, each of which is optionally substituted with one or more $R^7$.

In another embodiment $L^1$ is selected from the group consisting of $C_{1-6}$alkylene and $C_{1-6}$alkyloxy$C_{1-6}$alkylene, each of which is optionally substituted with one or more $R^6$; $X^1$ is selected from the group consisting of O and $NR^5$, $X^2$ is O, and $X^3$ is a bond; or $X^1$ is a bond, $X^2$ is O, and $X^3$ is selected from the group consisting of O and $NR^5$; and $R^1$ is selected from the group consisting of $C_{1-6}$alkylaryl, $C_{1-18}$alkylcarbonyloxy $C_{1-6}$alkyl, and $C_{1-18}$alkyloxycarbonyl$C_{1-6}$alkyl, each of which is optionally substituted with one or more $R^7$; or $R^1$ is $C_{1-6}$alkylaryl$C_{1-6}$alkyl substituted with one or more $R^7$.

In one embodiment $L^1$ is $C_{1-6}$alkylene optionally substituted with one or more $R^6$; $X^1$ and $X^2$ are each O, and $X^3$ is a bond; or $X^1$ is a bond, and $X^2$ and $X^3$ are each O; and $R^1$ is selected from the group consisting of $C_{3-12}$alkyl, aryl, aryl$C_{1-6}$alkyl, $C_{3-12}$alkylcarbonyloxy$C_{1-6}$alkyl, arylcarbonyloxy$C_{1-6}$alkyl, $C_{3-12}$alkyloxycarbonyl$C_{1-6}$alkyl, and aryloxycarbonyl$C_{1-6}$alkyl, each of which is optionally substituted with one or more $R^7$.

In one embodiment $L^1$ is $C_{1-6}$alkylene optionally substituted with one or more $R^6$; $X^1$ and $X^2$ are each O, and $X^3$ is a bond; or $X^1$ is a bond, and $X^2$ and $X^3$ are each O; and $R^1$ is selected from the group consisting of $C_{1-6}$alkylaryl, $C_{1-12}$alkylcarbonyloxy$C_{1-6}$alkyl, and $C_{1-12}$alkyloxycarbonyl$C_{1-6}$alkyl, each of which is optionally substituted with one or more $R^7$; or $R^1$ is $C_{1-6}$alkylaryl$C_{1-6}$alkyl substituted with one or more $R^7$.

In one embodiment $L^1$ is $C_{1-6}$alkylene optionally substituted with one or more $R^6$; $X^1$ and $X^2$ are each O, and $X^3$ is a bond; and $R^1$ is selected from the group consisting of aryl, aryl$C_{1-6}$alkyl, each of which is optionally substituted with one or more $R^7$.

In one embodiment $L^1$ is $C_{1-6}$alkylene optionally substituted with one or more $R^6$; $X^1$ and $X^2$ are each O, and $X^3$ is a bond; and $R^1$ is selected from the group consisting of $C_{1-6}$alkylaryl optionally substituted with one or more $R^7$, or $R^1$ is $C_{1-6}$alkylaryl$C_{1-6}$alkyl substituted with one or more $R^7$.

In one embodiment $L^1$ is $C_{1-6}$alkylene optionally substituted with one or more $R^6$; $X^1$ and $X^2$ are each O, and $X^3$ is a bond; and $R^1$ is selected from the group consisting of aryl and aryl$C_{1-6}$alkyl, each of which is optionally substituted with one or more $R^7$.

In one embodiment $L^1$ is $C_{1-6}$alkylene optionally substituted with one or more $R^6$; $X^1$ and $X^2$ are each O, and $X^3$ is a bond; and $R^1$ is selected from the group consisting of aryl $C_{1-6}$alkyl optionally substituted with one or more $R^7$.

In one embodiment, the compound of formula (II) is a compound of the formula (IIA), (IIB), (IIC), or (IID):

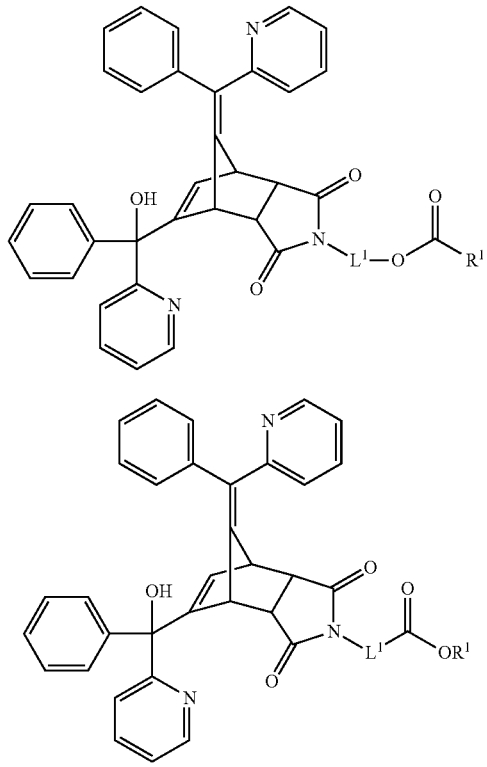

(IIA)

(IIB)

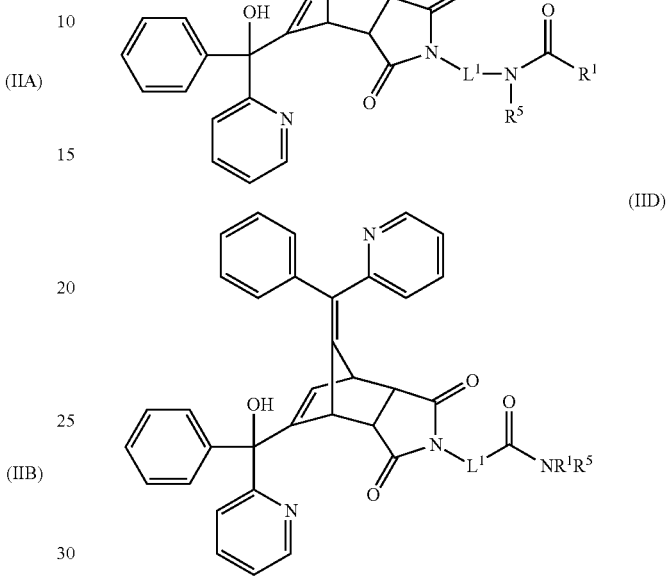

(IIC)

(IID)

wherein $L^1$, $R^1$, and $R^5$ are as defined in any of the embodiments relating to the compound of formula (I) or the compound of formula (II).

In one embodiment, the compound of formula (II) is a compound of the formula (IIA), (IIB), or (IIC). In another embodiment, the compound of formula (II) is a compound of the formula (IIA) or (IIB). In another embodiment, compound of formula (II) is a compound of the formula (IIA).

In one embodiment the compound of formula (II) is selected from the group consisting of:

| Cmpd | $L^1$ | $X^1$ | $X^2$ | $X^3$ | $R^1$ |
|------|-------|-------|-------|-------|-------|
| 8 | $CH_2$ | O | O | — | tBu |
| 9 | $CH_2$ | O | O | — | $(CH_2)_2CH_3$ |
| 10 | $CH_2$ | O | O | — | $(CH_2)_6CH_3$ |
| 11 | $CH_2$ | O | O | — | $(CH_2)_{10}CH_3$ |
| 12 | $CH_2$ | O | O | — | Ph |
| 13 | $CH_2$ | O | O | — | $C_6H_4$o-OMe |
| 14 | $CH_2$ | O | O | — | $C_6H_4$m-OMe |
| 15 | $CH_2$ | O | O | — | $C_6H_4$p-OMe |
| 16 | $CH_2$ | O | O | — | $CH_2$Ph |
| 324 | $CH_2$ | O | O | — | $CH_2C_6H_4$p-Me |
| 17 | $CH_2$ | O | O | — | $CHPh_2$ |
| 18 | $CH_2$ | O | O | — | $CH_2CH_2$Ph |
| 19 | $CH_2$ | O | O | — | CH=CHPh |
| 20 | $CH_2$ | O | O | — | 2-naphthyl |
| 109 | $CH_2CH_2$ | O | O | — | tBu |
| 110 | $CH_2CH_2$ | O | O | — | $(CH_2)_2CH_3$ |
| 111 | $CH_2CH_2$ | O | O | — | $(CH_2)_6CH_3$ |
| 112 | $CH_2CH_2$ | O | O | — | $(CH_2)_{10}CH_3$ |
| 113 | $CH_2CH_2$ | O | O | — | Ph |
| 114 | $CH_2CH_2$ | O | O | — | $C_6H_4$o-OMe |
| 115 | $CH_2CH_2$ | O | O | — | $C_6H_4$m-OMe |
| 116 | $CH_2CH_2$ | O | O | — | $C_6H_4$p-OMe |
| 117 | $CH_2CH_2$ | O | O | — | $CH_2$Ph |
| 118 | $CH_2CH_2$ | O | O | — | $CHPh_2$ |
| 119 | $CH_2CH_2$ | O | O | — | $CH_2CH_2$Ph |
| 120 | $CH_2CH_2$ | O | O | — | CH=CHPh |

-continued
| Cmpd | L¹ | X¹ | X² | X³ | R¹ |
|---|---|---|---|---|---|
| 121 | CH₂CH₂ | O | O | — | 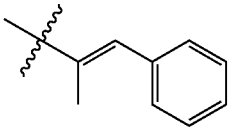 [SMILES: */C(C)=C/c1ccccc1] |
| 122 | CH₂CH₂ | O | O | — | 2-naphthyl |
| 123 | CH₂CH₂ | O | O | — | C≡CPh |
| 124 | CH₂CH₂ | O | O | — | 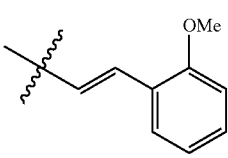 [SMILES: */C=C/c1ccccc1OC] |
| 125 | CH₂CH₂ | O | O | — | 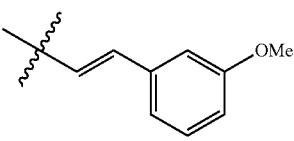 [SMILES: */C=C/c1cccc(OC)c1] |
| 126 | CH₂CH₂ | O | O | — | 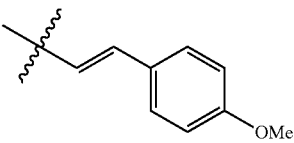 [SMILES: */C=C/c1ccc(OC)cc1] |
| 127 | CH₂CH₂ | O | O | — | 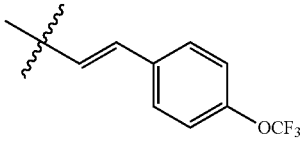 |
| 128 | CH₂CH₂ | O | O | — | 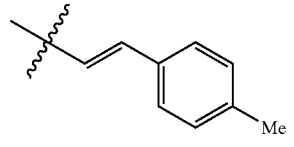 [SMILES: */C=C/c1ccc(C)cc1] |
| 335 | CH₂CH₂ | O | O | — | 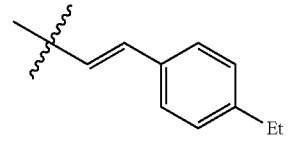 [SMILES: */C=C/c1ccc(CC)cc1] |
| 347 | CH₂CH₂ | O | O | — | 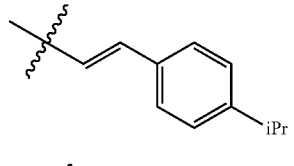 |
| 129 | CH₂CH₂ | O | O | — | 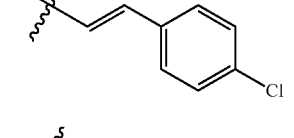 |
| 130 | CH₂CH₂ | O | O | — | 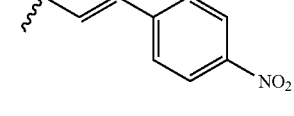 |

-continued

| Cmpd | L¹ | X¹ | X² | X³ | R¹ |
|---|---|---|---|---|---|
| 131 | CH₂CH₂ | O | O | — | -CH=CH-C₆H₄-NMe₂ (4-) |
| 337 | CH₂CH₂ | O | O | — | -CH=CH-C₆H₄-NHAc (4-) |
| 329 | CH₂CH₂ | O | O | — | -CH=CH-C₆H₄-SO₂Me (4-) |
| 132 | CH₂CH₂ | O | O | — | -CH=CH-C₆H₃(OMe)₂ (3,4-) |
| 133 | CH₂CH₂ | O | O | — | -CH=CH-C₆H₂(OMe)₃ (3,4,5-) |
| 134 | CH₂CH₂ | O | O | — | -CH=CH-C₆H₃Cl₂ (3,4-) |
| 135 | CH₂CHMe | O | O | — | CH=CHPh |
| 136 | CH₂CH₂CH₂ | O | O | — | CH=CHPh |
| 137 | CH₂(CH₂)₂CH₂ | O | O | — | CH=CHPh |
| 187 | CH₂CH₂ | O | O | — | -CH=CH-CH=CH-Ph |
| 188 | CH₂CH₂ | O | O | — | -CH=CH-(2-naphthyl) |
| 201 | CH₂CH₂OCH₂ | O | O | — | CHPh₂ |
| 204 | CH₂CH₂ | O | O | — | CH₂CH₂C(O)OPh |
| 342 | CH₂CH₂ | O | O | — | -C₆H₄-CH₂NH₂·TFA (4-) |

-continued

| Cmpd | $L^1$ | $X^1$ | $X^2$ | $X^3$ | $R^1$ |
|---|---|---|---|---|---|
| 343 | $CH_2CH_2$ | O | O | — | ![CH(NH_2·TFA)(CO_2Me)-] |
| 364 | $CH_2CH_2$ | $NR^5$ | O | — | $(CH_2)_6CH_3$ |
| 339 | $CH_2CH_2$ | $NR^5$ | O | — | $(CH_2)_{10}CH_3$ |
| 365 | $CH_2CH_2$ | $NR^5$ | O | — | CH=CHPh |
| 361 | $CH_2CH_2$ | $NR^5$ | O | — | -CH=CH-C_6H_4-p-OMe |
| 345 | $CH_2CH_2$ | $NR^5$ | O | — | -CH=CH-C_6H_4-p-OEt |
| 369 | $CH_2$ | — | O | O | $(CH_2)_7CH_3$ |
| 371 | $CH_2$ | — | O | O | $CH_2CH$=CHPh |

In another embodiment the compound of formula (II) is selected from the group consisting of:

| Cmpd | $L^1$ | $X^1$ | $X^2$ | $X^3$ | $R^1$ |
|---|---|---|---|---|---|
| 9 | $CH_2$ | O | O | — | $(CH_2)_2CH_3$ |
| 10 | $CH_2$ | O | O | — | $(CH_2)_6CH_3$ |
| 11 | $CH_2$ | O | O | — | $(CH_2)_{10}CH_3$ |
| 13 | $CH_2$ | O | O | — | $C_6H_4o$-OMe |
| 14 | $CH_2$ | O | O | — | $C_6H_4m$-OMe |
| 15 | $CH_2$ | O | O | — | $C_6H_4p$-OMe |
| 16 | $CH_2$ | O | O | — | $CH_2Ph$ |
| 324 | $CH_2$ | O | O | — | $CH_2C_6H_4p$-Me |
| 17 | $CH_2$ | O | O | — | $CHPh_2$ |
| 18 | $CH_2$ | O | O | — | $CH_2CH_2Ph$ |
| 19 | $CH_2$ | O | O | — | CH=CHPh |
| 20 | $CH_2$ | O | O | — | 2-naphthyl |
| 111 | $CH_2CH_2$ | O | O | — | $(CH_2)_6CH_3$ |
| 112 | $CH_2CH_2$ | O | O | — | $(CH_2)_{10}CH_3$ |
| 115 | $CH_2CH_2$ | O | O | — | $C_6H_4m$-OMe |
| 118 | $CH_2CH_2$ | O | O | — | $CHPh_2$ |
| 120 | $CH_2CH_2$ | O | O | — | CH=CHPh |
| 121 | $CH_2CH_2$ | O | O | — | -C(Me)=CH-Ph |
| 122 | $CH_2CH_2$ | O | O | — | 2-naphthyl |
| 123 | $CH_2CH_2$ | O | O | — | C≡CPh |
| 124 | $CH_2CH_2$ | O | O | — | -CH=CH-C_6H_4-o-OMe |

-continued
| Cmpd | L¹ | X¹ | X² | X³ | R¹ |
|---|---|---|---|---|---|
| 125 | $CH_2CH_2$ | O | O | — | 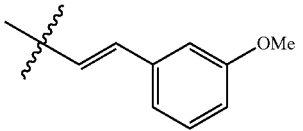 [SMILES: */C=C/c1cccc(OC)c1] |
| 126 | $CH_2CH_2$ | O | O | — | 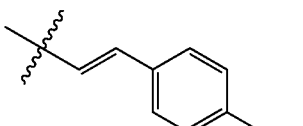 |
| 127 | $CH_2CH_2$ | O | O | — | 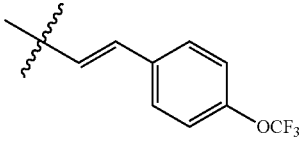 [SMILES: */C=C/c1ccc(OC(F)(F)F)cc1] |
| 128 | $CH_2CH_2$ | O | O | — | 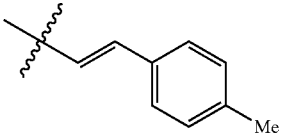 [SMILES: */C=C/c1ccc(C)cc1] |
| 335 | $CH_2CH_2$ | O | O | — | 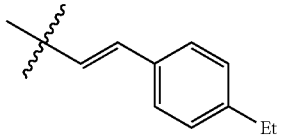 [SMILES: */C=C/c1ccc(CC)cc1] |
| 347 | $CH_2CH_2$ | O | O | — | 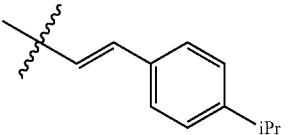 [SMILES: */C=C/c1ccc(C(C)C)cc1] |
| 129 | $CH_2CH_2$ | O | O | — | 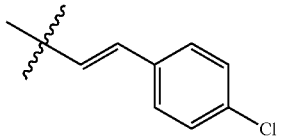 [SMILES: */C=C/c1ccc(Cl)cc1] |
| 130 | $CH_2CH_2$ | O | O | — | 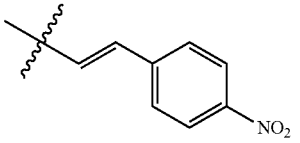 [SMILES: */C=C/c1ccc([N+](=O)[O-])cc1] |
| 131 | $CH_2CH_2$ | O | O | — | 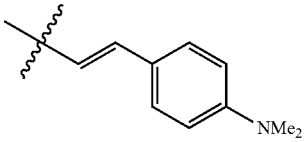 [SMILES: */C=C/c1ccc(N(C)C)cc1] |
| 337 | $CH_2CH_2$ | O | O | — | 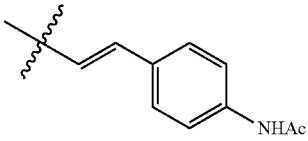 [SMILES: */C=C/c1ccc(NC(C)=O)cc1] |

-continued

| Cmpd | L¹ | X¹ | X² | X³ | R¹ |
|---|---|---|---|---|---|
| 329 | CH₂CH₂ | O | O | — | 4-(SO₂Me)-C₆H₄-CH=CH- |
| 132 | CH₂CH₂ | O | O | — | 3,4-(OMe)₂-C₆H₃-CH=CH- |
| 133 | CH₂CH₂ | O | O | — | 3,4,5-(OMe)₃-C₆H₂-CH=CH- |
| 134 | CH₂CH₂ | O | O | — | 3,4-Cl₂-C₆H₃-CH=CH- |
| 135 | CH₂CHMe | O | O | — | CH=CHPh |
| 136 | CH₂CH₂CH₂ | O | O | — | CH=CHPh |
| 137 | CH₂(CH₂)₂CH₂ | O | O | — | CH=CHPh |
| 187 | CH₂CH₂ | O | O | — | Ph-CH=CH-CH=CH- |
| 188 | CH₂CH₂ | O | O | — | 2-naphthyl-CH=CH- |
| 204 | CH₂CH₂ | O | O | — | CH₂CH₂C(O)OPh |
| 342 | CH₂CH₂ | O | O | — | 4-(CH₂NH₂·TFA)-C₆H₄- |
| 343 | CH₂CH₂ | O | O | — | -CH₂CH(NH₂·TFA)CO₂Me |
| 364 | CH₂CH₂ | NR⁵ | O | — | (CH₂)₆CH₃ |
| 339 | CH₂CH₂ | NR⁵ | O | — | (CH₂)₁₀CH₃ |
| 365 | CH₂CH₂ | NR⁵ | O | — | CH=CHPh |
| 361 | CH₂CH₂ | NR⁵ | O | — | 4-(OMe)-C₆H₄-CH=CH- |

-continued

| Cmpd | L¹ | X¹ | X² | X³ | R¹ |
|---|---|---|---|---|---|
| 345 | CH₂CH₂ | NR⁵ | O | — | 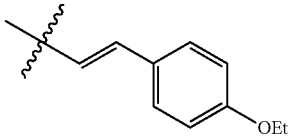 [SMILES: */C=C/c1ccc(OCC)cc1] |
| 369 | CH₂ | — | O | O | (CH₂)₇CH₃ |
| 371 | CH₂ | — | O | O | CH₂CH=CHPh |

In another embodiment the compound of formula (II) is selected from the group consisting of:

| Cmpd | L¹ | X¹ | X² | X³ | R¹ |
|---|---|---|---|---|---|
| 10 | CH₂ | O | O | — | (CH₂)₆CH₃ |
| 11 | CH₂ | O | O | — | (CH₂)₁₀CH₃ |
| 14 | CH₂ | O | O | — | C₆H₄m-OMe |
| 15 | CH₂ | O | O | — | C₆H₄p-OMe |
| 16 | CH₂ | O | O | — | CH₂Ph |
| 324 | CH₂ | O | O | — | CH₂C₆H₄p-Me |
| 17 | CH₂ | O | O | — | CHPh₂ |
| 18 | CH₂ | O | O | — | CH₂CH₂Ph |
| 19 | CH₂ | O | O | — | CH=CHPh |
| 20 | CH₂ | O | O | — | 2-naphthyl |
| 111 | CH₂CH₂ | O | O | — | (CH₂)₆CH₃ |
| 112 | CH₂CH₂ | O | O | — | (CH₂)₁₀CH₃ |
| 118 | CH₂CH₂ | O | O | — | CHPh₂ |
| 121 | CH₂CH₂ | O | O | — | 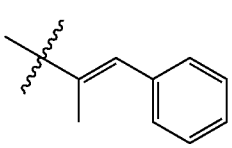 [SMILES: */C(C)=C/c1ccccc1] |
| 122 | CH₂CH₂ | O | O | — | 2-naphthyl |
| 123 | CH₂CH₂ | O | O | — | C≡CPh |
| 124 | CH₂CH₂ | O | O | — | 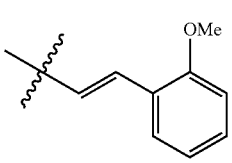 [SMILES: */C=C/c1ccccc1OC] |
| 126 | CH₂CH₂ | O | O | — | 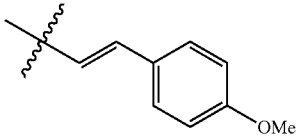 [SMILES: */C=C/c1ccc(OC)cc1] |
| 127 | CH₂CH₂ | O | O | — | 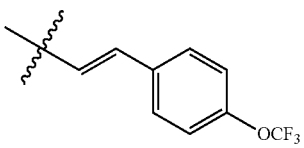 [SMILES: */C=C/c1ccc(OC(F)(F)F)cc1] |
| 335 | CH₂CH₂ | O | O | — | 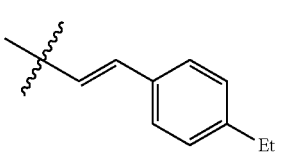 [SMILES: */C=C/c1ccc(CC)cc1] |

| Cmpd | L¹ | X¹ | X² | X³ | R¹ |
|---|---|---|---|---|---|
| 347 | CH₂CH₂ | O | O | — | 4-iPr-C₆H₄-CH=CH-CH₂- |
| 129 | CH₂CH₂ | O | O | — | 4-Cl-C₆H₄-CH=CH-CH₂- |
| 130 | CH₂CH₂ | O | O | — | 4-NO₂-C₆H₄-CH=CH-CH₂- |
| 337 | CH₂CH₂ | O | O | — | 4-NHAc-C₆H₄-CH=CH-CH₂- |
| 329 | CH₂CH₂ | O | O | — | 4-SO₂Me-C₆H₄-CH=CH-CH₂- |
| 134 | CH₂CH₂ | O | O | — | 3,4-Cl₂-C₆H₃-CH=CH-CH₂- |
| 135 | CH₂CHMe | O | O | — | CH=CHPh |
| 136 | CH₂CH₂CH₂ | O | O | — | CH=CHPh |
| 137 | CH₂(CH₂)₂CH₂ | O | O | — | CH=CHPh |
| 187 | CH₂CH₂ | O | O | — | Ph-CH=CH-CH=CH-CH₂- |
| 188 | CH₂CH₂ | O | O | — | (naphth-2-yl)-CH=CH-CH₂- |
| 204 | CH₂CH₂ | O | O | — | CH₂CH₂C(O)OPh |
| 342 | CH₂CH₂ | O | O | — | 4-(CH₂NH₂·TFA)-C₆H₄-CH₂- |
| 343 | CH₂CH₂ | O | O | — | -CH₂CH(NH₂·TFA)CO₂Me |

-continued

| Cmpd | L¹ | X¹ | X² | X³ | R¹ |
|---|---|---|---|---|---|
| 364 | CH₂CH₂ | NR⁵ | O | — | (CH₂)₆CH₃ |
| 339 | CH₂CH₂ | NR⁵ | O | — | (CH₂)₁₀CH₃ |
| 361 | CH₂CH₂ | NR⁵ | O | — | *trans*-CH₂CH=CH-C₆H₄-4-OMe |
| 345 | CH₂CH₂ | NR⁵ | O | — | *trans*-CH₂CH=CH-C₆H₄-4-OEt |
| 369 | CH₂ | — | O | O | (CH₂)₇CH₃ |
| 371 | CH₂ | — | O | O | CH₂CH=CHPh |

In another embodiment the compound of formula (II) is selected from the group consisting of:

| Cmpd | L¹ | X¹ | X² | X³ | R¹ |
|---|---|---|---|---|---|
| 16 | CH₂ | O | O | — | CH₂Ph |
| 324 | CH₂ | O | O | — | CH₂C₆H₄p-Me |
| 19 | CH₂ | O | O | — | CH=CHPh |
| 20 | CH₂ | O | O | — | 2-naphthyl |
| 111 | CH₂CH₂ | O | O | — | (CH₂)₆CH₃ |
| 118 | CH₂CH₂ | O | O | — | CHPh₂ |
| 121 | CH₂CH₂ | O | O | — | C(Me)=CH-Ph |
| 122 | CH₂CH₂ | O | O | — | 2-naphthyl |
| 123 | CH₂CH₂ | O | O | — | C≡CPh |
| 126 | CH₂CH₂ | O | O | — | *trans*-CH=CH-C₆H₄-4-OMe |
| 335 | CH₂CH₂ | O | O | — | *trans*-CH=CH-C₆H₄-4-Et |
| 347 | CH₂CH₂ | O | O | — | *trans*-CH=CH-C₆H₄-4-iPr |
| 129 | CH₂CH₂ | O | O | — | *trans*-CH=CH-C₆H₄-4-Cl |

-continued

| Cmpd | L¹ | X¹ | X² | X³ | R¹ |
|---|---|---|---|---|---|
| 337 | CH₂CH₂ | O | O | — | 4-(NHAc)-C₆H₄-CH=CH-* |
| 329 | CH₂CH₂ | O | O | — | 4-(SO₂Me)-C₆H₄-CH=CH-* |
| 136 | CH₂CH₂CH₂ | O | O | — | CH=CHPh |
| 342 | CH₂CH₂ | O | O | — | 4-(CH₂NH₂·TFA)-C₆H₄-* |
| 343 | CH₂CH₂ | O | O | — | -CH(NH₂·TFA)CO₂Me |
| 364 | CH₂CH₂ | NR⁵ | O | — | (CH₂)₆CH₃ |
| 339 | CH₂CH₂ | NR⁵ | O | — | (CH₂)₁₀CH₃ |
| 361 | CH₂CH₂ | NR⁵ | O | — | 4-(OMe)-C₆H₄-CH=CH-* |
| 345 | CH₂CH₂ | NR⁵ | O | — | 4-(OEt)-C₆H₄-CH=CH-* |

In one embodiment the stereochemical configuration at the bridgehead of the dicarboximide ring is endo.

Without wishing to be bound by theory, the applicant believes that the compounds of formula (I) and (II) are capable of acting like prodrugs that can be hydrolysed in vivo to release either NRB or an analogue thereof. For example, the compound of formula (II) wherein L¹ is CH₂, X¹ and X² are O, X³ is a bond, and R¹ is CH=CHPh upon hydrolysis releases NRB (and formaldehyde), while the compound of formula (II) wherein L¹ is CH₂CH₂, X¹ and X² are O, X³ is a bond, and R¹ is 2-naphthyl upon hydrolysis releases an N-(hydroxyethyl) analogue of NRB.

Advantageously, certain of these compounds may mask and/or delay the onset of toxic effects in vivo, relative to NRB, increasing the probability of a rodent ingesting a lethal dose.

In one embodiment the compound of formula (II) exhibits a delay in the onset of toxic effects, relative to NRB, of at least about 5, at least about 10, at least about 15, at least about 20, at least about 25, or about 30 minutes.

In another embodiment the compound of formula (II) exhibits a delay in the onset of toxic effects, relative to NRB, of at least about 5 minutes; preferably, about 8 minutes; more preferably, about 15 minutes; more preferably, about 30 minutes.

In one embodiment the compound of formula (II) exhibits a delay in the onset of toxic effects, relative to NRB, of from about 5 minutes to about 5 hours; from about 10 minutes to about 5 hours; from about 15 minutes to about 5 hours; from about 20 minutes to about 5 hours; from about 30 minutes to about 5 hours; 5 minutes to about 4 hours; from about 10 minutes to about 4 hours; from about 15 minutes to about 4 hours; from about 20 minutes to about 4 hours; from about 30 minutes to about 4 hours; 5 minutes to about 3 hours; from about 10 minutes to about 3 hours; from about 15 minutes to about 3 hours; from about 20 minutes to about 3 hours; from about 30 minutes to about 3 hours; 5 minutes to about 2 hours; from about 10 minutes to about 2 hours; from about 15 minutes to about 2 hours; from about 20 minutes to about 2 hours; from about 30 minutes to about 2 hours; 5 minutes to about 1.5 hours; from about 10 minutes to about 1.5 hours; from about 15 minutes to about 1.5 hours; from about 20 minutes to about 1.5 hours; or from about 30 minutes to about 1.5 hours.

In another embodiment the compound of formula (II) exhibits a delay in the onset of toxic effects, relative to NRB, of from about 5 minutes to about 2 hours; preferably about 8 minutes to about 1 hour; more preferably, from 15 minutes to 1 hour; more preferably, from 30 minutes to 1 hour.

In one embodiment, the compound of formula (I) is a compound of the formula (IIA), (IIB), (IIC), or (IID), wherein $L^1$ is $C_{1-6}$alkylene optionally substituted with one or more $R^6$; and $R^1$ is selected from the group consisting of $C_{3-12}$alkyl, aryl, $C_{1-6}$alkylaryl, aryl$C_{1-6}$alkyl, $C_{1-6}$alkylaryl$C_{1-6}$alkyl, $C_{1-6}$alkylcarbonyloxy$C_{1-6}$alkyl, arylcarbonyloxy$C_{1-6}$alkyl, $C_{1-6}$alkyloxycarbonyl$C_{1-6}$alkyl, and aryloxycarbonyl $C_{1-6}$alkyl, each of which is optionally substituted with one or more $R^7$, wherein the compound exhibits a delay in the onset of toxic effects, relative to NRB, of at least about 5 minutes.

In another aspect, the present invention provides a compound of formula (III):

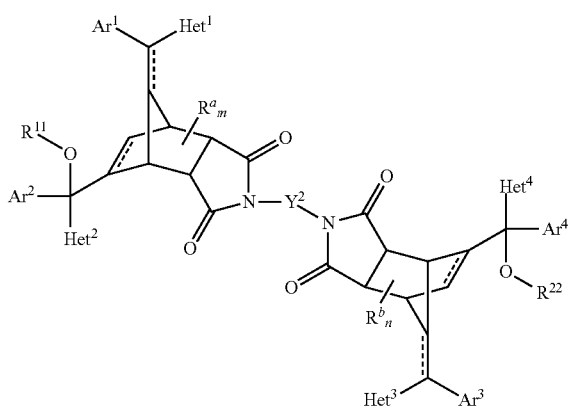

(III)

wherein:

$Ar^1$, $Ar^2$, $Ar^3$, and $Ar^4$ at each instance are independently a 6 to 10 membered monocyclic or bicyclic aryl ring, wherein the ring is optionally substituted with one or more $R^8$;

$Het^1$, $Het^2$, $Het^3$, and $Het^4$ at each instance are independently a 5 to 10 membered monocyclic or bicyclic heteroaryl ring comprising 1 to 4 ring nitrogen atoms, wherein the ring is optionally substituted with one or more $R^8$;

each dashed line and solid line together represent a double bond or a single bond;

$Y^2$ is

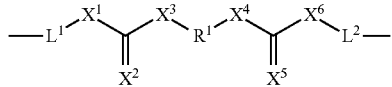

$L^1$ and $L^2$ are each independently selected from the group consisting of $C_{1-6}$alkylene, $C_{3-6}$cycloalkylene, arylene, heteroarylene, heterocyclylene, $C_{1-6}$alkyl$C_{3-6}$cycloalkylene, $C_{1-6}$alkylarylene, $C_{1-6}$alkylheteroarylene, $C_{1-6}$alkylheterocyclylene, $C_{3-6}$cycloalkyl$C_{1-6}$alkylene, aryl$C_{1-6}$alkylene, heteroaryl$C_{1-6}$alkylene, heterocyclyl$C_{1-6}$alkylene, $C_{1-6}$alkoxy$C_{1-6}$alkylene, $C_{3-6}$cycloalkyloxy$C_{1-6}$alkylene, aryloxy$C_{1-6}$alkylene, heteroaryloxy$C_{1-6}$alkylene, heterocyclyloxy$C_{1-6}$alkylene, $C_{1-6}$alkoxy$C_{3-6}$cycloalkylene, $C_{1-6}$alkoxyarylene, $C_{1-6}$alkoxyheteroalkylene, $C_{1-6}$alkoxyheterocyclylalkylene, $C_{1-6}$alkylthio$C_{1-6}$alkylene, $C_{3-6}$cycloalkylthio$C_{1-6}$alkylene, arylthio$C_{1-6}$alkylene, heteroarylthio$C_{1-6}$alkylene, heterocyclylthio$C_{1-6}$alkylene, $C_{1-6}$alkylthio$C_{3-6}$cycloalkylene, $C_{1-6}$alkylthioarylene, $C_{1-6}$alkylthioheteroalkylene, $C_{1-6}$alkylthioheterocyclylalkylene, $C_{1-6}$alkylamino$C_{1-6}$alkylene, $C_{3-6}$cycloalkylamino $C_{1-6}$alkylene, arylamino$C_{1-6}$alkylene, heteroamino $C_{1-6}$alkylene, heterocyclylamino$C_{1-6}$alkylene, $C_{1-6}$alkylamino$C_{3-6}$cycloalkylene, $C_{1-6}$alkylaminoarylene, $C_{1-6}$alkylaminoheteroalkylene, and $C_{1-6}$alkylaminoheterocyclylalkylene each of which is optionally substituted with one or more $R^6$;

$R^1$ is —$(R^2-Z)_q$—$R^3$—;

$R^2$ at each instance and $R^3$ are independently selected from the group consisting of $C_{2-12}$alkylene, $C_{3-8}$cycloalkylene, arylene, heterocyclylene, and heteroarylene, each of which is optionally substituted with one or more $R^7$;

Z at each instance is independently selected from the group consisting of $X^7$—C(=$X^8$)—$X^9$ and $X^{10}$;

$X^1$, $X^3$, $X^4$, and $X^6$ and $X^7$, $X^9$, and $X^{10}$ at each instance are independently selected from the group consisting of O, S, $NR^5$, and a bond, provided that $X^1$ and $X^3$ do not both represent a bond, $X^4$ and $X^6$ do not both represent a bond, and $X^7$ and $X^9$ do not both represent a bond;

$X^2$, $X^5$, and $X^8$ at each instance are independently selected from the group consisting of O, S, and $NR^5$;

q is an integer selected from 0 to 10;

$R^5$ at each instance is independently selected from the group consisting of hydrogen, $C_{1-6}$alkyl, $C_{3-6}$cycloalkyl, aryl, heterocyclyl, and heteroaryl;

$R^6$ at each instance is independently selected from the group consisting of hydroxyl, thiol, amino, cyano, nitro, halo, $C_{1-6}$alkyl, $C_{1-6}$haloalkyl, $C_{1-6}$alkoxy, and $C_{1-6}$haloalkoxy;

$R^7$ at each instance is independently selected from the group consisting of hydroxyl, thiol, amino, amido, acylamino, cyano, nitro, nitroso, azide, halo, cyanate, thiocyanate, isocyanate, isothiocyanate, oxo, imino, acyl, $C_{1-6}$alkyl, $C_{1-6}$haloalkyl, $C_{3-6}$cycloalkyl, aryl, heterocyclyl, heteroaryl, $C_{1-6}$alkoxy, $C_{1-6}$haloalkoxy, $C_{3-6}$cycloalkoxy, aryloxy, heterocyclyloxy, heteroaryloxy, $C_{1-6}$alkylcarbonyloxy, $C_{3-6}$cycloalkylcarbonyloxy, arylcarbonyloxy, heterocyclylcarbonyloxy, heteroarylcarbonyloxy, $C_{1-6}$alkyloxycarbonyl, $C_{3-6}$cycloalkyloxycarbonyl, aryloxycarbonyl, heterocyclyloxycarbonyl, heteroaryloxycarbonyl, sulfenyl, sulfonyl, sulfoxide, sulfate, sulfonate, sulfonamide, phosphate, phosphonate, phosphinate, phosphine, phosphite, carbonate, carbamate, and urea;

$R^8$ at each instance is selected from the group consisting of hydroxyl, thiol, amino, cyano, nitro, halo, $C_{1-6}$alkyl, $C_{1-6}$haloalkyl, $C_{1-6}$alkoxy, and $C_{1-6}$haloalkoxy;

$R^{11}$ and $R^{22}$ are each independently selected from the group consisting of hydrogen, $C_{1-6}$alkyl, and $C_{1-6}$haloalkyl;

$R^a$ and $R^b$ at each instance are each independently selected from the group consisting of halo, $C_{1-6}$alkyl, carboxyl, carboxyl$C_{1-6}$alkyl, amido$C_{1-6}$alkyl, acyloxy, sulfenyl, sulfoxide, sulfonyl, and aryl, wherein each $C_{1-6}$alkyl and aryl is optionally substituted with one or more $R^8$; and m and n are each an integer independently selected from 0 to 3; or a salt or solvate thereof.

In another aspect, the present invention provides a compound of formula (III), wherein $Ar^1$, $Ar^2$, $Ar^3$, $Ar^4$, $Het^1$, $Het^2$, $Het^3$, $Het^4$, each dashed line and solid line together, $Y^2$, $R^{11}$, $R^{22}$, $R^a$, $R^b$, m and n are as defined in the aspect above.

The following embodiments relate to the compound of formula (III).

In one embodiment $Ar^1$, $Ar^2$, $Ar^3$, and $Ar^4$ are each independently a phenyl ring optionally substituted with one or more $R^8$.

In one embodiment $Het^1$, $Het^2$, $Het^3$, and $Het^4$ are each independently a 5 or 6 membered monocyclic heteroaryl ring comprising 1 to 3 ring nitrogen atoms, wherein the ring is optionally substituted with one or more $R^a$. Preferably, $Het^1$, $Het^2$, $Het^3$, and $Het^4$ are each independently a 6 membered monocyclic heteroaryl ring comprising 1 to 3 ring nitrogen atoms, wherein the ring is optionally substituted with one or more $R^8$. More preferably, $Het^1$, $Het^2$, $Het^3$, and $Het^4$ are each independently pyridyl optionally substituted with one or more $R^8$.

In one embodiment each dashed line and solid line together represent a double bond.

In one embodiment m and n are each an integer independently selected from 0 to 1. Preferably, m and n are both 0.

In one embodiment $R^{11}$ and $R^{22}$ are each independently selected from the group consisting of hydrogen and $C_{1-6}$alkyl. Preferably, $R^{11}$ and $R^{22}$ are each independently selected from the group consisting of hydrogen and methyl. More preferably, $R^{11}$ and $R^{22}$ are each hydrogen.

In one embodiment, $R^7$ at each instance is independently selected from the group consisting of hydroxyl, thiol, amino, amido, acylamino, cyano, nitro, nitroso, azide, halo, cyanate, thiocyanate, isocyanate, isothiocyanate, oxo, imino, acyl, $C_{3-6}$cycloalkyl, aryl, heterocyclyl, heteroaryl, $C_{1-6}$alkoxy, $C_{1-6}$haloalkoxy, $C_{3-6}$cycloalkoxy, aryloxy, heterocyclyloxy, heteroaryloxy, $C_{1-6}$alkylcarbonyloxy, $C_{3-6}$cycloalkylcarbonyloxy, arylcarbonyloxy, heterocyclylcarbonyloxy, heteroarylcarbonyloxy, $C_{1-6}$alkyloxycarbonyl, $C_{3-6}$cycloalkyloxycarbonyl, aryloxycarbonyl, heterocyclyloxycarbonyl, heteroaryloxycarbonyl, sulfenyl, sulfonyl, sulfoxide, sulfate, sulfonate, sulfonamide, phosphate, phosphonate, phosphinate, phosphine, phosphite, carbonate, carbamate, and urea.

In another embodiment $R^7$ at each instance is independently selected from the group consisting of hydroxyl, thiol, amino, cyano, nitro, nitroso, azide, halo, cyanate, thiocyanate, isocyanate, isothiocyanate, oxo, $C_{1-6}$haloalkyl, $C_{3-6}$cycloalkyl, aryl, heterocyclyl, heteroaryl, $C_{1-6}$alkoxy, $C_{1-6}$haloalkoxy, $C_{3-6}$cycloalkoxy, aryloxy, heterocyclyloxy, and heteroaryloxy. In another embodiment $R^7$ at each instance is independently selected from the group consisting of hydroxyl, thiol, amino, cyano, nitro, halo, oxo, $C_{1-6}$alkyl, $C_{1-6}$haloalkyl, aryl, $C_{1-6}$alkoxy, $C_{1-6}$haloalkoxy, and aryloxy.

In another embodiment $R^7$ at each instance is independently selected from the group consisting of hydroxyl, thiol, amino, amido, acylamino, cyano, nitro, nitroso, azide, halo, cyanate, thiocyanate, isocyanate, isothiocyanate, oxo, acyl, $C_{1-6}$alkyl, $C_{1-6}$haloalkyl, aryl, $C_{1-6}$alkoxy, $C_{1-6}$haloalkoxy, aryloxy, $C_{1-6}$alkylcarbonyloxy, arylcarbonyloxy, $C_{1-6}$alkyloxycarbonyl, aryloxycarbonyl, sulfenyl, sulfonyl, sulfoxide, sulfate, sulfonate, sulfonamide, phosphate, phosphonate, carbonate, carbamate, and urea.

In yet another embodiment $R^7$ at each instance is independently selected from the group consisting of hydroxyl, thiol, amino, amido, acylamino, cyano, nitro, nitroso, azide, halo, cyanate, thiocyanate, isocyanate, isothiocyanate, oxo, acyl, $C_{1-6}$alkyl, $C_{1-6}$haloalkyl, aryl, $C_{1-6}$alkoxy, $C_{1-6}$haloalkoxy, aryloxy, $C_{1-6}$alkylcarbonyloxy, arylcarbonyloxy, $C_{1-6}$alkyloxycarbonyl, aryloxycarbonyl, sulfenyl, sulfonyl, sulfoxide, sulfate, sulfonate, sulfonamide, phosphate, and phosphonate.

In yet another embodiment, $R^7$ at each instance is independently selected from the group consisting of hydroxyl, thiol, amino, amido, acylamino, cyano, nitro, halo, oxo, acyl, $C_{1-6}$alkyl, $C_{1-6}$haloalkyl, aryl, $C_{1-6}$alkoxy, $C_{1-6}$haloalkoxy, aryloxy, $C_{1-6}$alkylcarbonyloxy, arylcarbonyloxy, $C_{1-6}$alkyloxycarbonyl, aryloxycarbonyl, sulfenyl, sulfonyl, sulfoxide, sulfate, sulfonate, sulfonamide, and phosphate.

In one embodiment $R^5$ at each instance is independently selected from the group consisting of hydrogen, $C_{1-6}$alkyl, and aryl. In another embodiment, $R^5$ at each instance is independently selected from the group consisting of hydrogen and $C_{1-6}$alkyl. In another embodiment, $R^5$ at each instance is hydrogen.

In one embodiment $Ar^1$, $Ar^2$, $Ar^3$, and $Ar^4$ are each independently a phenyl ring optionally substituted with one or more $R^8$; $Het^1$, $Het^2$, $Het^3$, and $Het^4$ are each independently pyridyl optionally substituted with one or more $R^8$; and each dashed line and solid line together represent a double bond; and n is 0.

In one embodiment the stereochemical configuration at the bridgehead of each dicarboximide ring is endo.

In one embodiment the compound is a compound of the formula (IV):

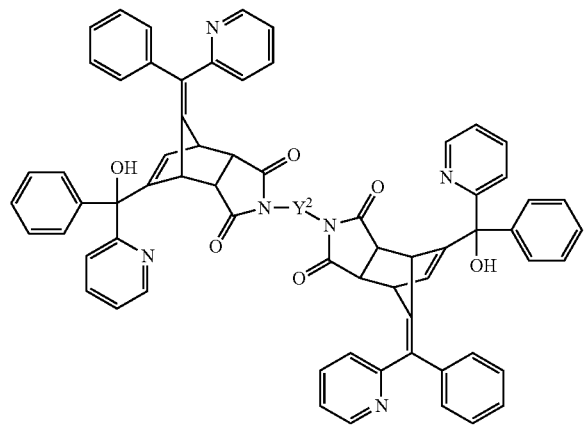

(IV)

wherein $Y^2$, $L^1$, $X^1$, $X^2$, $X^3$, $R^1$, $X^4$, $X^5$, $X^6$, and $L^2$ are as defined in any of the embodiments relating to the compound of formula (III).

The following embodiments relate to the compound of formula (III) and the compound of formula (IV).

In one embodiment $L^1$ is selected from the group consisting of $C_{1-6}$alkylene, $C_{3-6}$cycloalkylene, arylene, heteroarylene, heterocyclylene, $C_{1-6}$alkyl$C_{3-6}$cycloalkylene, $C_{1-6}$alkylarylene, $C_{1-6}$alkylheteroarylene, $C_{1-6}$alkylheterocyclylene, $C_{3-6}$cycloalkyl$C_{1-6}$alkylene, aryl$C_{1-6}$alkylene, heteroaryl$C_{1-6}$alkylene, heterocyclyl$C_{1-6}$alkylene, $C_{1-6}$alkoxy$C_{1-6}$alkylene, $C_{3-6}$cycloalkyloxy$C_{1-6}$alkylene, aryloxy$C_{1-6}$alkylene, heteroaryloxy$C_{1-6}$alkylene, heterocyclyloxy$C_{1-6}$alkylene, $C_{1-6}$alkylthio$C_{1-6}$alkylene, $C_{3-6}$cycloalkylthio$C_{1-6}$alkylene, arylthio$C_{1-6}$alkylene, heteroarylthio$C_{1-6}$alkylene, heterocyclylthio$C_{1-6}$alkylene, $C_{1-6}$alkylamino$C_{1-6}$alkylene, $C_{3-6}$cycloalkylamino$C_{1-6}$alkylene, arylamino$C_{1-6}$alkylene, heteroarylamino$C_{1-6}$alkylene, and heterocyclylamino$C_{1-6}$alkylene, each of which is optionally substituted with one or more $R^6$; and $L^2$ is selected from the group consisting of $C_{1-6}$alkylene, $C_{3-6}$cycloalkylene, arylene, heteroarylene, heterocyclylene, $C_{3-6}$cycloalkyl$C_{1-6}$alkylene, aryl$C_{1-6}$alkylene, heteroaryl$C_{1-6}$alkylene, heterocyclyl$C_{1-6}$alkylene, $C_{1-6}$alkoxy$C_{1-6}$alkylene, $C_{1-6}$alkoxy$C_{3-6}$cycloalkylene, $C_{1-6}$alkoxyarylene, $C_{1-6}$alkoxyheteroalkylene, $C_{1-6}$alkoxyheterocyclylalkylene, $C_{1-6}$alkylthio$C_{1-6}$alkylene, $C_{1-6}$alkylthio$C_{3-6}$cycloalkylene, $C_{1-6}$alkylthioarylene, $C_{1-6}$alkylthioheteroalkylene, $C_{1-6}$alkylthioheterocyclylalkylene, $C_{1-6}$alkylamino$C_{1-6}$alkylene, $C_{1-6}$alkylamino$C_{3-6}$cycloalkylene, $C_{1-6}$alkylaminoarylene, $C_{1-6}$alkylaminoheteroalkylene, and $C_{1-6}$alkylaminoheterocyclylalkylene, each of which is optionally substituted with one or more $R^6$.

In one embodiment $L^1$ is selected from the group consisting of $C_{1-6}$alkylene, $C_{3-6}$cycloalkylene, arylene, heteroarylene, heterocyclylene, $C_{1-6}$alkyl$C_{3-6}$cycloalkylene, $C_{1-6}$alkylarylene, $C_{1-6}$alkylheteroarylene, $C_{1-6}$alkylheterocyclylene, $C_{3-6}$cycloalkyl$C_{1-6}$alkylene, aryl$C_{1-6}$alkylene, heteroaryl$C_{1-6}$alkylene, heterocyclyl$C_{1-6}$alkylene, $C_{1-6}$alkoxy$C_{1-6}$alkylene, $C_{3-6}$cycloalkyloxy$C_{1-6}$alkylene, aryloxy$C_{1-6}$alkylene, heteroaryloxy$C_{1-6}$alkylene, and heterocyclyloxy$C_{1-6}$alkylene, each of which is optionally substituted with one or more $R^6$; and $L^2$ is selected from the group consisting of $C_{1-6}$alkylene, $C_{3-6}$cycloalkylene, arylene, heteroarylene, heterocyclylene, $C_{1-6}$alkyl$C_{3-6}$cycloalkylene, $C_{1-6}$alkylarylene, $C_{1-6}$alkylheteroarylene, $C_{1-6}$alkylheterocyclylene, $C_{3-6}$cycloalkyl$C_{1-6}$alkylene, aryl$C_{1-6}$alkylene, heteroaryl$C_{1-6}$alkylene, heterocyclyl$C_{1-6}$alkylene, $C_{1-6}$alkoxy$C_{1-6}$alkylene, $C_{1-6}$alkoxy$C_{3-6}$cycloalkylene, $C_{1-6}$alkoxyarylene, $C_{1-6}$alkoxyheteroalkylene, and $C_{1-6}$alkoxyheterocyclylalkylene, each of which is optionally substituted with one or more $R^6$.

In one embodiment $L^1$ and $L^2$ are each independently selected from the group consisting of $C_{1-6}$alkylene, $C_{1-6}$alkyl$C_{3-6}$cycloalkylene, $C_{1-6}$alkylarylene, $C_{3-6}$cycloalkyl$C_{1-6}$alkylene, aryl$C_{1-6}$alkylene, $C_{1-6}$alkoxy$C_{1-6}$alkylene, each of which is optionally substituted with one or more $R^6$.

In another embodiment $L^1$ is selected from the group consisting of $C_{1-6}$alkylene, $C_{1-6}$alkyl$C_{3-6}$cycloalkylene, $C_{1-6}$alkylarylene, $C_{3-6}$cycloalkyl$C_{1-6}$alkylene, aryl$C_{1-6}$alkylene, $C_{1-6}$alkoxy$C_{1-6}$alkylene, each of which is optionally substituted with one or more $R^6$; and $L^2$ is selected from the group consisting of $C_{1-6}$alkylene, $C_{1-6}$alkyl$C_{3-6}$cycloalkylene, $C_{1-6}$alkylarylene, $C_{3-6}$cycloalkyl$C_{1-6}$alkylene, aryl$C_{1-6}$alkylene, $C_{1-6}$alkoxy$C_{1-6}$alkylene, each of which is optionally substituted with one or more $R^6$. Preferably, $L^1$ is selected from the group consisting of $C_{1-6}$alkylene and $C_{1-6}$alkyloxy$C_{1-6}$alkylene, each of which is optionally substituted with one or more $R^6$; and $L^2$ is selected from the group consisting of $C_{1-6}$alkylene and $C_{1-6}$alkyloxy$C_{1-6}$alkylene, each of which is optionally substituted with one or more $R^6$.

In another embodiment $L^1$ is selected from the group consisting of $C_{1-6}$alkylene, $C_{1-6}$alkyl$C_{3-6}$cycloalkylene, $C_{1-6}$alkylarylene, $C_{3-6}$cycloalkyl$C_{1-6}$alkylene, aryl$C_{1-6}$alkylene, $C_{1-6}$alkoxy$C_1$alkylene, each of which is optionally substituted with one or more $R^6$; and $L^2$ is selected from the group consisting of $C_{1-6}$alkylene, $C_{1-6}$alkyl$C_{3-6}$cycloalkylene, $C_{1-6}$alkylarylene, $C_{3-6}$cycloalkyl$C_{1-6}$alkylene, aryl$C_{1-6}$alkylene, $C_1$alkoxy$C_{1-6}$alkylene, each of which is optionally substituted with one or more $R^6$. Preferably, $L^1$ is selected from the group consisting of $C_{1-6}$alkylene and $C_{1-6}$alkyloxy$C_1$alkylene, each of which is optionally substituted with one or more $R^6$; and $L^2$ is selected from the group consisting of $C_{1-6}$alkylene and $C_1$alkyloxy$C_{1-6}$alkylene, each of which is optionally substituted with one or more $R^6$.

In one embodiment $L^1$ and $L^2$ are each independently $C_{1-6}$alkylene optionally substituted with one or more $R^6$. More preferably, $L^1$ and $L^2$ are each independently $C_{1-4}$alkylene optionally substituted with one or more $R^6$. In another embodiment $L^1$ and $L^2$ are each independently saturated $C_{1-4}$alkylene.

In one embodiment $X^1$, $X^3$, $X^4$, and $X^6$ are each independently is selected from the group consisting of O, $NR^5$, and a bond. Preferably, $X^1$ and $X^6$ are each independently selected from the group consisting of O and $NR^5$ and $X^3$ and $X^4$ are each independently selected from the group consisting of O, $NR^5$, and a bond. More preferably, $X^1$ and $X^6$ are each O and $X^3$ and $X^4$ are each independently selected from the group consisting of O, $NR^5$, and a bond. More preferably, $X^1$ and $X^6$ are each O and $X^3$ and $X^4$ are each a bond.

In one embodiment $X^2$ and $X^5$ are each independently selected from the group consisting of O and $NR^5$. Preferably, $X^2$ and $X^5$ are each O.

In one embodiment $X^1$ and $X^2$ are each O and $X^3$ is a bond; $X^1$ and $X^2$ are each $NR^5$ and $X^3$ is a bond; $X^1$ is a bond and $X^2$ and $X^3$ are each O; or $X^1$ is a bond and $X^2$ and $X^3$ are each $NR^5$; and $X^4$ and $X^5$ are each O and $X^6$ is a bond; $X^4$ and $X^5$ are each $NR^5$ and $X^6$ is a bond; $X^4$ is a bond and $X^5$ and $X^6$ are each O; or $X^4$ is a bond and $X^5$ and $X^6$ are each $NR^5$. In another embodiment $X^1$ and $X^2$ are each O and $X^3$ is a bond; or $X^1$ is a bond and $X^2$ and $X^3$ are each O; and $X^4$ and $X^5$ are each O and $X^6$ is a bond; or $X^4$ is a bond and $X^5$ and $X^6$ are each O.

In one embodiment $X^1$, $X^2$, $X^5$, and $X^6$ are each O and $X^3$ and $X^4$ are each a bond.

In one embodiment $R^2$ at each instance and $R^3$ are independently selected from the group consisting of $C_{2-12}$alkylene, $C_{3-8}$cycloalkylene, and arylene, each of which is optionally substituted with one or more $R^7$. Preferably, $R^2$ at each instance and $R^3$ are independently selected from the group consisting of $C_{2-12}$alkylene and arylene, each of which is optionally substituted with one or more $R^7$. More preferably, $R^2$ at each instance and $R^3$ are independently selected from the group consisting of $C_{2-8}$alkylene and arylene, each of which is optionally substituted with one or more $R^7$.

In one embodiment, $R^2$ at each instance is independently $C_{2-6}$alkylene optionally substituted with one or more $R^7$; and $R^3$ is independently selected from the group consisting of $C_{2-8}$alkylene and arylene, each of which is optionally substituted with one or more $R^7$.

In one embodiment $X^7$, $X^9$, and $X^{10}$ at each instance are independently selected from the group consisting of O, $NR^5$, and a bond. Preferably, $X^7$, $X^9$, and $X^{10}$ at each instance are independently selected from the group consisting of O and a bond.

In one embodiment $X^8$ at each instance is independently selected from the group consisting of O and $NR^5$. Preferably, $X^8$ at each instance is O.

In one embodiment $X^7$, $X^9$, and $X^{10}$ at each instance are independently selected from the group consisting of O and a bond and $X^8$ at each instance is O.

In one embodiment Z at each instance is independently selected from O—C(=O), C(=O)—O, $NR^5$—C(=O), C(=O)—$NR^5$, O, and $NR^5$. In another embodiment Z at each instance is independently selected from O—C(=O), C(=O)—O, and O. In another embodiment Z at each instance is independently selected from O—C(=O) and C(=O)—O.

In one embodiment q is an integer from 0 to 5. Preferably, q is an integer from 0 to 3. More preferably, q is an integer from 0 to 2.

In one embodiment $L^1$ and $L^2$ are each independently selected from the group consisting of $C_{1-6}$alkylene, $C_{1-6}$alkyl$C_{3-6}$cycloalkylene, $C_{1-6}$alkylarylene, $C_{3-6}$cycloalkyl$C_{1-6}$alkylene, aryl$C_{1-6}$alkylene, $C_{1-6}$alkoxy$C_{1-6}$alkylene, each of which is optionally substituted with one or more $R^6$; $X^1$, $X^3$, $X^4$, and $X^6$ are each independently is selected from the group consisting of O, $NR^5$, and a bond; $X^2$ and $X^5$ are each independently selected from the group consisting of O and $NR^5$; $R^2$ at each instance and $R^3$ are independently selected from the group consisting of $C_{2-12}$alkylene, $C_{3-8}$cycloalkylene, and arylene, each of which is optionally substituted with one or more $R^7$; $X^7$, $X^9$, and $X^{10}$ at each instance are independently selected from the group consisting of O, $NR^5$, and a bond; $X^8$ at each instance is independently selected from the group consisting of O and $NR^5$; and q is an integer from 0 to 5.

In another embodiment $L^1$ is selected from the group consisting of $C_{1-6}$alkylene, $C_{1-6}$alkyl$C_{3-6}$cycloalkylene, $C_{1-6}$alkylarylene, $C_{3-6}$cycloalkyl$C_{1-6}$alkylene, aryl$C_{1-6}$alkylene, and $C_{1-6}$alkoxy$C_1$alkylene, each of which is optionally substituted with one or more $R^6$; $L^2$ is selected from the group consisting of $C_{1-6}$alkylene, $C_{1-6}$alkyl$C_{3-6}$cycloalkylene, $C_{1-6}$alkylarylene, $C_{3-6}$cycloalkyl$C_{1-6}$alkylene, aryl$C_{1-6}$alkylene, and $C_1$alkoxy$C_{1-6}$alkylene, each of which is optionally substituted with one or more $R^6$; $X^1$, $X^3$, $X^4$, and $X^6$ are each independently is selected from the group consisting of O, $NR^5$, and a bond; $X^2$ and $X^5$ are each independently selected from the group consisting of O and $NR^5$; $R^2$ at each instance and $R^3$ are independently selected from the group consisting of $C_{2-12}$alkylene, $C_{3-8}$cycloalkylene, and arylene, each of which is optionally substituted with one or more $R^7$; $X^7$, $X^9$, and $X^{10}$ at each instance are independently selected from the group consisting of O, $NR^5$, and a bond; $X^8$ at each instance is independently selected from the group consisting of O and $NR^5$; and q is an integer from 0 to 5.

In another embodiment $L^1$ and $L^2$ are each independently $C_{1-6}$alkylene optionally substituted with one or more $R^6$; $X^1$ and $X^6$ are each independently selected from the group consisting of O and $NR^5$ and $X^3$ and $X^4$ are each independently selected from the group consisting of O, $NR^5$, and a bond; $X^2$ and $X^5$ are each independently selected from the group consisting of O and $NR^5$; $R^2$ at each instance and $R^3$ are independently selected from the group consisting of $C_{2-12}$alkylene and arylene, each of which is optionally substituted with one or more $R^7$; $X^7$, $X^9$, and $X^{10}$ at each instance are independently selected from the group consisting of O, $NR^5$, and a bond; $X^8$ at each instance is independently selected from the group consisting of O and $NR^5$; and q is an integer from 0 to 5.

In another embodiment $L^1$ and $L^2$ are each independently $C_{1-6}$alkylene optionally substituted with one or more $R^6$; $X^1$, $X^3$, $X^4$, and $X^6$ are each independently is selected from the group consisting of O, $NR^5$, and a bond; $X^2$ and $X^5$ are each independently selected from the group consisting of O and $NR^5$; $X^1$ and $X^6$ are each independently selected from the group consisting of O and $NR^5$ and $X^3$ and $X^4$ are each independently selected from the group consisting of O, $NR^5$, and a bond; $X^2$ and $X^5$ are each independently selected from the group consisting of O and $NR^5$; $R^2$ at each instance and $R^3$ are independently selected from the group consisting of $C_{2-8}$alkylene and arylene, each of which is optionally substituted with one or more $R^7$; $X^7$, $X^9$, and $X^{10}$ at each instance are independently selected from the group consisting of O, $NR^5$, and a bond; $X^8$ at each instance is independently selected from the group consisting of O and $NR^5$; and q is an integer from 0 to 2.

In another embodiment $L^1$ and $L^2$ are each independently $C_{1-6}$alkylene optionally substituted with one or more $R^6$; $X^1$ and $X^6$ are each O and $X^3$ and $X^4$ are each independently selected from the group consisting of O, $NR^5$, and a bond; $X^2$ and $X^5$ are each independently selected from the group consisting of O and $NR^5$; $R^2$ at each instance and $R^3$ are independently selected from the group consisting of $C_{2-12}$alkylene and arylene, each of which is optionally substituted with one or more $R^7$; $X^7$, $X^9$, and $X^{10}$ at each instance are independently selected from the group consisting of O, $NR^5$, and a bond; $X^8$ at each instance is independently selected from the group consisting of O and $NR^5$; and q is an integer from 0 to 5.

In another embodiment $L^1$ and $L^2$ are each independently $C_{1-6}$alkylene optionally substituted with one or more $R^6$; $X^1$ and $X^6$ are each O and $X^3$ and $X^4$ are each a bond; $X^2$ and $X^5$ are each O; $R^2$ at each instance and $R^3$ are independently selected from the group consisting of $C_{2-12}$alkylene and arylene, each of which is optionally substituted with one or more $R^7$; $X^7$, $X^9$, and $X^{10}$ at each instance are independently selected from the group consisting of O and a bond and $X^8$ at each instance is O; and q is an integer from 0 to 3.

In another embodiment $L^1$ and $L^2$ are each independently $C_{1-4}$alkylene optionally substituted with one or more $R^6$; $X^1$ and $X^6$ are each O and $X^3$ and $X^4$ are each a bond; $X^2$ and $X^5$ are each O; $R^2$ at each instance and $R^3$ are independently selected from the group consisting of $C_{2-12}$alkylene and arylene, each of which is optionally substituted with one or more $R^7$; $X^7$, $X^9$, and $X^{10}$ at each instance are independently selected from the group consisting of O and a bond and $X^8$ at each instance is O; and q is an integer from 0 to 3.

In another embodiment $L^1$ and $L^2$ are each independently $C_{1-4}$alkylene optionally substituted with one or more $R^6$; $X^1$ and $X^6$ are each O and $X^3$ and $X^4$ are each a bond; $X^2$ and $X^5$ are each O; $R^2$ at each instance and $R^3$ are independently selected from the group consisting of $C_{2-8}$alkylene and arylene, each of which is optionally substituted with one or more $R^7$; $X^7$, $X^9$, and $X^{10}$ at each instance are independently selected from the group consisting of O and a bond and $X^8$ at each instance is O; and q is an integer from 0 to 3.

In another embodiment $L^1$ and $L^2$ are each independently selected from the group consisting of $C_{1-4}$alkylene optionally substituted with one or more $R^6$; $X^1$ and $X^6$ are each O and $X^3$ and $X^4$ are each a bond; $X^2$ and $X^5$ are each O; $R^2$ at each instance and $R^3$ are independently selected from the group consisting of $C_{2-8}$alkylene and arylene, each of which is optionally substituted with one or more $R^7$; $X^7$, $X^9$, and $X^{10}$ at each instance are independently selected from the group consisting of O and a bond and $X^8$ at each instance is O; and q is an integer from 0 to 2.

In another embodiment $L^1$ and $L^2$ are each independently selected from the group consisting of $C_{1-4}$alkylene optionally substituted with one or more $R^6$; $X^1$ and $X^6$ are each O and $X^3$ and $X^4$ are each a bond; $X^2$ and $X^5$ are each O; q is 0; and $R^3$ is selected from the group consisting of $C_{2-8}$alkylene and arylene, each of which is optionally substituted with one or more $R^7$.

In another embodiment $L^1$ and $L^2$ are each independently selected from the group consisting of $C_{1-4}$alkylene optionally substituted with one or more $R^6$; $X^1$ and $X^6$ are each O and $X^3$ and $X^4$ are each a bond; $X^2$ and $X^5$ are each O; q is 2; $R^2$ at each instance and $R^3$ are independently selected from the group consisting of $C_{2-8}$alkylene, each of which is optionally substituted with one or more $R^7$; Z is $X^7$—C(=$X^8$)—$X^9$; and $X^7$ and $X^9$ at each instance are independently selected from the group consisting of O and a bond and $X^8$ at each instance is O.

In another embodiment the compound of formula (IV) is a compound of formula (IVA):

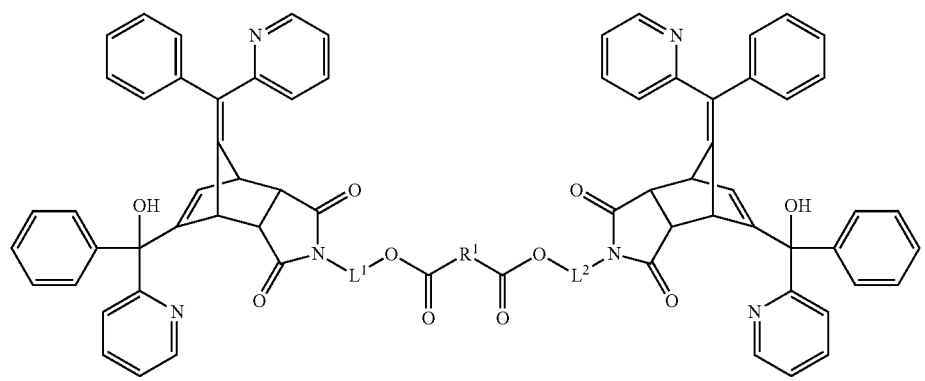

(IVA)

wherein $L^1$, $L^2$, and $R^1$ are as defined in any of the embodiments relating to the compound of formula (III) or the compound of formula (IV).

In one embodiment the compound of formula (IV) is selected from the group consisting of:

| Cmpd | $L^1/L^2$ | $X^1/X^6$ | $X^2/X^5$ | $X^3/X^4$ | $R^1$ |
|------|-----------|-----------|-----------|-----------|-------|
| 21 | $CH_2$ | O | O | — | $(CH_2)_2$ |
| 22 | $CH_2$ | O | O | — | $(CH_2)_4$ |
| 23 | $CH_2$ | O | O | — | $(CH_2)_6$ |
| 24 | $CH_2$ | O | O | — | $(CH_2)_8$ |
| 25 | $CH_2$ | O | O | — | $(CH_2)_{10}$ |
| 26 | $CH_2$ | O | O | — | $p\text{-}C_6H_4$ |
| 27 | $CH_2$ | O | O | — | $(CH_2)_2C(O)O(CH_2)_2OC(O)(CH_2)_2$ |
| 138 | $CH_2CH_2$ | O | O | — | $(CH_2)_2$ |
| 139 | $CH_2CH_2$ | O | O | — | $(CH_2)_4$ |
| 140 | $CH_2CH_2$ | O | O | — | $(CH_2)_6$ |
| 141 | $CH_2CH_2$ | O | O | — | $(CH_2)_8$ |
| 142 | $CH_2CH_2$ | O | O | — | $(CH_2)_{10}$ |
| 143 | $CH_2CH_2$ | O | O | — | $p\text{-}C_6H_4$ |
| 144 | $CH_2CH_2$ | O | O | — | $(CH_2)_2C(O)O(CH_2)_2OC(O)(CH_2)_2$ |

In one embodiment the stereochemical configuration at the bridgehead of each dicarboximide ring is endo.

Without wishing to be bound by theory, the applicant believes that the compounds of formula (III) and (IV), like the compounds of formula (I) and (II), are also capable of acting like prodrugs that upon hydrolysis in vivo release NRB or an analogue thereof.

In one embodiment the compound of formula (III) exhibits a delay in the onset of toxic effects, relative to NRB, of at least about 5, at least about 8, at least about 10, at least about 15, at least about 20, at least about 25, or about 30 minutes.

In another embodiment the compound of formula (III) exhibits a delay in the onset of toxic effects, relative to NRB, of from about 5 minutes to about 5 hours; from about 8 minutes to about 5 hours; from about 10 minutes to about 5 hours; from about 15 minutes to about 5 hours; from about 20 minutes to about 5 hours; from about 30 minutes to about 5 hours; 5 minutes to about 4 hours; from about 8 minutes to about 4 hours; from about 10 minutes to about 4 hours; from about 15 minutes to about 4 hours; from about 20 minutes to about 4 hours; from about 30 minutes to about 4 hours; 5 minutes to about 3 hours; from about 8 minutes to about 3 hours; from about 10 minutes to about 3 hours; from about 15 minutes to about 3 hours; from about 20 minutes to about 3 hours; from about 30 minutes to about 3 hours; 5 minutes to about 2 hours; from about 8 minutes to about 2 hours; from about 10 minutes to about 2 hours; from about 15 minutes to about 2 hours; from about 20 minutes to about 2 hours; from about 30 minutes to about 2 hours; 5 minutes to about 1.5 hours; from about 8 minutes to about 1.5 hours; from about 10 minutes to about 1.5 hours; from about 15 minutes to about 1.5 hours; from about 20 minutes to about 1.5 hours; or from about 30 minutes to about 1.5 hours.

In another aspect the present invention provides a compound of formula (V):

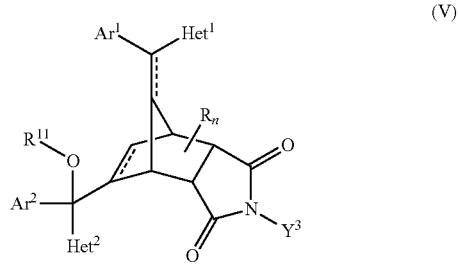

(V)

wherein $Ar^1$ and $Ar^2$ at each instance are independently a 6 to 10 membered monocyclic or bicyclic aryl ring, wherein the ring is optionally substituted with one or more $R^8$;

$Het^1$ and $Het^2$ at each instance are each independently a 5 to 10 membered monocyclic or bicyclic heteroaryl ring comprising 1 to 4 ring nitrogen atoms, wherein the ring is optionally substituted with one or more $R^8$;

each dashed line and solid line together represent a double bond or a single bond;

$Y^3$ is

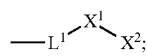

$L^1$ is selected from the group consisting of $C_{1-6}$alkylene, $C_{3-6}$cycloalkylene, arylene, heteroarylene, heterocyclylene, $C_{1-6}$alkylC$_{3-6}$cycloalkylene, $C_{1-6}$alkylarylene, $C_{1-6}$alkylheteroarylene, $C_{1-6}$alkylheterocyclylene, $C_{3-6}$cycloalkyl$C_{1-6}$alkylene, aryl$C_{1-6}$alkylene, heteroaryl$C_{1-6}$alkylene, and heterocyclyl$C_{1-6}$alkylene, each of which is optionally substituted with one or more $R^6$;

$X^1$ is selected from the group consisting of C(=O), C(=S), C(=NR$^5$), and a bond;

$X^2$ is selected from the group consisting of OH, SH, and NHR$^5$;

$R^5$ at each instance is independently selected from the group consisting of hydrogen, $C_{1-6}$alkyl, $C_{3-6}$cycloalkyl, aryl, heterocyclyl, and heteroaryl;

$R^6$ at each instance is independently selected from the group consisting of hydroxyl, thiol, amino, cyano, nitro, halo, $C_{1-6}$alkyl, $C_{1-6}$haloalkyl, $C_{1-6}$alkoxy, and $C_{1-6}$haloalkoxy;

$R^8$ at each instance is selected from the group consisting of hydroxyl, thiol, amino, cyano, nitro, halo, $C_{1-6}$alkyl, $C_{1-6}$haloalkyl, $C_{1-6}$alkoxy, and $C_{1-6}$haloalkoxy;

$R^{11}$ is selected from the group consisting of hydrogen, $C_{1-6}$alkyl, and $C_{1-6}$haloalkyl;

R at each instance is selected from the group consisting of halo, $C_{1-6}$alkyl, carboxyl, carboxyl$C_{1-6}$alkyl, amido$C_{1-6}$alkyl, acyloxy, sulfenyl, sulfoxide, sulfonyl, and aryl, wherein each $C_{1-6}$alkyl and aryl is optionally substituted with one or more $R^8$; and n is an integer selected from 0 to 3; or a salt or solvate thereof.

In another aspect, the present invention provides a compound of formula (V), wherein Ar$^1$, Ar$^2$, Het$^1$, Het$^2$, each dashed line and solid line together, $Y^3$, $R^{11}$, R, and n are as defined in the aspect above.

The following embodiments relate to the compound of formula (V).

In one embodiment Ar$^1$ and Ar$^2$ are each independently a phenyl ring optionally substituted with one or more $R^8$.

In one embodiment Het$^1$ and Het$^2$ are each independently a 5 or 6 membered monocyclic heteroaryl ring comprising 1 to 3 ring nitrogen atoms, wherein the ring is optionally substituted with one or more $R^8$. Preferably, Het$^1$ and Het$^2$ are each independently a 6 membered monocyclic heteroaryl ring comprising 1 to 3 ring nitrogen atoms, wherein the ring is optionally substituted with one or more $R^8$. More preferably, Het$^1$ and Het$^2$ are each independently pyridyl optionally substituted with one or more $R^8$.

In one embodiment each dashed line and solid line together represent a double bond.

In one embodiment n is 0 or 1. Preferably, n is 0.

In one embodiment $R^{11}$ is selected from the group consisting of hydrogen and $C_{1-6}$alkyl. Preferably, $R^{11}$ is selected from the group consisting of hydrogen and methyl. More preferably, $R^{11}$ is hydrogen.

In one embodiment $R^5$ at each instance is independently selected from the group consisting of hydrogen, $C_{1-6}$alkyl, and aryl. In another embodiment, $R^5$ at each instance is independently selected from the group consisting of hydrogen and $C_{1-6}$alkyl. In another embodiment, $R^5$ at each instance is hydrogen.

In one embodiment Ar$^1$ and Ar$^2$ are each independently a phenyl ring optionally substituted with one or more $R^8$; Het$^1$ and Het$^2$ are each independently pyridyl optionally substituted with one or more $R^8$; and each dashed line and solid line together represent a double bond; and n is 0.

In one embodiment the stereochemical configuration at the bridgehead of the dicarboximide ring is endo.

In one embodiment the compound is a compound of formula (VI):

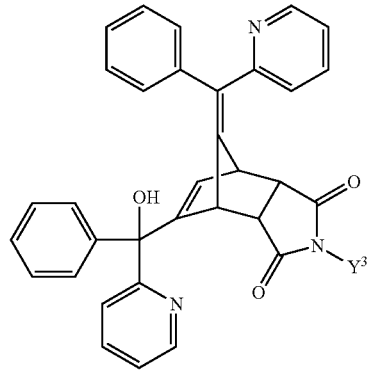

(VI)

wherein $Y^3$, $L^1$, $X^1$, and $X^2$ are as defined in any of the embodiments relating to the compound of formula (V).

The following embodiments relate to the compound of formula (V) and the compound of formula (VI).

In one embodiment $L^1$ is selected from the group consisting of $C_{1-6}$alkylene, $C_{1-6}$alkylarylene, aryl$C_{1-6}$alkylene, each of which is optionally substituted with one or more $R^6$. Preferably, $L^1$ is $C_{1-6}$alkylene optionally substituted with one or more $R^6$. More preferably, $L^1$ is $C_{1-4}$alkylene optionally substituted with one or more $R^6$. In one embodiment $L^1$ is saturated $C_{1-4}$alkylene.

In one embodiment $X^1$ is selected from the group consisting of C(=O), C(=S), C(=NR$^5$), and a bond. Preferably, $X^1$ is selected from the group consisting of C(=O) and a bond. More preferably, $X^1$ is a bond.

In one embodiment $X^2$ is selected from the group consisting of OH and NHR$^5$. Preferably, $X^2$ is OH or NH$_2$. More preferably, $X^2$ is OH.

In one embodiment $L^1$ is selected from the group consisting of $C_{1-6}$alkylene, $C_{1-6}$alkylarylene, aryl$C_{1-6}$alkylene, each of which is optionally substituted with one or more $R^6$; $X^1$ is selected from the group consisting of C(=O), C(=S), C(=NR$^5$), and a bond; and $X^2$ is selected from the group consisting of OH and NHR$^5$.

In one embodiment $L^1$ is selected from the group consisting of $C_{1-6}$alkylene, $C_{1-6}$alkylarylene, aryl$C_{1-6}$alkylene, each of which is optionally substituted with one or more $R^6$; $X^1$ is selected from the group consisting of C(=O) and a bond; and $X^2$ is selected from the group consisting of OH and NHR$^5$.

In one embodiment $L^1$ is selected from the group consisting of $C_{1-6}$alkylene, $C_{1-6}$alkylarylene, aryl$C_{1-6}$alkylene, each of which is optionally substituted with one or more $R^6$; $X^1$ is selected from the group consisting of C(=O) and a bond; and $X^2$ is selected from the group consisting of OH and NH$_2$.

In one embodiment $L^1$ is selected from the group consisting of $C_{1-6}$alkylene, $C_{1-6}$alkylarylene, aryl$C_{1-6}$alkylene, each of which is optionally substituted with one or more $R^6$; $X^1$ is a bond; and $X^2$ is selected from the group consisting of OH and NH$_2$.

In another embodiment $L^1$ is $C_{1-6}$alkylene optionally substituted with one or more $R^6$; $X^1$ is selected from the group consisting of C(=O) and a bond; and $X^2$ is selected from the group consisting of OH and NHR$^5$.

In another embodiment $L^1$ is $C_{1-6}$alkylene optionally substituted with one or more $R^6$; $X^1$ is selected from the group consisting of C(=O) and a bond; and $X^2$ is selected from the group consisting of OH and $NH_2$.

In another embodiment $L^1$ is $C_{1-6}$alkylene optionally substituted with one or more $R^6$; and $X^1$ is C=O and $X^2$ is OH; or $X^1$ is a bond and $X^2$ is selected from the group consisting of OH and $NH_2$.

In another embodiment $L^1$ is saturated $C_{1-4}$alkylene; and $X^1$ is C=O and $X^2$ is OH; or $X^1$ is a bond and $X^2$ is selected from the group consisting of OH and $NH_2$.

In another embodiment $L^1$ is $C_{1-4}$alkylene optionally substituted with one or more $R^6$; $X^1$ is a bond; and $X^2$ is selected from the group consisting of OH.

In another embodiment $L^1$ is $C_{1-4}$alkylene optionally substituted with one or more $R^6$; $X^1$ is a bond; and $X^2$ is selected from the group consisting of $NH_2$.

In one embodiment the compound of formula (VI) is selected from the group consisting of:

| Cmpd | $L^1$ | $X^1$ | $X^2$ |
|---|---|---|---|
| 102 | $CH_2CH_2$ | — | OH |
| 103 | $CH_2CHMe$ | — | OH |
| 104 | $CH_2CH_2CH_2$ | — | OH |
| 105 | $CH_2(CH_2)_2CH_2$ | — | OH |
| 106 | $CH_2CH_2$ | — | $NH_2$ |
| 107 | $CH_2$ | C(=O) | OH |

In one embodiment the stereochemical configuration at the bridgehead of the dicarboximide ring is endo.

The compounds of formula (V) and (VI) have rodenticidal activity and may be used as rodenticides.

In one embodiment the compound of formula (VI) exhibits toxic effects at a dosage and rate comparable to that of NRB.

In another embodiment the compound of formulae (VI) causes death in a rodent at a dosage and rate comparable to that of NRB. Preferably, the compound of formulae (VI) causes death in less than 4 hours; more preferably, less than 2 hours.

The compounds of formula (V) and (VI) may be converted into compounds of formulae (I) to (IV) for use as rodenticides. Without wishing to be bound by theory, the applicant believes that these compounds are capable of being hydrolysed in vivo to release compounds of formulae (V) and (VI).

The compounds of the invention may be prepared using methods known in the art, as outlined in the Examples below.

The norbornene dicarboximide core present in the compounds of the invention may be prepared, as described in U.S. Pat. No. 3,378,566 and U.S. Pat. No. 3,471,619, by the condensation of a fulvene of formula (XI) with a maleimide of formula (XII) under Diels Alder conditions (Scheme 1).

Scheme 1. Preparation of norbornene dicarboxamides by Diels Alder reaction.

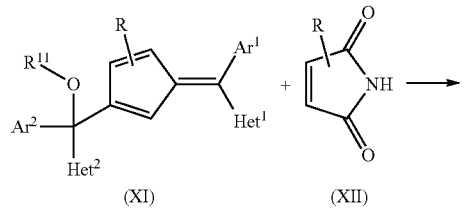

(XI)  (XII)

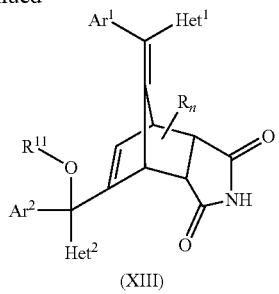

(XIII)

The reaction is typically carried out by heating the fulvene and maleimide in a suitable solvent. For example, in the preparation of NRB as described in the Examples below fulvenemethanol and maleimide were heated in toluene at 80° C. for 16 hours. The compound of formula (XIII) may be isolated from the reaction mixture and optionally purified by standard methods known in the art, such as filtration, recrystallisation, etc.

The fulvene of formula (XI) and the maleimide of formula (XII) may be commercially available or prepared using conventional synthetic organic chemistry methods. U.S. Pat. No. 3,378,566 and U.S. Pat. No. 3,471,619 describe several methods for obtaining compounds of formula (XI) and (XII).

The carbon-carbon double bonds in the norbornene dicarboxamide core of formula (XIII) may be saturated by, for example, hydrogenating the compound under an atmosphere of hydrogen in the presence of a suitable catalyst, such as palladium on carbon or platinum oxide, to provide the corresponding saturated or partially saturated compound of formula (XIII-A), (XIII-B), or (XIII-C) (Figure 1). The reaction may be carried out in a suitable solvent.

Saturation of one or both of the carbon-carbon double bonds in the norbornene dicarboxamide core may be carried out after functionalisation of the dicarboximide nitrogen—i.e. on a corresponding unsaturated compound of the formula (I) or precursor thereof. Other functional groups present in the compound to be saturated or partially saturated must be compatible with the reaction conditions used.

FIG. 1. Saturated and partially saturated derivatives of the compound of formula (XII).

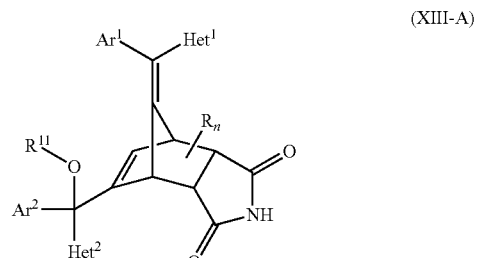

(XIII-A)

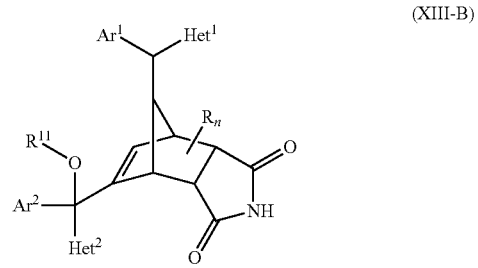

(XIII-B)

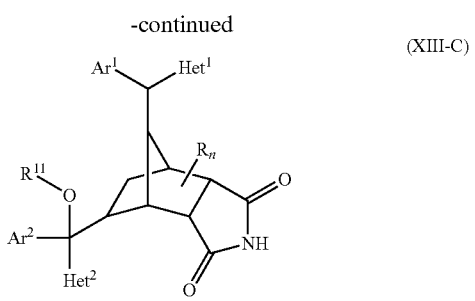

(XIII-C)

Endo-stereoisomers of the compounds of the invention may be isolated by, for example, recrystallising a stereoisomeric mixture of a compound of the invention or a suitable precursor thereof in an appropriate solvent. Several successive recrystallisations may be required to obtain the desired stereoisomeric purity or enrichment. Other suitable methods for purifying stereoisomers of the compounds of the invention will be apparent to those skilled in the art.

The optionally hydrogenated norbornene dicarboximide of formula (XIV) can be converted into the compounds of the invention of formula (I)-(VI) using synthetic chemistry techniques well known in the art.

Compounds of formula (I) wherein $X^1$ is O, $NR^5$, or S may be prepared by reacting a compound of formula (XIV) with an amino alcohol, diamine, or amino thiol of formula (XV) to provide a compound of formula (XVI) (Scheme 2).

The reaction may be carried out by heating the compounds of formula (XIV) and (XV) in a suitable solvent. For example, in the preparation of compound 102 ($X^1$=O) as described in the Examples below, NRB and ethanolamine were heated in dimethylformamide at 70° C. for 16 hours. Compound 106 ($X^1$=NH) was prepared by a similar procedure using ethylenediamine.

Compounds of formula (XV) are available commercially or accessible from commercially available precursors.

Compounds of formula (XVI) wherein $X^1$ is O, $NR^5$, or S may also be prepared by reacting a compound of formula (XIV) with a compound of formula (XV-A), wherein X is a suitable leaving group and P is a suitable protecting group, to form a compound of the formula (XVI-A) and then removing the protecting group (Scheme 2). Examples of suitable leaving groups include sulfonates, such as methanesulfonate and toluenesulfonate.

The reaction may be carried out in solvent using a suitable base. For example, as described in the Examples below, compound 106 ($X^1$=NH) was prepared by treating NRB in dimethylformamide with sodium hydride, followed by 2-((tert-butoxycarbonyl)amino)ethyl methanesulfonate.

The conditions for removal of the protecting group in a compound of formula (XVI-A) depend on the nature of the protecting group. For example, the tert-butyloxycarbonyl protecting group used in preparing compound 106 was removed using trifluoroacetic acid in dichloromethane. Protecting groups are well known in the art (see, for example, *Protective Groups in Organic Synthesis*, T. Green and P. Wuts, Wiley, 1991). Suitable protecting groups and conditions for their introduction and removal will be apparent to those skilled in the art.

It may be necessary to protect other reactive functional groups in the preparation of the compounds of the inventions. A person skilled in the art will be to select an appropriate protecting group strategy without undue experimentation.

Compounds of formula (XV-A) are also available commercially or from commercially available precursors.

Compounds of formula (I), wherein $X^1$ is O, $NR^5$, or S, can be prepared by reacting a compound of formula (XVI) with a compound of formula (XVII), wherein X is a suitable leaving group (Scheme 3). Suitable leaving groups include, for example, halogens, OH, carboxyates, etc.

Scheme 2. Preparation of compounds of formula (XVI) wherein $X^1$ is O, $NR^5$, or S.

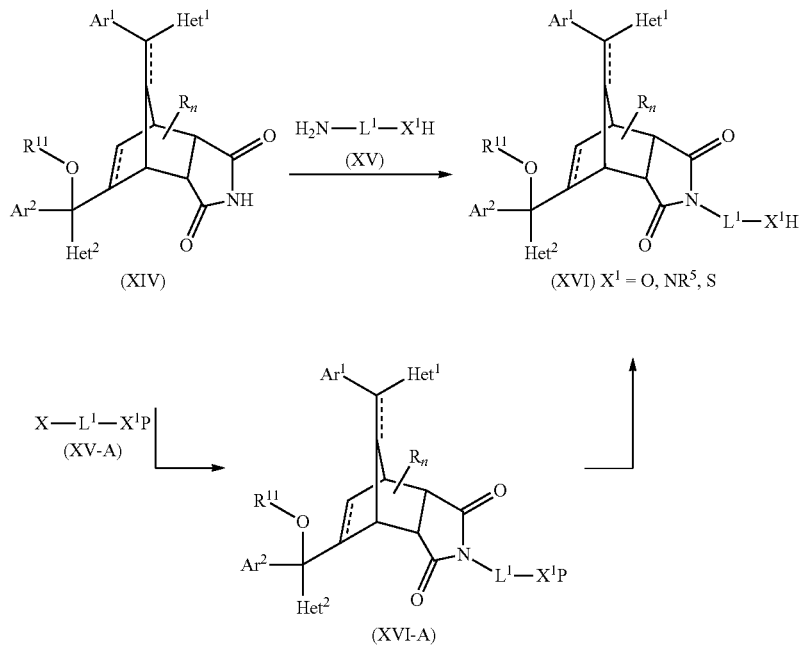

Scheme 3. Preparation of compounds of formula (I) from compounds of formula (XVI).

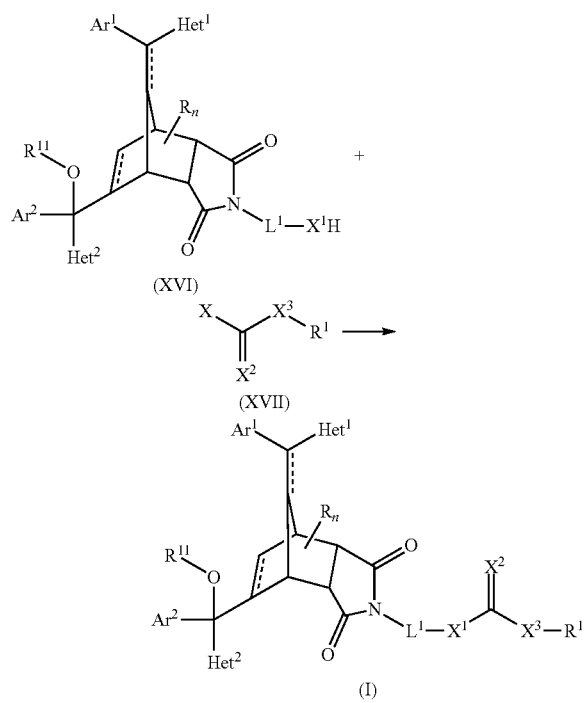

As depicted above in Scheme 3, $X^2$ and $X^3$ in the compound of formula (I) may be introduced from a compound of formula (XVII).

Accordingly, compounds of formula (I) wherein $X^2$ is O and $X^3$ is a bond may be prepared by reacting a compound of formula (XVII) wherein $X^2$ is O and $X^3$ is a bond with a compound of formula (XVI). The Examples demonstrate the preparation of various compounds of formula (I), such as compounds of formula (I) wherein $X^2$ is O and $X^3$ is a bond by this method.

Compounds of formula (XVII) may be commercially available or accessible from commercially available precursors. For example, compounds of formula (XVII) wherein X is chloro may be prepared from the corresponding carboxylic acid by reaction with e.g. thionyl chloride or oxalyl chloride.

In one embodiment, the compound of formula (XVII) is an acid chloride. In another embodiment, the compound of formula (XVII) is an anhydride. In another embodiment, the compound of formula (XVII) is a carboxylic acid. Other suitably functionalised compounds of formula (XVII) will be apparent to those skilled in the art.

The reaction between the compound of formula (XVII) and the compound of formula (XVI) may be carried out in the presence of acid or base, as appropriate. Examples of suitable bases include but are not limited to triethylamine, pyridine, and the like.

The reaction may also be carried in the presence of activating agents, if necessary, such as, 1-ethyl-3-(3-dimethylaminopropyl)carbodiimide (EDC), dicyclohexylcarbodiimide (DCC), 1-hydroxybenzotriazole (HOBT), and 4-dimethylaminopyridine (DMAP). A person skilled in the art will be able to determine suitable conditions for the reaction, such as temperatures, times, and solvents, and additional agents, if necessary, without undue experimentation.

For example, in the preparation of compound 126 as described in the Examples, compound 102 (a compound of formula (XVI) wherein $X^1$ is O) was reacted with 4-methoxycinnamoyl chloride in dimethylformamide, in the presence of triethylamine and dimethylaminopyridine. Compound 335 was prepared by a similar procedure using 4-ethylcinnamoyl chloride.

Compounds of formula (I) may also be prepared by reacting the compound of formula (XIV) with a compound of formula (XVIII), wherein X is a suitable leaving group (Scheme 4). Suitable leaving groups include, for example, halogens, sulfonates, etc.

Scheme 4. Preparation of compounds of formula (I) from compounds of formula (XIV).

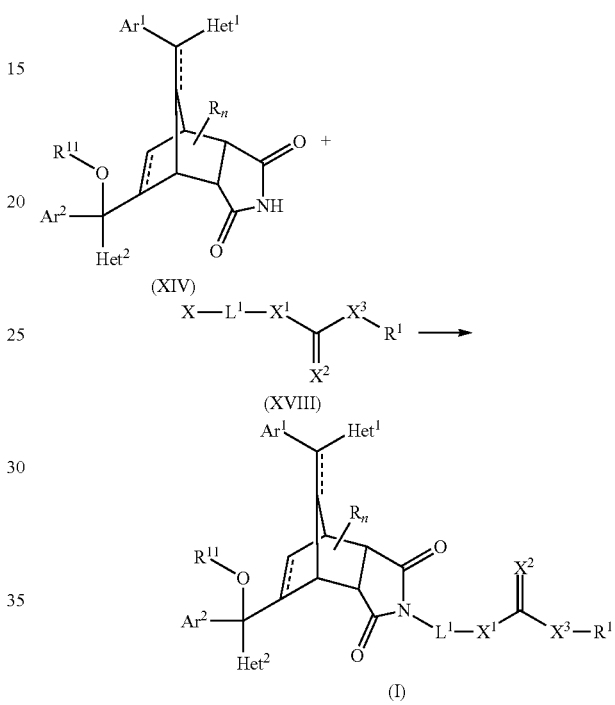

The reaction is typically carried out in the presence of base in a suitable solvent. The base used depends on the nature of X. Examples of suitable bases include but are not limited to potassium carbonate, caesium carbonate, sodium hydride, and the like.

The reaction may also be carried out in the presence of one or more reagents that improve the reactivity of the compound of formula (XVIII). For example, the reactivity of the compound of formula (XVIII) wherein X is a chlorine atom may be improved by conversion to the corresponding iodide in situ using sodium iodide.

A person skilled in the art will be able to select appropriate conditions for the reaction, such as temperatures, times, and solvents, etc. without undue experimentation.

The Examples demonstrate the preparation of various compounds of formula (I) by this method, such as compound of formula (I) wherein $X^1$ and $X^2$ are each O and $X^3$ is a bond and compounds of formula (I) wherein $X^1$ is a bond and $X^2$ and $X^3$ are each O.

For example, compound 19 ($X^1$ and $X^2$ are each O and $X^3$ is a bond) was prepared by reacting NRB with sodium hydride, followed by iodomethly cinnamate in dimethylformamide, as described in the Examples. Compound 19 was also prepared by reacting NRB with chloromethly cinnamate in the presence of potassium carbonate. Compound 324 was also prepared from NRB by a similar procedure, using chloromethyl p-methylphenylacetate as the compound of formula (XVIII) and cesium carbonate as base.

Compound 369 ($X^1$ is a bond and $X^2$ and $X^3$ are each O) was also prepared from NRB by a similar procedure, using octyl chloroacetate as the compound of formula (XVIII) and potassium carbonate as base.

Compounds of formula (XVIII) may be commercially available or prepared from commercially available compounds. For example, compounds of formula (XVIII), wherein X is halo may be halogenations of the corresponding $L^1$ group.

Compounds of formula (I), wherein $L^1$ is an ether, thioether, or amine (e.g. $C_{1-6}$alkoxy$C_{1-6}$alkyl) may be prepared by the method below in Scheme 5.

Scheme 5. Preparation of compounds of formula (I) from compounds of formula (XIV-B).

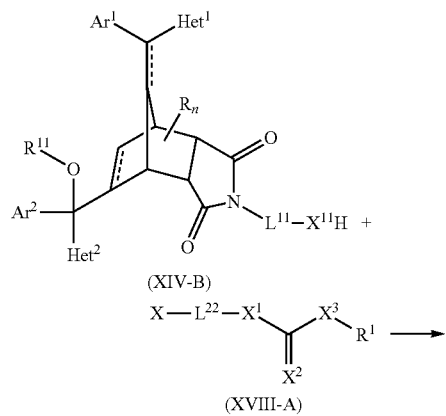

(XIV-B)

(XVIII-A)

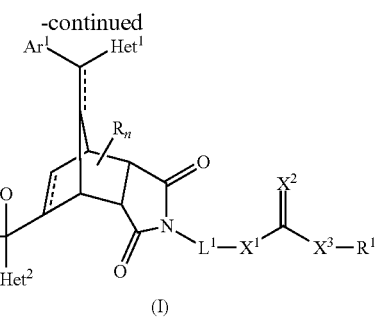

(I)

The method involves reacting a compound of formula (XIV-B), wherein $L^{11}$ is the first portion of $L^1$ and $X^{11}$ and H together represent hydroxyl, amine, or thiol, with a compound of the formula (XVIII-A) wherein $L^{22}$ is the second portion of $L^1$ and X is a suitable leaving group.

The reaction is typically carried out in the presence of a suitable base, such as sodium hydride. Displacement of X in the compound of formula (XVIII-A) by the hydroxyl, thiol, or amine group in the compound of formula (XIV-B) forms $L^1$ in the compound of formula (I).

Compounds of formula (III) contain similar functionality to the compounds of formula (I). The methods for preparing the compounds of formula (I) described above may also be used to prepare compounds of formula (III).

Compounds of formula (III) include two norbornene dicarboxamide units. Compounds of formula (III) wherein the two norbornene dicarboximide units are the same may be prepared by reacting two equivalents of a compound of formula (XIV) or (XIV-B)) with one equivalent of a compound of formula (XVIII-B) or (XVIII-C), respectively, wherein X is a suitable leaving group (Scheme 6). Suitable leaving groups include, for example, halogens.

Scheme 6. Preparation of compounds of formula (III).

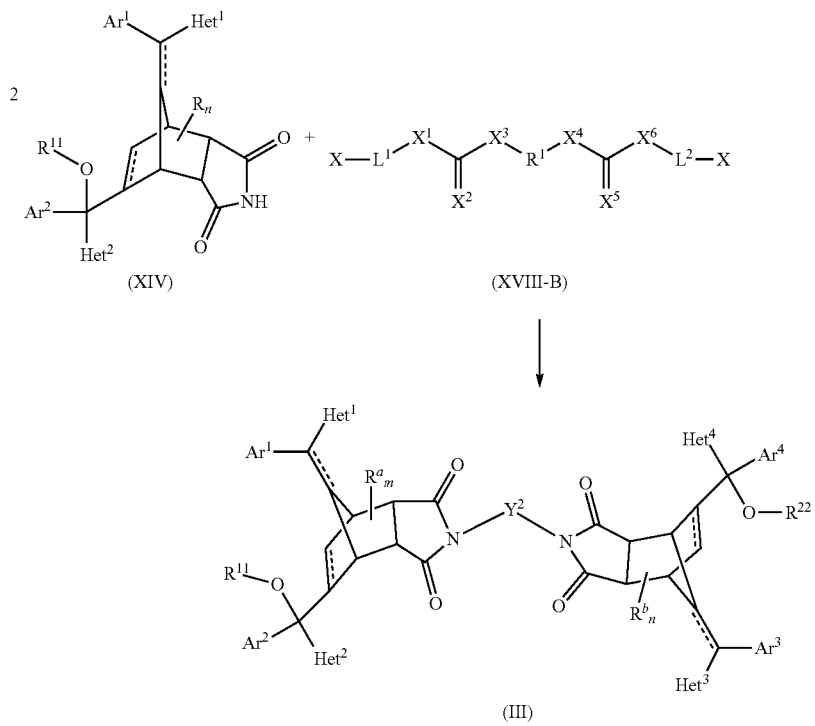

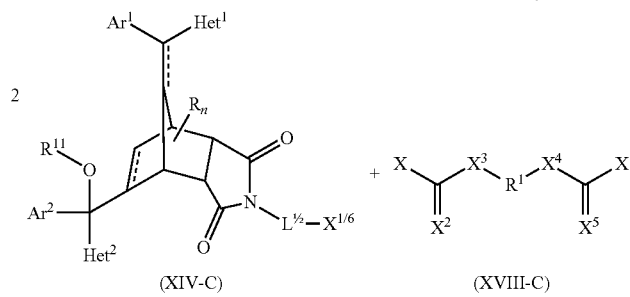

(XIV-C) (XVIII-C)

The reactions are typically carried out in the presence of a suitable base. The Examples demonstrate the preparation of various compounds by these methods. Compounds of formula (XVIII-B) or (XVIII-C) may be commercially available or prepared from commercially available precursors, as described in the examples, for example.

Compounds of formula (III) wherein the two norbornene dicarboximide units are different in structure may be prepared by, for example, selectively protecting one of the terminal reactive sites and coupling the first norbornene dicarboxamide unit, then removing the protecting group and coupling the second norbornene dicarboxamide unit. A person skilled in the art will be able to select an appropriate a protecting group strategy without undue experimentation.

Compounds of formula (V) may also be made by the methods for preparing the compounds of formula (I) described above. For example, compounds of formula (V) wherein $X^1$ is a bond may be prepared by the method described above for the compound of formula (XVI) (cf. Scheme 2).

Compounds of formula (V) wherein $X^1$ is not a bond may be prepared by reacting a compound of the formula (IV) with a compound of the formula (XX), wherein X is a suitable leaving group and P is a suitable protecting group, and then removing the protecting group (Scheme 7 Suitable leaving groups include, for example, halogens, sulfonates, etc.

Scheme 7. Preparation of compounds of formula (V) from compounds of formula (XIV).

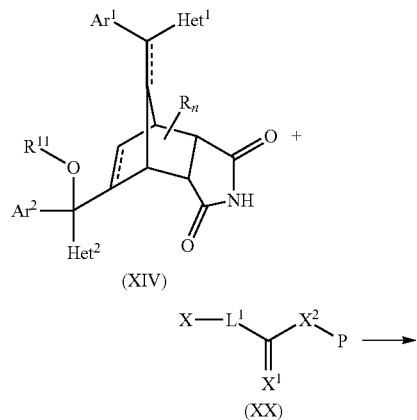

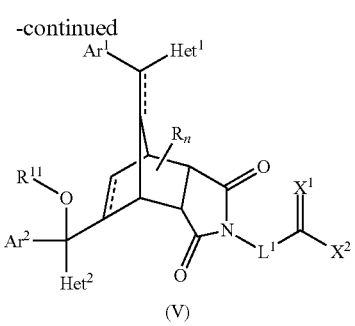

(V)

The reaction of a compound of formula (XIV) with a compound of formula (XX) may be carried out in a manner similar to that described above for the preparation of compounds of formula (I) in Scheme 4.

The reaction is typically carried out in solvent in the presence of a suitable base, such as potassium carbonate. The leaving group X may be activated to increase its reactivity with the compound of formula (XIV), as described above for the compound of formula (XVIII).

A person skilled in the art will be able to select appropriate protecting groups, and conditions for their introduction and removal.

For example, in the preparation of compound 107 as described in the Examples, NRB was reacted first with ethyl bromoacetate (a compound of the formula (XX), wherein $X^1$ is O) in the presence of potassium carbonate, and then treated with concentrated hydrochloric acid to remove the ester protecting group.

The compounds of the invention have rodenticidal activity. Accordingly, in one aspect the present invention provides a use of a compound of the present invention as a rodenticide.

In another aspect the present invention provides a rodenticidal composition comprising an effective amount of a compound of the invention; and one or more edible diluent or carrier materials.

In another aspect the present invention provides a use of a compound of the invention in the manufacture of a rodenticidal composition.

Preferably, the compound of the invention is a compound of formula (I) or (III); more preferably, a compound of formula (II) or (IV); more preferably, a compound of formula (II). In one embodiment the compound of formula (II) is a compound of formula (IIA).

The amount of a compound of the present invention that is effective against the target rodent, can be easily determined in vivo by simply feeding various amounts of the substance to the rodent, and determining if a poisonous effect (e.g., death or debilitation) is exhibited after a suitable pre-determined period of time.

In one embodiment the compound of the invention comprises 0.0001 to 5% by weight of the composition. Preferably, the compound of the invention comprises 0.001 to 2.5% by weight of the composition; more preferably, 0.1 to 1.5% by weight of the composition; more preferably, 0.5% by weight of the composition.

In one embodiment the composition comprises more than one compound of the invention.

In one embodiment the composition comprises an edible solid, liquid, or semi-solid material. Preferably, the edible solid, liquid, or semi-solid material is attractive to rodents. Examples of suitable solids include cracked corn, corn meal, mixtures of various grains (e.g., mixtures of corn, oats, and wheat), ground meat, and mixtures of meat and grain. Examples of suitable liquids include water, milk, syrup, carbonated flavoured liquids, lower alcohols and other organic solvents, mixtures of organic and aqueous solvents, and sweetened beverages. Examples of suitable semi-solids include animal fats and carbohydrate gums. Preferably, the edible solid, liquid, or semi-solid material is a solid food.

The composition may also comprise other ingredients commonly used in the formulation of rodenticides, for example, attractant chemicals, fertility reducing actives, insecticides, binders, antioxidants, sweeteners, flavourants, plastics, fillers, dyes, and encapsulants. The composition may also comprise bittering agents, such as Bitrex® (denatonium benzoate), as a means of lowering palatability to non-target interference. The composition may also include ingredients that prevent or inhibit bait degradation, for example, preservatives, such as fungicides. Other suitable ingredients will be apparent to those skilled in the art.

In one embodiment, the composition comprises another rodenticidal agent, in addition to one or more compounds of the invention. Suitable rodenticides include, for example, those listed in Krieger, R. I. (Ed.), *Handbook of Pesticide Toxicology: Principles (Second Edition)*, Academic Press: London, 2001.

The composition may be formulated in any form known in the art as suitable for the delivery of rodenticides. Examples of suitable formulations include baits in the form of granules, pellets, pastes, gels, or liquids and gnawing articles, such as briquettes, tablets, or blocks.

Any suitable method known in the art can be used to prepare the composition. In one embodiment the composition is prepared by dissolving a compound of the invention in a solvent and then adding the solution to a composition comprising edible material. The solvent may be subsequently removed. In another embodiment the composition is prepared by supplementing a composition comprising edible material with unsolvated compound. Other suitable methods will be apparent to those skilled in the art.

In another aspect the present invention provides a method of controlling rodents comprising making a rodenticidal composition of the invention available for consumption by the rodents.

In one embodiment, the method is for controlling a population of rodents. In one embodiment, the rodent population is controlled such that the number of rats in the population of rodents does not significantly increase. Preferably, the rodent population is controlled such that the number of rats in the population is reduced. More preferably, the rodent population is eliminated.

The term "rodent" as used herein means a vertebrate which is a member of the classes of the phylum Chordata and a member of the order Rodentia, class Mammalia. Preferably, the rodent is a member of the genus *Rattus*. More preferably, the rodent is a member of a species selected from the group consisting of *Rattus rattus, Rattus alexandrinus, Rattus norvegicus, Rattus hawaiiensis, Rattus argentiventer*, and *Rattus exulans*.

The rodenticidal composition may be made available for consumption by rodents by any suitable method known in the art.

In one embodiment the rodenticidal composition is provided at a site frequented by the rodents. Ideally, the amount of the composition provided at the site is sufficient to kill all of the rodents that frequent the site. However, it can be difficult to ascertain the number of rodents that frequent a site. In one embodiment the amount of the composition made available at the site is sufficient to kill at least one rodent. In another embodiment the amount is sufficient to kill at least five rodents, at least 10 rodents, at least 20 rodents, or at least 50 rodents.

In one embodiment the method is used for field control of rodents. Suitable bait formulations include cereal-based pellets or waxed blocks, pastes or gels. The bait formulation may be delivered by any suitable method known in the art where rodent control or eradication is desired. Suitable methods include deployment in bait stations, broadcast application by hand or from the air, or placement of bait within rodent burrows or other enclosed spaces.

The following non-limiting examples are provided to illustrate the present invention and in no way limit the scope thereof.

EXAMPLES

General Materials and Methods

All reagents were used as supplied unless otherwise stated. Solvents were purified by standard methods (Perrin, D. D. et al. *Purification of Laboratory Chemicals*; Pergamon Press: Oxford, 1980). Analytical thin layer chromatography (TLC) was carried out on pre-coated silica gel plates (Merck/UV$_{254}$) and products were visualized by UV fluorescence and/or staining. Potassium permanganate solution was the stain of choice. Flash chromatography was performed using silica gel (Riedel-de Haën, particle size 0.032-0.063 mm). Distillation was carried out using a Büchi GKR-51 Kugelrohr apparatus. Melting points in degrees Celsius (° C.) were measured on an Electrothermal® melting point apparatus and are uncorrected. Nuclear Magnetic Resonance (NMR) spectra were recorded on a Bruker AVANCE DRX400 ($^1$H, 400 MHz; $^{13}$C, 100 MHz) or a Bruker AVANCE 300 ($^1$H, 300 MHz; $^{13}$C, 75 MHz) spectrometer at 298 K. For $^1$H NMR data, chemical shifts are described in parts per million (ppm) relative to tetramethylsilane (δ 0.00) and are reported consecutively as position ($δ_H$), relative integral, multiplicity (s=singlet, bs=broad singlet, d=doublet, bd=broad doublet, t=triplet, q=quartet, dd=doublet of doublets, dt=doublet of triplets, qd=quartet of doublets, m=multiplet, bm=broad multiplet), coupling constant (J/Hz) and assignment. For $^{13}$C NMR data, chemical shifts (ppm) are referenced internally to CDCl$_3$ (δ 77.0) and are reported consecutively as position ($δ_C$) and degree of hybridization. Assignments were aided by DEPT135 and HSQC experiments. Infrared spectra were recorded on a Perkin-Elmer Spectrum One Fourier Transform Absorption peaks are reported in wavenumbers (v, cm$^{-1}$), with the major peaks assigned to the appropriate functional groups. Mass spectra were recorded on a VG-70SE mass spectrometer (EI, CI and FAB). High-resolution mass spectra were recorded at a nominal resolution of 5000. The purity of all target compounds was assigned using reverse-phase HPLC [Dionex P680 system using a Phenomenex Gemini $C_{18}$-Si column (50 mm×2 mm, 5 μm)]—eluted using a gradient of 100:0% AB to 5:95% AB over 15 min at 0.2 mL/min; where solvent A was water (0.1% formic acid) and solvent B was $CH_3CN$ (0.1% formic acid); with detection at 254 and 280 nm.

Experimental

Chemistry

Compounds of the invention were prepared using the procedures described below.

Chloromethyl Pivalate (41)

Compound 41 was prepared by a procedure similar to that of Iyer and co-workers (Iyer, R. P. et al. *Synth. Commun.* 1995, 25, 2739-2749). A mixture of pivaloyl chloride (8.56 g, 71 mmol), paraformaldehyde (2.13 g, 71 mmol) and zinc chloride (75 mg, 0.55 mmol) was stirred at 80° C. for 2 h. Purification by vacuum distillation afforded chloromethyl pivalate (41) as a colourless oil (6.29 g, 44.7 mmol, 59%). bp 80° C./15 mmHg [lit. bp 80-81° C./15 mmHg (Iyer, R. P.; Yu, D.; Ho, N.; Agrawal, S. *Synth. Commun.* 1995, 25, 2739-2749)]; $^1$H NMR (400 MHz, $CDCl_3$) δ 1.24 (9H, s, tBu), 5.72 (2H, s, $CH_2$).

Chloromethyl Octanoate (43)

Compound 43 was prepared by a procedure similar to that of Harada and co-workers (Harada, N. et al. *Synth. Commun.* 1995, 25, 767-772). To a vigorously stirring solution of octanoic acid (4.50 g, 31.2 mmol), sodium hydrogen carbonate (10.48 g, 124.8 mmol) and tetra-n-butylammonium hydrogen sulfate (1.06 g, 3.12 mmol) in water-dichloromethane (125 mL, 1:1 v/v) at 0° C. was added chloromethylchlorosulfate (5.15 g, 31.2 mmol) in dichloromethane (15 mL), and the reaction stirred at room temperature for a further 18 h. The mixture was diluted with dichloromethane (150 mL) and washed with brine (150 mL), dried over anhydrous magnesium sulfate and the solvent removed in vacuo. Purification by flash chromatography (hexane/ethyl acetate 9:1) afforded 43 as a yellow oil (5.28 g, 27.3 mmol, 88%). $^1$H NMR (400 MHz, $CDCl_3$) δ 0.86-0.90 (3H, m, Me), 1.24-1.37 (8H, m, $CH_3(CH_2)_4$), 1.60-1.71 (2H, m, $CH_2CH_2COO$), 2.36-2.40 (2H, m, $CH_2CH_2COO$), 5.71 (2H, s, $CH_2Cl$).

Alternatively, a similar procedure (Lu, M. C. et al. *J. Med. Chem.* 1987, 30, 273-278 and Iyer, R. P. et al. *Synth. Commun.* 1995, 25, 2739-2749) to that described for the preparation of 50 was followed using octanoic acid (3.0 g, 20.8 mmol) and thionyl chloride (1.5 mL), under reflux for 1 h. A mixture of crude octanoyl chloride, paraformaldehyde (624 mg, 20.8 mmol) and zinc chloride (21 mg, 0.16 mmol) was then stirred at 80° C. for 16 h. Purification by flash chromatography (hexane/ethyl acetate 19:1) afforded chloromethyl octanoate (43) as a colourless oil (1.7 g, 8.87 mmol, 43%).

Chloromethyl Dodecanoate (44)

A similar procedure (Lu, M. C. et al. *J. Med. Chem.* 1987, 30, 273-278 and Iyer, R. P. et al. *Synth. Commun.* 1995, 25, 2739-2749) to that described for the preparation of 50 was followed using dodecanoic acid (5.7 g, 28.4 mmol) and thionyl chloride (3.5 mL), under reflux for 1 h. A mixture of crude dodecanoyl chloride, paraformaldehyde (852 mg, 28.4 mmol) and zinc chloride (29 mg, 0.22 mmol) was then stirred at 80° C. for 16 h. Purification by flash chromatography (hexane/ethyl acetate 19:1) afforded chloromethyl dodecanoate (44) as a colourless oil (0.97 g, 3.91 mmol, 14%). $^1$H NMR (400 MHz, $CDCl_3$) δ 0.86-0.90 (3H, m, Me), 1.26-1.30 (16H, m, $Me(CH_2)_8$), 1.63-1.67 (2H, m, $CH_2CH_2COO$), 2.36-2.40 (2H, m, $CH_2CH_2COO$), 5.70 (2H, s, $CH_2Cl$).

Chloromethyl Benzoate (45)

A similar procedure (Iyer, R. P. et al. *Synth. Commun.* 1995, 25, 2739-2749) to that described for the preparation of 41 was followed using benzoyl chloride (10.0 g, 71 mmol), paraformaldehyde (2.13 g, 71 mmol) and zinc chloride (75 mg, 0.55 mmol), at 80° C. for 2 h. Purification by vacuum distillation afforded chloromethyl benzoate (45) as a colourless oil (5.93 g, 35.1 mmol, 49%). bp 100° C./0.5 mmHg [lit. bp 75-78° C./1.5 mmHg (Iyer, R. P. et al. *Synth. Commun.* 1995, 25, 2739-2749)]; $^1$H NMR (400 MHz, $CDCl_3$) δ 5.95 (2H, s, $CH_2$), 7.44-7.53 (2H, m, Ar), 7.58-7.64 (1H, m, Ar), 8.06-8.13 (2H, m, Ar).

Chloromethyl o-Methoxybenzoate (46)

A similar procedure (Iyer, R. P. et al. *Synth. Commun.* 1995, 25, 2739-2749) to that described for the preparation of 41 was followed using o-anisoyl chloride (5.0 g, 29 mmol), paraformaldehyde (883 mg, 29 mmol) and zinc chloride (31 mg, 0.2 mmol), at 80° C. for 2 h.

Purification by flash chromatography (hexane/ethyl acetate 4:1) afforded chloromethyl o-methoxybenzoate (46) as a yellow oil (2.5 g, 12.5 mmol, 42%). $^1$H NMR (300 MHz, $CDCl_3$) δ 3.92 (3H, s, OMe), 5.93 (2H, s, $CH_2$), 6.97-7.03 (2H, m, Ar), 7.50-7.56 (1H, m, Ar), 7.87-7.90 (1H, m, Ar).

Chloromethyl m-Methoxybenzoate (47)

A similar procedure (Lu, M. C. et al. *J. Med. Chem.* 1987, 30, 273-278 and Iyer, R. P. et al. *Synth. Commun.* 1995, 25, 2739-2749) to that described for the preparation of 50 was followed using m-anisic acid (4.1 g, 26.9 mmol) and thionyl chloride (4 mL), under reflux for 1 h. A mixture of crude m-anisoyl chloride, paraformaldehyde (808 mg, 26.9 mmol) and zinc chloride (28 mg, 0.21 mmol) was then stirred at 80° C. for 16 h. Purification by flash chromatography (hexane/ethyl acetate 19:1) afforded chloromethyl m-methoxybenzoate (47) as a pale green oil (1.4 g, 6.86 mmol, 26%). $^1$H NMR 3.86 (3H, s, OMe), 5.95 (2H, s, $CH_2$), 7.14-7.17 (1H, m, Ar), 7.36-7.40 (1H, m, Ar), 7.58-7.59 (1H, m, Ar), 7.66-7.69 (1H, m, Ar).

Chloromethyl p-Methoxybenzoate (48)

A similar procedure (Iyer, R. P. et al. *Synth. Commun.* 1995, 25, 2739-2749) to that described for the preparation of 41 was followed using p-anisoyl chloride (5.0 g, 29.4 mmol), paraformaldehyde (883 mg, 29.4 mmol) and zinc chloride (31 mg, 0.22 mmol), at 80° C. for 16 h. Purification by flash chromatography (hexane/ethyl acetate 4:1) afforded chloromethyl p-methoxybenzoate (48) as a yellow oil (0.74 g, 3.69 mmol, 12%). $^1$H NMR (300 MHz, $CDCl_3$) δ 3.87 (3H, s, OMe), 5.94 (2H, s, $CH_2$), 6.92-6.96 (2H, m, Ar), 8.01-8.06 (2H, m, Ar).

Chloromethyl Phenylacetate (49)

A similar procedure (Harada, N. et al. *Synth. Commun.* 1995, 25, 767-772) to that described for the preparation of 43 was followed using phenylacetic acid (4.50 g, 31.2 mmol), sodium hydrogen carbonate (10.48 g, 124.8 mmol) and tetra-n-butylammonium hydrogen sulfate (1.06 g, 3.12 mmol) in water-dichloromethane (125 mL, 1:1 v/v) and chloromethylchlorosulfate (5.15 g, 31.2 mmol) in dichloromethane (15 mL), at room temperature for 18 h. Purification by flash chromatography (hexane/ethyl acetate 9:1) afforded 49 as a yellow oil (1.81 g, 9.82 mmol, 31%).

Alternatively, a similar procedure (Lu, M. C. et al. *J. Med. Chem.* 1987, 30, 273-278 and Iyer, R. P. et al. *Synth. Commun.* 1995, 25, 2739-2749) to that described for the preparation of 50 was followed using phenylacetic acid (1.0 g, 7.34 mmol) and oxalyl chloride (2 mL), under reflux for 1 h. A mixture of crude phenylacetyl chloride, paraformaldehyde (220 mg, 7.34 mmol) and zinc chloride (7 mg, 0.05 mmol) was then stirred at 80° C. for 2 h. Purification by flash chromatography (hexane/ethyl acetate 4:1) afforded chloromethyl phenylacetate (49) as a colourless oil (0.47 g, 2.56 mmol, 35%).

Chloromethyl p-Methylphenylacetate (322)

A similar procedure (Harada, N. et al. *Synth. Commun.* 1995, 25, 767-772) to that described for the preparation of 43 was followed using 4-methylphenylacetic acid (2.27 g, 15.15 mmol), sodium hydrogen carbonate (5.09 g, 60.6 mmol) and tetra-n-butylammonium hydrogen sulfate (0.51 g, 1.52 mmol) in water-dichloromethane (62.5 mL, 1:1 v/v) and chloromethylchlorosulfate (2.50 g, 15.15 mmol) in dichloromethane (7.5 mL), at room temperature for 18 h. Purification by flash chromatography (hexane/ethyl acetate 9:1) afforded 322 as a colourless oil (2.42 g, 12.18 mmol, 80%).

Chloromethyl Diphenylacetate (50)

Compound 50 was prepared by a procedure similar to that of Lu and co-workers (Lu, M. C. et al. *J. Med. Chem.* 1987, 30, 273-278), and Iyer and co-workers (Iyer, R. P. et al. *Synth. Commun.* 1995, 25, 2739-2749). A solution of diphenylacetic acid (5.0 g, 23.6 mmol) in thionyl chloride (15 mL) was heated under reflux for 1 h. The excess thionyl chloride was removed in vacuo and the crude diphenylacetyl chloride was taken through to the next step without further purification. A mixture of crude diphenylacetyl chloride, paraformaldehyde (529 mg, 17.6 mmol) and zinc chloride (19 mg, 0.14 mmol) was then stirred at 80° C. for 2 h. Purification by flash chromatography (hexane/ethyl acetate 19:1) afforded chloromethyl diphenylacetate (50) as a colourless oil (1.71 g, 6.56 mmol, 37%). $^1$H NMR (300 MHz, CDCl$_3$) δ 5.07 (1H, s, CH), 5.73 (2H, s, CH$_2$), 7.23-7.36 (10H, m, Ar).

Chloromethyl Dihydrocinnamate (51)

A similar procedure (Lu, M. C. et al. *J. Med. Chem.* 1987, 30, 273-278 and Iyer, R. P. et al. *Synth. Commun.* 1995, 25, 2739-2749) to that described for the preparation of 50 was followed using dihydrocinnamic acid (150 mg, 0.36 mmol) and oxalyl chloride (0.5 mL), under reflux for 1 h. A mixture of crude dihydrocinnamoyl chloride, paraformaldehyde (242 mg, 8.06 mmol) and zinc chloride (8 mg, 0.06 mmol) was then stirred at 80° C. for 2 h. Purification by flash chromatography (hexane/ethyl acetate 10:1) afforded chloromethyl dihydrocinnamate (51) as a yellow oil (0.67 g, 3.4 mmol, 42%). $^1$H NMR (300 MHz, CDCl$_3$) δ 2.70 (2H, t, J=7.8 Hz, CH$_2$CO), 2.96 (2H, t, J=7.8 Hz, CH$_2$Ph), 5.70 (2H, s, CH$_2$Cl), 7.19-7.32 (5H, m, Ar).

Chloromethyl Cinnamate (52)

A similar procedure (Lu, M. C. et al. *J. Med. Chem.* 1987, 30, 273-278 and Iyer, R. P. et al. *Synth. Commun.* 1995, 25, 2739-2749) to that described for the preparation of 50 was followed using cinnamic acid (1.0 g, 6.75 mmol) and oxalyl chloride (2 mL), under reflux for 1 h. A mixture of crude cinnamoyl chloride, paraformaldehyde (202 mg, 6.75 mmol) and zinc chloride (7 mg, 0.05 mmol) was then stirred at 80° C. for 2 h. Purification by flash chromatography (hexane/ethyl acetate 4:1) afforded chloromethyl cinnamate (52) as a colourless oil (68 mg, 0.34 mmol, 5%); $^1$H NMR (400 MHz, CDCl$_3$) δ 5.85 (2H, s, CH$_2$), 6.43 (1H, d, J=16.1 Hz, CHCO), 7.39-7.43 (3H, m, Ar), 7.52-7.56 (2H, m, Ar), 7.78 (1H, d, J=16.1 Hz, CHPh).

Chloromethyl 2-Naphthoate (53)

A similar procedure (Lu, M. C. et al. *J. Med. Chem.* 1987, 30, 273-278 and Iyer, R. P. et al. *Synth. Commun.* 1995, 25, 2739-2749) to that described for the preparation of 50 was followed using 2-naphthoic acid (1.0 g, 5.8 mmol) and oxalyl chloride (2 mL), under reflux for 2 h. A mixture of crude 2-naphthoyl chloride, paraformaldehyde (174 mg, 5.8 mmol) and zinc chloride (6 mg, 0.04 mmol) was then stirred at 80° C. for 2 h. Purification by flash chromatography (hexane/ethyl acetate 4:1) afforded chloromethyl 2-naphthoate (53) as a colourless oil (80 mg, 0.36 mmol, 6%); $^1$H NMR (400 MHz, CDCl$_3$) δ 5.98 (2H, s, CH$_2$), 7.53-7.64 (2H, m, Ar), 7.87-7.96 (3H, m, Ar), 8.05-8.10 (1H, m, Ar), 8.65 (1H, s, Ar).

Dichloromethyl Succinate (60)

A similar procedure (Iyer, R. P. et al. *Synth. Commun.* 1995, 25, 2739-2749) to that described for the preparation of 41 was followed using succinoyl chloride (2.0 mL, 18.2 mmol), paraformaldehyde (1.1 g, 36 mmol) and zinc chloride (38 mg, 0.28 mmol), at 80° C. for 2 h. Purification by flash chromatography (hexane/ethyl acetate 10:1) afforded dichloromethyl succinate (60) as a colourless oil (1.0 g, 4.67 mmol, 26%); $^1$H NMR (400 MHz, CDCl$_3$) δ 2.76 (4H, s, 2×COCH$_2$), 5.72 (4H, s, 2×ClCH$_2$); $^{13}$C NMR (100 MHz, CDCl$_3$) δ 28.5 (CH$_2$, OCOCH$_2$), 68.8 (CH$_2$, ClCH$_2$), 170.0 (C, C=O).

Dichloromethyl Adipate (61)

A similar procedure (Iyer, R. P. et al. *Synth. Commun.* 1995, 25, 2739-2749) to that described for the preparation of 41 was followed using adipoyl chloride (2.0 mL, 13.7 mmol), paraformaldehyde (822 mg, 27 mmol) and zinc chloride (29 mg, 0.21 mmol), at 80° C. for 2 h. Purification by vacuum distillation afforded dichloromethyl adipate (61) as a colourless oil (0.52 g, 2.12 mmol, 15%). bp 175° C./0.65 mmHg [lit. bp 123° C./mm Hg (Rosnati, V. and Bovet, D. *Rend. ist. super sanita (Rome)* 1951, 15, 473-495)]; $^1$H NMR (400 MHz, CDCl$_3$) δ 1.70-1.76 (4H, m, 2×OCOCH$_2$CH$_2$), 2.42-2.46 (4H, m, 2×OCOCH$_2$), 5.72 (4H, s, 2×ClCH$_2$); $^{13}$C NMR (100 MHz, CDCl$_3$) δ 22.9-23.9 (CH$_2$, OCOCH$_2$CH$_2$), 33.0 (CH$_2$, OCOCH$_2$), 68.4 (CH$_2$, ClCH$_2$), 170.9 (C, C=O).

Dichloromethyl Suberate (62)

A similar procedure (Iyer, R. P. et al. *Synth. Commun.* 1995, 25, 2739-2749) to that described for the preparation of 41 was followed using suberoyl chloride (170 μL, 0.95 mmol), paraformaldehyde (56.9 mg, 1.89 mmol) and zinc chloride (2 mg, 15 μmol), at 80° C. for 16 h. Purification by flash chromatography (hexane/ethyl acetate 9:1) afforded dichloromethyl suberate (62) as a colourless oil (43 mg, 0.16 mmol, 17%); $^1$H NMR (400 MHz, CDCl$_3$) δ 1.35-1.40 (4H, m, 2×OCOCH$_2$CH$_2$CH$_2$), 1.63-1.70 (4H, m, 2×OCOCH$_2$CH$_2$), 2.37 (4H, t, J=7.4 Hz, 2×OCOCH$_2$), 5.70 (4H, s, 2×ClCH$_2$); $^{13}$C NMR (100 MHz, CDCl$_3$) δ 24.2 (CH$_2$, OCOCH$_2$CH$_2$CH$_2$), 28.4 (CH$_2$, OCOCH$_2$CH$_2$), 33.8 (CH$_2$, OCOCH$_2$), 68.5 (CH$_2$, ClCH$_2$), 171.5 (C, C=O); ν$_{max}$/cm$^{-1}$ 1029 and 1133 (C—O ester), 1750 (C=O ester), 2849 and 2936 (CH$_2$); m/z (CI+) 288 (MNH$_4^+$, 10%), 156 (100); (Found: MNH$_4^+$ 288.0761, C$_{10}$H$_{20}$$^{35}$Cl$_2$O$_4$N requires 288.0769).

Dichloromethyl Sebacate (63)

A similar procedure (Iyer, R. P. et al. *Synth. Commun.* 1995, 25, 2739-2749) to that described for the preparation of 41 was followed using sebacoyl chloride (5.0 mL, 23.4 mmol), paraformaldehyde (1.4 g, 46.6 mmol) and zinc chloride (50 mg, 0.36 mmol), at 80° C. for 2 h. Purification by flash chromatography (hexane/ethyl acetate 3:1) afforded dichloromethyl sebacate (63) as a colourless solid (2.8 g, 9.36 mmol, 40%). mp 34-38° C.; $^1$H NMR (300 MHz, CDCl$_3$) δ 1.32 (8H, bm, 2×OCO(CH$_2$)$_2$(CH$_2$)$_2$), 1.63-1.67 (4H, m, 2×OCOCH$_2$CH$_2$), 2.35 (4H, t, J=7.4 Hz, 2×OCOCH$_2$), 5.70 (4H, s, 2×ClCH$_2$); $^{13}$C NMR (75 MHz, CDCl$_3$) δ 24.3 (CH$_2$, OCO(CH$_2$)$_3$CH$_2$), 28.7-28.8 (CH$_2$, OCOCH$_2$(CH$_2$)$_2$), 33.8 (CH$_2$, OCOCH$_2$), 68.4 (CH$_2$, ClCH$_2$), 171.6 (C, C=O).

Dichloromethyl Dodecanedioate (64)

A similar procedure (Lu, M. C. et al. *J. Med. Chem.* 1987, 30, 273-278 and Iyer, R. P. et al. *Synth. Commun.* 1995, 25, 2739-2749) to that described for the preparation of 50 was followed using dodecaneclioic acid (1.0 g, 4.34 mmol) and oxalyl chloride (1.5 mL), under reflux for 1 h. A mixture of crude dodecanedioyl dichloride, paraformaldehyde (261 mg, 8.68 mmol) and zinc chloride (9 mg, 0.07 mmol) was then stirred at 80° C. for 16 h. Purification by flash chromatography (hexane/ethyl acetate 9:1) afforded dichloromethyl dodecanedioate (64) as a colourless solid (300 mg, 0.92 mmol, 21%). mp 40-42° C.; $^1$H NMR (400 MHz, CDCl$_3$) δ 1.25-1.32 (12H, m, 2×OCO(CH$_2$)$_2$(CH$_2$)$_3$), 1.61-1.68 (4H, m, 2×OCOCH$_2$CH$_2$), 2.36-2.40 (4H, m, 2×OCOCH$_2$), 5.70 (4H, s, 2×ClCH$_2$); $^{13}$C NMR (100 MHz, CDCl$_3$) δ 24.3-24.5 (CH$_2$, OCOCH$_2$CH$_2$), 28.7-29.1 (CH$_2$, OCO(CH$_2$)$_2$(CH$_2$)$_3$), 33.7-33.8 (CH$_2$, OCOCH$_2$), 68.4 (CH$_2$, ClCH$_2$), 171.5 (C, C=O); ν$_{max}$(NaCl)/cm$^{-1}$ 1132 and 1200 (C—O ester), 1750 (C=O ester); m/z (CI+) 344 (MNH$_4^+$, 56%), 212 (100); (Found: MNH$_4^+$ 344.1398, C$_{14}$H$_{28}$$^{35}$Cl$_2$O$_4$N requires 344.1395).

Ethylene Bis(Hydrogen Succinate) (67)

To a solution of succinic anhydride (2.0 g, 20 mmol) in pyridine (1.6 mL, 20 mmol) was added dropwise ethylene glycol (0.5 mL, 10 mmol) and the mixture refluxed for 16 h. The solvent was removed in vacuo to afford ethylene bis (hydrogen succinate) (67) as a colourless solid (2.50 g), which was used without further purification; $^1$H NMR (400 MHz, CDCl$_3$) δ 2.65-2.69 (8H, m, 2×HOOC(CH$_2$)$_2$), 4.32 (4H, s, COO(CH$_2$)$_2$); $^{13}$C NMR (400 MHz, CDCl$_3$) δ 28.9 (CH$_2$, HOOC(CH$_2$)$_2$), 62.4 (CH$_2$, COO(CH$_2$)$_2$), 171.9 (C, C=O), 177.9 (C, COOH).

Dichloromethyl Ethylene Bis(Hydrogen Succinate) (68)

A similar procedure (Lu, M. C. et al. *J. Med. Chem.* 1987, 30, 273-278 and Iyer, R. P. et al. *Synth. Commun.* 1995, 25, 2739-2749) to that described for the preparation of 50 was followed using 67 (1.0 g, 3.81 mmol) and thionyl chloride (2 mL), under reflux for 3 h. A mixture of crude ethylene bis (hydrogensuccinul)dichloride, paraformaldehyde (225 mg, 7.51 mmol) and zinc chloride (8 mg, 0.06 mmol) was then stirred at 80° C. for 2 h. Purification by flash chromatography (hexane/ethyl acetate 7:3) afforded dichloromethyl ethylene bis(hydrogen succinate) (68) as a colourless oil (126 mg, 0.35 mmol, 9%); $^1$H NMR (400 MHz, CDCl$_3$) δ 2.68-2.75 (8H, m, 2×ClCH$_2$OCO(CH$_2$)$_2$), 4.32 (4H, s, COO(CH$_2$)$_2$OCO), 5.72 (4H, s, 2×ClCH$_2$); $^{13}$C NMR (100 MHz, CDCl$_3$) δ 28.3-28.4 (ClCH$_2$OCOCH$_2$), 28.6-28.7 (CH$_2$, ClCH$_2$OCOCH$_2$CH$_2$), 62.3 (CH$_2$, COO(CH$_2$)$_2$OCO), 68.7 (CH$_2$, ClCH$_2$), 170.3 (C, C=O), 171.6 (C, C=O); ν$_{max}$(NaCl)/cm$^{-1}$ 1736 and 1761 (C=O); m/z (CI+) 376 (MNH$_4^+$, 7%), 193 (100); (Found: MNH$_4^+$ 376.0565, C$_{12}$H$_{20}$$^{35}$Cl$_2$NO$_8$ requires 376.0566).

cis,trans-α-Phenyl-α-[6-phenyl-6-(2-pyridyl)-2-fulvenyl]-2-pyridinemethanol (200)

Compound 200 was prepared by a procedure similar to that of Poos and co-workers (Mohrbacher, R. J.; Paragamian, V.; Carson, E. L.; Puma, B. M.; Rasmussen, C. R.; Meschino, J. A.; Poos, G. I. *J. Org. Chem.* 1966, 31, 2149-2159). To a solution of sodium ethoxide (15.6 g, 0.23 mol) and 2-benzoylpyridine (85.0 g, 0.46 mol) in absolute ethanol (220 mL) under nitrogen at 5° C. was added dropwise over 30 min. freshly distilled cyclopentadiene (15.4 mL, 0.23 mol). The mixture was stirred at 5° C. for a further 1.5 h, warmed to room temperature and left standing for 16 h. The resulting red-orange solid was collected by filtration, washed with cold ethanol (3×50 mL) and dried in vacuo to afford 200 as an orange solid (73.5 g), which was used without further purification. mp 164-168° C. [lit. mp 160-175° C. (Mohrbacher, R. J. et al. *J. Org. Chem.* 1966, 31, 2149-2159]; $^1$H NMR (300 MHz, CDCl$_3$) δ 5.97 (0.5H, t, J=3.9 and 1.9 Hz, trans H-1), 6.02 (0.5H, t, J=3.9 and 1.9 Hz, cis H-1), 6.13 (1H, s, OH), 6.33 (0.5H, dd, J=5.4 and 2.0 Hz, cis H-4), 6.38 (0.5H, dd, J=5.4 and 2.0 Hz, trans H-4), 6.54-6.58 (1H, m, H-3), 7.18-7.71 (16H, m, Ar), 8.54 (1H, dq, J=4.8, 1.7 and 1.0 Hz, αPyr), 8.60 (0.5H, dq, J=4.8, 1.7 and 1.0 Hz, cis αPyr), 8.69 (0.5H, dq, J=4.8, 1.7 and 1.0 Hz, trans αPyr).

5-(α-Hydroxy-α-2-pyridylbenzyl)-7-(α-2-pyridylbenzylidene)-5-norbornene-2,3-dicarboximide (NRB)

NRB was prepared by a procedure similar to that of Poos and co-workers (Mohrbacher, R. J.; Almond, H. R., Jr.; Carson, E. L.; Rosenau, J. D.; Poos, G. I. *J. Org. Chem.* 1966, 31, 2141-2148). A solution of fulvenylmethanol 200 (18.2 g, 44.0 mmol) and maleimide (4.3 g, 44.0 mmol) in toluene (180 mL) was stirred at 80° C. for 16 h. The reaction mixture was cooled in an ice bath and the resulting precipitate collected by filtration to afford NRB as a cream solid (22.2 g). mp 208-210° C. [lit. 190-198° C. (Mohrbacher, R. J. et al. *J. Org. Chem.* 1966, 31, 2141-2148)]. Recrystallisation from ethyl acetate afforded NRB as a mixture of predominately endo isomers (colourless crystals, 10.3 g, 20.1 mmol, 46%). mp 204-215° C.; $^1$H NMR (300 MHz, CDCl$_3$) δ 3.36-3.82 (2.2H, m, H-2, H-3, W/H-4), 3.84-3.87 (0.4H, m, 0.1H U/H-1 and 0.3H V/H-1), 3.95 (0.4H, m, Y/H-4), 4.11 (0.1H, m, U/H-4), 4.31 (0.3H, m, V/H-4), 4.44-4.47 (0.6H, m, W/H-1, Y/H-1), 5.63-5.67 (0.7H, m, V/H-6, Y/H-6), 5.83 (OH), 5.88 (OH), 6.06 (0.1H, m, U/H-6), 6.08 (0.2H, m, W/H-6), 6.80-7.58 (16H, m, Ar), 8.42-8.63 (2H, m, αPyr).

N-2'-Hydroxyethyl-5-(α-hydroxy-α-2-pyridylbenzyl)-7-(α-2-pyridylbenzylidene)-5-norbornene-2,3-dicarboximide (102)

Compound 102 was prepared by a procedure similar to that of Gasanov and co-workers (Gasanov, R. A. et al. *Russ. J. Appl. Chem.* 2004, 77, 2034-2035). A solution of NRB (25.0 g, 48.75 mmol) and ethanolamine (50 mL, 838 mmol) in dimethylformamide (125 mL) was heated at 70° C. for 16 h. The mixture was then allowed to cool, diluted with ethyl acetate (400 mL) and washed with water (400 mL). The separated aqueous phase was further extracted with ethyl acetate (2×200 mL) and the combined organic phases washed with brine (4×100 mL), dried over anhydrous magnesium sulfate, filtered and the solvent removed in vacuo. Purification by flash chromatography (hexane/ethyl acetate 1:4) afforded 102 as a white solid (21.0 g, 37.75 mmol, 77%). mp 160-167° C.; $^1$H NMR (400 MHz, CDCl$_3$) δ 3.32-3.90 (5H, m, CH$_2$CH$_2$OH, H-2, H-3, U/H-1, V/H-1, Y/H-4, W/H-4), 4.11 (0.14H, m, U/H-4), 4.32 (0.31H, m, V/H-4), 4.47 (0.37H, m, Y/H-1), 4.52 (0.18H, m, W/H-1), 5.10 (0.31H, s, OH), 5.12 (0.37H, s, OH), 5.57 (0.31H, dd, J=3.3 and 1.2 Hz, V/H-6), 5.61 (0.37H, dd, J=3.3 and 1.2 Hz, Y/H-6), 6.20 (0.14H, m, U/H-6), 6.25 (0.18H, dd, J=3.3 and 1.2 Hz, W/H-6), 6.28 (0.18H, s, OH), 6.30 (0.14H, s, OH), 6.81-7.62 (16H, m, Ar), 8.39-8.64 (2H, m, αPyr); $v_{max}$(NaCl)/cm$^{-1}$ 1697 (C=O amide), 3449 (OH); m/z (FAB+) 556 (MH$^+$, 94%), 538 (MH$^+$—H$_2$O, 100); (Found: MH$^+$ 556.2234, C$_{35}$H$_{30}$N$_3$O$_4$ requires 556.2236).

N-2'-Hydroxypropyl-5-(α-hydroxy-α-2-pyridylbenzyl)-7-(α-2-pyridylbenzylidene)-5-norbornene-2,3-dicarboximide (103)

A similar procedure (Gasanov, R. A. et al. *Russ. J. Appl. Chem.* 2004, 77, 2034-2035) to that described for the preparation of 102 was followed using NRB (400 mg, 0.8 mmol) and 1-amino-2-propanol (4.6 mL, 54.8 mmol) in dimethylformamide (4 mL), at 70° C. for 16 h. Purification by flash chromatography (hexane/ethyl acetate 1:2) afforded 103 as a colourless solid (290 mg, 0.51 mmol, 64%). mp 213-216° C.; $^1$H NMR (300 MHz, CDCl$_3$) δ 1.09-1.35 (3H, m, Me), 3.31-3.39 (0.1H, m, W/H-3), 3.40-3.72 (4H, m, 2H NCH$_2$, 0.8H V/H-2 and V/H-3, 0.2H W/H-2 and W/H-4, 1H Y/H-2 and Y/H-3), 3.82-3.94 (0.9H, m, 0.4H V/H-1 and 0.5H Y/H-4), 3.96-4.20 (1H, m, CHMe), 4.28-4.34 (0.4H, m, V/H-4), 4.44-4.54 (0.6H, m, 0.1H W/H-1 and 0.5H Y/H-1), 5.19-5.23 (1.2H, m, OH), 5.51-5.61 and 5.66-5.72 (0.8H, m, 0.4H V/H-6 and 0.5 Y/H-6), 6.14-6.17, 6.21-6.22 and 6.24-6.26 (0.9H, m, 0.1H W/H-6 and 0.8H OH), 6.76-7.61 (16H, m, Ar), 8.37-8.53 (1.4H, m, 0.8H 2V/αPyr, 0.1H W/αPyr and 0.5H Y/αPyr), 8.61-8.65 (0.6H, m, 0.1H W/αPyr and 0.5H Y/αPyr); $v_{max}$/cm$^{-1}$ 1134 and 1185 (C—O ester), 1586 (C=O imide), 1693 (C=O ester); m/z (EI+) 569 (M$^+$, 4%), 396 (100); (Found: M$^+$ 569.2316, C$_{36}$H$_{31}$N$_3$O$_4$ requires 569.2315).

N-3'-Hydroxypropyl-5-(α-hydroxy-α-2-pyridylbenzyl)-7-(α-2-pyridylbenzylidene)-5-norbornene-2,3-dicarboximide (104)

A similar procedure (Gasanov, R. A. et al. *Russ. J. Appl. Chem.* 2004, 77, 2034-2035) to that described for the preparation of 102 was followed using NRB (400 mg, 0.8 mmol) and 3-amino-1-propanol (4.2 mL, 54.8 mmol) in dimethylformamide (4 mL), at 70° C. for 16 h. Purification by flash chromatography (hexane/ethyl acetate 1:2) afforded 104 as a colourless solid (175 mg, 0.31 mmol, 38%). mp 103-110° C.; $^1$H NMR (400 MHz, CDCl$_3$) δ 1.63-1.83 (2H, m, NCH$_2$CH$_2$CH$_2$OH), 2.77-2.95 (1H, bs, NCH$_2$CH$_2$CH$_2$OH), 3.20-3.71 (6.1H, m, NCH$_2$CH$_2$CH$_2$OH, H-2, H-3, W/H-4), 3.89 (0.2H, m, V/H-1), 3.94 (0.7H, m, Y/H-4), 4.30 (0.2H, m, V/H-4), 4.47-4.50 (0.8H, m, W/H-1, Y/H-1), 5.61 (0.2H, m, V/H-6), 5.63 (0.7H, dd, J=3.2 and 1.1 Hz, Y/H-6), 5.66 (0.1H, s, OH), 5.72 (0.7H, s, OH), 5.76 (0.2H, s, OH), 6.11 (0.1H, m, W/H-6), 6.75-7.60 (16H, m, Ar), 8.44-8.64 (2H, m, αPyr); $v_{max}$(NaCl)/cm$^{-1}$ 1043 and 1169 (C—O ester), 1586 (C=O imide), 1695 (C=O ester); m/z (EI+) 569 (M$^+$, 2%), 231 (100); (Found: M$^+$ 569.2309, C$_{36}$H$_{31}$N$_3$O$_4$ requires 569.2315).

N-4'-Hydroxybutyl-5-(α-hydroxy-α-2-pyridylbenzyl)-7-(α-2-pyridylbenzylidene)-5-norbornene-2,3-dicarboximide (105)

A similar procedure (Gasanov, R. A. et al. *Russ. J. Appl. Chem.* 2004, 77, 2034-2035) to that described for the preparation of 102 was followed using NRB (400 mg, 0.8 mmol) and 4-amino-1-butanol (1.0 g, 11 mmol) in dimethylformamide (4 mL), at 70° C. for 16 h. Purification by flash chromatography (hexane/ethyl acetate 1:2) afforded 105 as a colourless solid (132 mg, 0.2 mmol, 28%). mp 98-110° C.; $^1$H NMR (300 MHz, CDCl$_3$) δ 1.47-1.99 (4H, m, NCH$_2$(CH$_2$)$_2$), 3.29-3.74 (6.1H, m, 4H NCH$_2$(CH$_2$)$_2$CH$_2$OH, 0.2H U/H-2 and U/H-3, 0.6H V/H-2 and V/H-3, 0.3H W/H-2, W/H-3 and W/H-4, 1H Y/H-2 and Y/H-3, CH$_2$OH), 3.88-3.99 (0.9H, m, 0.1H U/H-1, 0.3H V/H-1 and 0.5H Y/H-4), 4.08-4.14 (0.1H, m, U/H-4), 4.24-4.31 (0.3H, m, V/H-4), 4.42-4.50 (0.6H, m, 0.1H W/H-1 and 0.5H Y/H-1), 5.55-5.69 (1.8H, m, 0.3H V/H-6, 0.5H Y/H-6 and 1H OH), 6.02-6.10 (0.2H, m, 0.1H U/H-6 and 0.1H W/H-6), 6.74-7.60 (16H, m, Ar), 8.40-8.49 (1.4H, m, 0.2H 2U/αPyr, 0.6H 2V/αPyr, 0.1H W/αPyr and 0.5H Y/αPyr), 8.62-8.64 (0.6H, m, 0.1H W/αPyr and 0.5H Y/αPyr); $v_{max}$(NaCl)/cm$^{-1}$ 1042 and 1166 (C—O ester), 1586 (C=O imide), 1697 (C=O ester); m/z (FAB+) 584 (MH$^+$, 88%), 566 (100); (Found: MH$^+$ 584.2536, C$_{37}$H$_{34}$N$_3$O$_4$ requires 584.2549).

N-2'-Aminoethyl-5-(α-hydroxy-α-2-pyridylbenzyl)-7-(α-2-pyridylbenzylidene)-5-norbornene-2,3-dicarboximide (106)

Compound 106 was prepared over two steps by a procedure similar to that of van Vliet and co-workers (van Vliet, L. D. et al. *J. Med. Chem.* 2007, 50, 2326-2340).

To a solution of NRB (10.0 g, 19.57 mmol) in anhydrous DMF (60 mL) was added sodium hydride (1.57 g, 23.48 mmol, 60% w/w oil), and the mixture stirred at room temperature for 15 minutes, then at 80° C. for a further 15 minutes. To the mixture was then added 2-((tert-butoxycarbonyl)amino)ethyl methanesulfonate (5.15 g, 21.53 mmol) in dry DMF (7 mL), and the mixture stirred at 100° C. for 5 h. The reaction mixture was allowed to cool, poured onto ice/water and the resulting precipitate collected by filtration, washed with water (50 mL) and dried in vacuo. Purification by flash chromatography (hexane/ethyl acetate 1:1) afforded 5-(α-hydroxy-α-2-pyridylbenzyl)-7-(α-2-pyridylbenzylidene)-N-[(tert-butyloxy)carbonyl]-2'-aminoethyl-5-norbornene-2,3-dicarboximide as a pale brown solid (8.17 g, 12.48 mmol, 64%). $^1$H NMR (400 MHz, CDCl$_3$) δ 1.38-1.45 (9H, m, NHBoc), 3.15-3.89 (6.2H, m NCH$_2$CH$_2$NHBoc, H-2, H-3, W/H-4), 3.85-3.89 (0.4H, m, U/H-1, V/H-1), 3.91 (0.4H, Y/H-4), 4.11 (0.1H, m, U/H-4), 4.31 (0.3H, m, V/H-4), 4.46-4.51 (0.6H, m, W/H-1, Y/H-1), 5.36-6.19 (3H, H-6, OH, NHBoc), 6.75-7.65 (16H, m, Ar), 8.40-8.65 (2H, m, αPyr); m/z (ESI, 70 eV) 677 (MNa$^+$, 100%).

To a solution of 5-(α-hydroxy-α-2-pyridylbenzyl)-7-(α-2-pyridylbenzylidene)-N-[(tert-butyloxy)carbonyl]-2'-aminoethyl-5-norbornene-2,3-dicarboximide (4.0 g, 6.11 mmol) in dichloromethane (80 mL) was added trifluoroacetic acid (20 mL), and the mixture stirred at room temperature for 3 h. The solvent was removed in vacuo and the resultant oil triturated with diethyl ether, and the resulting solid then collected by filtration and dried in vacuo to afford 106 as a trifluoroacetate salt. The trifluoroacetate salt was then taken up in ethyl acetate (200 mL), washed with a saturated solution sodium hydrogen carbonate (20 mL), then water (20 mL), dried over magnesium sulfate, filtered and the solvent removed in vacuo to afford 106 as a white solid (3.0 g, 5.41 mmol, 88%), which was used without further purification. mp 100-105° C.; $^1$H NMR (400 MHz, CDCl$_3$) δ 2.75-2.95 (2H, m, NCH$_2$CH$_2$NH$_2$), 3.30-3.65 (4.18, NCH$_2$CH$_2$NH$_2$, H-2, H-3, W/H-4), 3.88-3.91 (0.82H, Y/H-4, V/H-1, U/H1), 4.10 (0.12H, m, U/H-4), 4.25 (0.31H, m, V/H-4), 4.39-4.46 (0.57H, m, W/H-1, Y/H-1), 5.69 (0.31H, m, V/H-6), 5.76 (0.39H, m, Y/H-6), 6.10 (0.12H, m, U/H-6), 6.15 (0.18H, m, W/H-6), 6.73-7.55 (16H, m, Ar), 8.31-8.62 (2H, m, αPyr); $v_{max}$/cm$^{-1}$ 1153 and 1218 (C—O ester), 1585 (C=O imide), 1695 (C=O ester), 3300 (NH$_2$); m/z (ESI, 70 eV) 555 (MH$^+$, 100%); (Found: M$^+$ 554.2313, C$_{35}$H$_{30}$N$_4$O$_3$ requires 554.2318).

Alternatively, a similar procedure (Gasanov, R. A. et al. *Russ. J. Appl. Chem.* 2004, 77, 2034-2035) to that described for the preparation of 102 was followed using NRB (600 mg, 1.2 mmol) and ethylenediamine (5.3 mL, 79.8 mmol) in dimethylformamide (6 mL), at 70° C. for 16 h. Purification by flash chromatography (dichloromethane/methanol 10:1) afforded 106 as a colourless solid (274 mg, 0.49 mmol, 42%).

N-Ethoxycarbonylmethyl-5-(α-hydroxy-α-2-pyridylbenzyl)-7-(α-2-pyridylbenzylidene)-5-norbornene-2,3-dicarboximide (207)

Compound 207 was prepared by a procedure similar to that of Hursthouse and co-workers (Hursthouse, M. B.; Khan, A.; Marson, C. M.; Porter, R. A. *Tetrahedron Lett.* 1995, 36, 33, 5979-5982). To a solution of NRB (1.0 g, 1.95 mmol) and potassium carbonate (270 mg, 1.95 mmol) in dimethylformamide (4 mL) was added ethyl bromoacetate (0.22 mL, 1.95 mmol) in dimethylformamide (2.5 mL). The mixture was stirred at room temperature for 2 h, taken up in chloroform (20 mL), washed with water (2×10 mL) and dried over anhydrous magnesium sulfate. The solvent was removed in vacuo with purification by flash chromatography (hexane/ethyl acetate 1:1) affording 207 as a colourless solid (900 mg, 1.5 mmol, 77%). mp 71-89° C.; $^1$H NMR (400 MHz, CDCl$_3$) δ 1.24-1.28 (3H, m, Me), 3.40 (0.1H, dd, J=8.0 and 4.4 Hz, W/H-3), 3.47 (0.3H, dd, J=7.8 and 4.6 Hz, Y/H-3), 3.57-3.60 (0.5H, m, V/H-2), 3.65-3.66 (0.1H, m, W/H-4), 3.69-3.77 (1.1H, m, 0.2H U/H-2 and U/H-3, 0.5H V/H-3, 0.1H W/H-2 and 0.3H Y/H-2), 3.87-3.91 (0.6H, m, 0.1H U/H-1 and 0.5H V/H-1), 3.95-3.97 (0.3H, m, Y/H-4), 3.99-4.00 (0.2H, m, CH$_2$N), 4.03-4.04 (0.3H, m, CH$_2$N), 4.11-4.22 (2.3H, m, 2H CH$_2$O, 0.1H U/H-4 and 0.2H CH$_2$N), 4.24 (0.2H, bs, CH$_2$N), 4.28 (0.7H, bs, CH$_2$N), 4.32-4.35 (0.7H, m, 0.2H CH$_2$N and 0.5H V/H-4), 4.37-4.38 (0.2H, m, CH$_2$N), 4.49-4.52 (0.4H, m, 0.1H W/H-1 and 0.3H Y/H-1), 5.48 (0.7H, s, OH), 5.52-5.55 (1.1H, m, 0.5H V/H-6, 0.3H Y/H-6 and 0.3H OH), 6.02-6.05 (0.2H, m, 0.1H U/H-6 and 0.1H W/H-6), 6.74-7.58 (16H, m, Ar), 8.38-8.39 (0.1H, m, U/αPyr), 8.42-8.51 (1.5H, m, 0.1H U/αPyr, 1H 2V/αPyr, 0.1H W/αPyr and 0.3H Y/αPyr), 8.61-8.62 (0.4H, m, 0.1H W/αPyr and 0.3H Y/αPyr); $v_{max}$/cm$^{-1}$ 1174 and 1211 (C—O ester), 1585 (C=O imide), 1711 (C=O ester); m/z (EI+) 597 (M$^+$, 6), 231 (100); (Found: M$^+$ 597.2263, C$_{37}$H$_{31}$N$_3$O$_5$ requires 597.2264).

N-Carboxymethyl-5-(α-hydroxy-α-2-pyridylbenzyl)-7-(α-2-pyridylbenzylidene)-5-norbornene-2,3-dicarboximide (107)

Compound 107 was prepared over two steps using procedures similar to those of Hursthouse and co-workers and Nitsche and co-workers, respectively (Hursthouse, M. B. et al. *Tetrahedron Lett.* 1995, 36, 33, 5979-5982 and Nitsche, B. et al. *J. Labelled Compd. Radiopharm.* 1987, 24, 6, 623-630).

To a solution of NRB (1.0 g, 1.95 mmol) and potassium carbonate (270 mg, 1.95 mmol) in dimethylformamide (4 mL) was added ethyl bromoacetate (0.22 mL, 1.95 mmol) in dimethylformamide (2.5 mL), and the mixture stirred at room temperature for 2 h. The mixture was then diluted with chloroform (20 mL), washed with water (2×10 mL), dried over anhydrous magnesium sulfate, filtered and the solvent removed in vacuo. Purification by flash chromatography (hexane/ethyl acetate 1:1) afforded N-ethoxycarbonylmethyl-5-(α-hydroxy-α-2-pyridylbenzyl)-7-(α-2-pyridylbenzylidene)-5-norbornene-2,3-dicarboximide as a white solid (900 mg, 1.5 mmol, 77%). $^1$H NMR (400 MHz, CDCl$_3$) δ 1.24-1.28 (3H, m, OCH$_2$CH$_3$), 3.40-4.50 (8H, m, OCH$_2$CH$_3$, NCH$_2$, H-1, H-2, H-3, H-4), 5.48 (0.4H, s, OH), 5.52 (0.5H, m, V/H-6), 5.53 (0.6H, s, OH), 5.55 (0.2H, m, Y/H-6), 6.02 (0.2H, m, U/H-6), 6.05 (0.1H, m, W/H-6), 6.74-7.58 (16H, m, Ar), 8.38-8.65 (2H, m, αPyr); m/z (EI+) 597 (M$^+$, 6), 231 (100).

A mixture of N-ethoxycarbonylmethyl-5-(α-hydroxy-α-2-pyridylbenzyl)-7-(α-2-pyridylbenzylidene)-5-norbornene-2,3-dicarboximide (100 mg, 0.17 mmol) and concentrated hydrochloric acid (1.5 mL) was stirred at 70° C. for 3 h. The solvent was removed in vacuo with purification by flash chromatography (chloroform/methanol 10:1) affording 107 as a white solid (38 mg, 0.07 mmol, 40%). mp>300° C.; $^1$H NMR (400 MHz, d$_6$-DMSO, HCl salt) δ 3.20-4.30 (6H, m, NCH$_2$, H-1, H-2, H-3, H-4), 5.57-5.67 (2H, m, H-6, OH), 6.80-7.78 (16H, m, Ar), 8.48-8.60 (2H, m, αPyr); $v_{max}$ (NaCl)/cm$^{-1}$ 1176 and 1236 (C—O ester), 1586 (C=O imide), 1706 (C=O acid), 3394 (OH acid); m/z (FAB+) 570 (MH$^+$, 70), 552 (MH$^+$-H$_2$O, 100); (Found: MH$^+$ 570.2027, C$_{35}$H$_{28}$N$_3$O$_5$ requires 570.2029).

5-(α-Hydroxy-α-2-pyridylbenzyl)-N-pivaloyloxymethyl-7-(α-2-pyridylbenzylidene)-5-norbornene-2,3-dicarboximide (8)

A similar procedure (Hursthouse, M. B.; Khan, A.; Marson, C. M.; Porter, R. A. *Tetrahedron Lett* 1995, 36, 33, 5979-5982) to that described for the preparation of 207 was followed using NRB (200 mg, 0.39 mmol) in dimethylformamide (2 mL), chloromethyl pivalate (41) (59 mg, 0.39 mmol) in dimethylformamide (0.5 mL), and potassium carbonate (54 mg, 0.39 mmol). Purification by flash chromatography (hexane/ethyl acetate 1:1) afforded 8 as a colourless solid (118 mg, 0.19 mmol, 48%). mp 95-98° C.; $^1$H NMR (400 MHz, CDCl$_3$) δ 1.18-1.19 (8.4H, m, tBu), 1.25-1.26 (0.6H, m, tBu), 3.38 (0.2H, dd, J=7.9 and 4.5 Hz, W/H-3), 3.45 (0.5H, dd, J=7.9 and 4.5 Hz, Y/H-3), 3.51-3.59 (0.4H, m, 0.2H U/H-2 and U/H-3, 0.2H V/H-2), 3.63-3.64 (0.2H, m, W/H-4), 3.67-3.76 (0.9H, m, 0.2H V/H-3, 0.2H W/H-2 and 0.5H Y/H-2), 3.88-3.92 (0.3H, m, 0.1H U/H-1 and 0.2H V/H-1), 4.00-4.01 (0.5H, dt, J=4.5 and 1.3 Hz, Y/H-4), 4.20-4.21

(0.1H, m, U/H-4), 4.35-4.36 (0.2H, dt, J=4.5 and 1.3 Hz, V/H-4), 4.49-4.52 (0.7H, m, 0.2H W/H-1 and 0.5H Y/H-1), 5.26-5.29 (0.7H, m, CH$_2$), 5.31-5.62 (3H, m, 1.3H CH$_2$, 0.2H V/H-6, 0.5H Y/H-6 and 1H OH), 6.04-6.06 (0.3H, m, 0.1H U/H-6 and 0.2H W/H-6), 6.71-7.57 (16H, m, Ar), 8.42-8.50 (0.6H, m, 0.2H 2U/αPyr and 0.4H 2VαPyr), 8.54-8.55 (0.7H, m, 0.2H W/αPyr and 0.5H Y/αPyr), 8.61-8.63 (0.7H, m, 0.2H W/αPyr and 0.5H Y/αPyr); ν$_{max}$(nujol)/cm$^{-1}$ 1140 and 1212 (C—O ester), 1586 (C=O imide), 1715 (C=O ester); m/z (FAB+) 626 (MH$^+$, 67%), 120 (100); (Found: MH$^+$ 626.2644, C$_{39}$H$_{36}$N$_3$O$_5$ requires 626.2655).

N-Butanoyloxymethyl-5-(α-hydroxy-α-2-pyridyl-benzyl)-7-(α-2-pyridylbenzylidene)-5-norbornene-2,3-dicarboximide (9)

Compound 9 was prepared by a procedure similar to that of Hursthouse and co-workers (Hursthouse, M. B. et al. *Tetrahedron Lett.* 1995, 36, 5979-5982), and Binderup and co-workers (Binderup, E. et al. *Synth. Commun.* 1984, 14, 857-864). To a mixture of butyric acid (426 uL, 4.6 mmol), water (5 mL), dichloromethane (5 mL), sodium hydrogen carbonate (1.46 g, 17.5 mmol) and tetrabutylammonium bromide (148 mg, 0.46 mmol) was added dropwise chloromethyl chlorosulfate (0.53 mL, 5.28 mmol) in dichloromethane (1.5 mL). The reaction was stirred at room temperature for 16 h and the organic layer separated, dried over anhydrous sodium sulfate and the solvent removed in vacuo. The crude chloromethyl butanoate was taken up in dimethylformamide (1 mL) and added to a solution of NRB (500 mg, 0.98 mmol) in dimethylformamide (2 mL), followed by potassium carbonate (135 mg, 0.98 mmol). The mixture was stirred at room temperature for 16 h, taken up in dichloromethane/water (1:1) (30 mL), washed with water (2×20 mL), dried over anhydrous magnesium sulfate and the solvent removed in vacuo. Purification by flash chromatography (hexane/ethyl acetate 1:1) afforded 9 as a colourless solid (375 mg, 0.61 mmol, 62%). mp 68-79° C.; $^1$H NMR (300 MHz, CDCl$_3$) δ 0.89-0.96 (3H, m, Me), 1.55-1.71 (2H, m, OCOCH$_2$CH$_2$), 2.25-2.35 (2H, m, OCOCH$_2$CH$_2$), 3.37-3.74 (2.2H, m, 0.2H U/H-2 and U/H-3, 0.6H V/H-2 and V/H-3, 0.6H W/H-2, W/H-3 and W/H-4, 0.8H Y/H-2 and Y/H-3), 3.86-3.93 (0.4H, m, 0.1H U/H-1 and 0.3H V/H-1), 3.96-4.02 (0.4H, m, Y/H-4), 4.19-4.24 (0.1H, m, U/H-1), 4.37-4.43 (0.3H, m, V/H-4), 4.50-4.59 (0.6H, m, 0.2H W/H-1 and 0.4H Y/H-1), 5.30-5.35 (0.7H, m, 0.3H V/H-6 and 0.4H Y/H-6), 5.44-5.64 (3H, m, 2H NCH$_2$O and 1H OH), 6.03-6.08 (0.3H, m, 0.1H U/H-6 and 0.2H W/H-6), 6.75-7.58 (16H, m, Ar), 8.37-8.44 (0.8H, m, 0.2H 2U/αPyr and 0.6H 2VαPyr), 8.49-8.51 (0.6H, m, 0.2H W/αPyr and 0.4H Y/αPyr), 8.58-8.63 (0.6H, m, 0.2H-1 W/αPyr and 0.4H Y/αPyr); ν$_{max}$/cm$^{-1}$ 1041 and 1208 (C—O ester), 1585 (C=O imide), 1713 (C=O ester); m/z (ESI) 612 (MH$^+$, 100%); (Found: MH$^+$ 612.2489, C$_{38}$H$_{34}$N$_3$O$_5$ requires 612.2493).

5-(α-Hydroxy-α-2-pyridylbenzyl)-N-octanoyloxymethyl-7-(α-2-pyridylbenzylidene)-5-norbornene-2,3-dicarboximide (10)

A similar procedure (Hursthouse, M. B. et al. *Tetrahedron Lett.* 1995, 36, 5979-5982) to that described for the preparation of 8 was followed using NRB (5.88 g, 11.46 mmol) in dimethylformamide (100 mL), chloromethyl octanoate (43) (5.90 g, 20.5 mmol) in dimethylformamide (25 mL), cesium carbonate (4.48 g, 13.75 mmol) and tetra-n-butylammonium iodide (0.42 g, 1.15 mmol), at room temperature for 16 h. Purification by flash chromatography (hexane/ethyl acetate 2:1) afforded 10 as a pale yellow solid (7.0 g, 10.48 mmol, 91%). $^1$H NMR (300 MHz, CDCl$_3$) δ 0.85-0.89 (3H, m, (CH$_2$)$_6$CH$_3$), 1.21-1.28 (8H, m, (CH$_2$)$_4$CH$_3$), 1.55-1.69 (2H, m, CH$_2$CH$_2$(CH$_2$)$_4$CH$_3$), 2.29-2.37 (2H, m, CH$_2$(CH$_2$)$_5$CH$_3$), 3.36-3.74 (2.2H, m, H-2, H-3, W/H-4), 3.86-3.91 (0.4H, m, U/H-1, V/H-1), 3.97-4.00 (0.4H, m, Y/H-4), 4.20-4.22 (0.1H, m, U/H-4), 4.36-4.39 (0.3H, m, V/H-4), 4.50-4.54 (0.6H, m, W/H-1, Y/H-1), 5.28-5.60 (2.7H, m, NCH$_2$O, V/H-6, Y/H-6), 6.03 (0.2H, m, W/H-6), 6.07 (0.1H, m, U/H-6), 6.74-7.58 (16H, m, Ar), 8.40-8.63 (2H, m, αPyr), ν$_{max}$/cm$^{-1}$ 1040 and 1214 (C—O ester), 1585 (C=O imide), 1712 (C=O ester); m/z (ESI) 668 (MH$^+$, 1%), 650 (MH$^+$-H$_2$O, 100%); (Found: MH$^+$ 668.3123, C$_{42}$H$_{42}$N$_3$O$_5$ requires 668.3119).

Alternatively, a similar procedure (Hursthouse, M. B. et al. *Tetrahedron Lett.* 1995, 36, 5979-5982) to that described for the preparation of 8 was followed using NRB (500 mg, 0.98 mmol) in dimethylformamide (2 mL), chloromethyl octanoate (43) (377 mg, 1.96 mmol) in dimethylformamide (0.5 mL) and potassium carbonate (135 mg, 0.98 mmol), at room temperature for 16 h. Purification by flash chromatography (hexane/ethyl acetate 2:1) afforded 10 as an oily residue (367 mg, 0.55 mmol, 56%).

N-Dodecanoyloxymethyl-5-(α-hydroxy-α-2-pyridyl-benzyl)-7-(α-2-pyridylbenzylidene)-5-norbornene-2,3-dicarboximide (11)

A similar procedure (Hursthouse, M. B. et al. *Tetrahedron Lett.* 1995, 36, 5979-5982) to that described for the preparation of 8 was followed using NRB (500 mg, 0.98 mmol) in dimethylformamide (2 mL), chloromethyl dodecanoate (44) (488 mg, 1.96 mmol) in dimethylformamide (0.5 mL) and potassium carbonate (135 mg, 0.98 mmol), at room temperature for 16 h. Purification by flash chromatography (hexane/ethyl acetate 2:1) afforded 11 as a colourless oil (231 mg, 0.32 mmol, 32%). $^1$H NMR (300 MHz, CDCl$_3$) δ 0.85-0.89 (3H, m, Me), 1.20-1.36 (16H, m, OCO(CH$_2$)$_2$(CH$_2$)$_8$), 1.55-1.68 (2H, m, OCOCH$_2$CH$_2$), 2.29-2.36 (2H, m, OCOCH$_2$), 3.36 (0.2H, dd, J=9.0 and 3.0 Hz, W/H-3), 3.42 (0.4H, dd, J=9.0 and 3.0 Hz, Y/H-3), 3.48-3.74 (1.6H, m, 0.2H U/H-2 and U/H-3, 0.6H V/H-2 and V/H-3, 0.4H W/H-2 and W/H-4, 0.4H Y/H-2), 3.86-3.92 (0.4H, m, 0.1H U/H-1 and 0.3H V/H-1), 3.98-3.99 (0.4H, m, Y/H-4), 4.20-4.21 (0.1H, m, U/H-4), 4.37-4.38 (0.3H, m, V/H-4), 4.51-4.54 (0.6H, m, 0.2H W/H-1 and 0.4H Y/H-1), 5.29-5.33 (0.7H, m, NCH$_2$O), 5.43-5.60 (3H, m, 1.3H NCH$_2$O, 0.3H V/H-6, 0.4H Y/H-6 and 1H OH), 6.03-6.07 (0.3H, m, 0.1H U/H-6 and 0.2H W/H-6), 6.75-7.58 (16H, m, Ar), 8.39-8.46 (0.7H, m, 0.1H U/αPyr and 0.6H 2VαPyr), 8.51-8.52 (0.7H, m, 0.1H U/αPyr, 0.2H W/αPyr and 0.4H Y/αPyr), 8.60-8.61 (0.6H, m, 0.2H W/αPyr and 0.4H Y/αPyr); ν$_{max}$/cm$^{-1}$ 1041 and 1209 (C—O ester), 1585 (C=O imide), 1715 (C=O ester); m/z (ESI) 724 (MH$^+$, 1%), 706 (MH$^+$-H$_2$O, 100); (Found: MH$^+$ 724.3747, C$_{46}$H$_{50}$N$_3$O$_5$ requires 724.3745).

N-Benzoyloxymethyl-5-(α-hydroxy-α-2-pyridylbenzyl)-7-(α-2-pyridylbenzylidene)-5-norbornene-2,3-dicarboximide (12)

A similar procedure (Hursthouse, M. B. et al. *Tetrahedron Lett.* 1995, 36, 5979-5982) to that described for the preparation of 8 was followed using NRB (200 mg, 0.39 mmol) in dimethylformamide (2 mL), chloromethyl benzoate (45) (66 mg, 0.39 mmol) in dimethylformamide (0.5 mL) and potassium carbonate (54 mg, 0.39 mmol), at room temperature for 16 h. Purification by flash chromatography (hexane/ethyl acetate 1:1) afforded 12 as a colourless solid (180 mg, 0.28 mmol, 71%). mp 94-96, 105-108° C.; $^1$H NMR (400 MHz, CDCl$_3$) δ 3.41-3.44 (0.2H, dd, J=8.0 and 4.4 Hz, W/H-3), 3.48-3.52 (0.4H, dd, J=7.9 and 4.6 Hz, Y/H-3), 3.54-3.63 (0.5H, m, 0.2H U/H-2 and U/H-3 and 0.3H V/H-2), 3.65-3.67 (0.2H, m, W/H-2), 3.70-3.79 (0.9H, m, 0.3H V/H-3, 0.3H W/H-2 and 0.4H Y/H-2), 3.91-3.95 (0.4H, m, 0.1H U/H-1 and 0.3H V/H-1), 4.02-4.03 (0.4H, m, Y/H-4), 4.23-4.24 (0.1H, m, U/H-4), 4.39-4.40 (0.3H, m, V/H-4), 4.54-4.56 (0.6H, m, 0.2H W/H-1 and 0.4H Y/H-1), 5.53-5.58 (1.9H, m, 0.3H V/H-6, 0.4H Y/H-6 and 1.2H CH$_2$), 5.64 (0.3H, s, OH), 5.65 (0.2H, s, OH), 5.68-5.75 (0.6H, m, CH$_2$ and OH), 5.82-5.86 (0.7H, m, CH$_2$ and OH), 6.11-6.12 (0.3H, m, 0.1H U/H-6 and 0.2H W/H-6), 6.74-7.59 (19.2H, m, Ar), 8.01-8.03 (1.8H, m, OCOPh), 8.40-8.50 (1.4H, m, 0.2H 2U/αPyr, 0.6H 2V/αPyr, 0.2H W/αPyr and 0.4H Y/αPyr), 8.61-8.62 (0.6H, m, 0.2H W/αPyr and 0.4H Y/αPyr); ν$_{max}$(NaCl)/cm$^{-1}$ 1092 and 1265 (C—O ester), 1585 (C=O imide), 1720 (C=O ester); m/z (FAB+) 646 (MH$^+$, 8%), 120 (100); (Found: MH$^+$ 646.2349, C$_{41}$H$_{32}$N$_3$O$_5$ requires 646.2342).

5-(α-Hydroxy-α-2-pyridylbenzyl)-N-o-methoxybenzoyloxymethyl-7-(α-2-pyridylbenzylidene)-5-norbornene-2,3-dicarboximide (13)

A similar procedure (Hursthouse, M. B. et al. *Tetrahedron Lett.* 1995, 36, 5979-5982) to that described for the preparation of 8 was followed using NRB (500 mg, 0.98 mmol) in dimethylformamide (2 mL), chloromethyl o-methoxybenzoate (46) (393 mg, 1.96 mmol) in dimethylformamide (1 mL) and potassium carbonate (135 mg, 0.98 mmol), at room temperature for 16 h. Purification by flash chromatography (hexane/ethyl acetate 1:1) afforded 13 as a colourless solid (432 mg, 0.64 mmol, 65%). mp 83-88° C.; $^1$H NMR (300 MHz, CDCl$_3$) δ 3.39-3.43 (0.2H, m, W/H-3), 3.45-3.49 (0.5H, m, Y/H-3), 3.53 (0.3H, dd, J=9.0 and 6.0 Hz, V/H-2), 3.64-3.77 (1H, m, 0.3H V/H-3, 0.2H W/H-2 and 0.5H Y/H-2), 3.80 and 3.83 (3H, s, OMe), 3.90-3.94 (0.3H, m, V/H-1), 4.00-4.05 (0.5H, m, Y/H-4), 4.37-4.42 (0.3H, m, V/H-4), 4.50-4.57 (0.7H, m, 0.2H W/H-1 and 0.5H Y/H-1), 5.49-5.57 (2.3H, m, 2H CH$_2$, 0.3H V/H-6 or OH), 5.65-5.68, 5.79-5.84 (1.5H, m, 0.3H V/H-6 or OH, 0.5H Y/H-6 and 0.7H OH), 6.08-6.09 (0.2H, m, W/H-6), 6.72-7.78 (20H, m, Ar), 8.37-8.43 (1.3H, m, 0.6H 2V/αPyr, 0.2H W/αPyr and 0.5H Y/αPyr), 8.58-8.60 (0.7H, m, 0.2H W/αPyr and 0.5H Y/αPyr); ν$_{max}$/cm$^{-1}$ 1124 and 1235 (C—O ester), 1584 (C=O imide), 1713 (C=O ester); m/z (ESI) 676 (MH$^+$, 10%), 658 (MH$^+$-H$_2$O, 100); (Found: MH$^+$ 676.2448, C$_{42}$H$_{34}$N$_3$O$_6$ requires 676.2442).

5-(α-Hydroxy-α-2-pyridylbenzyl)-N-m-methoxybenzoyloxymethyl-7-(α-2-pyridylbenzylidene)-5-norbornene-2,3-dicarboximide (14)

A similar procedure (Hursthouse, M. B. et al. *Tetrahedron Lett.* 1995, 36, 5979-5982) to that described for the preparation of 8 was followed using NRB (500 mg, 0.98 mmol) in dimethylformamide (2 mL), chloromethyl m-methoxybenzoate (47) (393 mg, 1.96 mmol) in dimethylformamide (1 mL) and potassium carbonate (135 mg, 0.98 mmol, at room temperature for 16 h. Purification by flash chromatography (hexane/ethyl acetate 1:1) afforded 14 as a colourless solid (224 mg, 0.33 mmol, 34%). mp 171-180° C.; $^1$H NMR (300 MHz, CDCl$_3$) δ 3.40 (0.2H, dd, J=7.5 and 4.5 Hz, W/H-3), 3.47 (0.5H, dd, J=9.0 and 6.0 Hz, Y/H-3), 3.56 (0.3H, dd, J=7.5 and 4.5 Hz, V/H-2), 3.65-3.66 (0.2H, m, W/H-4), 3.70-3.79 (4H, m, 3H OMe, 0.3H V/H-3, 0.2H W/H-2 and 0.5H Y/H-2), 3.91-3.94 (0.3H, m, V/H-1), 4.00-4.03 (0.5H, m, Y/H-4), 4.41-4.42 (0.3H, m, V/H-4), 4.54-4.56 (0.7H, m, 0.2H W/H-1 and 0.5H Y/H-1), 5.54-5.76 and 5.82-5.87 (3.8H, m, 2H CH$_2$, 0.3H V/H-6, 0.5H Y/H-6 and 1H OH), 6.11-6.13 (0.2H, m, W/H-6), 6.75-7.62 (20H, m, Ar), 8.41-8.48 (1.3H, m, 0.6H 2V/αPyr, 0.2H W/αPyr and 0.5H Y/αPyr), 8.59-8.61 (0.7H, m, 0.2H W/αPyr and 0.5H Y/αPyr); ν$_{max}$/cm$^{-1}$ 1040 and 1218 (C—O ester), 1586 (C=O imide), 1712 (C=O ester); m/z (ESI) 676 (MH$^+$, 3%), 658 (MH$^+$-H$_2$O, 100); (Found: MH$^+$ 676.2452, C$_{42}$H$_{34}$N$_3$O$_6$ requires 676.2442).

5-(α-Hydroxy-α-2-pyridylbenzyl)-N-p-methoxybenzoyloxymethyl-7-(α-2-pyridylbenzylidene)-5-norbornene-2,3-dicarboximide (15)

A similar procedure (Hursthouse, M. B. et al. *Tetrahedron Lett.* 1995, 36, 5979-5982) to that described for the preparation of 8 was followed using NRB (200 mg, 0.39 mmol) in dimethylformamide (1 mL), chloromethyl p-methoxybenzoate (48) (157 mg, 0.78 mmol) in dimethylformamide (0.5 mL) and potassium carbonate (54 mg, 0.39 mmol), at room temperature for 16 h. Purification by flash chromatography (hexane/ethyl acetate 1:1) afforded 15 as a colourless solid (172 mg, 0.25 mmol, 65%). mp 94-112° C.; $^1$H NMR (400 MHz, CDCl$_3$) δ 1.40 (0.2H, dd, J=8.0 and 4.4 Hz, W/H-3), 3.47 (0.4H, dd, J=8.0 and 4.8 Hz, Y/H-3), 3.53-3.62 (0.5H, m, 0.2H U/H-2 and U/H-3, 0.3H V/H-2), 3.65-3.67 (0.2H, m, W/H-4), 3.68-3.78 (0.9H, m, 0.3H V/H-3, 0.2H W/H-2 and 0.4H Y/H-2), 3.84 and 3.85 (3H, s, OMe), 3.91-3.95 (0.4H, m, 0.1H U/H-1 and 0.3H V/H-1), 4.00-4.04 (0.4H, m, Y/H-4), 4.22-4.24 (0.1H, m, U/H-4), 4.34-4.40 (0.3H, m, V/H-4), 4.51-4.56 (0.6H, m, 0.2H W/H-1 and 0.4H Y/H-1), 5.51-5.54, 5.59-5.60, 5.64-5.70 and 5.78-5.81 (3.7H, m, 2H CH$_2$, 0.3H V/H-6, 0.4H Y/H-6 and 10H), 6.10-6.12 (0.3H, m, 0.1H U/H-6 and 0.2H W/H-6), 6.71-7.61 and 7.95-8.02 (20H, m, Ar), 8.41-8.54 (1.4H, m, 0.2H 2U/αPyr, 0.6H 2V/αPyr, 0.2H W/αPyr and 0.4H Y/αPyr), 8.61-8.65 (0.6H, m, 0.2H W/αPyr and 0.4H Y/αPyr); ν$_{max}$/cm$^1$ 1079 and 1251 (C—O ester), 1584 (C=O imide), 1712 (C=O ester); m/z (ESI) 676 (MH$^+$, 1%), 658 (MH$^+$-H$_2$O, 100); (Found: MH$^+$ 676.2434, C$_{42}$H$_{34}$N$_3$O$_6$ requires 676.2442).

5-(α-Hydroxy-α-2-pyridylbenzyl)-N-phenylacetyloxymethyl-7-(α-2-pyridylbenzylidene)-5-norbornene-2,3-dicarboximide (16)

A similar procedure (Hursthouse, M. B. et al. *Tetrahedron Lett.* 1995, 36, 5979-5982) to that described for the preparation of 8 was followed using NRB (2.78 g, 5.43 mmol) in dimethylformamide (20 mL), chloromethyl phenylacetate (49) (1.20 g, 6.52 mmol) in dimethylformamide (7.5 mL) and cesium carbonate (2.12 g, 6.52 mmol), at room temperature for 16 h. Purification by flash chromatography (hexane/ethyl acetate 2:1) afforded 16 as a pale yellow solid (2.10 g, 3.18 mmol, 59%). mp 71-78° C.; $^1$H NMR (300 MHz, CDCl$_3$) δ 3.35-3.71 (4.2H, m, CH$_2$Ph, H-2, H-3, W/H-4), 3.87-3.94 (0.4H, m, U/H-1, V/H-1), 4.00 (0.4H, m, Y/H-4), 4.11 (0.1H, m, U/H-4), 4.28 (0.3H, m, V/H-4), 4.43-4.46 (0.6H, m, W/H-1, Y/H-1), 5.30-5.62 (3.7H, m, NCH$_2$O, V/H-6, Y/H-6, OH), 6.04 (0.1H, m, U/H-6), 6.07 (0.2H, m, W/H-6), 6.74-7.59 (21H, m, Ar), 8.46-8.65 (2H, m, αPyr); ν$_{max}$/cm$^{-1}$ 1138 and 1211 (C—O ester), 1585 (C=O imide), 1714 (C=O ester); m/z (FAB+) 660 (100%); (Found: MH$^+$ 660.2501, C$_{42}$H$_{34}$N$_3$O$_5$ requires 660.2498).

Alternatively, a similar procedure (Hursthouse, M. B. et al. *Tetrahedron Lett.* 1995, 36, 5979-5982) to that described for the preparation of 8 was followed using NRB (200 mg, 0.39 mmol) in dimethylformamide (2 mL), chloromethyl phenylacetate (49) (144 mg, 0.78 mmol) in dimethylformamide (0.4 mL) and potassium carbonate (54 mg, 0.39 mmol), at room temperature for 16 h. Purification by flash chromatography (hexane/ethyl acetate 1:2) afforded 16 as a colourless solid (50 mg, 0.08 mmol, 19%).

5-(α-Hydroxy-α-2-pyridylbenzyl)-N-4-methylphenylacetoyloxymethyl-7-(α-2-pyridylbenzylidene)-5-norbornene-2,3-dicarboximide (324)

A similar procedure (Hursthouse, M. B. et al. *Tetrahedron Lett.* 1995, 36, 5979-5982) to that described for the preparation of 8 was followed using NRB (2.29 g, 4.48 mmol) in dimethylformamide (20 mL), chloromethyl p-methylphenylacetate (322) (1.0 g, 5.38 mmol) in dimethylformamide (7.5 mL) and cesium carbonate (1.75 g, 6.52 mmol), at room temperature for 16 h. Purification by flash chromatography (hexane/ethyl acetate 4:1) afforded 324 as a white solid (2.01 g, 2.98 mmol, 67%). mp 80-85° C.; $^1$H NMR (300 MHz, CDCl$_3$) δ 3.35-3.73 (7.2H, m, CH$_2$Ph, Me, H-2, H-3, W/H-4), 3.88-3.91 (0.4H, m, U/H-1, V/H-1), 3.99 (0.4H, m, Y/H-4), 4.19 (0.1H, m, U/H-4), 4.35 (0.3H, m, V/H-4), 4.49-4.53 (0.6H, m, W/H-1, Y/H-1), 5.30-5.61 (3.7H, m, NCH$_2$O, V/H-6, Y/H-6, OH), 6.04 (0.1H, m, U/H-6), 6.07 (0.2H, m, W/H-6), 6.74-7.58 (20H, m, Ar), 8.42-8.64 (2H, m, αPyr); $v_{max}$(NaCl)/cm$^{-1}$ 1127, 1214 (C—O ester), 1585 (C═O imide), 1714 (C═O ester); m/z (ESI, 70 eV) 696 (MNa$^+$, 100%); (Found MNa$^+$ 696.2469), C$_{43}$H$_{35}$N$_3$NaO$_5$ requires 696.2472.

N-Diphenylacetyloxymethyl-5-(α-hydroxy-α-2-pyridylbenzyl)-7-(α-2-pyridylbenzylidene)-5-norbornene-2,3-dicarboximide (17)

A similar procedure (Hursthouse, M. B. et al. *Tetrahedron Lett.* 1995, 36, 5979-5982) to that described for the preparation of 8 was followed using NRB (200 mg, 0.39 mmol) in dimethylformamide (2 mL), chloromethyl diphenylacetate (50) (102 mg, 0.39 mmol) in dimethylformamide (0.5 mL) and potassium carbonate (54 mg, 0.39 mmol), at room temperature for 16 h. Purification by flash chromatography (hexane/ethyl acetate 2:1) afforded 17 as a colourless solid (42 mg, 0.06 mmol, 15%). mp 113-115° C.; $^1$H NMR (400 MHz, CDCl$_3$) δ 3.35 (0.7H, dd, J=7.9 and 4.6 Hz, Y/H-3), 3.41 (0.3H, dd, J=7.9 and 4.9 Hz, V/H-2), 3.58-3.67 (1H, m, V/H-3 and Y/H-2), 3.86-3.89 (0.3H, m, V/H-1), 3.96 (0.7H, dt, J=4.6 and 1.4 Hz, Y/H-4), 4.29 (0.3H, dt, J=4.5 and 1.5 Hz, V/H-4), 4.45-4.48 (0.7H, m, Y/H-1), 5.05 (0.7H, s, Y/CHPh$_2$), 5.06 (0.3H, s, V/CHPh$_2$), 5.36 (0.5H, s, H$_a$/CH$_2$), 5.39 (0.5H, s, H$_b$/CH$_2$), 5.46-5.49 (2H, m, 0.6H V/H-6 and V/OH, 1.4H Y/H-6 and Y/OH), 5.64-5.66 (1H, m, CH$_2$), 6.70-7.58 (26H, m, Ar), 8.47-8.50 (1.3H, m, 0.6H 2V/αPyr and 0.7H Y/αPyr), 8.62-8.63 (0.7H, m, Y/αPyr); $v_{max}$(NaCl)/cm$^{-1}$ 1139 and 1215 (C—O ester), 1585 (C═O imide), 1715 (C═O ester); m/z (ESI+) 736 (MH$^+$, 27%), 120 (100); (Found: MH$^+$ 736.2814, C$_{48}$H$_{38}$N$_3$O$_5$ requires 736.2811).

N-Dihydrocinnamoyloxymethyl-5-(α-hydroxy-α-2-pyridylbenzyl)-7-(α-2-pyridylbenzylidene)-5-norbornene-2,3-dicarboximide (18)

Compound 18 was prepared by a procedure similar to that of Hursthouse and co-workers (Hursthouse, M. B. et al. *Tetrahedron Lett.* 1995, 36, 5979-5982), and Bodor and co-workers (Bodor, N. et al. *J. Org. Chem.* 1983, 48, 5280-5284). To a solution of chloromethyl dihydrocinnamate (51) (155 mg, 0.78 mmol) in acetone (1.5 mL) was added sodium iodide (117 mg, 0.78 mmol), and the mixture stirred at room temperature for 3 h. The solvent was removed in vacuo and the crude iodomethyl dihydrocinnamate was taken through to the next step without further purification. A solution of NRB (200 mg, 0.39 mmol), iodomethyl dihydrocinnamate and potassium carbonate (54 mg, 0.39 mmol) in dimethylformamide (1.5 mL) was stirred at room temperature for 16 h. The mixture was then taken up in chloroform (15 mL), washed with water (2×10 mL), dried over anhydrous magnesium sulfate and the solvent removed in vacuo. Purification by flash chromatography (hexane/ethyl acetate 1:2) afforded 18 as a colourless solid (15 mg, 0.02 mmol, 6%). mp 89-94° C.; $^1$H NMR (300 MHz, CDCl$_3$) δ 2.66-2.71 (2H, m, OCOCH$_2$), 2.94-2.99 (2H, m, CH$_2$Ph), 3.36-3.40 (0.2H, m, W/H-3), 3.42-3.47 (0.3H, m, Y/H-3), 3.52-3.56 (0.7H, m, 0.4H U/H-2 and U/H-3, 0.3H V/H-2), 3.62-3.74 (1H, m, 0.3H V/H-3, 0.4H W/H-2 and W/H-4, 0.3H Y/H-2), 3.85-3.94 (0.5H, m, 0.2H U/H-1 and 0.3H V/H-1), 3.98-4.00 (0.3H, m, Y/H-4), 4.18-4.24 (0.2H, m, U/H-4), 4.35-4.40 (0.3H, m, V/H-4), 4.48-4.49 (0.5H, m, 0.2H W/H-1 and 0.3H Y/H-1), 5.29-5.33 (0.6H, m, 0.3H V/H-6 and 0.3H Y/H-6), 5.43-5.60 (3H, m, 2H NCH$_2$O and 1H OH), 6.03-6.07 (0.4H, m, 0.2H U/H-6 and 0.2H W/H-6), 6.74-7.63 (21H, m, Ar), 8.42-8.52 (1.5H, m, 0.4H 2U/αPyr, 0.4H 2V/αPyr, 0.2H W/αPyr and 0.3H Y/αPyr), 8.63-8.65 (0.5H, m, 0.2H W/αPyr and 0.3H Y/αPyr); $v_{max}$(NaCl)/cm$^{-1}$ 1141 and 1214 (C—O ester), 1582 (C═O imide), 1717 (C═O ester); m/z (ESI+) 674 (MH$^+$, 100%), 656 (MH$^+$-H$_2$O, 15); (Found: MH$^+$ 674.2649, C$_{43}$H$_{36}$N$_3$O$_5$ requires 674.2665).

N-Cinnamoyloxymethyl-5-(α-hydroxy-α-2-pyridylbenzyl)-7-(α-2-pyridylbenzylidene)-5-norbornene-2,3-dicarboximide (19)

Compound 19 was prepared by a procedure similar to that of Hursthouse and co-workers (Hursthouse, M. B. et al. *Tetrahedron Lett.* 1995, 36, 5979-5982), and Bodor and co-workers (Bodor, N. et al. *J. Org. Chem.* 1983, 48, 5280-5284). To a solution of NRB (9.5 g, 18.6 mmol) in dimethylformamide (75 mL) under nitrogen at 0° C. was cautiously added, batchwise, sodium hydride (0.82 g, 20.5 mmol, 60% w/w in mineral oil), and the mixture stirred at 0° C. for a further 0.5 h. A solution of iodomethyl cinnamate (5.9 g, 20.5 mmol) in dimethylformamide (25 mL) was then added slowly, and the mixture left to stir at room temperature overnight. The reaction was then diluted with ethyl acetate and washed with brine. The aqueous phase was further extracted with ethyl acetate and the combined organic phases washed with brine, dried over anhydrous magnesium sulfate and the solvent removed in vacuo. Purification by column chromatography (hexane/ethyl acetate 4:1) afforded 19 as a white solid (10.0 g, 14.9 mmol, 80%). mp 108-113° C.; $^1$H NMR (400 MHz, CDCl$_3$) δ 3.35-3.75 (2.2H, m, H-2, H-3, W/H-4), 3.90-3.94 (0.4H, m, U/H-1, V/H-1), 4.00 (0.4H, m, Y/H-4), 4.22 (0.1H, m, U/H-4), 4.37 (0.3H, m, V/H-4), 4.51-4.57 (0.6H, m, W/H-1, Y/H-1), 5.42-5.73 (2.7H, m, NCH$_2$O, V/H-6, Y/H-6), 6.07 (0.2H, m, W/H-6), 6.11 (0.1H, m, U/H-6), 6.40-6.50 (1H, m, OCOCH), 6.75-7.59 (21H, m, Ar), 7.70-7.75 (1H, m, CHPh), 8.48-8.64 (2H, m, αPyr); $v_{max}$/cm$^{-1}$ 1144 and 1202 (C—O ester), 1584 (C═O imide), 1712 (C═O ester); m/z (FAB+) 672 (MH$^+$, 100%); (Found: MH$^+$ 672.2486, C$_{43}$H$_{34}$N$_3$O$_5$ requires 672.2498).

Alternatively, a similar procedure (Hursthouse, M. B. et al. *Tetrahedron Lett.* 1995, 36, 5979-5982) to that described for the preparation of 8 was followed using NRB (174 mg, 0.34 mmol) in dimethylformamide (1.5 mL), chloromethyl cinnamate (52) (68 mg, 0.34 mmol) in dimethylformamide (0.5 mL) and potassium carbonate (47 mg, 0.34 mmol), at room temperature for 16 h. Purification by flash chromatography (hexane/ethyl acetate 4:1, then 1:1) afforded 19 as a colourless solid (28 mg, 0.04 mmol, 12%).

5-(α-Hydroxy-α-2-pyridylbenzyl)-2'-naphthoyloxymethyl-7-(α-2-pyridylbenzylidene)-5-norbornene-2,3-dicarboximide (20)

A similar procedure (Hursthouse, M. B. et al. *Tetrahedron Lett.* 1995, 36, 5979-5982) to that described for the preparation of 8 was followed using NRB (184 mg, 0.36 mmol) in dimethylformamide (1.5 mL), chloromethyl 2-naphthoate (53) (80 mg, 0.36 mmol) in dimethylformamide (0.5 mL) and potassium carbonate (47 mg, 0.34 mmol), at room temperature for 16 h. Purification by flash chromatography (hexane/ethyl acetate 4:1, then 1:1) afforded 20 as a colourless solid (80 mg, 0.11 mmol, 32%). mp 108-112° C.; $^1$H NMR (400 MHz, CDCl$_3$) δ 3.51 (0.8H, dd, J=7.9 and 4.5 Hz, Y/H-3), 3.60 (0.2H, dd, J=7.9 and 5.0 Hz, V/H-2), 3.74-3.81 (1H, m, 0.2H V/H-3 and 0.8H Y/H-2), 3.94-3.96 (0.2H, m, V/H-1), 4.03-4.04 (0.8H, m, Y/H-4), 4.39-4.40 (0.2H, m, V/H-4), 4.54-4.57 (0.8H, m, Y/H-1), 5.55-5.57 (1.8H, m, 0.2H V/H-6, 0.8H Y/H-6 and 0.8H OH), 5.61-5.63 (1.2H, m, CH$_2$ and OH), 5.87 (0.1H, s, H$_a$/CH$_2$), 5.88 (0.4H, s, H$_a$/CH$_2$), 5.89 (0.1H, s, H$_b$/CH$_2$), 5.90 (0.4H, s, H$_b$/CH$_2$), 6.73-7.61 (18H, m, Ar), 7.86-7.95 (3H, m, Ar), 8.02-8.05 (1H, m, Ar), 8.48-8.52 (1.2H, m, 0.4H 2V/αPyr and 0.8H Y/αPyr), 8.59-8.64 (1.8H, m, 0.8H Y/αPyr and 1H Ar); $v_{max}$/cm$^{-1}$ 1079 and 1263 (C—O ester), 1585 (C=O imide), 1712 (C=O ester); m/z (FAB+) 696 (MH$^+$, 9%), 120 (100); (Found: MH$^+$ 696.2504, C$_{45}$H$_{34}$N$_3$O$_5$ requires 696.2498).

5-(α-Hydroxy-α-2-pyridylbenzyl)-N-2'-pivaloyloxyethyl-7-(α-2-pyridylbenzylidene)-5-norbornene-2,3-dicarboximide (109)

Compound 9 was prepared by a procedure similar to that of Nagao and co-workers (Nagao, Y. et al. *Tetrahedron Lett.* 1988, 29, 6133-6136). A solution of 102 (78 mg, 0.14 mmol) and pivaloyl chloride (34 μL, 0.28 mmol) in pyridine (0.6 mL) was stirred at room temperature for 30 min. The solvent was removed in vacuo with purification by flash chromatography (chloroform/methanol 200:1) affording 109 as a colourless oil (66 mg, 0.1 mmol, 74%); $^1$H NMR (300 MHz, CDCl$_3$) δ 1.13 and 1.18 (9H, bs, tBu), 3.33-3.43 (0.6H, m, 0.2H W/H-3 and 0.4H Y/H-3), 3.45-3.54 (0.5H, m, 0.2H U/H-2 and U/H-3 and 0.3H V/H-2), 3.56-3.90 (3.5H, m, 2H NCH$_2$, 0.1H U/H-1, 0.6H V/H-1 and V/H-3, 0.4H W/H-1 and W/H-2, 0.4H Y/H-2), 3.94-3.96 (0.4H, m, Y/H-4), 4.13-4.31 (2.4H, m, 2H CH$_2$O, 0.1H U/H-4 and 0.3H V/H-4), 4.46-4.49 (0.6H, m, 0.2H W/H-1 and 0.4H Y/H-1), 5.50-5.57 (1.4H, m, 0.3H V/H-6, 0.4H Y/H-6 and 0.7H OH), 5.62 (0.3H, s, OH), 6.00-6.04 (0.3H, m, 0.1H U/H-6 and 0.2H W/H-6), 6.73-7.61 (16H, m, Ar), 8.40-8.50 (1.4H, m, 0.2H 2U/αPyr, 0.6H 2V/αPyr, 0.2H W/αPyr and 0.4H Y/αPyr), 8.62-8.63 (0.6H, m, 0.2H W/αPyr and 0.4H Y/αPyr); $v_{max}$(NaCl)/cm$^{-1}$ 1151 and 1183 (C—O ester), 1585 (C=O imide), 1704 (C=O ester); m/z (EI+) 639 (M$^+$, 2%), 57 (100); (Found: M$^+$ 639.2729, C$_{40}$H$_{37}$N$_3$O$_5$ requires 639.2733).

N-2'-Butanoyloxyethyl-5-(α-hydroxy-α-2-pyridylbenzyl)-7-(α-2-pyridylbenzylidene)-5-norbornene-2,3-dicarboximide (110)

Compound 110 was prepared by a procedure similar to that of Bartalucci and co-workers (Bartalucci, G.; Bianchini, R.; Catelani, G.; D'Andrea, F.; Guazzelli, L. *Eur. J. Org. Chem.* 2007, 588-595). To a solution of 102 (250 mg, 0.48 mmol) in dimethylformamide (1.5 mL) was added butyric acid (50 mg, 0.57 mmol), EDC (112 mg, 0.57 mmol) and 4-dimethylaminopyridine (cat.), and the mixture stirred at room temperature for 1 h. The solvent was removed in vacuo and the residue taken up in ethyl acetate (10 mL), washed with an aqueous solution of sodium hydrogen carbonate (5 mL), then brine (5 mL), dried over anhydrous sodium sulphate and the solvent removed in vacuo. Purification by flash chromatography (hexane/ethyl acetate 1:2) afforded 110 as a colourless solid (142 mg, 0.21 mmol, 47%). mp 125-130° C.; $^1$H NMR (300 MHz, CDCl$_3$) δ 0.87-0.94 (3H, m, Me), 1.53-1.67 (2H, m, CH$_2$Me), 2.11-2.25 (2H, m, CH$_2$CH$_2$Me), 3.33-3.43 (0.85H, m, 0.15H W/H-3 and 0.7H Y/H-3), 3.46-3.50 (0.15H, m, V/H-2), 3.55-3.89 (3.3H, m, 2H NCH$_2$, 0.3H V/H-1 and V/H-3, 0.3H W/H-2 and W/H-4, 0.7H Y/H-2), 3.93-3.95 (0.7H, m, Y/H-4), 4.16-4.35 (2.15H m, 2H CH$_2$O and 0.15H V/H-4), 4.46-4.49 (0.85H, m, 0.15H W/H-1 and 0.7H Y/H-1), 5.51-5.58 (1.7H, m, 0.3H V/H-6, 1.4H Y/H-6 and 0.85H OH), 5.65 (0.15H, s, OH), 6.04-6.05 (0.15H, m, W/H-6), 6.84-7.57 (16H, m, Ar), 8.47-8.48 (1.15H, m, 0.3H 2V/αPyr, 0.15H W/αPyr and 0.7H Y/αPyr), 8.61-8.62 (0.85, m, 0.15H W/αPyr and 0.7H Y/αPyr); $v_{max}$(NaCl)/cm$^{-1}$ 1167 and 1280 (C—O ester), 1584 (C=O imide), 1705 (C=O ester); m/z (EI+) 626 (MH$^+$, 26%), 538 (100); (Found: MH$^+$ 626.2647, C$_{39}$H$_{36}$N$_3$O$_5$ requires 626.2649).

5-(α-Hydroxy-α-2-pyridylbenzyl)-N-2'-octanoyloxyethyl-7-(α-2-pyridylbenzylidene)-5-norbornene-2,3-dicarboximide (111)

A similar procedure (Lu, M. C. et al. *J. Med. Chem.* 1987, 30, 273-278 and Nagao, Y. et al. *Tetrahedron Lett.* 1988, 29, 6133-6136) to that described for the preparation of 117 was followed using octanoic acid (4.43 g, 30.74 mmol) and thionyl chloride (20 mL), under reflux for 2 h. A solution of 102 (12.0 g, 21.55 mmol), triethylamine (4.6 mL, 33.3 mmol), dimethylaminopyridine (0.26 g, 2.16 mmol) and crude octanoyl chloride in dimethylformamide (150 mL) was then stirred at room temperature for 16 h. Purification by flash chromatography (hexane/ethyl acetate 2:1) afforded 111 as an off-white solid (9.92 g, 14.66 mmol, 68%). mp 60-65° C.; $^1$H NMR (300 MHz, CDCl$_3$) δ 0.84-0.88 (3H, m, (CH$_2$)$_6$CH$_3$), 1.24-1.29 (8H, m, (CH$_2$)$_4$CH$_3$), 1.55-1.60 (2H, m, CH$_2$CH$_2$(CH$_2$)$_4$CH$_3$), 2.12-2.26 (2H, m, CH$_2$(CH$_2$)$_5$CH$_3$), 3.33-3.85 (4.15H, NCH$_2$CH$_2$O, H-2, H-3, W/H-4), 3.86-3.89 (0.47H, m, U/H-1, V/H-1), 3.94 (0.38H, m, Y/H-4), 4.14 (0.13H, m, U/H-4), 4.21-4.32 (2.34H, m, NCH$_2$CH$_2$O, V/H-4), 4.43-4.53 (0.53H, m, W/H-1, Y/H-1), 5.50 (0.34H, m, V/H-6), 5.53 (0.38H, m, Y/H-6), 5.55 (0.13, s, U/OH), 5.56 (0.15, s, W/OH), 5.57 (0.38, s, Y/OH), 5.63 (0.34H, s, V/OH), 6.01 (0.13H, m, U/H-6), 6.05 (0.15H, m, W/H-6), 6.75-7.56 (16H, m, Ar), 8.42-8.62 (2H, m, αPyr); $v_{max}$(NaCl)/cm$^{-1}$ 1185 and 1251 (C—O ester), 1583 (C=O imide), 1706 (C=O ester); m/z (ESI, 70 eV) 704 (MNa$^+$, 100%); (Found: MH$^+$ 682.3267, C$_{43}$H$_{44}$N$_3$O$_5$ requires 682.3275).

Alternatively, a similar procedure (Bartalucci, G.; Bianchini, R.; Catelani, G.; D'Andrea, F.; Guazzelli, L. *Eur. J. Org. Chem.* 2007, 588-595) to that described for the preparation of 110 was followed using 102 (250 mg, 0.48 mmol), octanoic acid (82 mg, 0.57 mmol), EDC (112 mg, 0.57 mmol) and 4-dimethylaminopyridine (cat.) in dimethylformamide (1.5 mL), at room temperature for 1 h. Purification by flash chromatography (hexane/ethyl acetate 2:1) afforded 111 as a colourless oil (230 mg, 0.34 mmol, 70%).

N-2'-Dodecanoyloxyethyl-5-(α-hydroxy-α-2-pyridylbenzyl)-7-(α-2-pyridylbenzylidene)-5-norbornene-2,3-dicarboximide (112)

A similar procedure (Lu, M. C. et al. *J. Med. Chem.* 1987, 30, 273-278 and Nagao, Y. et al. *Tetrahedron Lett.* 1988, 29, 6133-6136) to that described for the preparation of 117 was followed using dodecanoic acid (144 mg, 0.72 mmol) and thionyl chloride (0.6 mL), under reflux for 2 h. A solution of 102 (200 mg, 0.36 mmol) and crude dodecanoyl chloride in pyridine (2 mL) was then stirred at room temperature for 16 h. Purification by flash chromatography (hexane/ethyl acetate 2:1) afforded 112 as a colourless oily residue (124 mg, 0.17 mmol, 47%). $^1$H NMR (400 MHz, CDCl$_3$) δ 0.83-0.91 (3H, t, J=6.6 Hz, Me), 1.19-1.34 (16H, m, OCO(CH$_2$)$_2$(CH$_2$)$_8$), 1.52-1.64 (2H, m, OCOCH$_2$CH$_2$), 2.20-2.28 (2H, m, OCOCH$_2$), 3.33 (0.1H, dd, J=8.0 and 4.6 Hz, W/H-3), 3.39 (0.4H, dd, J=8.0 and 4.6 Hz, Y/H-3), 3.47 (0.5H, dd, J=7.8 and 5.0 Hz, V/H-2), 3.57-3.67 (2.1H, m, 1H NCH$_2$, 0.5H V/H-3, 0.2H W/H-4 and W/H-4, 0.4H Y/H-2), 3.76-3.84 (1H, m, NCH$_2$), 3.87-3.89 (0.5H, m, V/H-1), 3.93-3.94 (0.4H, m, Y/H-4), 4.13-4.26 (2H, m, CH$_2$O), 4.30-4.32 (0.5H, m, V/H-4), 4.47-4.50 (0.5H, m, 0.1H W/H-1 and 0.4H Y/H-1), 5.51 (0.5H, dd, J=3.3 and 1.2 Hz, V/H-6), 5.54 (0.4H, dd, J=3.4 and 1.2 Hz, Y/H-6), 5.59 (0.5H, s, OH), 5.65 (0.5H, s, OH), 6.04-6.06 (0.1H, m, W/H-6), 6.75-7.58 (16H, m, Ar), 8.43-8.49 (1.5H, m, 1H 2V/αPyr, 0.1H W/αPyr, 0.4H VαPyr), 8.61-8.64 (0.5H, m, 0.111 W/αPyr and 0.4H Y/αPyr); ν$_{max}$ (NaCl)/cm$^{-1}$ 1119 and 1188 (C—O ester), 1585 (C=O imide), 1705 (C=O ester); m/z (FAB+) 738 (MH$^+$, 100%); (Found: MH$^+$ 738.3909, C$_{47}$H$_{52}$N$_3$O$_5$ requires 738.3907).

N-2'-Benzoyloxyethyl-5-(α-hydroxy-α-2-pyridylbenzyl)-7-(α-2-pyridylbenzylidene)-5-norbornene-2,3-dicarboximide (113)

A similar procedure (Nagao, Y. et al. *Tetrahedron Lett.* 1988, 29, 6133-6136) to that described for the preparation of 109 was followed using 102 (100 mg, 0.18 mmol) and benzoyl chloride (42 μL, 0.36 mmol) in pyridine (0.78 mL), at room temperature for 1 h. Purification by flash chromatography (hexane/ethyl acetate 1:2) afforded 113 as a colourless solid (89 mg, 0.13 mmol, 75%). mp 74-78, 97-95° C.; $^1$H NMR (400 MHz, CDCl$_3$) δ 3.35 (0.1H, dd, J=7.9 and 4.5 Hz, W/H-3), 3.41 (0.4H, dd, J=7.9 and 4.5 Hz, Y/H-3), 3.49-3.69 (1.6H, m, 0.2H U/H-2 and U/H-3, 0.8H V/H-2 and V/H-3, 0.2H W/H-1 and W/H-4, 0.4H Y/H-2), 3.72-3.86 (1H, m, 0.5H CH$_2$O, 0.1H U/H-1 and 0.4H V/H-1), 3.89-4.01 (1.9H, m, 1.5H CH$_2$O and 0.4H Y/H-4), 4.13-4.14 (0.1H, m, U/H-4), 4.31-4.32 (0.4H, m, V/H-4), 4.37-4.57 (2.5H, m, 2H NCH$_2$, 0.1H W/H-1 and 0.4H Y/H-1), 5.55-5.59 (0.8H, m, 0.4H V/H-6 and 0.4H Y/H-6), 5.65 and 5.70 (1H, s, OH), 6.03-6.08 (0.2H, m, 0.1H U/H-6 and 0.1H W/H-6), 6.74-7.60 (19H, m, Ar), 7.90-8.03 (2H, m, OCOAr), 8.41-8.50 (1.5H, m, 0.8H 2V/αPyr, 0.2H 2U/αPyr, 0.1H W/αPyr and 0.4H Y/αPyr), 8.63-8.65 (0.5H, m, 0.1H W/αPyr and 0.4H Y/αPyr); ν$_{max}$ (NaCl)/cm$^{-1}$ 1122 and 1273 (C—O ester), 1585 (C=O imide), 1701 (C=O ester); m/z (FAB+) 660 (MH$^+$, 92%), 642 (100); (Found: MH$^+$ 660.2501, C$_{42}$H$_{34}$N$_3$O$_5$ requires 660.2498).

5-(α-Hydroxy-α-2-pyridylbenzyl)-N-2'-o-methoxybenzoyloxyethyl-7-(α-2-pyridylbenzylidene)-5-norbornene-2,3-dicarboximide (114)

A similar procedure (Nagao, Y. et al. *Tetrahedron Lett.* 1988, 29, 6133-6136) to that described for the preparation of 109 was followed using 102 (300 mg, 0.57 mmol) and o-anisoyl chloride (195 mg, 1.14 mmol) in pyridine (2 mL), at room temperature for 2 h. Purification by flash chromatography (hexane/ethyl acetate 1:2) afforded 114 as a colourless oil (314 mg, 0.46 mmol, 80%). $^1$H NMR (300 MHz, CDCl$_3$) δ 3.35 (0.15H, dd, J=7.9 and 4.5 Hz, W/H-3), 3.41 (0.6H, dd, J=7.9 and 4.5 Hz, Y/H-3), 3.45-3.56 (0.3H, m, 0.1H U/H-2 and U/H-3, 0.2H V/H-2), 3.59-3.80 (1.35H, m, 0.05H U/H-1, 0.4H V/H-1 and V/H-3, 0.3H W/H-2 and W/H-4, 0.6H Y/H-2), 3.83-4.00 (2.6H, m, 2H NCH$_2$ and 0.6H Y/H-4), 4.07 (3H, s, OMe), 4.10-4.16 (0.05H, m, UH-4), 4.27-4.28 (0.2H, m, V/H-4), 4.33-4.54 (2.65H, m, 2H CH$_2$O, 0.05H W/H-1 and 0.6H Y/H-1), 5.52-5.65 (1.8H, m, 0.2H V/H-6, 0.6H Y/H-6 and 1H OH), 5.99-6.04 (0.2H, m, 0.05H UH-6 and 0.15H W/H-6), 6.72-7.77 (19H, m, Ar), 8.17-8.20 (1H, m, Ar), 8.41-8.53 (1.25H, m, 0.1H 2U/αPyr, 0.4H 2V/αPyr, 0.15H W/αPyr and 0.6H Y/αPyr), 8.62-8.65 (0.75, m, 0.15H W/αPyr and 0.6H Y/αPyr); ν$_{max}$(NaCl)/cm$^{-1}$ 1164 and 1239 (C—O ester), 1584 (C=O imide), 1700 (C=O ester); m/z (EI+) 690 (MH$^+$, 22%), 135 (100); (Found: MH$^+$ 690.2592, C$_{43}$H$_{36}$N$_3$O$_6$ requires 690.2599).

5-(α-Hydroxy-α-2-pyridylbenzyl)-N-2'-m-methoxybenzoyloxyethyl-7-(α-2-pyridylbenzylidene)-5-norbornene-2,3-dicarboximide (115)

A similar procedure (Bartalucci, G.; Bianchini, R.; Catelani, G.; D'Andrea, F.; Guazzelli, L. *Eur. J. Org. Chem.* 2007, 588-595) to that described for the preparation of 110 was followed using 102 (300 mg, 0.57 mmol), m-anisic acid (105 mg, 0.68 mmol), EDC (133 mg, 0.68 mmol) and 4-dimethylaminopyridine (cat.) in dimethylformamide (2 mL), at room temperature for 16 h. Purification by flash chromatography (hexane/ethyl acetate 1:2) afforded 14 as a colourless solid (235 mg, 0.34 mmol, 60%). mp 151-161° C.; $^1$H NMR (300 MHz, CDCl$_3$) δ 3.34 (0.15H, dd, J=8.1 and 4.5 Hz, W/H-3), 3.40 (0.6H, dd, J=7.8 and 4.8 Hz, Y/H-3), 3.47-3.57 (0.3H, m, 0.1H U/H-2 and U/H-3, 0.2H V/H-2), 3.60-3.68 (1.15H, m, 0.05H U/H-1, 0.2H V/H-3, 0.3H W/H-2 and W/H-4, 0.6H Y/H-2), 3.71-4.00 (5.8H, m, 3H OMe, 2H NCH$_2$, 0.2H V/H-1 and 0.6H Y/H-4), 4.13-4.16 (0.05H, m, U/H-4), 4.30-4.54 (2.95, m, 2H CH$_2$O, 0.2H V/H-4, 0.15H W/H-1 and 0.6H Y/H-1), 5.56-5.78 (1.8H, m, 0.2H V/H-6, 0.6H Y/H-6 and 1H OH), 6.03-6.04 (0.05H, m, U/H-6), 6.07-6.08 (0.15H, m, W/H-6), 6.75-7.62 (20H, m, Ar), 8.37-8.47 (1.25H, m, 0.1H 2U/αPyr, 0.4H 2V/αPyr, 0.15H W/αPyr and 0.6H Y/αPyr), 8.62-8.63 (0.75, m, 0.15H W/αPyr and 0.6H Y/αPyr); ν$_{max}$(NaCl)/cm$^{-1}$ 1115 and 1255 (C—O ester), 1584 (C=O imide), 1705 (C=O ester); m/z (EI+) 690 (MH$^+$, 17%), 135 (100); (Found: MH$^+$ 690.2572, C$_{43}$H$_{36}$N$_3$O$_6$ requires 690.2599).

5-(α-Hydroxy-α-2-pyridylbenzyl)-N-2'-p-methoxybenzoyloxyethyl-7-(α-2-pyridylbenzylidene)-5-norbornene-2,3-dicarboximide (116)

A similar procedure (Nagao, Y. et al. *Tetrahedron Lett.* 1988, 29, 6133-6136) to that described for the preparation of 109 was followed using 102 (300 mg, 0.57 mmol) and p-anisoyl chloride (195 mg, 1.14 mmol) in pyridine (2 mL), at room temperature for 2 h. Purification by flash chromatography (hexane/ethyl acetate 1:2) afforded 15 as a colourless solid (223 mg, 0.32 mmol, 57%). mp 87-97° C.; $^1$H NMR (300 MHz, CDCl$_3$) δ 3.34 (0.15H, dd, J=7.9 and 4.5 Hz, W/H-3), 3.40 (0.6H, dd, J=7.9 and 4.5 Hz, Y/H-3), 3.46-3.53 (0.3H, m, 0.1H U/H-2 and UH-3, 0.2H V/H-2), 3.58-3.78 (1.35H, m, 0.05H U/H-1, 0.4H V/H-1 and V/H-3, 0.3H W/H-2 and W/H-4, 0.6H Y/H-2), 3.82 (3H, s, OMe), 3.86-3.99 (2.6H, m, 2H NCH$_2$ and 0.6H Y/H-4), 4.13-4.16 (0.05H, m, U/H-4), 4.30-4.55 (2.95, m, 2H CH$_2$O, 0.2H V/H-4, 0.15H W/H-1 and 0.6H Y/H-1), 5.54-5.55 (0.2H, m, V/H-6), 5.58-5.59 (0.6H, m, Y/H-6), 5.62, 5.64, 5.70 (1H, s, OH), 6.03-6.06 (0.2H, m, 0.05H U/H-6 and 0.15H W/H-6), 6.74-7.57, 7.84-7.93 (20H, m, Ar), 8.40-8.49 (1.25H, m, 0.1H 2U/αPyr, 0.4H 2V/αPyr, 0.15H W/αPyr and 0.6H Y/αPyr), 8.62-8.65 (0.75, m, 0.15H W/αPyr and 0.6H Y/αPyr); ν$_{max}$(NaCl)/cm$^{-1}$ 1168 and 1255 (C—O ester), 1584 (C=O imide), 1701 (C=O ester); m/z (EI+) 690 (MH$^+$, 18%), 135 (100); (Found: MH$^+$ 690.2568, C$_{43}$H$_{36}$N$_3$O$_6$ requires 690.2599).

5-(α-Hydroxy-α-2-pyridylbenzyl)-N-2'-phenylacetyloxyethyl-7-(α-2-pyridylbenzylidene)-5-norbornene-2,3-dicarboximide (117)

Compound 117 was prepared by a procedure similar to that of Lu and co-workers (Lu, M. C. et al. *J. Med. Chem.* 1987, 30, 273-278) and Nagao and co-workers (Nagao, Y. et al. *Tetrahedron Lett.* 1988, 29, 6133-6136). A solution of phenylacetic acid (49 mg, 0.35 mmol) in oxalyl chloride (1 mL) was heated under reflux for 3 h. The excess oxalyl chloride was removed in vacuo and the crude phenylacetyl chloride was taken through to the next step without further purification. A solution of 102 (200 mg, 0.36 mmol) and crude phenylacetyl chloride in pyridine (2 mL) was then stirred at room temperature for 16 h. The solvent was removed in vacuo with purification by flash chromatography (hexane/ethyl acetate 1:2) affording 117 as a colourless solid (8 mg, 0.01 mmol, 3%). mp 76-79, 82-88° C.; $^1$H NMR (300 MHz, CDCl$_3$) δ 3.34 (0.5H, dd, J=7.8 and 4.5 Hz, Y/H-3), 3.41 (0.5H, dd, J=8.0 and 5.0 Hz, V/H-2), 3.49-3.52 and 3.58-3.65 (4H, m, 2H CH$_2$Ph, 1H NCH$_2$, 0.5H V/H-3 and 0.5H Y/H-2), 3.77-3.88 (1.5H, m, 1H NCH$_2$ and 0.5H V/H-1), 3.92-3.94 (0.5H, m, Y/H-4), 4.21-4.25 (2H, t, J=5.4 Hz, CH$_2$O), 4.30-4.31 (0.5H, m, V/H-4), 4.45-4.48 (0.5H, m, Y/H-1), 5.48-5.49 (0.5H, m, V/H-6), 5.51 (0.5H, dd, J=3.3 and 1.2 Hz, Y/H-6), 5.57 (0.5H, s, OH), 5.62 (0.5H, s, OH), 6.73-7.60 (21H, m, Ar), 8.45-8.49 (1.5H, m, 1H 2V/αPyr and 0.5H Y/αPyr), 8.63-8.65 (0.5H, m, Y/αPyr); ν$_{max}$/cm$^{-1}$ 1152 and 1190 (C—O ester), 1585 (C=O imide), 1704 (C=O ester); m/z (FAB+) 674 (MH$^+$, 33%), 120 (100); (Found: MH$^+$ 674.2654, C$_{43}$H$_{36}$N$_3$O$_5$ requires 674.2655).

N-2'-Diphenylacetyloxyethyl-5-(α-hydroxy-α-2-pyridylbenzyl)-7-(α-2-pyridylbenzylidene 5-norbornene-2,3-dicarboximide (118)

A similar procedure (Lu, M. C. et al. *J. Med. Chem.* 1987, 30, 273-278 and Nagao, Y. et al. *Tetrahedron Lett.* 1988, 29, 6133-6136) to that described for the preparation of 117 was followed using diphenylacetic acid (98 mg, 0.46 mmol) and oxalyl chloride (1 mL), under reflux for 3 h. A solution of 102 (128 mg, 0.23 mmol) and crude diphenylacetyl chloride in pyridine (2 mL) was then stirred at room temperature for 16 h. Purification by flash chromatography (hexane/ethyl acetate 1:2) afforded 118 as an oily residue (122 mg, 0.16 mmol, 71%); $^1$H NMR (400 MHz, CDCl$_3$) δ 3.19 (0.2H, dd, J=7.9 and 4.5 Hz, W/H-3), 3.25-3.31 (0.8H, m, 0.1H U/H-2 or U/H-3, 0.2H V/H-2 and 0.5H Y/H-3), 3.40 (0.1H, dd, J=7.9 and 4.5 Hz, U/H-2 or U/H-3), 3.44 (0.2H, dd, J=7.9 and 4.7 Hz, V/H-3), 3.50 (0.7H, dd, J=7.9 and 4.9 Hz, 0.2H W/H-2 and 0.5H Y/H-2), 3.61-3.92 (2.5H, m, 2H NCH$_2$, 0.1H U/H-1, 0.2H V/H-1 and 0.2H W/H-4), 3.96 (0.5H, dt, J=4.6 and 1.5 Hz, Y/H-4), 4.10-4.11 (0.1H, m, U/H-4), 4.24 (0.2H, dt, J=4.5 and 1.4 Hz, V/H-4), 4.28-4.44 (2.7H, m, 2H CH$_2$O, 0.2H W/H-1 and 0.5H Y/H-1), 5.02 and 5.04 (1.1H, s, 1H CHPh$_2$ and 0.1H OH), 5.49 (0.2H, dd, J=3.2 and 1.2 Hz, V/H-6), 5.54 (0.5H, dd, J=3.3 and 1.3 Hz, Y/H-6), 5.60 and 5.63 (0.9H, s, OH), 5.96 (0.1H, dd, J=3.3 and 1.2 Hz, U/H-6), 6.00 (0.2H, dd, J=3.3 and 1.2 Hz, W/H-6), 6.78-7.65 (26H, m, Ar), 8.43-8.45 (0.7H, m, 0.2H W/αPyr and 0.5H Y/αPyr), 8.48-8.55 (0.6H, m, 0.2H 2U/αPyr and 0.4H 2V/αPyr), 8.69-8.70 (0.7H, m, 0.2H W/αPyr and 0.5H Y/αPyr); ν$_{max}$(NaCl)/cm$^{-1}$ 1149 and 1187 (C—O ester), 1585 (C=O imide), 1704 (C=O ester); m/z (FAB+) 750 (MH$^+$, 25%), 120 (100); (Found: MH$^+$ 750.2962, C$_{49}$H$_{40}$N$_3$O$_5$ requires 750.2968).

N-2'-Dihydrocinnamoyloxyethyl-5-(α-hydroxy-α-2-pyridylbenzyl)-7-(α-2-pyridylbenzylidene)-5-norbornene-2,3-dicarboximide (119)

A similar procedure (Lu, M. C. et al. *J. Med. Chem.* 1987, 30, 273-278 and Nagao, Y. et al. *Tetrahedron Lett.* 1988, 29, 6133-6136) to that described for the preparation of 117 was followed using dihydrocinnamic acid (54 mg, 0.36 mmol) and oxalyl chloride (1 mL), under reflux for 3 h. A solution of 102 (100 mg, 0.18 mmol) and crude dihydrocinnamyl chloride in pyridine (2 mL) was then stirred at room temperature for 16 h. Purification by flash chromatography (hexane/ethyl acetate 1:1, then chloroform/methanol 100:1) afforded 119 as a colourless oil (11 mg, 0.02 mmol, 9%); $^1$H NMR (400 MHz, CDCl$_3$) δ 2.52-2.62 (2H, m, CH$_2$CH$_2$Ph), 2.85-2.98 (2H, t, J=7.9 Hz, CH$_2$CH$_2$Ph), 3.29 (0.1H, dd, J=7.9 and 4.4 Hz, W/H-3), 3.34 (0.4H, dd, J=7.8 and 4.5 Hz, Y/H-3), 3.42 (0.5H, dd, J=7.9 and 4.9 Hz, V/H-2), 3.55-3.66 (2.1H, m, 1H NCH$_2$, 0.5H V/H-3, 0.4H Y/H-2, 0.2H W/H-1 and W/H-4), 3.75-3.84 (1H, m, NCH$_2$), 3.86-3.88 (0.5H, m, V/H-1), 3.91 (0.4H, dt, J=4.5 and 1.2 Hz, Y/H-4), 4.18-4.27 (2H, m, CH$_2$O), 4.29-4.31 (0.5H, m, V/H-4), 4.44-4.48 (0.5H, m, 0.1H W/H-1 and 0.4H Y/H-1), 5.50 (0.5H, dd, J=3.4 and 1.2 Hz, V/H-6), 5.53 (0.4H, dd, J=3.3 and 1.2 Hz, Y/H-6), 5.58 (0.5H, s, OH), 5.64 (0.5H, s, OH), 6.03-6.05 (0.1H, m, W/H-6), 6.74-7.60 (21H, m, Ar), 8.45-8.48 (1.5H, m, 1H 2V/αPyr, 0.1H W/αPyr and 0.4H Y/αPyr), 8.62-8.64 (0.5H, m, 0.1H W/αPyr and 0.4H Y/αPyr); ν$_{max}$(NaCl)/cm$^{-1}$ 1160 and 1180 (C—O ester), 1585 (C=O imide), 1703 (C=O ester); m/z (FAB+) 688 (MH$^+$, 4%), 120 (100); (Found: MH$^+$ 688.2807, C$_{44}$H$_{38}$N$_3$O$_5$ requires 688.2812).

N-2'-Cinnamoyloxyethyl-5-(α-hydroxy-α-2-pyridylbenzyl)-7-(α-2-pyridylbenzylidene)-5-norbornene-2,3-dicarboximide (120)

A similar procedure (Lu, M. C. et al. *J. Med. Chem.* 1987, 30, 273-278 and Nagao, Y. et al. *Tetrahedron Lett.* 1988, 29, 6133-6136) to that described for the preparation of 117 was followed using cinnamic acid (54 mg, 0.40 mmol) and oxalyl chloride (1 mL), under reflux for 3 h. A solution of 102 (100 mg, 0.18 mmol) and crude cinnamoyl chloride in pyridine (1.5 mL) was then stirred at room temperature for 16 h. Purification by flash chromatography (hexane/ethyl acetate 1:1, then chloroform/methanol 50:1) afford 120 as a colourless oil (60 mg, 0.09 mmol, 49%); $^1$H NMR (300 MHz, CDCl$_3$) δ 3.34 (0.1H, dd, J=7.9 and 4.6 Hz, W/H-3), 3.41 (0.5H, dd, J=7.9 and 4.6 Hz, Y/H-3), 3.48 (0.4H, dd, J=8.0 and 4.9 Hz, V/H-2), 3.60-3.79 (2.1H, m, 1H NCH$_2$, 0.4H V/H-3, 0.2H W/H-2 and W/H-4, 0.5H Y/H-2), 3.84-3.96 (1.9H, m, 1H NCH$_2$, 0.4H V/H-1 and 0.5H Y/H-4), 4.28-4.42 (2.4H, m, 2H CH$_2$O and 0.4H V/H-4), 4.44-4.50 (0.6H, m, 0.1H W/H-1 and 0.5H Y/H-1), 5.53 (0.4H, dd, J=3.3 and 1.3 Hz, V/H-6), 5.56 (0.5H, dd, J=3.2 and 1.2 Hz, Y/H-6), 5.60 (0.1H, s, W/OH), 5.62 (0.5H, s, Y/OH), 5.68 (0.4H, s, V/OH), 6.06 (0.1H, dd, J=3.3 and 1.2 Hz, W/H-6), 6.24 (0.1H, d, J=16.0 Hz, OCOCH), 6.33 (0.9H, d, J=16.0 Hz, OCOCH), 6.74-7.68 (22H, m, 1H CHPh and 20H Ar), 8.45-8.48 (0.4H, m, VαPyr), 8.50-8.53 (1H, m, 0.4H V/αPyr, 0.1H W/αPyr and 0.5H Y/αPyr), 8.61-8.63 (0.6H, m, 0.1H W/αPyr and 0.5H Y/αPyr); $v_{max}$(NaCl)/cm$^{-1}$ 1168 and 1202 (C—O ester), 1585 (C=O imide), 1713 (C=O ester); m/z (FAB+) 686 (MH$^+$, 63%), 131 (100); (Found: MH$^+$ 686.2651, $C_{44}H_{36}N_3O_5$ requires 686.2655).

5-(α-Hydroxy-α-2-pyridylbenzyl)-N-2'-α-methylcinnamoyloxyethyl-7-(α-2-pyridylbenzylidene)-5-norbornene-2,3-dicarboximide (121)

A similar procedure (Lu, M. C. et al. *J. Med. Chem.* 1987, 30, 273-278 and Nagao, Y. et al. *Tetrahedron Lett.* 1988, 29, 6133-6136) to that described for the preparation of 117 was followed using α-methylcinnamic acid (1.23 g, 7.61 mmol) and oxalyl chloride (5 mL), under reflux for 3 h. A solution of 102 (2.11 g, 3.79 mmol), triethylamine (1.2 mL, 8.75 mmol), dimethylaminopyridine (46 mg, 0.38 mmol) and crude α-methylcinnamoyl chloride in dimethylformamide (20 mL) was then stirred at room temperature for 16 h. Purification by flash chromatography (hexane/ethyl acetate 2:1) afforded 121 as a white solid (2.24 g, 3.2 mmol, 84%). mp 75-80° C.; $^1$H NMR (300 MHz, CDCl$_3$) δ 2.03-2.08 (3H, m, Me), 3.40-3.96 (5H, m, NCH$_2$CH$_2$O, H-2, H-3, U/H-1, V/H-1, Y/H-4, W/H-4), 4.15 (0.13H, m, U/H-4), 4.27-4.42 (2.31H, m, NCH$_2$CH$_2$O, V/H-4), 4.47-4.51 (0.56H, m, Y/H-1, W/H-1), 5.53 (0.31H, m, V/H-6), 5.57 (0.38H, m, Y/H-6), 5.59 (0.13H, m, U/OH), 5.61 (0.18H, m, W/OH), 5.63 (0.38H, m, Y/OH), 5.68 (0.31H, m, V/OH), 6.03 (0.13H, m, U/H-6), 6.06 (0.18H, m, W/H-6), 6.72-7.63 (22H, m, COC(Me)=CH, Ar), 8.41-8.65 (2H, m, αPyr); $v_{max}$(NaCl)/cm$^{-1}$ 1113 and 1247 (C—O ester), 1585 (C=O imide), 1701 (C=O ester); m/z (ESI, 70 eV) 722 (MNa$^+$, 100%); (Found: MH$^+$700.2812, $C_{45}H_{37}N_3O_5$ requires 700.2820).

Alternatively, a similar procedure (Lu, M. C. et al. *J. Med. Chem.* 1987, 30, 273-278 and Nagao, Y. et al. *Tetrahedron Lett.* 1988, 29, 6133-6136) to that described for the preparation of 117 was followed using α-methylcinnamic acid (117 mg, 0.72 mmol) and oxalyl chloride (1 mL), under reflux for 16 h. A solution of 102 (200 mg, 0.36 mmol) and crude α-methylcinnamoyl chloride in pyridine (2 mL) was then stirred at 70° C. for 16 h. Purification by flash chromatography (hexane/ethyl acetate 1:2) afforded 121 as a colourless solid (16 mg, 0.02 mmol, 3%).

5-(α-Hydroxy-α-2-pyridylbenzyl)-N-[2'-(2"-naphthoyloxy)ethyl]-7-(α-2-pyridylbenzylidene)-5-norbornene-2,3-dicarboximide (122)

A similar procedure (Lu, M. C. et al. *J. Med. Chem.* 1987, 30, 273-278 and Nagao, Y. et al. *Tetrahedron Lett.* 1988, 29, 6133-6136) to that described for the preparation of 117 was followed using 2-naphthoic acid (124 mg, 0.72 mmol) and oxalyl chloride (1 mL), under reflux for 3 h. A solution of 102 (100 mg, 0.18 mmol) and crude 2-naphthoyl chloride in pyridine (2 mL) was then stirred at room temperature for 16 h. Purification by flash chromatography (hexane/ethyl acetate 2:1) gave 122 (ca. 90% pure). Further purification by RP-HPLC afforded 122 as a colourless solid (26 mg, 0.04 mmol, 10%). mp 112-116° C.; $^1$H NMR (300 MHz, CDCl$_3$) δ 3.35 (0.2H, dd, J=7.8 and 4.4 Hz, W/H-3), 3.42 (0.4H, dd, J=8.1 and 4.6 Hz, Y/H-3), 3.49 (0.4H, dd, J=8.1 and 4.8 Hz, V/H-2), 3.60-3.70 (1.2H, m, 0.4H V/H-3, 0.4H W/H-2 and W/H-4, 0.4H Y/H-2), 3.76-3.85 (1H, m, NCH$_2$), 3.89-3.92 (0.4H, m, V/H-1), 3.94-4.06 (1.4H, m, 1H CH$_2$N and 0.4H Y/H-4), 4.30-4.32 (0.4H, m, V/H-4), 4.42-4.58 (2.6H, m, 2H CH$_2$O, 0.2H W/H-1 and 0.4H Y/H-1), 5.56 (0.4H, dd, J=3.3 and 1.2 Hz, V/H-6), 5.60 (0.4H, dd, J=3.3 and 1.2 Hz, Y/H-6), 5.64 (0.2H, s, OH), 5.68 (0.4H, s, OH), 5.74 (0.4H, s, OH), 6.08-6.10 (0.2H, m, W/H-6), 6.73-7.61 and 7.80-7.99 (22H, m, Ar), 8.44-8.54 (2.4H, m, 1H Ar, 0.8H 2V/αPyr, 0.2H W/HαPyr and 0.4H Y/αPyr), 8.61-8.64 (0.6H, m, 0.2H W/αPyr and 0.4H Y/αPyr); $v_{max}$(NaCl)/cm$^{-1}$ 1196 and 1283 (C—O ester), 1585 (C=O imide), 1705 (C=O ester); m/z (FAB+) 710 (MH$^+$, 75%), 120 (100); (Found: MH$^+$ 710.2665, $C_{46}H_{36}N_3O_5$ requires 710.2655).

5-(α-Hydroxy-α-2-pyridylbenzyl)-N-2'-phenylpropioyloxyethyl-7-(α-2-pyridylbenzylidene)-5-norbornene-2,3-dicarboximide (123)

A similar procedure (Lu, M. C. et al. *J. Med. Chem.* 1987, 30, 273-278 and Nagao, Y. et al. *Tetrahedron Lett.* 1988, 29, 6133-6136) to that described for the preparation of 117 was followed using phenylpropiolic acid (105 mg, 0.72 mmol) and oxalyl chloride (1 mL), under reflux for 2 h. A solution of 102 (200 mg, 0.36 mmol) and crude phenylpropioyl chloride in pyridine (1.5 mL) was then stirred at 70° C. for 16 h. Purification by flash chromatography (hexane/ethyl acetate 1:2) afforded 123 as a colourless solid (18 mg, 0.03 mmol, 7%). mp 97-103° C.; $^1$H NMR (400 MHz, CDCl$_3$) δ 3.38-3.41 (0.1H, m, W/H-3), 3.44 (0.6H, dd, J=7.8 and 4.6 Hz, Y/H-3), 3.53 (0.3H, dd, J=8.0 and 4.8 Hz, V/H-2), 3.63-3.75 (2.1H, m, 1H NCH$_2$, 0.3H V/H-3, 0.2H W/H-2 and W/H-4, 0.6H Y/H-2), 3.85-3.96 (1.9H, m, 1H NCH$_2$, 0.3H V/H-1 and 0.6H Y/H-4), 4.21-4.22 (0.3H, m, V/H-4), 4.30-4.42 (2.7H, m, 2H CH$_2$O, 0.1H W/H-1 and 0.6H Y/H-1), 5.54-5.61 (1.6H, m, 0.3H V/H-6, 0.6H Y/H-6 and 0.6H OH), 6.08-6.10 (0.1H, m, W/H-6), 6.24 (0.1H, s, OH), 6.48 and 6.49 (0.3H, s, OH), 6.77-7.71 (21H, m, Ar), 8.43-8.54 (1.3H, m, 2H V/αPyr, 0.1H W/αPyr and 0.6H Y/αPyr), 8.69-8.70 (0.7H, m, 0.1H W/αPyr and 0.6H Y/αPyr); $v_{max}$/cm$^{-1}$ 1080 and 1241 (C—O ester), 1585 (C=O imide), 1711 (C=O ester); m/z (FAB+) 684 (MH$^+$, 54%), 120 (100); (Found: MH$^+$ 684.2503, $C_{44}H_{34}N_3O_5$ requires 684.2498).

5-(α-Hydroxy-α-2-pyridylbenzyl)-N-[2'-(2"-methoxycinnamoyloxy)ethyl]-7-(α-2-pyridyl benzylidene)-5-norbornene-2,3-dicarboximide (124)

A similar procedure (Lu, M. C. et al. *J. Med. Chem.* 1987, 30, 273-278 and Nagao, Y. et al. *Tetrahedron Lett.* 1988, 29, 6133-6136) to that described for the preparation of 117 was followed using 2-methoxycinnamic acid (128 mg, 0.72 mmol) and thionyl chloride (1 mL), under reflux for 2 h. A solution of 102 (200 mg, 0.36 mmol) and crude 2-methoxycinnamoyl chloride in pyridine (2 mL) was then stirred at room temperature for 2 h. Purification by flash chromatography (hexane/ethyl acetate 1:1) afforded 124 as a colourless solid (112 mg, 0.16 mmol, 44%). mp 101-108° C.; $^1$H NMR (400 MHz, CDCl$_3$) δ 3.35-3.38 (0.1H, m, W/H-3), 3.41 (0.6H, dd, J=8.0 and 4.8 Hz, Y/H-3), 3.48 (0.3H, dd, J=8.0 and 4.8 Hz, V/H-2), 3.61-3.82 (2.1H, m, 1H NCH$_2$, 0.3H V/H-3, 0.2H W/H-2 and W/H-4, 0.6H Y/H-2), 3.85-3.92 (4.3H, m, 3H OMe, 1H NCH$_2$ and 0.3H V/H-3), 3.94-3.96 (0.6H, m, Y/H-4), 4.27-4.45 (2.3H, m, 2H CH$_2$O and 0.3H V/H-4), 4.47-4.49 (0.7H, m, 0.1H W/H-1 and 0.6H Y/H-1), 5.53-5.60 (1H, m, 0.3H V/H-6, 0.6H Y/H-6 and 0.1H OH), 5.64 (0.7H, s, OH), 5.70 (0.2H, s, OH), 6.08 (0.1H, dd, J=3.2 and 1.2 Hz, W/H-6), 6.36 (0.1H, d, J=16.1 Hz, OCOCH), 6.42 (0.9H, d, J=16.1 Hz, OCOCH), 6.74-7.56 (20H, m, Ar), 7.91

(0.1H, d, J=16.1 Hz, CHAr), 7.92 (0.9H, d, J=16.1 Hz, CHAr), 8.44-8.52 (1.3H, m, 0.6H 2V/αPyr, 0.1H W/αPyr and 0.6H Y/αPyr), 8.60-8.62 (0.7H, m, 0.1H W/αPyr and 0.6H Y/αPyr); $v_{max}/cm^{-1}$ 1160 and 1246 (C—O ester), 1584 (C=O imide), 1698 (C=O ester); m/z (FAB+) 716 (MH$^+$, 9%), 120 (100); (Found: MH$^+$ 716.2760, $C_{45}H_{38}N_3O_6$ requires 716.2761).

5-(α-1-hydroxy-α-2-pyridylbenzyl)-N-[2'-(3''-methoxycinnamoyloxy)ethyl]-7-(α-2-pyridyl benzylidene)-5-norbornene-2,3-dicarboximide (125)

A similar procedure (Lu, M. C. et al. *J. Med. Chem.* 1987, 30, 273-278 and Nagao, Y. et al. *Tetrahedron Lett.* 1988, 29, 6133-6136) to that described for the preparation of 117 was followed using 3-methoxycinnamic acid (128 mg, 0.72 mmol) and thionyl chloride (1 mL), under reflux for 2 h. A solution of 102 (200 mg, 0.36 mmol) and crude 3-methoxycinnamoyl chloride in pyridine (2 mL) was then stirred at room temperature for 16 h. Purification by flash chromatography (hexane/ethyl acetate 1:1) afforded 125 as a colourless solid (120 mg, 0.17 mmol, 47%). mp 100-104° C.; $^1$H NMR (300 MHz, CDCl$_3$) δ 3.41 (0.2H, dd, J=8.0 and 4.8 Hz, Y/H-3), 3.48 (0.8H, dd, J=8.0 and 4.8 Hz, V/H-2), 3.64-3.96 (7H, m, 3H OMe, 2H NCH$_2$, 1.6H V/H-1 and V/H-3, 0.4H Y/H-2 and Y/H-4), 4.30-4.36 (2.8H, m, 2H CH$_2$O and 0.8H V/H-4), 4.46-4.48 (0.2H, m, Y/H-1), 5.63-5.69 (2H, m, 0.8H V/H-6, 0.2H Y/H-6 and 1H OH), 6.31 (1H, d, J=15.9 Hz, OCOCH), 6.71-7.70 (21H, m, 1H CHAr OCOCH and 20H Ar), 8.46-8.53 (1.8H, m, 1.6H 2V/αPyr and 0.2H Y/αPyr), 8.62-8.63 (0.2H, m, Y/αPyr); $v_{max}/cm^{-1}$ 1160 and 1246 (C—O ester), 1584 (C=O imide), 1698 (C=O ester); m/z (FAB+) 716 (MH$^+$, 9%), 120 (100); (Found: MH$^+$ 716.2760, $C_{45}H_{38}N_3O_6$ requires 716.2761).

5-(α-Hydroxy-α-2-pyridylbenzyl)-N-[2'-(4''-methoxycinnamoyloxy)ethyl]-7-(α-2-pyridyl benzylidene)-5-norbornene-2,3-dicarboximide (126)

A similar procedure (Lu, M. C. et al. *J. Med. Chem.* 1987, 30, 273-278 and Nagao, Y. et al. *Tetrahedron Lett.* 1988, 29, 6133-6136) to that described for the preparation of 117 was followed using 4-methoxycinnamic acid (9.63 g, 54.1 mmol) and thionyl chloride (40 mL), under reflux for 3 h. A solution of 102 (15.05 g, 27.0 mmol), triethylamine (8.6 mL, 62.1 mmol), dimethylaminopyridine (330 mg, 2.7 mmol) and crude 4-methoxycinnamoyl chloride in dimethylformamide (150 mL) was then stirred at room temperature for 5 h. Purification by flash chromatography (hexane/ethyl acetate 2:1) afforded 126 as a white solid (18.03 g, 25.24 mmol, 93%). mp 125-130° C.; $^1$H NMR (300 MHz, CDCl$_3$) δ 3.35-3.91 (4.63H, m, NCH$_2$CH$_2$O, H-2, H-3, U/H-1, V/H-1, W/H-4), 3.83-3.85 (3H, m, OMe), 3.95 (0.37H, m, Y/H-4), 4.15 (0.15H, m, U/H-4), 4.28-4.44 (2.3H, m, NCH$_2$CH$_2$O, V/H-4), 4.47-4.50 (0.55H, m, W/H-1, Y/H-1), 5.53 (0.30H, dd, J=3.4 and 1.2 Hz, V/H-6), 5.56 (0.37H, dd, J=3.4 and 1.2 Hz, Y/H-6), 5.57 (0.33H, s, W/OH, U/OH), 5.61 (0.37H, s, Y/OH), 5.67 (0.30H, s, V/OH), 6.03 (0.15H, dd, J=3.4 and 1.2 Hz, U/H-6), 6.06 (0.18H, dd, J=3.4 and 1.2 Hz, W/H-6), 6.14 (0.33H, d, J=15.8 Hz, COCH=CH), 6.22 (0.67H, d, J=15.8 Hz, COCH=CH), 6.70-7.65 (21H, m, Ar and COCH=CH), 8.40-8.62 (2H, m, αPyr); $v_{max}/cm^{-1}$ 1163 and 1251 (C—O ester), 1633 (C=O imide), 1705 (C=O ester); m/z (FAB+) 716 (MH$^+$, 60%), 116 (100); (Found: MH$^+$ 716.2765, $C_{45}H_{38}N_3O_6$ requires 716.2761).

Alternatively, a similar procedure (Lu, M. C. et al. *J. Med. Chem.* 1987, 30, 273-278 and Nagao, Y. et al. *Tetrahedron Lett.* 1988, 29, 6133-6136) to that described for the preparation of 117 was followed using 4-methoxycinnamic acid (131 mg, 0.72 mmol) and thionyl chloride (0.5 mL), under reflux for 1.5 h. A solution of 102 (200 mg, 0.36 mmol) and crude 4-methoxycinnamoyl chloride in pyridine (2 mL) was then stirred at 70° C. for 30 min. Purification by flash chromatography (dichloromethane/methanol 20:1 then 50:1) afforded 126 as a colourless solid (167 mg, 0.23 mmol, 63%).

5-(α-Hydroxy-α-2-pyridylbenzyl)-7-(α-2-pyridylbenzylidene)-N-[2'-(4''-trifluoromethoxy cinnamoyloxy)ethyl]-5-norbornene-2,3-dicarboximide (127)

A similar procedure (Lu, M. C. et al. *J. Med. Chem.* 1987, 30, 273-278 and Nagao, Y. et al. *Tetrahedron Lett.* 1988, 29, 6133-6136) to that described for the preparation of 117 was followed using 4-trifluoromethoxycinnamic acid (167 mg, 0.72 mmol) and thionyl chloride (1 mL), under reflux for 2 h. A solution of 102 (200 mg, 0.36 mmol) and crude 4-trifluoromethoxycinnamoyl chloride in pyridine (2 mL) was then stirred at room temperature for 16 h. Purification by flash chromatography (hexane/ethyl acetate 2:1) afforded 127 as a colourless solid (120 mg, 0.16 mmol, 43%). mp 100-105° C.; $^1$H NMR (300 MHz, CDCl$_3$) δ 3.35 (0.1H, dd, J=7.8 and 4.5 Hz, W/H-3), 3.41 (0.8H, dd, J=7.8 and 4.5 Hz, Y/H-3), 3.49 (0.1H, dd, J=8.0 and 5.0 Hz, V/H-2), 3.61-3.79 (2.1H, m, 1H NCH$_2$, 0.1H V/H-3, 0.2H W/H-2 and W/H-4, 0.8H Y/H-2), 3.86-3.96 (1.9H, m, 1H NCH$_2$, 0.1H V/H-1 and 0.8H Y/H-4), 4.29-4.45 (2.1H, m, 2H CH$_2$O, 0.1H V/H-4), 4.48-4.51 (0.9H, m, 0.1H W/H-1 and 0.8H Y/H-1), 5.52-5.57 (0.9H, m, 0.1H V/H-6 and 0.8H Y/H-6), 5.64 (0.9H, s, OH), 5.70 (0.1H, s, OH), 6.07 (0.1H, dd, J=3.4 and 1.0 Hz, W/H-6), 6.20 (0.1H, d, J=16.0 Hz, OCOCH), 6.31 (0.9H, d, J=16.0 Hz, OCOCH), 6.75-7.66 (21H, m, 1H CHAr and 20H Ar), 8.44-8.51 (1.1H, m, 0.2H 2V/αPyr, 0.1H W/αPyr and 0.8H Y/αPyr), 8.61-8.63 (0.9H, m, 0.1H W/αPyr and 0.8H Y/αPyr); $v_{max}/cm^{-1}$ 1164 and 1205 (C—O ester), 1586 (C=O imide), 1697 (C=O ester); m/z (FAB+) 770 (MH$^+$, 79%), 752 (MH$^+$-H$_2$O, 100); (Found: MH$^+$ 770.2472, $C_{45}H_{35}F_3N_3O_6$ requires 770.2478).

5-(α-Hydroxy-α-2-pyridylbenzyl)-N-[2'-(4''-methylcinnamoyloxy)ethyl)]-7-(α-2-pyridyl benzylidene)-5-norbornene-2,3-dicarboximide (128)

A similar procedure (Lu, M. C. et al. *J. Med. Chem.* 1987, 30, 273-278 and Nagao, Y. et al. *Tetrahedron Lett.* 1988, 29, 6133-6136) to that described for the preparation of 117 was followed using 4-methylcinnamic acid (117 mg, 0.72 mmol) and thionyl chloride (1 mL), under reflux for 2 h. A solution of 102 (200 mg, 0.36 mmol) and crude 4-methylcinnamoyl chloride in pyridine (2 mL) was then stirred at room temperature for 2 h. Purification by flash chromatography (hexane/ethyl acetate 1:2) afforded 128 as a colourless solid (160 mg, 0.23 mmol, 64%). mp 100-104, 106-110° C.; $^1$H NMR (300 MHz, CDCl$_3$) δ 2.35 (3H, s, Me), 3.35 (0.1H, dd, J=8.1 and 4.5 Hz, W/H-3), 3.41 (0.6H, dd, J=8.0 and 4.6 Hz, Y/H-3), 3.48 (0.3H, dd, J=7.8 and 4.8 Hz, V/H-2), 3.60-3.78 (2.1H, m, 1H NCH$_2$, 0.3H V/H-3, 0.2H W/H-2 and W/H-4, 0.6H Y/H-2), 3.84-3.96 (1.9H, m, 1H NCH$_2$, 0.3H V/H-1 and 0.6H Y/H-4), 4.26-4.43 (2.3H, m, 2H CH$_2$O and 0.3H V/H-4), 4.45-4.49 (0.7H, m, 0.1H W/H-1 and 0.6H Y/H-1), 5.54-5.68 (1.9H, m, 0.3H V/H-6, 0.6H Y/H-6 and 1H OH), 6.06 (0.1H, dd, J=3.3 and 1.4 Hz, W/H-6), 6.20 (0.3H, d, J=16.0 Hz, OCOCH), 6.28 (0.7H, d, J=16.0 Hz, OCOCH), 6.74-7.65 (21H, m, 1H CHAr and 20H Ar), 8.43-8.52 (1.3H, m, 0.6H 2V/αPyr, 0.1H W/αPyr and 0.6H Y/αPyr), 8.61-8.63 (0.7H, m, 0.1H W/αPyr and 0.6H Y/αPyr); $v_{max}/cm^{-1}$ 1117 and 1162 (C—O ester), 1584 (C=O imide), 1700 (C=O ester); m/z (FAB+) 700 (MH$^+$, 64%), 145 (100); (Found: MH$^+$ 700.2812, $C_{45}H_{38}N_3O_5$ requires 700.2812).

N-[2'-(4"-Ethylcinnamoyloxy)ethyl]-5-(α-hydroxy-α-2-pyridylbenzyl)-7-(α-2-pyridyl benzylidene)-5-norbornene-2,3-dicarboximide (335)

A similar procedure (Lu, M. C. et al. *J. Med. Chem.* 1987, 30, 273-278 and Nagao, Y. et al. *Tetrahedron Lett.* 1988, 29, 6133-6136) to that described for the preparation of 117 was followed using 4-ethylcinnamic acid (1.36 g, 7.71 mmol) and thionyl chloride (15 mL), under reflux for 3 h. A solution of 102 (2.14 g, 3.85 mmol), triethylamine (1.23 mL, 8.86 mmol), dimethylaminopyridine (47 mg, 0.39 mmol) and crude 4-ethylcinnamoyl chloride in dimethylformamide (20 mL) was then stirred at room temperature for 5 h. Purification by flash chromatography (hexane/ethyl acetate 1:1) afforded 335 as a white solid (1.15 g, 1.62 mmol, 42%). mp 90-95° C.; $^1$H NMR (300 MHz, CDCl$_3$) δ 1.22-1.28 (3H, m, CH$_2$CH$_3$), 2.62-2.70 (2H, m, CH$_2$CH$_3$), 3.35-3.90 (4.61H, m, NCH$_2$CH$_2$O, H-2, H-3, U/H-1, V/H-1, W/H-4), 3.94 (0.39H, m, Y/H-4), 4.14 (0.11H, m, U/H-4), 4.28-4.35 (2.33H, m, NCH$_2$CH$_2$O, V/H-4), 4.47-4.50 (0.56H, m, W/H-1, Y/H-1), 5.52 (0.33H, dd, J=3.4 and 1.2 Hz, V/H-6), 5.56 (0.39H, dd, J=3.4 and 1.2 Hz, Y/H-6), 5.62 (0.72H, s), 5.67 (0.28H, s), 6.06 (0.11H, dd, J=3.4 and 1.2 Hz, UH-6), 6.08 (0.17H, dd, J=3.4 and 1.2 Hz, W/H-6), 6.23 (0.28H, d, J=15.8 Hz, COCH=CH), 6.31 (0.72H, d, J=15.8 Hz, COCH=CH), 6.74-7.66 (21H, m, Ar and COCH=CH), 8.46-8.64 (2H, m, αPyr); $v_{max}$ (NaCl)/cm$^{-1}$ 1162, 1248 (C—O ester), 1585 (C=O imide), 1702 (C=O ester); m/z (ESI, 70 eV) 736 (MNa$^+$, 100%); (Found MNa$^+$ 736.2774, $C_{46}H_{39}N_3NaO_5$ requires 736.2782).

5-(α-Hydroxy-α-2-pyridylbenzyl)-N-[2'-(4"-isopropylcinnamoyloxy)ethyl]-7-(α-2-pyridyl benzylidene)-5-norbornene-2,3-dicarboximide (347)

Compound 347 was prepared by a procedure similar to that of Schwartz and co-workers (Schwartz, E. et al. *Macromolecules* 2011, 44, 4735-4741). To a solution of 102 (1.0 g, 1.80 mmol), 4-isopropylcinnamic acid (0.22 g, 1.13 mmol), triethylamine (0.47 mL, 3.40 mmol) and dimethylaminopyridine (12 mg, 0.10 mmol) in dichloromethane (15 mL) was added 1-ethyl-3-(3-dimethylaminopropyl)carbodiimide (0.24 g, 1.24 mmol), and the mixture stirred at room temperature for 24 h. The reaction mixture was then diluted with dichloromethane (75 mL) and washed with brine (2×100 mL). The aqueous phase was adjusted to pH 7 with a 10% aqueous solution of citric acid, and the organic phase further washed with brine (2×100 mL). The aqueous phase was then extracted with dichloromethane (2×100 mL) and the combined organic extracts dried over anhydrous sodium sulfate and the solvent removed in vacuo. Purification by flash chromatography (hexane/ethyl acetate 1:3) afforded 347 as an off-white solid (0.55 g, 0.75 mmol, 73%). $^1$H NMR (300 MHz, CDCl$_3$) δ 1.24-1.26 (6H, m, CH(CH$_3$)$_2$), 2.87-2.96 (1H, m, CH(CH$_3$)$_2$), 3.33-3.90 (4.67H, m, NCH$_2$CH$_2$O, H-2, H-3, U/H-1, V/H-1, W/H-4), 3.94 (0.33H, m, Y/H-4), 4.13 (0.13H, m, U/H-4), 4.28-4.35 (2.36H, m, NCH$_2$CH$_2$O, V/H-4), 4.6-4.49 (0.51H, m, W/H-1, Y/H-1), 5.53 (0.36H, dd, J=3.4 and 1.2 Hz, V/H-6), 5.56 (0.33H, dd, J=3.4 and 1.2 Hz, Y/H-6), 5.62 (0.69H, s), 5.68 (0.318H, s), 6.03 (0.13H, dd, J=3.4 and 1.2 Hz, U/H-6), 6.05 (0.18H, dd, J=3.4 and 1.2 Hz, W/H-6), 6.23 (0.31H, d, J=15.8 Hz, COCH=CH), 6.31 (0.69H, d, J=15.8 Hz, COCH=CH), 6.70-7.66 (21H, m, Ar and COCH=CH), 8.41-8.63 (2H, m, αPyr); mp 95-100° C.; $v_{max}$ (NaCl)/cm$^{-1}$ 1174, 1250 (C—O ester), 1585 (C=O imide), 1696 (C=O ester); m/z (ESI, 70 eV) 750 (MNa$^+$, 100%); (Found MNa$^+$ 750.2939), $C_{47}H_{41}N_3NaO_5$ requires 750.2938.

N-[2'-(4"-Chlorocinnamoyloxy)ethyl]-5-(α-hydroxy-α-2-pyridylbenzyl)-7-(α-2-pyridylbenzylidene)-5-norbornene-2,3-dicarboximide (129)

A similar procedure (Lu, M. C. et al. *J. Med. Chem.* 1987, 30, 273-278 and Nagao, Y. et al. *Tetrahedron Lett.* 1988, 29, 6133-6136) to that described for the preparation of 117 was followed using 4-chlorocinnamic acid (131 mg, 0.72 mmol) and thionyl chloride (1 mL), under reflux for 2 h. A solution of 102 (200 mg, 0.36 mmol) and crude 4-chlorocinnamoyl chloride in pyridine (2 mL) was then stirred at room temperature for 16 h. Purification by flash chromatography (hexane/ethyl acetate 1:1) afforded 129 as a colourless solid (90 mg, 0.12 mmol, 17%). mp 100-111° C.; $^1$H NMR (300 MHz, CDCl$_3$) δ 3.34 (0.1H, dd, J=7.8 and 4.5 Hz, W/H-3), 3.40 (0.7H, dd, J=7.8 and 4.5 Hz, Y/H-3), 3.48 (0.2H, dd, J=8.0 and 5.0 Hz, V/H-2), 3.60-3.76 (2.1H, m, 1H NCH$_2$, 0.2H V/H-3, 0.2H W/H-2 and W/H-4, 0.7H Y/H-2), 3.84-3.96 (1.9H, m, 1H NCH$_2$, 0.2H V/H-1 and 0.7H Y/H-4), 4.27-4.42 (2.2H, m, 2H CH$_2$O and 0.2H V/H-4), 4.46-4.50 (0.8H, m, 0.1H W/H-1 and 0.7H Y/H-1), 5.52-5.62 (1.9H, m, 0.2H V/H-6, 0.7H Y/H-6 and 1H OH), 6.06-6.07 (0.1H, m, W/H-6), 6.19 (0.1H, d, J=16.0 Hz, OCOCH), 6.30 (0.9H, d, J=16.0 Hz, OCOCH), 6.74-7.63 (21H, m, 1H CHAr and 20H Ar), 8.45-8.52 (1.2H, m, 0.4H 2V/αPyr, 0.1H W/αPyr and 0.7H Y/αPyr), 8.61-8.64 (0.8H, m, 0.1H W/αPyr and 0.7H Y/αPyr); $v_{max}$/cm$^{-1}$ 1088 and 1165 (C—O ester), 1585 (C=O imide), 1699 (C=O ester); m/z (FAB+) 720 (MH$^+$, 17%), 120 (100); (Found: MH$^+$ 720.2276, $C_{44}H_{35}{}^{35}ClN_3O_5$ requires 720.2265).

5-(α-Hydroxy-α-2-pyridylbenzyl)-N-[2'-(4"-nitrocinnamoyloxy)ethyl]-7-(α-2-pyridylbenzylidene)-5-norbornene-2,3-dicarboximide (130)

A similar procedure (Lu, M. C. et al. *J. Med. Chem.* 1987, 30, 273-278 and Nagao, Y. et al. *Tetrahedron Lett.* 1988, 29, 6133-6136) to that described for the preparation of 117 was followed using 4-nitrocinnamic acid (32 mg, 0.16 mmol) and thionyl chloride (0.5 mL), under reflux for 1 h. A solution of 102 (92 mg, 0.16 mmol) and crude 4-nitrocinnamoyl chloride in pyridine (1 mL) was then stirred at room temperature for 16 h. Purification by flash chromatography (hexane/ethyl acetate 1:1) afforded 130 as a colourless solid (11 mg, 0.02 mmol, 9%). mp 105-110° C.; $^1$H NMR (400 MHz, CDCl$_3$) δ 3.37-3.44 (0.8H, m, 0.3H W/H-3 and 0.5H Y/H-3), 3.46-3.53 (0.2H, m, V/H-2), 3.59-3.74 (2.3H, m, 1H NCH$_2$, 0.2H V/H-3, 0.6H W/H-2 and W/H-4, 0.5H Y/H-2), 3.81-3.95 (1.7H, m, 1H NCH$_2$, 0.2H V/H-1 and 0.5H Y/H-4), 4.26-1.31 and 4.36-4.39 (2.2H, m, 2H CH$_2$O and 0.2 V/H-4), 4.48-4.50 (0.8H, m, 0.3H W/H-1 and 0.5H Y/H-1), 5.52-5.63 (1.7H, m, 0.2H V/H-6, 0.5H Y/H-6 and 1H OH), 6.03-6.08 (0.6H, m, 0.3H OCOCH and 0.3H W/H-6), 6.31 (0.1H, d, J=16.0 Hz, OCOCH), 6.46 (0.6H, d, J=16.0 Hz, OCOCH), 6.76-7.72 (21H, m, 1H CHAr and 20H Ar), 8.19-8.25 (2H, m, Ar), 8.45-8.51 (1.2H, m, 0.4H 2V/αPyr, 0.3H W/αPyr and 0.5H Y/αPyr), 8.63-8.64 (0.8H, m, 0.3H W/αPyr and 0.5H Y/αPyr); $v_{max}$/cm$^{-1}$ 1169 and 1344 (C—O ester), 1586 (C=O imide), 1702 (C=O ester); m/z (FAB+) 731 (MH$^+$, 17%), 120 (100); (Found: MH$^+$ 731.2506, $C_{44}H_{35}N_4O_7$ requires 731.2506).

N-[2'-(4"-((Dimethylamino)cinnamoyloxy)ethyl]-5-(α-hydroxy-α-2-pyridylbenzyl)-7-(α-2-pyridylbenzylidene)-5-norbornene-2,3-dicarboximide (131)

Compound 131 was prepared by a procedure similar to that of Kalgutkar and co-workers (Kalgutkar, A. S. et al. *J. Med. Chem.* 2000, 43, 2860-2870). To a mixture of 4-(dimethylamino)cinnamic acid (76 mg, 0.40 mmol), dicyclohexylcarbodiimide (88 mg, 0.43 mmol) and 4-dimethylaminopyridine (5 mg) in dry dichloromethane (9 mL) was added 102 (247 mg, 0.4 mmol) in dichloromethane (10 mL), and the mixture heated under reflux for 16 h. The mixture was taken up in water (30 mL), extracted with ethyl acetate (2×30 mL), dried over anhydrous magnesium sulfate and the solvent removed in vacuo. Purification by flash chromatography (hexane/ethyl acetate 1:1) afforded 131 as a yellow solid (58 mg, 0.08 mmol, 18%). mp 121-126° C.; $^1$H NMR (300 MHz, CDCl$_3$) δ 2.97-3.06 (6H, m, NMe$_2$), 3.34-3.38 (0.1H, m, W/H-3), 3.40 (0.4H, dd, J=8.2 and 3.4 Hz, Y/H-3), 3.47-3.52 (0.5H, m, V/H-2), 3.57-3.72 (2.1H, m, 1H NCH$_2$, 0.5H V/H-3, 0.2H W/H-2 and W/H-4, 0.4H Y/H-2), 3.82-3.92 (1.5H, m, 1H NCH$_2$ and 0.5H V/H-1), 3.94-3.96 (0.4H, m, Y/H-4), 4.24-4.38 (2.5H, m, 2H CH$_2$O and 0.5H V/H-4), 4.45-4.48 (0.5H, m, 0.1H W/H-1 and 0.4H Y/H-1), 5.53-5.66 (1.9H, m, 0.5H V/H-6, 0.4H Y/H-6 and 1H OH), 6.05-6.06 (0.1H, m, W/H-6), 6.10-6.15 (1H, m, OCOCH), 6.64-7.60 (21H, m, 0.1H CHAr and 20H Ar), 8.46-8.53 (1.5H, m, 1H 2V/αPyr, 0.1H W/αPyr and 0.4HY/αPyr), 8.62-8.63 (0.5H, m, 0.1H W/αPyr and 0.4H Y/αPyr); ν$_{max}$/cm$^{-1}$ 1154 and 1256 (C—O ester), 1599 (C=O imide), 1702 (C=O ester); m/z (FAB+) 729 (MH$^+$, 4%), 120 (100); (Found: MH$^+$ 729.3080, C$_{46}$H$_{41}$N$_4$O$_5$ requires 729.3077).

N-[2'-(4"-Acetamidocinnamoyloxy)ethyl]-5-(α-hydroxy-α-2-pyridylbenzyl)-7-(α-2-pyridyl benzylidene)-5-norbornene-2,3-dicarboximide (337)

A similar procedure (Schwartz, E. et al. *Macromolecules* 2011, 44, 4735-4741) to that previously described for the preparation of 347 was followed using 2 (1.50 g, 2.70 mmol), 4-acetamidocinnamic acid (0.50 g, 2.46 mmol), 1-ethyl-3-(3-dimethylaminopropyl)carbodiimide (1.04 g, 5.60 mmol), triethylamine (1.24 mL, 8.91 mmol) and dimethylaminopyridine (60 mg, 0.49 mmol) in dichloromethane (25 mL), at room temperature for 72 h. Purification by flash chromatography (hexane/ethyl acetate 1:4) afforded 337 as a white solid (2.0 g, 2.69 mmol, 99%). mp 125-130° C.; $^1$H NMR (300 MHz, CDCl$_3$) δ 2.17 (3H, s, NHAc), 3.35-3.90 (4.16H, m, NCH$_2$CH$_2$O, H-2, H-3, W/H-4), 3.83-3.95 (0.84H, m, U/H-1, V/H-1, Y/H-4), 4.14 (0.14H, m, U/H-4), 4.28-4.38 (2.32H, m, NCH$_2$CH$_2$O, V/H-4), 4.43-4.47 (0.54H, m, W/H-1, Y/H-1), 5.53 (0.32H, dd, J=3.4 and 1.2 Hz, V/H-6), 5.55 (0.38H, dd, J=3.4 and 1.2 Hz, Y/H-6), 5.59 (s, OH), 5.60 (s, OH), 5.63 (s, OH), 5.69 (s, OH), 6.06 (0.14H, dd, J=3.4 and 1.2 Hz, U/H-6), 6.06 (0.16H, dd, J=3.4 and 1.2 Hz, W/H-6), 6.17 (0.30H, d, J=15.8 Hz, COCH=CH), 6.26 (0.70H, d, J=15.8 Hz, COCH=CH), 6.74-7.61 (21H, m, Ar and COCH=CH), 8.40-8.63 (2H, m, αPyr); m/z (ESI, 70 eV) 765 (MNa$^+$, 100%); (Found MNa$^+$ 765.2684, C$_{46}$H$_{38}$N$_4$NaO$_6$ requires 765.2687).

5-(α-Hydroxy-α-2-pyridylbenzyl)-N-[2'-(4"-methylsulfonylcinnamoyloxy)ethyl]-7-(α-2-pyridyl benzylidene)-5-norbornene-2,3-dicarboximide (329)

A similar procedure (Lu, M. C. et al. *J. Med. Chem.* 1987, 30, 273-278 and Nagao, Y. et al. *Tetrahedron Lett.* 1988, 29, 6133-6136) to that described for the preparation of 117 was followed using 4-methylsulfonylcinnamic acid (1.32 g, 5.83 mmol) and thionyl chloride (15 mL), under reflux for 3 h. A solution of 2 (1.63 g, 2.92 mmol), triethylamine (0.9 mL, 6.71 mmol), dimethylaminopyridine (36 mg, 0.29 mmol) and crude 4-methylsulfonylcinnamoyl chloride in dimethylformamide (5 mL) was then stirred at room temperature for 18 h, with purification by flash chromatography (hexane/ethyl acetate 1:2) affording 329 as a white solid (1.21 g, 1.58 mmol, 54%). mp 105-110° C.; $^1$H NMR (400 MHz, CDCl$_3$) 3.07 (3H, s, SO$_2$Me), δ 3.35-3.97 (5H, m, NCH$_2$CH$_2$O, H-2, H-3, U/H-1, V/H-1, W/H-4, Y/H-4), 4.14 (0.12H, m, U/H-4), 4.31 (0.33H, m, V/H-4), 4.33-4.38 (2H, m, NCH$_2$CH$_2$O), 4.47-4.50 (0.55H, m, W/H-1, Y/H-1), 5.53 (0.33H, dd, J=3.4 and 1.2 Hz, V/H-6), 5.55 (0.39H, dd, J=3.4 and 1.2 Hz, Y/H-6), 5.62 (0.39H, s, Y/OH), 5.64 (0.12H, s, U/OH), 5.66 (0.16H, s, W/OH), 5.68 (0.33H, s, V/OH), 6.04 (0.15H, dd, J=3.4 and 1.2 Hz, U/H-6), 6.07 (0.16H, dd, J=3.4 and 1.2 Hz, W/H-6), 6.31-6.36 (0.28H, m, COCH=CH), 6.45-6.50 (0.72H, m, COCH=CH), 6.70-7.70 (21H, m, Ar and COCH=CH), 7.93-7.96 (2H, m, H-3", H-5"), 8.41-8.63 (2H, m, αPyr); ν$_{max}$ (NaCl)/cm$^{-1}$ 1147, 1246 (C—O ester), 1585 (C=O imide), 1700 (C=O ester); m/z (ESI, 70 eV) 786 (MNa$^+$, 100%); (Found MNa$^+$ 786.2221, C$_{45}$H$_{37}$N$_3$NaO$_7$S requires 786.2244).

N-[2'-(3",4"-Dimethoxycinnamoyloxy)ethyl]-5-(α-hydroxy-α-2-pyridylbenzyl)-7-(α-2-pyridylbenzylidene)-5-norbornene-2,3-dicarboximide (132)

A similar procedure (Lu, M. C. et al. *J. Med. Chem.* 1987, 30, 273-278 and Nagao, Y. et al. *Tetrahedron Lett.* 1988, 29, 6133-6136) to that described for the preparation of 117 was followed using 3,4-dimethoxycinnamic acid (140 mg, 0.67 mmol) and thionyl chloride (0.5 mL), under reflux for 1 h. A solution of 102 (184 mg, 0.34 mmol) and crude 3,4-dimethoxycinnamoyl chloride in pyridine (4 mL) was then stirred at 70° C. for 16 h. Purification by flash chromatography (dichloromethane/methanol 20:1) afforded 132 as a colourless solid (84 mg, 0.1 mmol, 33%). mp 85-95° C.; $^1$H NMR (300 MHz, CDCl$_3$) δ 3.35 (0.1H, dd, J=7.8 and 4.5 Hz, W/H-3), 3.41 (0.4H, dd, J=7.8 and 4.8 Hz, Y/H-3), 3.48 (0.4H, dd, J=8.0 and 5.0 Hz, V/H-2), 3.54-3.79 (2.2H, m, 1H NCH$_2$, 0.2H U/H-2 and U/H-3, 0.4H V/H-3, 0.211 W/H-2 and W/H-4, 0.4H Y/H-2), 3.86-4.00 (7.9H, m, 6H OMe, 1H NCH$_2$, 0.1H U/H-1, 0.4H V/H-1 and 0.4H Y/H-4), 4.14-4.15 (0.1H, m, U/H-4), 4.32-4.41 (2.4H, m, 2H CH$_2$O and 0.4H V/H-4), 4.46-4.49 (0.5H, m, 0.1H W/H-1 and 0.4H Y/H-1), 5.52-5.61 (1.4H, m, 0.4H V/H-6, 0.4H Y/H-6 and 0.6H OH), 5.68 (0.4H, s, OH), 6.03-6.06 (0.2H, m, 0.1H U/H-6 and 0.1H W/H-6), 6.15 (0.1H, d, J=15.9 Hz, OCOCH), 6.22 (0.9H, d, J=15.9 Hz, OCOCH), 6.75-7.63 (20H, m, 1H CHAr and 19H Ar), 8.40-8.52 (1.5H, m, 0.2H 2U/αPyr, 0.8H 2V/αPyr, 0.1H W/αPyr and 0.4HY/αPyr), 8.60-8.62 (0.5H, m, 0.1H W/αPyr and 0.4H Y/αPyr); ν$_{max}$/cm$^{-1}$ 1158 and 1259 (C—O ester), 1584 (C=O imide), 1705 (C=O ester); m/z (FAB+) 746 (MH$^+$, 57%), 191 (100); (Found: MH$^+$ 746.2855, C$_{46}$H$_{40}$N$_3$O$_7$ requires 746.2866).

5-(α-Hydroxy-α-2-pyridylbenzyl)-7-(α-2-pyridylbenzylidene)-N-[2'-(3",4",5"-trimethoxy cinnamoyloxy)ethyl]-5-norbornene-2,3-dicarboximide (133)

A similar procedure (Lu, M. C. et al. *J. Med. Chem.* 1987, 30, 273-278 and Nagao, Y. et al. *Tetrahedron Lett.* 1988, 29, 6133-6136) to that described for the preparation of 117 was followed using 3,4,5-trimethoxycinnamic acid (224 mg, 0.9 mmol) and thionyl chloride (0.5 mL), under reflux for 2 h. A solution of 102 (243 mg, 0.4 mmol) and crude 3,4,5-trimethoxycinnamoyl chloride in pyridine (2 mL) was then stirred at 70° C. for 3 h. Purification by flash chromatography (hexane/ethyl acetate 1:1) afforded 133 as a colourless solid (90 mg, 0.1 mmol, 29%). mp 109-113° C.; $^1$H NMR (300 MHz, CDCl$_3$) δ 3.34 (0.1H, dd, J=8.0 and 4.4 Hz, W/H-3), 3.41-3.47 (0.3H, m, Y/H-3), 3.49-3.53 (0.5H, m, V/H-2), 3.60-3.75 and 3.78-3.95 (13.1H, m, 9H OMe, 2H NCH$_2$, 0.3H U/H-1, U/H-2 and U/H-3, 1H V/H-3 and V/H-4, 0.2H W/H-2 and W/H-4, 0.6H Y/H-2 and Y/H-4), 4.15-4.16 (0.1H, m, U/H-4), 4.32-4.43 (2.5H, m, 2H CH$_2$O and 0.5H V/H-4), 4.46-4.50 (0.4H, m, 0.1H W/H-1 and 0.3H Y/H-1), 5.52-5.67 (1.8H, m, 0.5H V/H-6, 0.3H Y/H-6 and 1H OH), 6.02-6.07 (0.2H, m, 0.1H U/H-6 and 0.1H W/H-6), 6.19-6.33 m, OCOCH), 6.72-7.62 and 7.97-8.04 (19H, m, 18H Ar and 1H CHAr), 8.40-8.52 (1.6H, m, 0.2H 2U/αPyr, 1H 2V/αPyr, 0.1H W/αPyr and 0.3H Y/αPyr), 8.61-8.62 (0.4H, m, 0.1H W/αPyr and 0.3H Y/αPyr); ν$_{max}$/cm$^{-1}$ 1127 and 1275 (C—O ester), 1584 (C=O imide), 1706 (C=O ester); m/z (FAB+) 776 (MH$^+$, 6%), 95 (100); (Found: MH$^+$ 776.2970, C$_{47}$H$_{42}$N$_3$O$_8$ requires 776.2972).

N-[2'-(3",4"-Dichlorocinnamoyloxy)ethyl]-5-(α-hydroxy-α-2-pyridylbenzyl)-7-(α-2-pyridyl benzylidene)-5-norbornene-2,3-dicarboximide (134)

A similar procedure (Lu, M. C. et al. *J. Med. Chem.* 1987, 30, 273-278 and Nagao, Y. et al. *Tetrahedron Lett.* 1988, 29, 6133-6136) to that described for the preparation of 117 was followed using 3,4-dichlorocinnamic acid (131 mg, 0.72 mmol) and thionyl chloride (1 mL), under reflux for 2 h. A solution of 102 (200 mg, 0.36 mmol) and crude 3,4-dichlorocinnamoyl chloride in pyridine (2 mL) was then stirred at room temperature for 2 h. Purification by flash chromatography (hexane/ethyl acetate 2:1) afforded 134 as a colourless solid (68 mg, 0.09 mmol, 25%). mp 99-104° C.; $^1$H NMR (300 MHz, CDCl$_3$) δ 3.40 (0.8H, dd, J=8.0 and 4.6 Hz, Y/H-3), 3.48 (0.2H, dd, J=8.0 and 5.0 Hz, V/H-2), 3.61-3.73 (2H, m, 1H NCH$_2$, 0.2H V/H-3 and 0.8H Y/H-2), 3.85-3.96 (2H, m, 1H NCH$_2$, 0.2H V/H-1 and 0.8H Y/H-4), 4.28-4.37 (2.2H, m, 2H CH$_2$O, 0.2H V/H-4), 4.48-4.51 (0.8H, m, Y/H-1), 5.52-5.53 (0.2H, m, V/H-6), 5.54 (0.8H, dd, J=3.2 and 1.4 Hz, Y/H-6), 5.62 (1H, s, OH), 6.31 (1H, d, J=15.9 Hz, OCOCH), 6.75-7.61 (20H, m, 1H CHAr and 19H Ar), 8.47-8.51 (1.2H, m, 0.4H 2V/αPyr and 0.8H Y/αPyr), 8.61-8.64 (0.8H Y/αPyr); ν$_{max}$/cm 1169 (C—O ester), 1584 (C=O imide), 1700 (C=O ester); m/z (FAB+) 754 (MH$^+$, 17%), 736 (MH$^+$-H$_2$O, 12), 120 (100); (Found: MH$^+$ 754.1861, C$_{44}$H$_{34}$$^{35}$Cl$_2$N$_3$O$_5$ requires 754.1876).

N-2'-Cinnamoyloxypropyl-5-(α-hydroxy-α-2-pyridylbenzyl)-7-(α-2-pyridylbenzylidene)-5-norbornene-2,3-dicarboximide (135)

A similar procedure (Lu, M. C. et al. *J. Med. Chem.* 1987, 30, 273-278 and Nagao, Y. et al. *Tetrahedron Lett.* 1988, 29, 6133-6136) to that described for the preparation of 117 was followed using cinnamic acid (53 mg, 0.36 mmol) and oxalyl chloride (0.5 mL), under reflux for 3 h. A solution of 103 (100 mg, 0.04 mmol) and crude cinnamoyl chloride in pyridine (1 mL) was then stirred at 70° C. for 16 h. Purification by flash chromatography (hexane/ethyl acetate 1:1) afforded 135 as a colourless solid (25 mg, 0.08 mmol, 20%). mp 97-103° C.; $^1$H NMR (400 MHz, CDCl$_3$) δ 1.19-1.48 (3H, in Me), 3.36-3.95 (6H, m, 2H NCH$_2$, 1H CHMe, 1.2H V/H-1, V/H-2 and V/H-3, 0.3H W/H-2, W/H-3 and W/H-4, 1.5H Y/H-2, Y/H-3 and Y/H-4), 4.26-4.28 (0.4H, m, V/H-4), 4.42-4.44 (0.6H, m, 0.1H W/H-1 and 0.5H Y/H-1), 5.21-5.33 and 5.50-5.57 (1.9H, m, 0.4H V/H-6, 0.5H Y/H-6 and 1H OH), 5.99-6.01 (0.1H, m, W/H-6), 6.34-6.47 (1.1H, m, 1H OCOCH and 0.1H Ar), 6.70-7.76 (21.9H, m, 1H CHPh and 20.9H Ar), 8.45-8.53 (1.4H, m, 0.8H 2V/αPyr, 0.1H W/αPyr and 0.5H Y/αPyr), 8.60-8.63 (0.6H, m, 0.1H W/αPyr and 0.5H Y/αPyr); ν$_{max}$/cm$^{-1}$ 1082 and 1242 (C—O ester), 1585 (C=O imide), 1710 (C=O ester); m/z (FAB+) 700 (MH$^+$, 70%), 120 (100); (Found: MH$^+$ 700.2805, C$_{45}$H$_{38}$N$_3$O$_5$ requires 700.2812).

N-3'-Cinnamoyloxypropyl-5-(α-hydroxy-α-2-pyridylbenzyl)-7-(α-2-pyridylbenzylidene)-5-norbornene-2,3-dicarboximide (136)

A similar procedure (Lu, M. C. et al. *J. Med. Chem.* 1987, 30, 273-278 and Nagao, Y. et al. *Tetrahedron Lett.* 1988, 29, 6133-6136) to that described for the preparation of 117 was followed using cinnamic acid (53 mg, 0.36 mmol) and oxalyl chloride (0.5 mL), under reflux for 3 h. A solution of 104 (102 mg, 0.18 mmol) and crude cinnamoyl chloride in pyridine (1 mL) was then stirred at 70° C. for 16 h. Purification by flash chromatography (hexane/ethyl acetate 1:2) gave 136 (ca. 75% pure). Further purification by RP-HPLC afforded 136 as a colourless solid (19 mg, 0.03 mmol, 15%). mp 79-83° C.; $^1$H NMR (400 MHz, CDCl$_3$) δ 1.88-2.06 (2H, m, NCH$_2$CH$_2$CH$_2$O) 3.34-4.22 (4.2H, m, H-2, H-3, W/H-4, NCH$_2$CH$_2$CH$_2$O), 3.89-3.91 (0.4H, m, U/H-1, V/H-1), 3.95 (0.4H, m, Y/H-4), 4.13-4.22 (2.1H, m, NCH$_2$CH$_2$CH$_2$O, U/H-4), 4.30 (0.3H, m, V/H-4), 4.44-4.48 (0.6H, m, Y/H-1, W/H-1), 5.59 (0.3H, m, V/H-6), 5.63 (0.4H, m, Y/H-6), 5.67 (1H, s, OH), 6.06 (0.1H, m, U/H-6), 6.09 (0.2H, m, W/H-6), 6.46 (1H, d, J=15.6 Hz, COCH=CH), 6.73-7.74 (22H, m, COCH=CH, Ar), 8.42-8.65 (2H, m, αPyr); ν$_{max}$/cm$^{-1}$ 1042 and 1168 (C—O ester), 1584 (C=O imide), 1697 (C=O ester); m/z (FAB+) 700 (MH$^+$, 25%), 120 (100); (Found: MH$^+$ 700.2812, C$_{45}$H$_{38}$N$_3$O$_5$ requires 700.2812).

Alternatively, a similar procedure (Lu, M. C. et al. *J. Med. Chem.* 1987, 30, 273-278 and Nagao, Y. et al. *Tetrahedron Lett.* 1988, 29, 6133-6136) to that described for the preparation of 117 was followed using cinnamic acid (53 mg, 0.36 mmol) and oxalyl chloride (0.5 mL), under reflux for 3 h. A solution of 104 (102 mg, 0.18 mmol) and crude cinnamoyl chloride in pyridine (1 mL) was then stirred at 70° C. for 16 h. Purification by flash chromatography (hexane/ethyl acetate 1:2) gave 136 (ca. 75% pure). Further purification by RP-HPLC afforded 136 as a colourless solid (19 mg, 0.03 mmol, 15%).

N-4'-Cinnamoyloxybutyl-5-(α-hydroxy-α-2-pyridylbenzyl)-7-(α-2-pyridylbenzylidene)-5-norbornene-2,3-dicarboximide (137)

A similar procedure (Lu, M. C. et al. *J. Med. Chem.* 1987, 30, 273-278 and Nagao, Y. et al. *Tetrahedron Lett.* 1988, 29, 6133-6136) to that described for the preparation of 117 was followed using cinnamic acid (53 mg, 0.36 mmol) and oxalyl chloride (0.5 mL), under reflux for 3 h. A solution of 105 (105 mg, 0.18 mmol) and crude cinnamoyl chloride in pyridine (1 mL) was then stirred at 70° C. for 16 h. Purification by flash chromatography (hexane/ethyl acetate 1:2) gave 137 (ca. 80% pure). Further purification by RP-HPLC afforded 137 as a colourless solid (44 mg, 0.06 mmol, 34%). mp 82-87° C.; $^1$H NMR (400 MHz, CDCl$_3$) δ 1.54-1.77 (4H, m, NCH$_2$(CH$_2$)$_2$), 3.34-3.64 (4.2H, m, 2H NCH$_2$, 0.6H V/H-2 and V/H-3, 0.6H W/H-2, W/H-3 and W/H-4, 1H Y/H-2 and Y/H-3), 3.89-3.91 (0.3H, m, V/H-1), 3.93-3.95 (0.5H, m, Y/H-4), 4.20-4.23 (2H, m, CH$_2$O), 4.27-4.28 (0.3H, m, V/H-4), 4.42-4.46 (0.7H, m, 0.2H W/H-1 and 0.5H Y/H-1), 5.58-5.71 (1.8H, m, 0.3H V/H-6, 0.5H Y/H-6 and 1H OH), 6.06-6.07 (0.2H, m, W/H-6), 6.43 (1H, d, J=16.0 Hz, OCOCH), 6.74-7.63 (21H, m, Ar), 7.68 (1H, d, J=16.0 Hz, CHPh), 8.43-8.48 (1.3H, m, 0.6H 2V/αPyr, 0.2H W/αPyr and 0.5H Y/αPyr), 8.63-8.64 (0.7H, m, 0.2H W/αPyr and 0.5H Y/αPyr); $v_{max}$/cm$^{-1}$ 1028 and 1168 (C—O ester), 1584 (C=O imide), 1695 (C=O ester); m/z (FAB+) 714 (MH$^+$, 14%), 149 (100); (Found: MH$^+$ 714.2971, C$_{46}$H$_{40}$N$_3$O$_5$ requires 714.2968).

5-(α-Hydroxy-α-2-pyridylbenzyl)-N-[2'-(5"-phenyl-2"E,4"E-pentadienoyloxy)ethyl]-7-(α-2-pyridylbenzylidene)-5-norbornene-2,3-dicarboximide (187)

A similar procedure (Lu, M. C. et al. *J. Med. Chem.* 1987, 30, 273-278 and Nagao, Y. et al. *Tetrahedron Lett.* 1988, 29, 6133-6136) to that described for the preparation of 117 was followed using 5-phenyl-2E,4E-pentadienoic acid (125 mg, 0.72 mmol) and thionyl chloride (1 mL), under reflux for 2 h. A solution of 102 (200 mg, 0.36 mmol) and crude 5-phenyl-2E,4E-pentadienoyl chloride in pyridine (2 mL) was then stirred at 70° C. for 16 h. Purification by flash chromatography (hexane/ethyl acetate 1:1) afforded 187 as a colourless solid (8 mg, 0.004 mmol, 3%). mp 99-104° C.; $^1$H NMR (300 MHz, CDCl$_3$) δ 3.34-3.45 (0.7H, m, 0.3H W/H-3 and 0.4H Y/H-4), 3.49-3.53 (0.3H, m, V/H-2), 3.58-3.73 (2.3H, m, 1H NCH$_2$, 0.3H V/H-3, 0.6H W/H-2 and W/H-4, 0.4H Y/H-2), 3.82-3.96 (1.7H, m, 1H NCH$_2$, 0.3H V/H-1 and 0.4H Y/H-4), 4.26-4.44 (3H, m, 2H CH$_2$O, 0.3H V/H-4, 0.3H W/H-1 and 0.4H Y/H-1), 5.51-5.66 (1.7H, m, 0.3H V/H-6, 0.4H Y/H-6 and 1H OH), 5.82-6.06 (0.9H, m, 0.6H=CH and 0.3H W/H-6), 6.32 (0.4H, d, J=15.9 Hz, =CH), 6.73-7.67 (24H, m, 3H=CH and 21H Ar), 8.48-8.51 (1.3H, m, 0.6H 2V/αPyr, 0.3H W/αPyr and 0.4H Y/αPyr), 8.65-8.67 (0.7H, m, 0.3H W/αPyr and 0.4H Y/αPyr); $v_{max}$/cm (C—O ester), (C=O imide), (C=O ester); m/z (FAB+) (Found: MH$^+$, C$_{45}$H$_{38}$N$_3$O$_6$ requires). m/z (FAB+) 712 (MH$^+$, 9%), 120 (100); (Found: MH$^+$ 712.2811, C$_{46}$H$_{38}$N$_3$O$_5$ requires 712.2812).

5-(α-Hydroxy-α-2-pyridylbenzyl)-N-[2'-(2"-naphthylacryloyloxy)ethyl]-7-(α-2-pyridyl benzylidene)-5-norbornene-2,3-dicarboximide (188)

A similar procedure (Lu, M. C. et al. *J. Med. Chem.* 1987, 30, 273-278 and Nagao, Y. et al. *Tetrahedron Lett.* 1988, 29, 6133-6136) to that described for the preparation of 117 was followed using 3-(2-naphthyl)-acrylic acid (143 mg, 0.72 mmol) and thionyl chloride (1 mL), under reflux for 2 h. A solution of 102 (200 mg, 0.36 mmol) and crude 3-(2-naphthyl)-acryloyl chloride in pyridine (2 mL) was then stirred at 70° C. for 16 h. Purification by flash chromatography (hexane/ethyl acetate 1:1) afforded 188 as a colourless residue (5 mg, 0.007 mmol, 2%); $^1$H NMR (300 MHz, CDCl$_3$) δ 3.42 (0.6H, dd, J=7.8 and 4.5 Hz, Y/H-3), 3.50 (0.4H, dd, J=7.8 and 4.8 Hz, V/H-2), 3.62-3.96 (4H, m, 2H NCH$_2$, 0.8H V/H-3 and V/H-1, 1.2H Y/H-2 and Y/H-4), 4.24-4.41 (2.4H, m, 2H CH$_2$O and 0.4H V/H-4), 4.48-4.51 (0.6H, m, Y/H-1), 5.53-5.64 (1.7H, m, 0.4H V/H-6, 0.6H Y/H-6, 0.7H OH), 5.69 (0.3H s, OH), 6.44 (1H, d, J=16.2 Hz, OCOCH), 6.74-7.93 (24H, m, 1H CHAr and 23H Ar), 8.42-8.54 (1.4H, m, 0.8H 2V/αPyr and 0.6H Y/αPyr), 8.61-8.63 (0.6H, m, Y/αPyr); $v_{max}$/cm (C—O ester), (C=O imide), (C=O ester); m/z (FAB+) 736 (MH$^+$, 27%), 120 (100); (Found: MH$^+$ 736.2808, C$_{48}$H$_{38}$N$_3$O$_5$ requires 736.2812).

N-[2'-(Diphenylacetyloxymethyloxy)ethyl]-5-(α-hydroxy-α-2-pyridylbenzyl)-7-(α-2-pyridyl benzylidene)-5-norbornene-2,3-dicarboximide (201)

Compound 201 was prepared by a procedure similar to that of Miki and co-workers (Miki, T. et al. *J. Med. Chem.* 2002, 45, 4571-4580). To a solution of 102 (100 mg, 0.18 mmol) in dimethylformamide (1.2 mL) was added 164 (61 mg, 0.23 mmol) in dimethylformamide (0.5 mL) followed by sodium hydride (9.2 mg, 0.23 mmol). The mixture was stirred at room temperature for 4 h with a further addition of sodium hydride (9.2 mg, 0.23 mmol) after 2 h. The mixture was taken up in ethyl acetate (10 mL) and washed with water (10 mL), saturated sodium hydrogen carbonate (10 mL), and brine (10 mL). The organic extract was dried over anhydrous sodium sulfate and the solvent removed in vacuo, with purification by flash chromatography (hexane/ethyl acetate 1:1) affording 201 (ca. 75% pure). Further purification by RP-HPLC afforded 201 as a colourless residue (8 mg, 0.01 mmol, 6%); $^1$H NMR (300 MHz, CDCl$_3$) δ 3.22 (0.4H, dd, J=7.8 and 4.5 Hz, W/H-3), 3.28 (0.5H, dd, J=7.8 and 4.5 Hz, Y/H-3), 3.33 (0.1H, dd, J=8.1 and 4.8 Hz, V/H-2), 3.46-3.74 (3.4H, m, 1H CHPh$_2$, 1H NCH$_2$, 0.1H V/H-3, 0.8H W/H-2 and W/H-4, 0.5H Y/H-2), 3.79-3.92 (1.6H, m, 1H NCH$_2$, 0.1H V/H-1 and 0.5H Y/H-4), 4.29-4.46 (5H, m, 2H OCH$_2$O, 2H CH$_2$CH$_2$O, 0.1H V/H-4, 0.4H W/H-1 and 0.5H Y/H-1), 5.46-5.57 (1.6H, m, 0.1H V/H-6, 0.5H Y/H-6 and 1H OH), 6.01 (0.4H, dd, J=3.3 and 1.2 Hz, W/H-6), 6.73-7.62 (26H, m, Ar), 8.38-8.40 and 8.45-8.49 (1.1H, m, 0.2H 2V/αPyr, 0.4H W/αPyr and 0.5H Y/αPyr), 8.64-8.65 (0.9H, m, 0.4H W/αPyr and 0.5H Y/αPyr); $v_{max}$/cm$^{-1}$ 1186 and 1219 (C—O ester), 1586 (C=O imide), 1703 (C=O ester); m/z (FAB+) 780 (MH$^+$, 25%), 120 (100); (Found: MH$^+$ 780.3090, C$_{50}$H$_{42}$N$_3$O$_6$ requires 780.3074).

Monophenyl Succinate (205)

To a stirred suspension of sodium hydride (212 mg, 5.3 mmol) in anhydrous tetrahydrofuran (1 mL) was added a solution of phenol (500 mg, 5.3 mmol) in anhydrous tetrahydrofuran (1 mL) and the mixture stirred at room temperature for 1 h. A solution of succinic anhydride (530 mg, 5.3 mmol) in anhydrous tetrahydrofuran (2 mL) was added and the mixture stirred at room temperature for a further 10 min. The reaction mixture was quenched with water (10 mL), acidified with an aqueous solution of hydrochloric acid (2M), extracted with dichloromethane (3×10 mL) and dried over anhydrous magnesium sulfate. The solvent was removed in vacuo with purification by flash chromatography (hexane/ethyl acetate 7:3) affording 205 as a colourless solid (60 mg, 0.3 mmol, 6%); $^1$H NMR (400 MHz, CDCl$_3$) δ 2.78-2.92 (4H, m, 2×CH$_2$), 7.07-7.09 (2H, m, Ar), 7.19-7.27 (1H, m, Ar), 7.34-7.39 (2H, m, Ar).

5-(α-Hydroxy-α-2-pyridylbenzyl)-N-2'-(monophenyl)succinoyloxyethyl-7-(α-2-pyridyl benzylidene)-5-norbornene-2,3-dicarboximide (204)

A similar procedure (Lu, M. C. et al. *J. Med. Chem.* 1987, 30, 273-278 and Nagao, Y. et al. *Tetrahedron Lett.* 1988, 29, 6133-6136) to that previously described for the preparation of 117 was followed using 205 (140 mg, 0.72 mmol) and oxalyl chloride (1 mL), under reflux for 1 h. A solution of 102 (200 mg, 0.36 mmol) and crude 4-oxo-4-phenoxybutanoyl chloride in pyridine (2 mL) was then stirred at 0° C., warming to room temperature over 16 h. Purification by flash chromatography (hexane/ethyl acetate 1:2) afforded 204 as a colourless solid (28.9 mg, 0.04 mmol, 11%). mp 74-78° C.; $^1$H NMR (400 MHz, CDCl$_3$) δ 2.56-2.76 (2H, m, CH$_2$COOPh), 2.79-2.95 (2H, m, CH$_2$OCOCH$_2$), 3.29-3.32 (0.2H, m, W/H-3), 3.34-3.70 (3H, m, 1H NCH$_2$, 0.4H V/H-2 and V/H-3, 0.4H W/H-2 and W/H-4, 1.2H Y/H-2 and Y/H-3), 3.76-3.87 (1.2H, m, 1H NCH$_2$ and 0.2H V/H-1), 3.91-3.92 (0.6H, m, Y/H-4), 4.18-4.50 (3H, m, 2H CH$_2$O and 0.2H V/H-4, 0.2H W/H-1 and 0.6H Y/H-1), 5.49-5.68 (1.8H, m, 0.2H V/H-6, 0.6H Y/H-6 and 1H OH), 6.05-6.06 (0.2H, m, W/H-6), 6.73-7.58 (21H, m, Ar), 8.41-8.48 (1.2H, m, 0.4H 2V/αPyr, 0.2H W/αPyr and 0.6H Y/αPyr), 8.60-8.64 (0.8H, m, 0.211 W/αPyr and 0.6H Y/αPyr); $v_{max}$/cm$^{-1}$ 1136 and 1192 (C—O ester), 1585 (C=O imide), 1701 (C=O ester); m/z (FAB+) 732 (MH$^+$, 25%), 120 (100); (Found: MH$^+$ 732.2710, C$_{45}$H$_{38}$N$_3$O$_7$ requires 732.2710).

N-[2'-(4-Aminomethylbenzoyloxy)ethyl]-5-(α-hydroxy-α-2-pyridylbenzyl)-7-(α-2-pyridylbenzylidene)-5-norbornene-2,3-dicarboximide trifluoroacetate (342)

A similar procedure (Schwartz, E. et al. Macromolecules 2011, 44, 4735-4741) to that previously described for the preparation of 347 was followed using 2 (1.0 g, 1.80 mmol), N-(t-butyloxycarbonyl)-4-aminomethylbenzoic acid (0.50 g, 1.98 mmol), 1-ethyl-3-(3-dimethylaminopropyl)carbodiimide (0.41 g, 2.16 mmol), triethylamine (0.82 mL, 5.93 mmol) and dimethylaminopyridine (44 mg, 0.36 mmol) in dichloromethane (25 mL), at room temperature for 18 h. Purification by flash chromatography (hexane/ethyl acetate 1:1) afforded N-[2'-(t-butyloxycarbonyl-4-aminomethylbenzoyloxy)ethyl]-5-(α-hydroxy-α-2-pyridylbenzyl)-7-(α-2-pyridylbenzylidene)-5-norbornene-2,3-dicarboximide as a white solid (0.62 g, 0.79 mmol, 44%). mp 110-115° C.; $^1$H NMR (400 MHz, CDCl$_3$) δ 1.47 (9H, br s, NHBoc), 3.30-4.50 (10H, m, NCH$_2$CH$_2$O, CH$_2$NHBoc, H-1, H-2, H-3, H-4), 4.90 (1H, br s, NHBoc), 5.53 (0.3H, m, V/H-6), 5.57 (0.4H, m, Y/H-6), 5.61 (OH), 5.63 (OH), 5.64 (OH), 5.70 (OH), 6.03 (0.1H, m, U/H-6), 6.06 (0.2H, m, W/H-6), 6.75-7.60 (18H, m, Ar), 7.84-7.93 (2H, m, Ar), 8.42-8.63 (2H, m, αPyr); $v_{max}$ (NaCl)/cm$^{-1}$ 1153, 1214 (C—O ester), 1586 (C=O imide), 1707 (C=O ester); m/z (ESI, 70 eV) 811 (MNa$^+$, 100%); (Found MNa$^+$ 811.3104), C$_{48}$H$_{44}$N$_4$NaO$_7$ requires 811.3102. To a solution of N-[2'-(t-butyloxycarbonyl-4-aminoethylbenzoyloxy)ethyl]-5-(α-hydroxy-α-2-pyridylbenzyl)-7-(α-2-pyridylbenzylidene)-5-norbornene-2,3-dicarboximide (0.55 g, 0.70 mmol) in dichloromethane (7 mL) was added trifluoroacetic acid (3 mL), and the mixture stirred at room temperature for 5 h. The solvent was removed in vacuo and the resultant oil triturated with diethyl ether, and the resulting solid then collected by filtration and dried in vacuo to afford 342 as a trifluoroacetate salt (white solid; 0.53 g, 0.66 mmol, 95%). $^1$H NMR (400 MHz, d$_6$-DMSO) δ 3.50-4.50 (10H, m, NCH$_2$CH$_2$O, CH$_2$NH$_2$.TFA, H-1, H-2, H-3, H-4), 5.67 (0.3H, m, V/H-6), 5.70 (0.4H, m, Y/H-6), 5.91 (0.1H, m, U/H-6), 5.97 (0.2H, m, W/H-6), 7.00-8.00 (20H, m, Ar), 8.45-8.70 (2H, m, αPyr); $v_{max}$ (NaCl)/cm$^{-1}$ 1125, 1180 (C—O ester), 1611 (C=O imide), 1674 (C=O ester); m/z (ESI, 70 eV) 689 (MH$^+$, 100%); (Found MH$^+$ 689.2758), C$_{43}$H$_{37}$N$_4$O$_5$ requires 689.2759.

5-(α-Hydroxy-α-2-pyridylbenzyl)-N-[2'-(α-methylaspartoyloxy)ethyl]-7-(α-2-pyridylbenzylidene)-5-norbornene-2,3-dicarboximide trifluoroacetate (343)

A similar procedure (Schwartz, E. et al. Macromolecules 2011, 44, 4735-4741) to that previously described for the preparation of 347 was followed using 2 (1.00 g, 1.80 mmol), N-(tert-butyloxy)carbonyl-α-methylaspartic acid (0.67 g, 2.69 mmol), 1-ethyl-3-(3-dimethylaminopropyl)carbodiimide (0.41 g, 2.16 mmol), triethylamine (0.82 mL, 5.93 mmol) and dimethylaminopyridine (44 mg, 0.36 mmol) in dichloromethane (25 mL), at room temperature for 18 h. Purification by flash chromatography (hexane/ethyl acetate 1:1) afforded N-[2'-(t-butyloxycarbonyl-α-methylaspartoyloxy)ethyl]-5-(α-hydroxy-α-2-pyridylbenzyl)-7-(α-2-pyridylbenzylidene)-5-norbornene-2,3-dicarboximide as a white solid (0.55 g, 0.70 mmol, 39%). mp 87-92° C.; $^1$H NMR (400 MHz, CDCl$_3$) δ 1.48 (9H, br s, NHBoc), 2.55-2.95 (2H, m, CH$_2$CHNHBoc), 3.30-4.50 (12H, m, NCH$_2$CH$_2$O, CHNHBoc, Me, H-1, H-2, H-3, H-4), 5.51 (0.3H, m, V/H-6), 5.55 (0.4H, m, Y/H-6), 6.03 (0.1H, m, U/H-6), 6.05 (0.2H, m, W/H-6), 6.70-7.65 (16H, m, Ar), 8.41-8.63 (2H, m, αPyr); $v_{max}$ (NaCl)/cm$^{-1}$ 1147, 1217 (C—O ester), 1586 (C=O imide), 1706 (C=O ester); m/z (ESI, 70 eV) 807 (MNa$^+$, 100%); (Found MNa$^+$ 807.3001), C$_{45}$H$_{44}$N$_4$NaO$_9$ requires 809.2998. To a solution of N-[2'-(t-butyloxycarbonyl-α-methylaspartoyloxy)ethyl]-5-(α-hydroxy-α-2-pyridylbenzyl)-7-(α-2-pyridylbenzylidene)-5-norbornene-2,3-dicarboximide (0.55 g, 0.70 mmol) in dichloromethane (7 mL) was added trifluoroacetic acid (3 mL), and the mixture stirred at room temperature for 5 h. The solvent was removed in vacuo and the resultant oil triturated with diethyl ether, and the resulting solid then collected by filtration and dried in vacuo to afford 343 as a trifluoroacetate salt (white solid; 0.52 g, 0.65 mmol, 93%). $^1$H NMR (400 MHz, d$_6$-DMSO) 82.85-2.90 (2H, m, CH$_2$CHNH$_2$.TFA), 3.30-4.50 (12H, m, NCH$_2$CH$_2$O, CHNH$_2$.TFA, Me, H-1, H-2, H-3, H-4), 5.62 (0.3H, m, V/H-6), 5.65 (0.4H, m, Y/H-6), 5.90 (0.1H, m, U/H-6), 5.95 (0.2H, m, W/H-6), 7.00-7.7.90 (16H, m, Ar), 8.45-8.70 (2H, m, αPyr); $v_{max}$ (NaCl)/cm$^{-1}$ 1127, 1178 (C—O ester), 1614 (C=O imide), 1679 (C=O ester); m/z (ESI, 70 eV) 685 (MH$^+$, 100%); (Found MH$^+$ 685.2675), C$_{40}$H$_{37}$N$_4$O$_7$ requires 685.2657.

5-(α-Hydroxy-α-2-pyridylbenzyl)-7-(α-2-pyridylbenzylidene)-N-succinoyloxymethyl-5-norbornene-2,3-dicarboximide dimer (21)

A similar procedure (Hursthouse, M. B. et al. *Tetrahedron Lett.* 1995, 36, 5979-5982) to that described for the preparation of 8 was followed using NRB (200 mg, 0.39 mmol) in dimethylformamide (2 mL), dichloromethyl succinate (60) (42 mg, 0.20 mmol) in dimethylformamide (0.5 mL) and potassium carbonate (54 mg, 0.40 mmol), at room temperature for 16 h. Purification by flash chromatography (chloroform/methanol 100:1) afforded 21 as a colourless solid (40 mg, 0.03 mmol, 17%). mp 129-148° C.; $^1$H NMR (300 MHz, CDCl$_3$) δ 2.65-2.71 (4H, m, 2×OCOCH$_2$), 3.38-3.76 (4.3H, m, H-1, H-2, H-3 and H-4), 3.87-3.93 (0.4H, m, H-1, H-2, H-3 and H-4), 3.98-3.99 (1.1H, m, H-1, H-2, H-3 and H-4), 4.17-4.19 (0.4H, m, H-1, H-2, H-3 and H-4), 4.34-4.35 (0.4H, m, H-1, H-2, H-3 and H-4), 4.49-4.51 (1.4H, m, H-1, H-2, H-3 and H-4), 5.30-5.34 (1.5H, m, NCH$_2$O and OH), 5.48-5.64 (5.1H, m, NCH$_2$O, H-6 and OH), 5.79-5.80 (0.6H, m, NCH$_2$O, H-6 and OH), 6.04-6.07 (0.8H, m, H-6 and OH), 6.74-7.61 (32H, m, Ar), 8.42-8.47 (1.2H, m, αPyr), 8.55-8.56 (1.3H, m, αPyr), 8.61-8.62 (1.5H, m, αPyr); $v_{max}$(NaCl)/cm$^{-1}$ 1144 and 1265 (C—O ester), 1585 (C=O imide), 1716 (C=O ester); m/z (FAB+) 1165 (MH$^+$, 14%), 397 (100); (Found: MH$^+$ 1165.4106, C$_{72}$H$_{57}$N$_6$O$_{13}$ requires 1165.4136).

N-Adipoyloxymethyl-5-(α-hydroxy-α-2-pyridylbenzyl)-7-(α-2-pyridylbenzylidene)-5-norbornene-2,3-dicarboximide dimer (22)

A similar procedure (Hursthouse, M. B. et al. *Tetrahedron Lett.* 1995, 36, 5979-5982) to that described for the preparation of 8 was followed using NRB (100 mg, 0.20 mmol) in dimethylformamide (1 mL), dichloromethyl adipate (61) (24 mg, 0.10 mmol) in dimethylformamide (0.5 mL) and potassium carbonate (27 mg, 0.20 mmol), at room temperature for 16 h. Purification by flash chromatography (chloroform/methanol 100:1) afforded 22 as a colourless solid (40 mg, 0.03 mmol, 16%). mp 117-124° C.; $^1$H NMR (300 MHz, CDCl$_3$) δ 1.56-1.80 (4H, m, 2×OCOCH$_2$CH$_2$), 2.26-2.48 (4H, m, 2×OCOCH$_2$), 3.37-3.78 (4.5H, m, H-1, H-2, H-3 and H-4), 3.84-3.92 (0.7H, m; H-1, H-2, H-3 and H-4), 3.97-3.99 (0.9H, bm, H-1, H-2, H-3 and H-4), 4.16-4.21 (0.2H, bm, H-1, H-2, H-3 and H-4), 4.32-4.39 (0.5H, bm, H-1, H-2, H-3 and H-4), 4.45-4.55 (1.2H, bm, H-1, H-2, H-3 and H-4), 5.28-5.36 (1.4H, m, NCH$_2$O and OH), 5.42-5.61 (5.4H, m, NCH$_2$O, H-6 and OH), 5.74, 5.75 (0.5H, bs, OH), 5.82 (0.1H, bs, OH), 6.03-6.06 (0.6H, m, H-6 and OH), 6.74-7.58 (32H, m, Ar), 8.43-8.54 (2.8H, m, αPyr), 8.61-8.62 (1.2H, m, αPyr); ν$_{max}$(NaCl)/cm$^{-1}$ 1139 and 1216 (C—O ester), 1585 (C=O imide), 1717 (C=O ester); m/z (FAB+) 1193 (MH$^+$ 33%), 397 (100); (Found: MH$^+$ 1193.4463, C$_{74}$H$_{61}$N$_6$O$_{10}$ requires 1193.4449).

5-(α-Hydroxy-α-2-pyridylbenzyl)-7-(α-2-pyridylbenzylidene)-N-suberoyloxymethyl-5-norbornene-2,3-dicarboximide dimer (23)

A similar procedure (Hursthouse, M. B. et al. *Tetrahedron Lett.* 1995, 36, 5979-5982 and Bodor, N. et al. *J. Org. Chem.* 1983, 48, 5280-5284) to that described for the preparation of 18 was followed using dichloromethyl suberate (62) (44 mg, 0.16 mmol) and sodium iodide (49 mg, 0.32 mmol) in acetone (0.5 mL), at room temperature for 3 h. A solution of NRB (164 mg, 0.32 mmol), crude diiodomethyl suberoate and potassium carbonate (50 mg, 0.36 mmol) in dimethylformamide (1.5 mL) was then stirred at room temperature for 48 hours. Purification by flash chromatography (hexane/ethyl acetate 1:2) afforded 23 as a colourless solid (15 mg, 0.01 mmol, 6%). mp 112-116° C.; $^1$H NMR (300 MHz, CDCl$_3$) δ 1.20-1.41 (4H, m, 2×OCOCH$_2$CH$_2$CH$_2$), 1.49-1.76 (4H, m, 2×OCOCH$_2$CH$_2$), 2.21-2.44 (4H, m, 2×OCOCH$_2$), 3.36 (0.6H, dd, J=8.1 and 4.5 Hz, W/H-3), 3.43 (0.8H, dd, J=7.8 and 4.5 Hz, Y/H-3), 3.52-3.74 (3.2H, m, 1.2H V/H-2 and V/H-3, 1.2H W/H-2 and W/H-4 and 0.8H Y/H-2), 3.86-3.92 (0.6H, m, V/H-1), 3.95-4.03 (0.8H, m, Y/H-4), 4.34-4.39 (0.6H, m, V/H-4), 4.48-4.59 (1.4H, m, 0.6H W/H-1 and 0.8H Y/H-1), 5.27 (0.85H, s, H$_a$NCH$_2$O), 5.30 (0.85H, s, H$_b$NCH$_2$O), 5.45-5.58 (5.3H, m, 2.3H NCH$_2$O, 0.6H V/H-6, 0.8H Y/H-6 and 1.6H OH), 5.74 (0.4H, s, OH), 6.05-6.06 (0.6H, m, W/H-6), 6.73-7.60 (32H, m, Ar), 8.48-8.54 (2.6H, m, 1.2H 2V/αPyr, 0.6H W/αPyr, 0.8H Y/αPyr), 8.62-8.64 (1.4H, m, 0.611 W/αPyr and 0.8H Y/αPyr); ν$_{max}$/cm$^{-1}$ 1118 and 1211 (C—O ester), 1584 (C=O imide), 1715 (C=O ester); m/z (FAB+) 1221 (MH$^+$, 28%), 397 (100); (Found: MH$^+$ 1221.4771, C$_{76}$H$_{65}$N$_6$O$_{10}$ requires 1221.4762).

5-(α-Hydroxy-α-2-pyridylbenzyl)-7-(α-2-pyridylbenzylidene)-N-sebacoyloxymethyl-5-norbornene-2,3-dicarboximide dimer (24)

A similar procedure (Hursthouse, M. B. et al. *Tetrahedron Lett.* 1995, 36, 5979-5982) to that described for the preparation of 8 was followed using NRB (100 mg, 0.20 mmol) in dimethylformamide (1 mL), dichloromethyl sebacate (63) (29 mg, 0.10 mmol) in dimethylformamide (0.2 mL) and potassium carbonate (27 mg, 0.20 mmol), at room temperature for 48 h. Purification by flash chromatography (chloroform/methanol 100:1) afforded 24 as a colourless solid (101 mg, 0.08 mmol, 81%). mp 113-121° C.; $^1$H NMR (400 MHz, CDCl$_3$) δ 1.23-1.37 (8H, bm, 2×OCO(CH$_2$)$_2$(CH$_2$)$_2$), 1.55-1.67 (4H, bm, 2×OCOCH$_2$CH$_2$), 2.26-2.38 (4H, m, 2×OCOCH$_2$), 3.37 (0.4H, dd, J=7.9 and 4.5 Hz, W/H-3), 3.43 (0.9H, dd, J=7.9 and 4.5 Hz, Y/H-3), 3.50-3.59 (0.9H, m, 0.4H U/H-2 and U/H-3 and 0.5H V/H-2), 3.62-3.74 (2.2H, m, 0.5H V/H-3, 0.8H W/H-2 and W/H-4 and 0.9H Y/H-2), 3.88-3.92 (0.7H, m, 0.2H U/H-1 and 0.5H V/H-1), 3.98 (0.9H, dt, J=4.4 and 1.3 Hz, Y/H-4), 4.19-4.20 (0.2H, m, U/H-4), 4.36-4.37 (0.5H, m, V/H-4), 4.50-4.53 (1.3H, m, 0.4H W/H-1 and 0.9H Y/H-1), 5.28-5.31 (1.4H, m, NCH$_2$O), 5.42-5.60 (4H, m, 2.6H NCH$_2$O, 0.5H V/H-6, 0.9H Y/H-6), 5.74 (2H, s, OH), 6.03 (0.2H, dd, J=3.3 and 1.1 Hz, U/H-6), 6.05 (0.4H, dd, J=3.3 and 1.1 Hz, W/H-6), 6.74-7.59 (32H, m, Ar), 8.41-8.48 (1.4H, m, 0.4H 2U/αPyr and 1H 2VαPyr), 8.52-8.53 (1.3H, m, 0.4H W/αPyr and 0.9H Y/αPyr) 8.61-8.63 (1.3H, m, 0.4H W/αPyr and 0.9H Y/αPyr); ν$_{max}$(NaCl)/cm$^{-1}$ 1152 and 1211 (C—O ester), 1585 (C=O imide), 1718 (C=O ester); m/z (FAB+) 1249 (MH$^+$, 19%), 397 (100); (Found: MH$^+$ 1249.5065, C$_{78}$H$_{69}$N$_6$O$_{10}$ requires 1249.5075).

N-Dodecanedioyloxymethyl-5-(α-hydroxy-α-2-pyridylbenzyl)-7-(α-2-pyridylbenzylidene)-5-norbornene-2,3-dicarboximide dimer (25)

A similar procedure (Hursthouse, M. B. et al. *Tetrahedron Lett.* 1995, 36, 5979-5982) to that described for the preparation of 8 was followed using NRB (200 mg, 0.39 mmol) in dimethylformamide (1 mL), dichloromethyl dodecanedioate (64) (66 mg, 0.20 mmol) in dimethylformamide (0.2 mL) and potassium carbonate (54 mg, 0.39 mmol), at room temperature for 48 h. Purification by flash chromatography (hexane/ethyl acetate 1:2) afforded 25 as a colourless solid (60 mg, 0.05 mmol, 12%). mp 105-110° C.; $^1$H NMR (300 MHz, CDCl$_3$) δ 1.20-1.39 (12H, bm, 2×OCO(CH$_2$)$_2$(CH$_2$)$_3$), 1.54-1.73 (4H, m, 2×OCOCH$_2$CH$_2$), 2.28-2.40 (4H, m, 2×OCOCH$_2$), 3.43 (1.5H, dd, J=7.8 and 4.5 Hz, Y/H-3), 3.52 (0.5H, dd, J=8.1 and 5.0 Hz, V/H-2), 3.66-3.74 (2H, m, 0.5H V/H-3, 1.5H Y/H-2), 3.88-3.92 (0.5H, m, V/H-1), 3.98-4.00 (1.5H, m, Y/H-4), 4.35-4.37 (0.5H, m, V/H-4), 4.50-4.53 (1.5H, m, Y/H-1), 5.28-5.32 (2H, m, NCH$_2$O), 5.46-5.59 (5.5H, m, 2H NCH$_2$O, 0.5H V/H-6, 1.5H Y/H-6 and 1.6H OH), 5.74 (0.4H, s, OH), 6.74-7.59 (32H, m, Ar), 8.48-8.54 (2.5H, m, 1H 2V/αPyr and 1.5H Y/αPyr), 8.62-8.64 (1.5H, m, 1.5H Y/αPyr); ν$_{max}$/cm$^{-1}$ 1149 and 1209 (C—O ester), 1585 (C=O imide), 1713 (C=O ester); m/z (ESI+) 1277 (MH$^+$, 28%), 627 (100); (Found: MH$^+$ 1277.5441, C$_{76}$H$_{65}$N$_6$O$_{10}$ requires 1277.5383).

5-(α-Hydroxy-α-2-pyridylbenzyl)-7-(α-2-pyridylbenzylidene)-N-terephthaloyloxymethyl-5-norbornene-2,3-dicarboximide dimer (26)

A similar procedure (Hursthouse, M. B. et al. *Tetrahedron Lett.* 1995, 36, 5979-5982) to that described for the preparation of 8 was followed using NRB (200 mg, 0.39 mmol) in dimethylformamide (1 mL), dichloromethyl terephthalate (65) (53 mg, 0.20 mmol) in dimethylformamide (0.2 mL) and potassium carbonate (54 mg, 0.39 mmol), at room temperature for 48 h. Purification by flash chromatography (hexane/ethyl acetate 1:2) afforded 26 as a colourless solid (49 mg, 0.04 mmol, 21%). mp 150-157° C.; $^1$H NMR (400 MHz, CDCl$_3$) δ 3.42 (0.5H, dd, J=8.0 and 4.4 Hz, W/H-3), 3.49 (0.8H, dd, J=8.0 and 4.4 Hz, Y/H-3), 3.55-3.65 and 3.70-3.80 (3.2H, 0.4H U/H-2 and U/H-3, 1H V/H-2 and V/H-3, 1H W/H-1 and W/H-2, 0.8H Y/H-2), 3.90-3.95 (0.7H, m, 0.2H U/H-1 and 0.5H V/H-1), 3.99-4.05 (0.8H, m, Y/H-4), 4.19-4.23 (0.2H, m, U/H-4), 4.35-4.40 (0.5H, m, V/H-4), 4.48-4.56 (1.3H, bm, 0.5H W/H-1 and 0.8H Y/H-1), 5.53-5.57 (3.4H, m, NCH$_2$O and OH), 5.64-5.74 (2.3H, m, 1H NCH$_2$O and OH, 0.5H V/H-6, 0.8H Y/H-6), 5.82-5.86 (1.3H, m, NCH$_2$O and OH), 6.09-6.16 (0.7H, m, 0.2H U/H-6 and 0.5H W/H-6), 6.26 (0.3H, s, OH), 6.74-7.60 (32H, m, Ar), 8.04-8.16 (4H, m, Ar), 8.41-8.50 (2.7H, m, 0.4H 2U/αPyr, 1H 2U/αPyr, 0.5H W/αPyr and 0.8H Y/αPyr), 8.62-8.63 (1.3H, m, 0.5H W/αPyr and 0.8HαPyr); $v_{max}$/cm$^{-1}$ 1079 and 1241 (C—O ester), 1585 (C=O imide), 1713 (C=O ester); m/z (FAB+) 1213 (MH$^+$, 4%), 120 (100); (Found: MH$^+$ 1213.4124, C$_{76}$H$_{57}$N$_6$O$_{10}$ requires 1213.4136).

N-[α-(Ethylenebis(hydrogensuccinoyloxy))methyl]-5-(α-hydroxy-α-2-pyridylbenzyl)-7-(α-2-pyridyl-benzylidene)-5-norbornene-2,3-dicarboximide dimer (27)

A similar procedure (Hursthouse, M. B. et al. *Tetrahedron Lett.* 1995, 36, 5979-5982 and Bodor, N. et al. *J. Org. Chem.* 1983, 48, 5280-5284) to that described for the preparation of 18 was followed using dichloromethyl ethylene bis(hydrogen succinate) (68) (56 mg, 0.2 mmol) and sodium iodide (30 mg, 0.2 mmol) in acetone (1.5 mL), at room temperature for 3 h. A solution of NRB (200 mg, 0.39 mmol), crude diiodomethyl ethylene bis(hydrogen succinate) and potassium carbonate (54.0 mg, 0.40 mmol) in dimethylformamide (2 mL) was then stirred at room temperature for 16 h. Purification by flash chromatography (chloroform/methanol 100:1, then hexane/ethyl acetate 4:1 to 3:2) afforded 27 as an oily colourless solid (68 mg, 0.05 mmol, 26%). mp 49° C.; $^1$H NMR (400 MHz, CDCl$_3$) δ 2.61-2.73 (8H, m, 2×NCH$_2$OCO(CH$_2$)$_2$), 3.37 (0.6H, dd, J=7.9 and 4.4 Hz, W/H-3), 3.44 (1H, dd, J=7.9 and 4.6 Hz, Y/H-3), 3.50-3.74 (3H, m, 0.4H U/H-2 and U/H-3, 0.4H V/H-2 and V/H-3, 1.2H W/H-2 and W/H-4 and 1H Y/H-2), 3.87-3.91 (0.4H, m, 0.2H U/H-1 and 0.2H V/H-1), 3.97 (1H, dt, J=4.4 and 1.2 Hz, Y/H-4), 4.18-4.19 (0.2H, m, U/H-4), 4.26-4.36 (4.2H, m, 0.2H V/H-4, 4H COO(CH$_2$)$_2$OCO), 4.50-4.51 (1.6H, m, 0.6H W/H-1 and 1H Y/H-1), 5.30-5.34 (1.3H, m, NCH$_2$O and OH), 5.47-5.60 (5.9H, m, 4.7H NCH$_2$O and OH, 0.2H V/H-6, 1H Y/H-6), 6.04 (0.2H, dd, J=3.3 and 1.2 Hz, U/H-6), 6.06 (0.6H, dd, J=3.2 and 1.0 Hz, W/H-6), 6.75-7.59 (32H, m, Ar), 8.42-8.54 (2.4H, m, 0.4H 2U/αPyr, 0.4H 2V/αPyr, 0.6H W/αPyr and 1HY/αPyr), 8.62-8.63 (1.6H, m, 0.6H W/αPyr and 1H Y/αPyr); $v_{max}$ (NaCl)/cm$^{-1}$ 1147 and 1214 (C—O ester), 1586 (C=O imide), 1714 (C=O ester); m/z (FAB+) 1309 (MH$^+$, 8%), 120 (100); (Found: MH$^+$ 1309.4546, C$_{78}$H$_{65}$N$_6$O$_{14}$ requires 1309.4559).

5-(α-Hydroxy-α-2-pyridylbenzyl)-7-(α-2-pyridyl-benzylidene)-N-2'-succinoyloxyethyl-5-norbornene-2,3-dicarboximide dimer (138)

A similar procedure (Nagao, Y. et al. *Tetrahedron Lett.* 1988, 29, 6133-6136) to that described for the preparation of 109 was followed using 102 (200 mg, 0.36 mmol) and succinyl chloride (21 μL, 0.18 mmol) in pyridine (2 mL), at 70° C. for 16 h. Purification by flash chromatography (dichloromethane/methanol 20:1) afforded 138 as a colourless solid (10 mg, 0.008 mmol, 2%). mp 120-128° C.; $^1$H NMR (300 MHz, CDCl$_3$) δ 2.41-2.60 (4H, m, OCO(CH$_2$)$_2$COO), 3.33 (0.1H, dd, J=8.0 and 4.8 Hz, W/H-3), 3.93 (0.9H, dd, J=7.8 and 4.6 Hz, Y/H-3), 3.47-3.52 (1H, m, V/H-2), 3.55-3.67 (4.1H, m, 2H NCH$_2$, 1H V/H-3, 0.2H W/H-2 and W/H-4, 0.9H Y/H-2), 3.73-3.84 (2H, m, NCH$_2$), 3.85-3.89 (1H, m, V/H-1), 3.92-3.94 (0.9H, m, Y/H-4), 4.13-4.31 (5H, m, 4H 2×CH$_2$O, 1H V/H-4), 4.46-4.49 (1H, m, 0.1H W/H-1 and 0.9HY/H-1), 5.51-5.72 (3.9H, m, 1H V/H-6, 0.9HY/H-6 and 2H OH), 6.01-6.05 (0.1H, m, W/H-6), 6.74-7.61 (32H, m, Ar), 8.38-8.50 (3H, m, 2H V/αPyr, 0.1H W/αPyr and 0.9H Y/αPyr), 8.62-8.64 (1H, m, 0.1H W/αPyr and 0.9H Y/αPyr); $v_{max}$/cm$^{-1}$ 1041 and 1153 (C—O ester), 1584 (C=O imide), 1700 (C=O ester); m/z (FAB+) 1193 (MH$^+$, 4%), 149 (100); (Found: MH$^+$ 1193.4454, C$_{74}$H$_{61}$N$_6$O$_{10}$ requires 1193.4449).

N-2'-Adipoyloxyethyl-5-(α-hydroxy-α-2-pyridyl-benzyl)-7-(α-2-pyridylbenzylidene)-5-norbornene-2,3-dicarboximide dimer (139)

A similar procedure (Nagao, Y. et al. *Tetrahedron Lett.* 1988, 29, 6133-6136) to that described for the preparation of 109 was followed using 102 (200 mg, 0.36 mmol) and adipoyl chloride (26 μL, 0.18 mmol) in pyridine (2 mL), at 70° C. for 16 h. Purification by flash chromatography (dichloromethane/methanol 20:1) afforded 139 as a colourless solid (33 mg, 0.03 mmol, 8%). mp 110-116° C.; $^1$H NMR (300 MHz, CDCl$_3$) δ 1.51-1.76 (4H, bm, 2×OCOCH$_2$CH$_2$), 2.12-2.47 (4H, m, 2×OCOCH$_2$), 3.40 (0.1H, dd, J=8.0 and 4.4 Hz, W/H-3), 3.46 (0.8H, dd, J=8.0 and 4.4 Hz, Y/H-3), 3.52-3.60, 3.62-3.73 and 3.82-3.90 (7.2H, m, 4H 2×NCH$_2$, 0.2H U/H-2 and U/H-3, 2H V/H-2 and V/H-3, 0.2H W/H-2 and W/H-4, 0.8H Y/H-2), 3.94-3.98 (1.1H, m, 0.1H U/H-1 and 1H V/H-1), 4.00-4.02 (0.8H, m, Y/H-4), 4.09-4.10, 4.18-4.33 and 4.36-4.40 (5.1H, m, 4H 2×CH$_2$OCO, 0.1H U/H-4 and 1H V/H-4), 4.53-4.55 (0.9H, m, 0.1H1, V/H-1 and 0.8H Y/H-1), 5.60-5.76 (3.8H, m, 1H V/H-6, 0.8H Y/H-6 and 2H OH), 6.11-6.16 (0.2H, m, 0.1H U/H-6 and 0.1H W/H-6), 6.88-7.80 (32H, m, Ar), 8.56-8.65 (3.1H, m, 0.2H 2U/αPyr, 2H 2V/αPyr, 0.1H W/αPyr and 0.8H Y/αPyr), 8.79-8.80 (0.9H, m, 0.1H W/αPyr and 0.8H Y/αPyr); $v_{max}$/cm$^{-1}$ 1042 and 1186 (C—O ester), 1585 (C=O imide), 1698 (C=O ester); m/z (FAB+) 1221 (MH$^+$, 60%), 397 (100); (Found: MH$^+$ 1221.4751, C$_{76}$H$_{65}$N$_6$O$_{10}$ requires 1221.4762).

5-(α-Hydroxy-α-2-pyridylbenzyl)-7-(α-2-pyridyl-benzylidene)-N-2'-suberoyloxyethyl-5-norbornene-2,3-dicarboximide dimer (140)

A similar procedure (Nagao, Y. et al. *Tetrahedron Lett.* 1988, 29, 6133-6136) to that described for the preparation of 109 was followed using 102 (200 mg, 0.36 mmol) and suberoyl chloride (32 μL, 0.18 mmol) in pyridine (2 mL), at 70° C. for 16 h. Purification by flash chromatography (hexane/ethyl acetate 1:1) afforded 140 as a colourless solid (6 mg, 0.005 mmol, 2%). mp 104-112° C.; $^1$H NMR (300 MHz, CDCl$_3$) δ 1.22-1.39 (4H, m, 2×OCO(CH$_2$)$_2$CH$_2$), 1.47-1.84 (4H, m, 2×OCOCH$_2$CH$_2$), 2.18-2.29 (4H, m, J=7.5 Hz, 2×OCOCH$_2$), 3.32 (0.2H, dd, J=8.0 and 4.6 Hz, W/H-3), 3.38 (0.6H, dd, J=7.8 and 4.5 Hz, Y/H-3), 3.46 (1.2H, dd, J=7.8 and 4.8 Hz, V/H-2), 3.55-3.67 (4.2H, m, 2H NCH$_2$, 1.2H V/H-3, 0.4H W/H-2 and W/H-4, 0.6H Y/H-2), 3.75-3.84 (2H, m, NCH$_2$), 3.86-3.89 (1.2H, m, V/H-1), 3.92 (0.6H, dt, J=4.5 and 1.5 Hz, Y/H-4), 4.15-4.26 (4H, m, 2×CH$_2$OCO), 4.29 (1.2H, dt, J=4.6 and 1.4 Hz, V/H-4), 4.45-4.49 (0.8H, m, 0.2H W/H-1 and 0.6H Y/H-1); 5.50-5.62 (3.8H, m, 1.2H V/H-6, 0.6H Y/H-6 and 2H OH), 6.03-6.05 (0.2H, m, W/H-6), 6.74-

7.61 (32H, m, Ar), 8.46-8.50 (3.2H, m, 2.4H 2V/αPyr, 0.2H W/αPyr and 0.6H Y/αPyr), 8.62-8.64 (0.8H, m, 0.2H W/αPyr and 0.6H Y/αPyr); $v_{max}$/cm$^{-1}$ 1127 and 1186 (C—O ester), 1585 (C=O imide), 1701 (C=O ester); m/z (FAB+) 1249 (MH$^+$, 11%), 391 (100); (Found: MH$^+$ 1249.5078, $C_{78}H_{69}N_6O_{10}$ requires 1249.5075).

5-(α-Hydroxy-α-2-pyridylbenzyl)-7-(α-2-pyridyl-benzylidene)-N-2'-sebacoyloxyethyl-5-norbornene-2,3-dicarboximide dimer (141)

A similar procedure (Nagao, Y. et al. *Tetrahedron Lett.* 1988, 29, 6133-6136) to that described for the preparation of 109 was followed using 102 (200 mg, 0.36 mmol) and sebacoyl chloride (43 mg, 0.18 mmol) in pyridine (2 mL), at 70° C. for 16 h. Purification by flash chromatography (dichloromethane/methanol 50:1) afforded 141 as a colourless solid (61 mg, 0.05 mmol, 27%). mp 97-107° C.; $^1$H NMR (400 MHz, CDCl$_3$) δ 1.19-1.35 (8H, m, CO(CH$_2$)$_2$(CH$_2$)$_4$(CH$_2$)$_2$CO), 1.48-1.64 (4H, m, COCH$_2$(CH$_2$)$_4$CH$_2$CH$_2$CO), 2.10-2.29 (4H, m, COCH$_2$(CH$_2$)$_6$CH$_2$CO), 3.33-3.83 (8.2, m, NCH$_2$CH$_2$O, H-2, H-3, W/H-4), 3.87-3.89 (1H, m, U/H-1, V/H-1), 3.93-3.94 (0.8H, m, Y/H-4), 4.12-4.13 (0.2H, m, U/H-4), 4.18-4.25 (4H, m, NCH$_2$CH$_2$O), 4.33 (0.8H, m, V/H-4), 4.45-4.48 (1H, m, W/H-1, Y/H-1), 5.51-5.59 (2.6H, m, V/H-6, Y/H-6, OH), 5.65 (1H, s, OH), 6.01-6.05 (0.4H, m, U/H-6, W/H-6), 6.74-7.59 (32H, m, Ar), 8.40-8.63 (4H, m, αPyr); $v_{max}$/cm$^{-1}$ 1122 and 1166 (C—O ester), 1585 (C=O imide), 1700 (C=O ester); m/z (FAB+) 1277 (MH$^+$, 8%), 120 (100); (Found: MH$^+$ 1277.5386, $C_{80}H_{73}N_6O_{10}$ requires 1277.5388).

N-2'-Dodecanedioyloxyethyl-5-(α-hydroxy-α-2-pyridylbenzyl)-7-(α-2-pyridylbenzylidene)-5-norbornene-2,3-dicarboximide dimer (142)

A similar procedure (Lu, M. C. et al. *J. Med. Chem.* 1987, 30, 273-278 and Nagao, Y. et al. *Tetrahedron Lett.* 1988, 29, 6133-6136) to that previously described for the preparation of 117 was followed using dodecanedioic acid (46 mg, 0.18 mmol) and oxalyl chloride (0.5 mL), under reflux for 16 h. A solution of 102 (200 mg, 0.36 mmol) and crude dodecanedioyl chloride in pyridine (2 mL) was then stirred at 70° C. for 16 h. Purification by flash chromatography (hexane/ethyl acetate 2:1) afforded 142 as a colourless solid (5 mg, 0.004 mmol, 1%). mp 70-77° C.; $^1$H NMR (300 MHz, CDCl$_3$) δ 1.16-1.35 (12H, m, 2×OCO(CH$_2$)$_2$(CH$_2$)$_3$), 1.45-1.69 (4H, m, 2×OCOCH$_2$CH$_2$), 2.11-2.29 (4H, m, 2×OCOCH$_2$), 3.32 (0.1H, dd, J=8.0 and 4.4 Hz, W/H-3), 3.38 (0.9H, dd, J=8.0 and 4.7 Hz, Y/H-3), 3.46-3.50 and 3.55-3.66 (5.1H, m, 2H NCH$_2$, 0.2H U/H-2 and U/H-3, 1.8H V/H-2 and V/H-3, 0.2H W/H-2 and W/H-4, 0.9H Y/H-2), 3.75-3.84 (2H, m, NCH$_2$), 3.85-3.89 (1H, m, 0.1H U/H-1 and 0.9H V/H-1), 3.92 (0.9H, dt, J=5.0 and 1.6 Hz, Y/H-4), 4.16-4.25 and 4.29-4.31 (5H, m, 4H 2×CH$_2$OCO, 0.1H U/H-4 and 0.9H V/H-4), 4.45-4.48 (1H, m, 0.1H W/H-1 and 0.9H Y/H-1), 5.50 (1H, bdd, J=3.4 and 1.4 Hz, 0.9H V/H-6 and 0.1H OH), 5.53 (1H, bdd, J=3.3 and 1.4 Hz, 0.9H Y/H-6 and 0.1H OH), 5.57 (0.9H, s, OH), 5.63 (0.9H, s, OH), 6.01-6.02 (0.1H, m, U/H-6), 6.03-6.04 (0.1H, m, W/H-6), 6.73-7.61 (32H, m, Ar), 8.45-8.51 (3H, m, 0.2H 2U/αPyr, 1.8H 2V/αPyr, 0.1H W/αPyr and 0.9H Y/αPyr), 8.61-8.64 (1H, m, 0.1H W/αPyr and 0.9H Y/αPyr); $v_{max}$/cm$^{-1}$ 1041 and 1166 (C—O ester), 1585 (C=O imide), 1699 (C=O ester); m/z (FAB+) 1305 (MH$^+$, 18%), 120 (100); (Found: MH$^+$ 1305.5711, $C_{82}H_{77}N_6O_{10}$ requires 1305.5701).

5-(α-Hydroxy-α-2-pyridylbenzyl)-7-(α-2-pyridyl-benzylidene)-N-2'-terephthaloyloxyethyl-5-norbornene-2,3-dicarboximide dimer (143)

A similar procedure (Bartalucci, G. et al. *Eur. J. Org. Chem.* 2007, 588-595) to that described for the preparation of 110 was followed using 102 (181 mg, 0.33 mmol), terephthalic acid (28 mg, 0.17 mmol), DCC (67 mg, 0.33 mmol) and 4-dimethylaminopyridine (11 mg, 0.09 mmol) in dimethylformamide (1.1 mL), at room temperature for 48 h. Purification by flash chromatography (hexane/ethyl acetate 3:7) afforded 143 as a colourless solid (19 mg, 0.02 mmol, 5%). mp 133-139° C.; $^1$H NMR (300 MHz, CDCl$_3$) δ 3.33-3.37 (0.3H, m, W/H-3), 3.40-3.44, 3.47-3.59 and 3.63-3.68 (4H, m, 2H V/H-2 and V/H-3, 0.6H W/H-2 and W/H-4, 1.4H Y/H-2 and Y/H-3), 3.74-3.79 (2H, m, NCH$_2$), 3.86-3.90 (1H, m, V/H-1), 3.93-4.02 (2.7H, m, 2H NCH$_2$ and 0.7H Y/H-4), 4.31-4.32 (1H, m, V/H-4), 4.38-4.56 (5H, m, 4H 2×CH$_2$O, 0.3H W/H-1 and 0.7H Y/H-1), 5.53-5.58 (2.2H, m, 1H V/H-6, 0.7H Y/H-6 and 0.5H OH), 5.65 (1.5H, s, OH), 6.06-6.07 (0.3H m, W/H-6), 6.75-7.61 (32.7H, m, Ar), 7.88-7.90 (0.3H, m, Ar), 7.98 (3H, dd, J=8.2 and 1.6 Hz, Ar), 8.46-8.49 (3H, m, 2H 2V/αPyr, 0.3H W/αPyr and 0.7H Y/αPyr), 8.62-8.64 (1H, m, 0.3H W/αPyr and 0.7H Y/αPyr); $v_{max}$/cm$^{-1}$ 1122 and 1270 (C—O ester), 1644 (C=O imide), 1699 (C=O ester).

N-[2'-Ethylenebis(hydrogensuccinoyloxy)ethyl]-5-(α-hydroxy-α-2-pyridylbenzyl)-7-(α-2-pyridylbenzylidene)-5-norbornene-2,3-dicarboximide dimer (144)

Compound 144 was prepared by a procedure similar to that of Bartalucci and co-workers (Bartalucci, G. et al. *Eur. J. Org. Chem.* 2007, 588-595). To a solution of 102 (200 mg, 0.36 mmol) in dimethylformamide (1.2 mL) was added ethylene bis(hydrogensuccinate) (47 mg, 0.18 mmol), EDC (69 mg, 0.36 mmol) and 4-dimethylaminopyridine (11 mg, 0.1 mmol), and the mixture stirred at room temperature for 48 h. The solvent was removed in vacuo and the residue taken up in ethyl acetate (10 mL), washed with an aqueous solution of sodium hydrogen carbonate (5 mL), then brine (5 mL), dried over anhydrous sodium sulfate and the solvent removed in vacuo. Purification by flash chromatography (hexane/ethyl acetate 1:2) afforded 144 as a colourless solid (7 mg, 0.005 mmol, 1%). mp 104-112° C.; $^1$H NMR (300 MHz, CDCl$_3$) δ 2.53-2.66 (8H, m), 3.33-3.93 (10H, m, NCH$_2$CH$_2$O, H-2, H-3, V/H-1, W/H-4, Y/H-4), 4.19-4.35 (9H, m, NCH$_2$CH$_2$O, OCH$_2$CH$_2$O, V/H-4), 4.44-4.47 (1H, m, W/H-1, Y/H-1), 5.50-5.54 (3.8H, m, V/H-6, Y/H-6, OH), 6.04-6.05 (0.2H, m, W/H-6), 6.74-7.59 (32H, m, Ar), 8.46-8.64 (4H, m, αPyr); $v_{max}$/cm$^{-1}$ 1041 and 1149 (C—O ester), 1585 (C=O imide), 1699 (C=O ester); m/z (FAB+) 1338 (MH$^+$, 5%), 120 (100); (Found: MH$^+$ 1337.4861, $C_{80}H_{69}N_6O_{14}$ requires 1337.4872).

5-(α-Hydroxy-α-2-pyridylbenzyl)-N-2'-octanamido-ethyl-7-(α-2-pyridylbenzylidene)-5-norbornene-2,3-dicarboximide (364)

A similar procedure (Schwartz, E. et al. *Macromolecules* 2011, 44, 4735-4741) to that previously described for the preparation of 347 was followed using 106 (0.8 g, 0.7 mmol), octanoic acid (0.1 g, 0.8 mmol), 1-ethyl-3-(3-dimethylaminopropyl)carbodiimide (0.16 g, 0.8 mmol), triethylamine (0.1 mL, 0.8 mmol) and dimethylaminopyridine (9 mg, 0.07 mmol) in dichloromethane (10 mL), at room temperature for 24 h. Purification by flash chromatography (hexane/ethyl acetate 1:5) afforded 364 as a white solid (0.28 g, 0.4 mmol, 57%). $^1$H NMR (300 MHz, CDCl$_3$) δ 0.83-0.89 (3H, m, (CH$_2$)$_6$CH$_3$), 1.24-1.28 (8H, m, (CH$_2$)$_4$CH$_3$), 1.56-1.61 (2H, m, CH$_2$CH$_2$(CH$_2$)$_4$CH$_3$), 2.03-2.12 (2H, m, CH$_2$(CH$_2$)$_5$CH$_3$), 3.35-3.80 (6.2H, NCH$_2$CH$_2$NHCO, H-2, H-3, W/H-4), 3.85-3.88 (0.5H, m, U/H-1, V/H-1), 3.91 (0.3H, m, Y/H-4), 4.09 (0.1H, m, U/H-4), 4.34 (0.4H, m, V/H-4), 4.49-4.54 (0.5H, m, W/H-1, Y/H-1), 5.46 (1H, s, OH), 5.56 (0.4H, m, V/H-6), 5.59 (0.3H, m, Y/H-6), 6.18 (0.1H, m, U/H-6), 6.24 (0.2H, m, W/H-6), 6.30-7.60 (16H, m, Ar), 8.40-8.65 (2H, m, αPyr).

N-2'-Dodecanamidoethyl-5-(α-hydroxy-α-2-pyridylbenzyl)-7-(α-2-pyridylbenzylidene)-5-norbornene-2,3-dicarboximide (339)

A similar procedure (Schwartz, E. et al. *Macromolecules* 2011, 44, 4735-4741) to that previously described for the preparation of 347 was followed using 106 (1.20 g, 2.16 mmol), dodecanoic acid (0.48 g, 2.38 mmol), 1-ethyl-3-(3-dimethylaminopropyl)carbodiimide (0.46 g, 2.38 mmol), triethylamine (1.0 mL, 7.14 mmol) and dimethylaminopyridine (26 mg, 0.22 mmol) in dichloromethane (25 mL), at room temperature for 24 h. Purification by flash chromatography (hexane/ethyl acetate 1:3) afforded 339 as a white solid (1.24 g, 1.68 mmol, 78%). mp 66-70° C.; $^1$H NMR (300 MHz, CDCl$_3$) δ 0.85-0.90 (3H, m, (CH$_2$)$_{10}$CH$_3$), 1.22-1.32 (16H, m, (CH$_2$)$_8$CH$_3$), 1.52-1.61 (2H, m, CH$_2$CH$_2$(CH$_2$)$_8$CH$_3$), 2.05-2.13 (2H, m, CH$_2$(CH$_2$)$_9$CH$_3$), 3.30-3.78 (6.18H, m, NCH$_2$CH$_2$NHCO, H-2, H-3, W/H-4), 3.85-3.91 (0.82H, m, U/H-1, V/H-1, Y/H-4), 4.09 (0.12H, m, U/H-4), 4.34 (0.34H, m, V/H-4), 4.49-4.53 (0.54H, m, W/H-1, Y/H-1), 5.46 (s, OH), 5.56 (0.34H, m, V/H-6), 5.59 (0.36H, m, Y/H-6), 6.18 (0.12H, m, U/H-6), 6.21 (s, OH), 6.22 (s, OH), 6.25 (0.18H, m, W/H-6), 6.39 (m, NH), 6.51 (m, NH), 6.69 (m, NH), 6.780-7.59 (16H, m, Ar), 8.39-8.65 (2H, m, αPyr); m/z (ESI, 70 eV) 759 (MNa$^+$, 100%); (Found MNa$^+$ 759.3881, C$_{47}$H$_{52}$N$_4$NaO$_4$ requires 759.3894).

N-2'-Cinnamamidoethyl-5-(α-hydroxy-α-2-pyridylbenzyl)-7-(α-2-pyridylbenzylidene)-5-norbornene-2,3-dicarboximide (365)

A similar procedure (Schwartz, E. et al. *Macromolecules* 2011, 44, 4735-4741) to that previously described for the preparation of 347 was followed using 106 (0.8 g, 0.7 mmol), cinnamic acid (0.1 g, 0.8 mmol), 1-ethyl-3-(3-dimethylaminopropyl)carbodiimide (0.16 g, 0.8 mmol), triethylamine (0.1 mL, 0.8 mmol) and dimethylaminopyridine (9 mg, 0.07 mmol) in dichloromethane (10 mL), at room temperature for 24 h. Purification by flash chromatography (hexane/ethyl acetate 1:5) afforded 365 as a white solid (0.5 g, 0.7 mmol, 99%). $^1$H NMR (300 MHz, CDCl$_3$) δ 3.32-3.95 (7H, m, NCH$_2$CH$_2$NHCO, H-2, H-3, U/H-1, V/H-1, W/H-4, Y/H-4), 4.08 (0.1H, m, U/H-4), 4.36 (0.3H, m, V/H-4), 4.50-4.53 (0.6H, m, W/H-1, Y/H-1), 5.41 (0.3H, s, OH), 5.43 (0.4H, s, OH), 5.59 (0.3H, dd, m, V/H-6), 5.62 (0.4H, m, Y/H-6), 5.84 (0.1H, s, U/OH), 5.88 (0.2H, s, W/OH), 6.25 (0.1H, m, U/H-6), 6.30 (0.2H, m, W/H-6), 6.33-6.39 (1H, m, COCH=CH), 6.79-7.61 (22H, m, Ar and COCH=CH), 8.40-8.60 (2H, m, αPyr).

5-(α-Hydroxy-α-2-pyridylbenzyl)-N-[2'-(4"-methoxycinnamamido)ethyl]-7-(α-2-pyridylbenzylidene)-5-norbornene-2,3-dicarboximide (361)

A similar procedure (Schwartz, E. et al. Macromolecules 2011, 44, 4735-4741) to that previously described for the preparation of 347 was followed using 106 (0.8 g, 0.7 mmol), 4-methoxycinnamic acid (0.1 g, 0.8 mmol), 1-ethyl-3-(3-dimethylaminopropyl)carbodiimide (0.16 g, 0.8 mmol), triethylamine (0.1 mL, 0.8 mmol) and dimethylaminopyridine (9 mg, 0.07 mmol) in dichloromethane (10 mL), at room temperature for 24 h. Purification by flash chromatography (hexane/ethyl acetate 1:5) afforded 361 as a white solid (0.4 g, 0.6 mmol, 85%). $^1$H NMR (300 MHz, CDCl$_3$) δ 3.35-3.91 (6.6H, m, NCH$_2$CH$_2$NHCO, H-2, H-3, U/H-1, V/H-1, W/H-4), 3.83-3.85 (3H, m, OMe), 3.95 (0.4H, m, Y/H-4), 4.15 (0.1H, m, U/H-4), 4.33 (0.3H, m, V/H-4), 4.47-4.50 (0.6H, m, W/H-1, Y/H-1), 5.46 (0.6H, s, OH), 5.53 (0.3H, dd, m, V/H-6), 5.56 (0.4H, m, Y/H-6), 5.77 (0.4, s, OH), 6.20-6.40 (1.3H, m, COCH=CH, W/H-6, U/H-6), 6.70-7.65 (21H, m, Ar and COCH=CH), 8.40-8.62 (2H, m, αPyr).

N-[2'-(4"-Ethoxycinnamamido)ethyl]-5-(α-hydroxy-α-2-pyridylbenzyl)-7-(α-2-pyridylbenzylidene)-5-norbornene-2,3-dicarboximide (345)

A similar procedure (Schwartz, E. et al. Macromolecules 2011, 44, 4735-4741) to that previously described for the preparation of 345 was followed using 106 (0.57 g, 1.03 mmol), 4-ethoxycinnamic acid (0.41 g, 2.16 mmol), 1-ethyl-3-(3-dimethylaminopropyl)carbodiimide (0.45 g, 2.35 mmol), triethylamine (0.82 mL, 5.93 mmol) and dimethylaminopyridine (44 mg, 0.36 mmol) in dichloromethane (20 mL), at room temperature for 24 h. Purification by flash chromatography (hexane/ethyl acetate 1:1) afforded 345 as a white solid (0.77 g, 1.06 mmol, 59%). mp 110-115° C.; $^1$H NMR (300 MHz, CDCl$_3$) δ 1.40-1.45 (6.6H, m, 3H, m, OCH$_2$CH$_3$), 3.30-3.80 (6.16H, m, NCH$_2$CH$_2$NHCO, H-2, H-3, W/H-4), 3.85-3.90 (0.84H, m, U/H-1, V/H-1, Y/H-4), 4.02-4.10 (2.15H, m, OCH$_2$CH$_3$, U/H-4), 4.35 (0.31H, m, V/H-4), 4.49-4.52 (0.54H, m, W/H-1, Y/H-1), 5.47 (s, OH), 5.48 (s, OH), 5.59 (0.31H, m, V/H-6), 5.62 (0.38H, m, Y/H-6), 5.72 (s, OH), 5.76 (s, OH), 6.19-6.40 (1.31H, m, COCH=CH, W/H-6, U/H-6), 6.75-7.60 (21H, m, Ar and COCH=CH), 8.40-8.63 (2H, m, αPyr); ν$_{max}$ (NaCl)/cm$^{-1}$ 1174, 1222 (C—O ester), 1586 (C=O imide), 1696 (C=O ester), 3325 (N—H amide); m/z (ESI, 70 eV) 751 (MNa$^+$, 100%); (Found MNa$^+$ 751.2903), C$_{46}$H$_{40}$N$_4$NaO$_5$ requires 751.2891.

5-(α-Hydroxy-α-2-pyridylbenzyl)-N-octyloxycarbonylmethyl-7-(α-2-pyridylbenzylidene)-5-norbornene-2,3-dicarboximide (369)

A similar procedure (Hursthouse, M. B.; Khan, A.; Marson, C. M.; Porter, R. A. *Tetrahedron Lett.* 1995, 36, 33, 5979-5982) to that described for the preparation of 207 was followed using NRB (0.37 g, 0.7 mmol) and potassium carbonate (0.25 g, 1.8 mmol) in dimethylformamide (5 mL), and octyl chloroacetate (0.32 g, 1.5 mmol) in dimethylformamide (2 mL), and the mixture stirred at room temperature for 2 h. Purification by flash chromatography (hexane/ethyl acetate 2:1) afforded 369 as a white solid (0.34 g, 0.5 mmol, 71%). $^1$H NMR (400 MHz, CDCl$_3$) δ 0.87-0.90 (3H, m, O(CH$_2$)$_7$CH$_3$), 1.26-1.30 (10H, m, OCH$_2$CH$_2$(CH$_2$)$_5$CH$_3$), 1.61-1.63 (2H, m, OCH$_2$CH$_2$(CH$_2$)$_5$CH$_3$), 3.40-4.56 (8H, m, OCH$_2$(CH$_2$)$_6$CH$_3$, NCH$_2$, H-1, H-2, H-3, H-4), 5.48 (0.5H, s, OH), 5.52 (0.3H, m, V/H-6), 5.53 (0.5H, s, OH), 5.55 (0.4H, m, Y/H-6), 6.02 (0.1H, m, U/H-6), 6.04 (0.2H, m, W/H-6), 6.70-7.60 (16H, m, Ar), 8.40-8.60 (2H, m, αPyr).

N-Cinnamoxycarbonylmethyl-5-(α-hydroxy-α-2-pyridylbenzyl)-7-(α-2-pyridylbenzylidene)-5-norbornene-2,3-dicarboximide (371)

A similar procedure (Hursthouse, M. B.; Khan, A.; Marson, C. M.; Porter, R. A. *Tetrahedron Lett.* 1995, 36, 33, 5979-5982) to that described for the preparation of 207 was followed using NRB (0.49 g, 1.0 mmol) and potassium carbonate (0.33 g, 2.4 mmol) in dimethylformamide (5 mL), and cinnamyl chloroacetate (0.3 g, 1.4 mmol) in dimethylformamide (2 mL), and the mixture stirred at room temperature for 2 h. Purification by flash chromatography (hexane/ethyl acetate 3:2) afforded 371 as a white solid (0.63 g, 0.9 mmol, 90%). $^1$H NMR (400 MHz, CDCl$_3$) δ 3.40-4.55 (8H, m, CH$_2$CH=CH, NCH$_2$, H-1, H-2, H-3, H-4), 5.48 (0.5H, s, OH), 5.52 (0.3H, m, V/H-6), 5.53 (0.5H, s, OH), 5.55 (0.4H, m, Y/H-6), 6.03 (0.1H, m, U/H-6), 6.05 (0.2H, m, W/H-6), 6.21-6.29 (1H, m, CH$_2$CH=CH), 6.60-7.60 (22H, m, CH$_2$CH=CH, Ar), 8.40-8.60 (2H, m, αPyr).

Experimental

Pharmacology

Rat Caudal Artery and Aortic Ring Isolation and Recording of Contractile Force

Male Wistar rats (150-250 g) were obtained from Charles River Italia (Milano, Italy) and killed by decapitation. Ventral caudal artery was isolated, placed in Tyrode solution at room temperature and cleaned of extraneous fatty and connective tissue under a dissection microscope. All vessels were cut into rings 2 mm long, mounted on a custom-built plexiglass support by means of two intraluminal tungsten wires and placed in 20 mL double-jacketed organ baths filled with Tyrode solution of the following composition (mM): NaCl 125, KCl 5, CaCl$_2$ 2.7, MgSO$_4$ 1, KH$_2$PO$_4$ 1.2, NaHCO$_3$ 25 and glucose 11, maintained at 37° C., pH 7.35, bubbled with 95% O$_2$ and CO$_2$. The endothelium was removed by gently rubbing the lumen of the rings with a very thin rough-surfaced tungsten wire (caudal artery). The mechanical activity of the rings was detected by means of an isometric force transducer (Ugo Basile, Comerio, Italy) coupled to a pen recorder (Ugo Basile, Comerio, Italy). Rings were passively stretched to impose a resting tension (2 g) and were allowed to equilibrate for 60 min. After equilibration, each ring was repeatedly simulated with both KCl (90 mM) and phenylephrine (10 μM) until reproducible responses were obtained. To verify the absence of the endothelium, rings contracted with 1 μM phenylephrine were exposed to 2 μm carbamylcholine. The absence of the endothelium was revealed by the lack of carbamylcholine-induced relaxation. Each compound was tested for the vasoconstrictor activity at a concentration of 50 μM, which has been previously reported to be the one evoking the maximal response to norbormide. The contractile responses to the compounds were expressed as percent of the 90 mM KCl response.

Hydrolytic Stability Assay

Compounds of the invention were subjected to a 1 h hydrolytic stability appraisal [200 μL total volume, at a final compound concentration of 200 μM, 2.5% DMSO overall, 37° C., n=3] using Tyrode solution for those candidates which displayed vasoconstrictory activity in the rat caudal artery contractile experiment, and phosphate buffer (0.1 M, pH 7.4) for those revealed to be non-vasoconstricting pre-cleavage. Analysis was by RP-LCMS at an injection volume of 5 μL.

Rat Serum Assay

The hydrolytic stability of compounds of the invention in rat blood was evaluated using in vitro rat serum obtained from Sigma-Aldrich and stored at −78° C. Similar assay conditions to those reported by Li Di and co-workers (Int. J. Pharm. 2005, 297, 110-119) were followed [200 μL total volume, 80% rat serum (diluting with phosphate buffer (0.1 M, pH 7.4)), at a final compound concentration of 200 μM, 2.5% DMSO overall, 37° C., 3 h, n=3] using an Eppendorf Thermomixer Compact. Reactions were quenched by transferring 150 μL of the incubation mixture to 450 μL of ice-cold acetonitrile, affording a final compound/NRB or NRB analogue concentration of 50 μM. Samples were centrifuged at 14,500×g for 15 min using an Eppendorf Mini Spin Plus centrifuge, at ambient temperature. 400 μL of the supernatant was removed and transferred to clean tubes. Analysis was by RP-LCMS at an injection volume of 20 μL. Each compound and corresponding NRB or NRB analogue were subjected to external calibration curves at 50 μM, 100 μM and 200 μM to allow conversion of absorbance unit area into nmol, from which the percentage of NRB or NRB analogue released from each compound was calculated.

Rat Liver S9 Fraction Assay

The hydrolytic stability of compounds of the invention was also evaluated in vitro using rat liver S9 fraction (20 mg/mL), pooled from male rat (Sprague-Dawley), obtained from Sigma-Aldrich, diluted to 1 mg/mL with phosphate buffer (0.1 M, pH 7.4) and stored at −78° C. Similar assay conditions to those reported by Li Di and co-workers (Int. J. Pharm. 2005, 297, 110-119) were followed [200 μL total volume, 1 mg/mL rat liver S9 fraction (diluting with phosphate buffer (0.1 M, pH 7.4)), at a final compound concentration of 200 μM, 2.5% DMSO overall, 37° C., 6 h, n=3]. The assay protocol followed is as that described above for the rat serum assay, with an adjusted end-point of 6 h.

Simulated Gastric Fluid (SGF) Assay

All in vivo candidates were subjected to a 1 h hydrolytic stability appraisal in the presence of SGF, without pepsin (United States Pharmacopoeia 24) [200 μL total volume, sodium chloride solution (0.03 M) acidified to pH 1.2 with concentrated hydrochloric acid, at a final compound concentration of 200 μM, 2.5% DMSO overall, 37° C., n=3], to investigate any potential chemical instabilities that may occur in the acidic environment of the stomach prior to uptake. Analysis was by RP-LCMS at an injection volume of 5 μL.

In Vivo Experiments and Palatability Trials

Sprague Dawley rats (150-200 g) were used to appraise the rodenticidal activity of the compounds put forward for in vivo evaluation. Briefly, prior to administration the compounds were dissolved in 0.2 M hydrochloric acid (5% DMSO overall), to the desired dose, and without delay either injected intravenously, via the tail, or orally gavaged. All treated animals were housed in a quiet room and monitored every minute (i.v) or every 15 min (oral) to verify early signs of toxicity.

In the palatability trials, Sprague Dawley rats (ca. 250 g) were presented with 1% w/w compound (n=6) or 0.5% w/w compound (n=5) in a peanut butter bait, following 3 days 'pre-baiting' with a peanut butter formulation free of toxicant.

Results

TABLE 1

In vitro evaluation for vasoconstrictory activity of selected compound of formula (I).

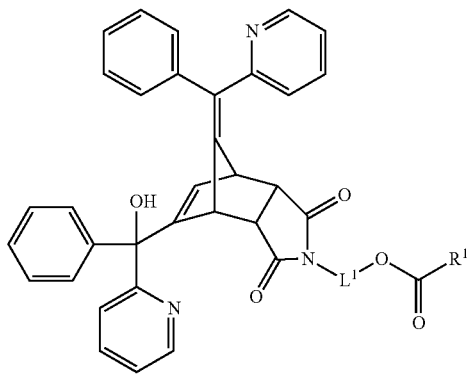

| Cmpd | L¹ | R¹ | Yield (%) | Vasoconstriction[a] |
|---|---|---|---|---|
| 8 | $CH_2$ | t-Bu | 48 | ≥132 |
| 9 | $CH_2$ | $(CH_2)_2CH_3$ | 62 | 86 |
| 10 | $CH_2$ | $(CH_2)_6CH_3$ | 91 | 0 |
| 11 | $CH_2$ | $(CH_2)_{10}CH_3$ | 32 | 0 |
| 12 | $CH_2$ | Ph | 71 | ≥132 |
| 13 | $CH_2$ | $C_6H_4$o-OMe | 65 | 90 |
| 14 | $CH_2$ | $C_6H_4$m-OMe | 34 | 0 |
| 15 | $CH_2$ | $C_6H_4$p-OMe | 65 | 0 |
| 16 | $CH_2$ | $CH_2$Ph | 59 | 15 |
| 324 | $CH_2$ | $CH_2C_6H_4$p-Me | 67 | 17 |
| 17 | $CH_2$ | $CHPh_2$ | 15 | 0 |
| 18 | $CH_2$ | $CH_2CH_2$Ph | 6 | 13 |
| 19 | $CH_2$ | CH=CHPh | 80 | 0 |
| 20 | $CH_2$ | 2-Naph | 32 | 0 |
| 109 | $CH_2CH_2$ | t-Bu | 74 | ≥132 |
| 110 | $CH_2CH_2$ | $(CH_2)_2CH_3$ | 40 | ≥132 |
| 111 | $CH_2CH_2$ | $(CH_2)_6CH_3$ | 65 | 0 |
| 112 | $CH_2CH_2$ | $(CH_2)_{10}CH_3$ | 47 | 0 |
| 113 | $CH_2CH_2$ | Ph | 75 | ≥132 |
| 114 | $CH_2CH_2$ | o-OMePh | 80 | ≥132 |
| 115 | $CH_2CH_2$ | m-OMePh | 58 | 52 |
| 116 | $CH_2CH_2$ | p-OMePh | 41 | ≥132 |
| 117 | $CH_2CH_2$ | $CH_2$Ph | 3 | ≥132 |
| 118 | $CH_2CH_2$ | $CHPh_2$ | 71 | 0 |
| 119 | $CH_2CH_2$ | $CH_2CH_2$Ph | 9 | ≥132 |
| 120 | $CH_2CH_2$ | CH=CHPh | 49 | 66 |
| 121 | $CH_2CH_2$ | CMe=CHPh | 3 | 0 |
| 122 | $CH_2CH_2$ | 2-Naph | 10 | 0 |
| 123 | $CH_2CH_2$ | C≡CPh | 7 | 0 |
| 124 | $CH_2CH_2$ | (CH=CH-C₆H₄-o-OMe) | 44 | 23 |
| 125 | $CH_2CH_2$ | (CH=CH-C₆H₄-m-OMe) | 47 | 80 |
| 126 | $CH_2CH_2$ | (CH=CH-C₆H₄-p-OMe) | 63 | 0 |

TABLE 1-continued
In vitro evaluation for vasoconstrictory activity of selected compound of formula (I).
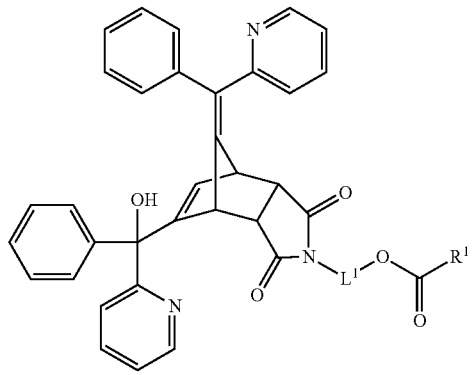
| Cmpd | L¹ | R¹ | Yield (%) | Vasoconstriction[a] |
|---|---|---|---|---|
| 127 | $CH_2CH_2$ | 4-OCF₃-styryl | 43 | 0 |
| 128 | $CH_2CH_2$ | 4-Me-styryl | 64 | 42 |
| 335 | $CH_2CH_2$ | 4-Et-styryl | 42 | 19 |
| 347 | $CH_2CH_2$ | 4-iPr-styryl | 73 | 0 |
| 129 | $CH_2CH_2$ | 4-Cl-styryl | 17 | 0 |
| 130 | $CH_2CH_2$ | 4-NO₂-styryl | 9 | 20 |
| 131 | $CH_2CH_2$ | 4-NMe₂-styryl | 18 | 30 |

TABLE 1-continued
In vitro evaluation for vasoconstrictory activity of selected compound of formula (I).
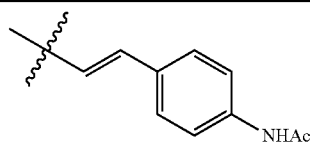
| Cmpd | L¹ | R¹ | Yield (%) | Vasoconstriction[a] |
|---|---|---|---|---|
| 337 | CH$_2$CH$_2$ | 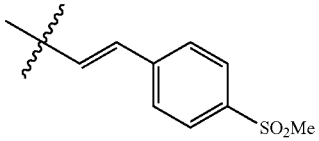 [SMILES: */C=C/c1ccc(S(C)(=O)=O)cc1] | 99 | 97 |
| 329 | CH$_2$CH$_2$ | 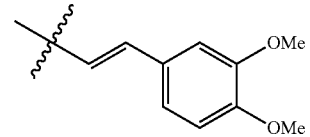 [SMILES: */C=C/c1ccc(OC)c(OC)c1] | 54 | 88 |
| 132 | CH$_2$CH$_2$ | 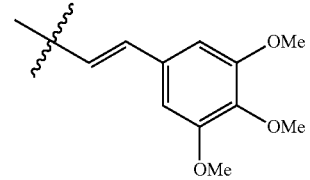 [SMILES: */C=C/c1cc(OC)c(OC)c(OC)c1] | 33 | 120 |
| 133 | CH$_2$CH$_2$ | 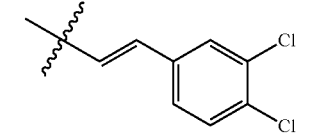 [SMILES: */C=C/c1ccc(Cl)c(Cl)c1] | 29 | 30 |
| 134 | CH$_2$CH$_2$ | 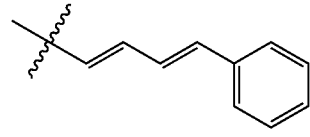 [SMILES: */C=C/C=C/c1ccccc1] | 25 | 0 |
| 135 | CH$_2$CHMe | CH=CHPh | 20 | 0 |
| 136 | CH$_2$CH$_2$CH$_2$ | CH=CHPh | 15 | 0 |
| 137 | CH$_2$(CH$_2$)$_2$CH$_2$ | CH=CHPh | 34 | 0 |
| 187 | CH$_2$CH$_2$ | 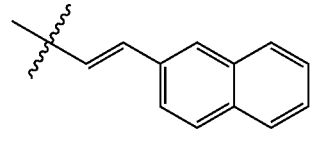 [SMILES: */C=C/c1ccc2ccccc2c1] | 3 | 0 |
| 188 | CH$_2$CH$_2$ |  | 2 | 0 |

TABLE 1-continued

In vitro evaluation for vasoconstrictory activity of selected compound of formula (I).

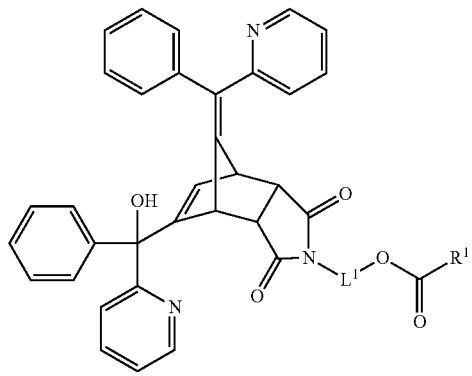

| Cmpd | $L^1$ | $R^1$ | Yield (%) | Vasoconstriction[a] |
|---|---|---|---|---|
| 201 | $CH_2CH_2OCH_2$ | $CHPh_2$ | 6 | ≥132 |
| 204 | $CH_2CH_2$ | $CH_2CH_2C(O)OPh$ | 11 | 0 |
| 342 | $CH_2CH_2$ | 4-(aminomethyl)phenyl·TFA | 42[b] | 136 |
| 343 | $CH_2CH_2$ | $CH_2CH(NH_2·TFA)CO_2Me$ | 36[b] | 140 |

[a]Maximum contractile effect as a % of 90 mM KCl contraction (rat caudal artery); stereoisomeric mixture of NRB = 132%;
[b]over two steps.

TABLE 2

In vitro evaluation for vasoconstrictory activity of selected compounds of formula (I).

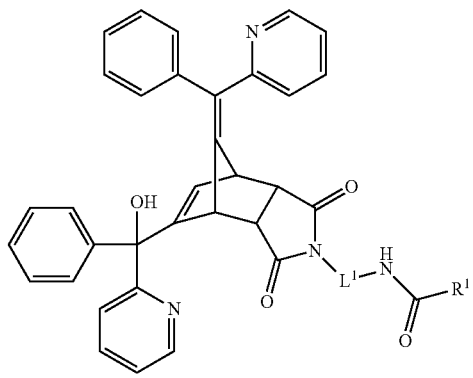

| Cmpd | $L^1$ | $R^1$ | Yield (%) | Vasoconstriction[a] |
|---|---|---|---|---|
| 364 | $CH_2CH_2$ | $(CH_2)_6CH_3$ | 57 | 21 |
| 339 | $CH_2CH_2$ | $(CH_2)_{10}CH_3$ | 78 | 0 |
| 365 | $CH_2CH_2$ | $CH=CHPh$ | 99 | 43 |
| 361 | $CH_2CH_2$ | CH=CH-(4-OMe-C6H4) | 85 | 21 |

TABLE 2-continued

In vitro evaluation for vasoconstrictory activity of selected compounds of formula (I).

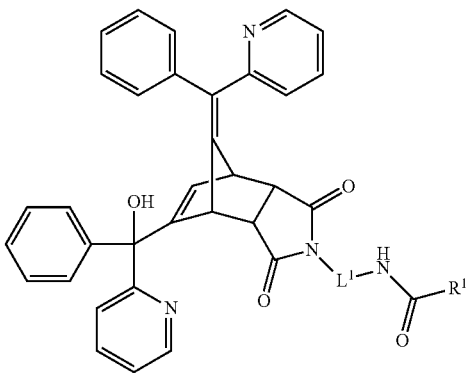

| Cmpd | L$^1$ | R$^1$ | Yield (%) | Vasoconstriction$^a$ |
|---|---|---|---|---|
| 345 | CH$_2$CH$_2$ | (CH=CH-C$_6$H$_4$-OEt) | 59 | 0 |

$^a$Maximum contractile effect as a % of 90 mM KCl contraction (rat caudal artery); stereoisomeric mixture of NRB = 132%.

TABLE 3

In vitro evaluation for vasoconstrictory activity of selected compounds of formula (I).

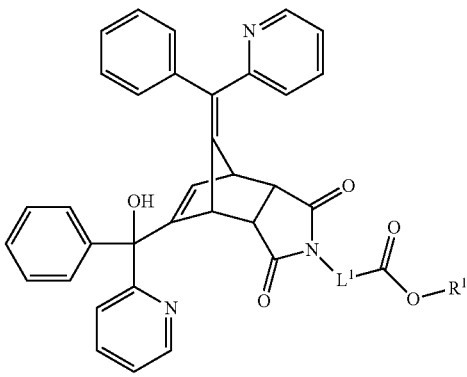

| Cmpd | L$^1$ | R$^1$ | Yield (%) | Vasoconstriction$^a$ |
|---|---|---|---|---|
| 369 | CH$_2$ | (CH$_2$)$_7$CH$_3$ | 71 | 0 |
| 371 | CH$_2$ | CH$_2$CH=CHPh | 90 | 0 |

$^a$Maximum contractile effect as a % of 90 mM KCl contraction (rat caudal artery); stereoisomeric mixture of NRB = 132%.

TABLE 4

Pre-cleavage vasoconstrictory activity, in vitro hydrolytic stability (low pH, rat blood and liver enzymes) and in vivo lethality of NRB and selected compounds of formula (I) in rats.

| Cmpd | Vasoconstriction$^a$ | % NRB released | | | In vivo lethality (i.v.) | In vivo lethality (oral) |
| | | Hydrolytic Stability | Rat Serum$^d$ | Rat Liver S9$^e$ | | |
|---|---|---|---|---|---|---|
| endo-NRB | 132 | — | — | — | yes$^{f,g}$ | yes$^{h,i}$ |
| 8 | ≥132 | 0$^b$ | — | — | — | — |
| 9 | 86 | 0$^b$ | — | — | — | — |
| 10 | 0 | 20$^c$ | 89.1 ± 1.2 | 73.0 ± 5.2 | yes$^f$ | yes$^h$ |

TABLE 4-continued

Pre-cleavage vasoconstrictory activity, in vitro hydrolytic stability
(low pH, rat blood and liver enzymes) and in vivo lethality of
NRB and selected compounds of formula (I) in rats.

| | | % NRB released | | | In vivo | In vivo |
|---|---|---|---|---|---|---|
| Cmpd | Vasocon-striction[a] | Hydrolytic Stability | Rat Serum[d] | Rat Liver S9[e] | lethality (i.v.) | lethality (oral) |
| 11 | 0 | 20[c] | 83.2 ± 1.8 | — | — | — |
| 12 | ≥132 | 0[b] | — | — | — | — |
| 13 | 90 | 0[b] | — | — | — | — |
| 14 | 0 | 0[c] | 64.2 ± 3.0 | 53.1 ± 3.3 | — | — |
| 15 | 0 | 0[c] | 67.7 ± 3.1 | — | — | — |
| 16 | 15 | 0[b], <5[c] | 100.0 ± 0.1 | 86.0 ± 2.8 | yes[f] | yes[h,i] |
| 324 | 17 | — | — | — | — | yes[h,i] |
| 17 | 0 | 0[c] | 29.1 ± 1.0 | 12.4 ± 0.3 | nt[j] | no[h] |
| 18 | 13 | 0[b] | — | — | — | — |
| 19 | 0 | 0[c] | 76.9 ± 0.5 | 55.4 ± 2.4 | yes[f] | yes[h,i] |
| 20 | 0 | 0[c] | 31.3 ± 2.7 | 20.2 ± 0.8 | yes[f] | no[h] |
| 111 | 0 | 20[c] | 87.9 ± 0.7 | 48.5 ± 8.5 | — | — |
| 112 | 0 | 0[c] | 19.3 ± 1.3 | — | — | — |
| 118 | 0 | 0[c] | <5 | 9.0 ± 0.7 | yes[f] | no[h] |
| 120 | 66 | 0[c] | 14.1 ± 0.4 | — | — | — |
| 121 | 0 | 0[c] | 19.1 ± 1.3 | — | — | — |
| 122 | 0 | 0[c] | 14.4 ± 3.0 | 14.1 ± 0.5 | yes[f] | yes[h,i] |
| 123 | 0 | 0[c] | 84.5 ± 2.0 | 55.6 ± 4.1 | yes[f] | yes[h,i] |
| 126 | 0 | 0[c] | 24.2 ± 0.4 | 5.0 ± 0.3 | yes[f] | yes[h,i] |
| 127 | 0 | 0[c] | 17.0 ± 2.2 | — | — | — |
| 335 | 19 | — | — | — | — | yes[h] |
| 347 | 0 | — | — | — | — | yes[h] |
| 129 | 0 | 0[c] | 18.9 ± 1.3 | 8.0 ± 2.4 | yes[f] | yes[h,i] |
| 337 | 97 | — | — | — | — | yes[h] |
| 329 | 88 | — | — | — | — | yes[h] |
| 134 | 0 | 0[c] | 19.6 ± 2.8 | — | — | — |
| 135 | 0 | 0[c] | 33.8 ± 6.1 | — | — | — |
| 136 | 0 | 0[c] | 76.5 ± 5.7 | 18.2 ± 2.7 | yes[f] | yes[h] |
| 137 | 0 | 0[c] | 81.0 ± 0.8 | — | — | — |
| 342 | 136 | — | — | — | — | yes[h] |
| 343 | 149 | — | — | — | — | yes[h,i] |
| 364 | 21 | — | — | — | — | yes[h,i] |
| 339 | 0 | — | — | — | — | yes[h] |
| 361 | 21 | — | — | — | — | yes[h,i] |
| 345 | 0 | — | — | — | — | yes[h,i] |
| 369 | 0 | — | — | — | — | no[h] |
| 371 | 0 | — | — | — | — | no[h] |

[a]Maximum contractile effect as a % of 90 mM KCl contraction (rat caudal artery, n = 3), stereoisomeric mixture of NRB = 132%;

[b]for compounds exhibiting vasoconstriction, Tyrode solution (37° C., 1 h, n = 3);

[c]for compounds not exhibiting vasoconstriction, simulated gastric fluid without pepsin (pH 1.2, 37° C., 1 h, n = 3);

[d]80% rat serum (37° C., 3 h, n = 3);

[e]1 mg/mL rat liver S9 fraction (37° C., 6 h, n = 3);

[f]20 mg/Kg (rat, i.v., n = 2);

[g]10 mg/Kg (rat, i.v., n = 2);

[h]40 mg/Kg (rat, oral, n = 2);

[i]20 mg/Kg (rat, oral, n = 2);

[j]solubility problems encountered preventing injection by i.v. nt = not tested.

TABLE 5

In vitro evaluation for vasoconstrictory activity of selected compounds of formula (III).

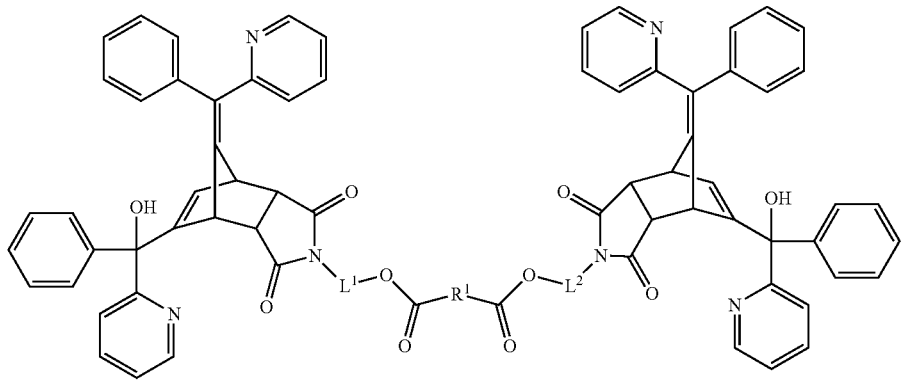

| Cmpd | $L^1/L^2$ | $R^1$ | Yield (%) | Vasoconstriction[a] |
|---|---|---|---|---|
| 21 | $CH_2$ | $(CH_2)_2$ | 17 | 0 |
| 22 | $CH_2$ | $(CH_2)_4$ | 16 | 0 |
| 23 | $CH_2$ | $(CH_2)_6$ | 6 | 0 |
| 24 | $CH_2$ | $(CH_2)_8$ | 81 | 0 |
| 25 | $CH_2$ | $(CH_2)_{10}$ | 12 | 0 |
| 26 | $CH_2$ | $p(C_6H_4)$ | 21 | 0 |
| 27 | $CH_2$ | $(CH_2)_2C(O)O(CH_2)_2OC(O)(CH_2)_2$ | 26 | 0 |
| 138 | $CH_2CH_2$ | $(CH_2)_2$ | 1 | 0 |
| 139 | $CH_2CH_2$ | $(CH_2)_4$ | 3 | 20 |
| 140 | $CH_2CH_2$ | $(CH_2)_6$ | 5 | 0 |
| 141 | $CH_2CH_2$ | $(CH_2)_8$ | 27 | 0 |
| 142 | $CH_2CH_2$ | $(CH_2)_{10}$ | 1 | 0 |
| 143 | $CH_2CH_2$ | $p(C_6H_4)$ | 5 | 0 |
| 144 | $CH_2CH_2$ | $(CH_2)_2C(O)O(CH_2)_2OC(O)(CH_2)_2$ | 1 | 0 |

[a]Maximum contractile effect as a % of 90 mM KCl contraction (rat caudal artery); stereoisomeric mixture of NRB = 132%.

TABLE 6

Pre-cleavage vasoconstrictory activity, in vitro hydrolytic stability (low pH, rat blood and liver enzymes) and in vivo lethality of NRB and selected compounds of formula (III) in rats.

| Cmpd | Vasoconstriction[a] | Hydrolytic Stability[b] | % NRB released Rat Serum[c] | Rat Liver S9[d] | In vivo lethality (i.v.) | In vivo lethality (oral) |
|---|---|---|---|---|---|---|
| endo-NRB | 132 | — | — | — | yes[e,f] | yes[g,h] |
| 21 | 0 | 0 | 29.6 ± 5.4 | — | — | — |
| 22 | 0 | 0 | 13.4 ± 0.2 | — | — | — |
| 23 | 0 | 0 | 14.9 ± 5.0 | — | — | — |
| 24 | 0 | 0 | 8.6 ± 0.5 | 6.2 ± 0.2 | no[e] | — |
| 25 | 0 | 0 | <5 | — | — | — |
| 26 | 0 | 0 | <5 | — | — | — |
| 27 | 0 | 0 | 20.8 ± 0.7 | — | — | — |
| 138 | 0 | 0 | 7.7 ± 0.2 | — | — | — |
| 139 | 20 | 0 | 11.7 ± 1.6 | — | — | — |
| 140 | 0 | 0 | 9.9 ± 1.3 | — | — | — |
| 141 | 0 | 0 | <5 | <5 | no[f] | — |
| 142 | 0 | 0 | <5 | — | — | — |
| 143 | 0 | 0 | 27.5 ± 1.4 | — | — | — |
| 144 | 0 | 0 | 14.5 ± 0.8 | <5 | no[f] | — |

[a]Maximum contractile effect as a % of 90 mM KCl contraction (rat caudal artery, n = 3), stereoisomeric mixture of NRB = 132%;
[b]simulated gastric fluid without pepsin (pH 1.2, 37° C., 1 h,n = 3);
[c]80% rat serum (37° C., 3 h,n = 3);
[d]1 mg/mL rat liver S9 fraction (37° C., 6 h,n = 3);
[e]20 mg/Kg (rat, i.v., n = 2);
[f]10 mg/Kg (rat, iv., n = 2);
[g]40 mg/Kg (rat, oral, n = 2);
[h]20 mg/Kg (rat, oral, n = 2).

TABLE 7

In vitro evaluation for vasoconstrictory activity of selected compounds of formula (V).

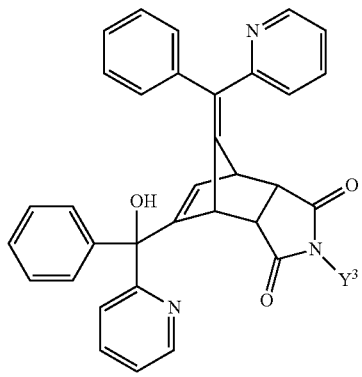

| Cmpd | $Y^3$ | Yield (%) | Vasoconstriction[a] |
|---|---|---|---|
| 102 | $CH_2CH_2OH$ | 77 | ≥132 |
| 103 | $CH_2CHMeOH$ | 64 | 67 |
| 104 | $CH_2CH_2CH_2OH$ | 38 | ≥132 |
| 105 | $CH_2CH_2CH_2CH_2OH$ | 28 | 100 |
| 106 | $CH_2CH_2NH_2$ | 56 (2 steps) | ≥132 |
| 107 | $CH_2CO_2H$ | 40 (2 steps) | ≥132 |

[a]Maximum contractile effect as a % of 90 mM KCl contraction (rat caudal artery); stereoisomeric mixture of NRB = 132%.

TABLE 8

Pre-cleavage vasoconstrictory activity, in vitro hydrolytic stability (low pH, rat blood and liver enzymes) and in vivo lethality of NRB and selected compounds of formula (V) in rats.

| Cmpd | Vasoconstriction[a] | In vivo lethality (i.v.) | In vivo lethality (oral) |
|---|---|---|---|
| endo-NRB | 132 | yes[b] | yes[c,d] |
| 102 | ≥132 | yes[b] | yes[c,d] |
| 103 | 67 | — | — |
| 104 | ≥132 | yes[b] | yes[c] |
| 105 | 100 | — | — |
| 106 | ≥132 | yes[b] | — |
| 107 | ≥132 | yes[b] | — |

[a]Maximum contractile effect as a % of 90 mM KCl contraction (rat caudal artery, n = 3), stereoisomeric mixture of NRB = 132%;
[b]20 mg/Kg (rat, i.v., n = 3),
[c]40 mg/Kg (rat, oral, n = 3),
[d]20 mg/Kg (rat, oral, n = 3).

TABLE 9

In vivo lethality for NRB and selected compounds of formula (I) in rats.

| Cmpd | Onset of Symptoms[b,c,d] (min) | Time to Death (min)[c] |
|---|---|---|
| endo-NRB | 5 | 35[d] |
| 10 | 15 | not lethal |
| 16 | 15 | 90[d] |
| 324 | 15 | 60[d] |
| 19 | 20 | 90[d] |
| 111 | 15 | >120[e] |
| 121 | 20 | not lethal |
| 123 | 15 | 35[d] |
| 126 | 25 | 50[d] |
| 335 | 15 | 90[e] |

TABLE 9-continued

In vivo lethality for NRB and selected compounds of formula (I) in rats.

| Cmpd | Onset of Symptoms[b,c,d] (min) | Time to Death (min)[c] |
|---|---|---|
| 347 | 20 | not lethal |
| 136 | 20 | not lethal |
| 339 | 200 | 300[e] |
| 345 | 15 | 65[d] |

[a]20 mg/Kg (rat, oral);
[b]visual signs of distress (laboured/irregular breathing, lethargy, tail twitching), consistent with NRB-like symptoms;
[c]mean time;
[d]n = 2;
[e]n = 1.

TABLE 10

Palatability (no-choice) trial observations for NRB and selected compounds of formula (I) in rats.

| | Palatability Trial[a] | | | |
|---|---|---|---|---|
| Cmpd | Bait consumed (g) (of 5 g) | Ave. bait consumed (as % of body mass) | Maximum toxicant consumed (mg/kg) | N° of deaths |
| endo-NRB | 1.9 ± 0.5 | — | — | 3/6 |
| 19 | 4.3 ± 0.2 | — | — | 5/5[b] |
| 126 | 4.0 ± 0.4 | — | — | 5/6 |
| PB | 5.0 ± 0.2 | — | — | 0/6 |

[a]rats presented with 1% w/w toxicant (n = 6, male rats only) in a peanut butter bait following 3 days 'pre-feeding' with a peanut butter formulation free of toxicant;
[b]one rat removed from the trial due to irregular pre-feeding habits.
PB = Peanut butter only.

TABLE 11

Palatability (no-choice) trial observations for NRB and selected compounds of formula (I) in rats.

| | Palatability Trial[a] | | | |
|---|---|---|---|---|
| Cmpd | Bait consumed (g) (of 3 g) | Ave. bait consumed (% of body mass) | Maximum toxicant consumed (mg/kg) | N° of deaths |
| endo-NRB | 1.30 | 0.65 | 66 | 4/6 |
| 10 | 1.65 | 0.84 | 64 | 6/6 |
| 16 | 1.15 | 0.53 | 42 | 5/6 |
| 324 | 2.00 | 1.01 | 80 | 6/6 |
| 111 | 1.00 | 0.48 | 40 | 6/6 |
| 121 | 2.10 | 1.03 | 85 | 6/6 |
| 335 | 2.23 | 1.08 | 87 | 6/6 |
| 342 | 1.37 | 0.61 | 46 | 4/6 |
| PB | 3.12 | 1.61 | — | 0/6 |

[a]rats presented with 1% w/w toxicant (n = 6, 3 male and 3 female rats) in a peanut butter bait following 3 days 'pre-feeding' with a peanut butter formulation free of toxicant.
PB = Peanut butter only.

TABLE 12

Palatability (no-choice) trial observations for NRB and selected compounds of formula (I) in rats.

| | Palatability Trial[a] | | | |
|---|---|---|---|---|
| Cmpd | Bait consumed (g) (of 3 g) | Ave. bait consumed (as % of body mass) | Maximum toxicant consumed (mg/kg) | N° of deaths |
| endo-NRB | 0.37 | 0.26 | 26 | 3/6 |
| 347 | 1.3 | 0.58 | 44 | 3/6 |
| 339 | 1.97 | 0.89 | 67 | 3/6 |
| 339[b] | 0.7 | 0.34 | 50 | 5/6 |
| 345 | 1.55 | 0.54 | 41 | 2/6 |
| PB | 3.17 | 1.51 | — | 0/6 |

[a]rats presented with 1% w/w toxicant (n = 6, 3 male and 3 female rats) in a peanut butter bait following 3 days 'pre-feeding' with a peanut butter formulation free of toxicant;
[b]2% w/w toxicant.
PB = Peanut butter only.

TABLE 13

Palatability (choice) trial observations for NRB and selected compounds of formula (I) in rats.

| | Palatability Trial[a] | | | |
|---|---|---|---|---|
| Cmpd | Ave. Toxic bait consumed (g) | Ave. toxic bait consumed (% of body mass) | Maximum toxicant consumed (mg/kg) | N° of deaths |
| NRB | 1.05 | 0.30 | 31 | 5/12 |
| 19 | 1.81 | 0.54 | 40 | 2/12 |
| 126 | 1.98 | 0.60 | 47 | 10/12 |

[a]rats presented with a choice of standard lab pellets (20 g) and a bait containing 1% w/w toxicant (20 g) for 2 days following 3 days 'pre-feeding' with a choice of standard lab pellets and a bait formulation free of toxicant (n = 12); 20 g of fresh bait presented each day.

TABLE 14

Palatability (choice) trial observations for NRB and selected compounds of formula (I) in rats.

| | Palatability Trial[a] | | | |
|---|---|---|---|---|
| Cmpd | Ave. Toxic bait consumed (g) | Ave. toxic bait consumed (% of body mass) | Maximum toxicant consumed (mg/kg) | N° of deaths |
| NRB | 1.07 | 0.34 | 33 | 2/12 |
| 19 | 1.16 | 0.33 | 24 | 1/12 |
| 126 | 1.62 | 0.45 | 38 | 8/11[b] |

[a]rats presented with a choice of EPA diet (20 g) and a bait containing 1% w/w toxicant (20 g) for 2 days following 3 days 'pre-feeding' with a choice of EPA diet and a bait formulation free of toxicant (n = 12); 20 g of fresh bait presented each day;
[b]one rat was excluded because it was found to be pregnant.

TABLE 15

Palatability (choice) trial observations for NRB and selected compounds of formula (I) in rats.

| | Palatability Trial[a] | | | |
|---|---|---|---|---|
| Cmpd | Ave. Toxic bait consumed (g) | Ave. toxic bait consumed (% of body mass) | Maximum toxicant consumed (mg/kg) | N° of deaths |
| NRB | 2.81 | 0.64 | 64 | 5/12 |
| 324 | 2.92 | 0.90 | 68 | 5/12 |
| 121 | 2.70 | 0.82 | 69 | 3/12 |
| 335 | 3.32 | 0.94 | 80 | 7/12 |
| 339 | 3.71 | 1.23 | 92 | 3/12 |

[a]rats presented with a choice of EPA diet (20 g) and a bait containing 1% w/w toxicant (20 g) for 2 days following 3 days 'pre-feeding' with a choice of EPA diet and a bait formulation free of toxicant (n = 2); 20 g of fresh bait presented each day.

It is not the intention to limit the scope of the invention to the abovementioned examples only. As would be appreciated by a skilled person in the art, many variations are possible without departing from the scope of the invention.

INDUSTRIAL APPLICATION

The present invention relates to compounds that have rodenticidal activity and can be used to control destructive rodents, such as rats.

The invention claimed is:
1. A compound of the formula (I):

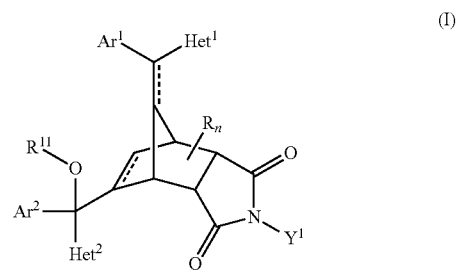

wherein:
Ar$^1$ and Ar$^2$ are each independently a 6 to 10 membered monocyclic or bicyclic aryl ring, wherein the ring is optionally substituted with one or more R$^8$;
Het$^1$ and Het$^2$ are each independently a 5 to 10 membered monocyclic or bicyclic heteroaryl ring comprising 1 to 4 ring nitrogen atoms, wherein the ring is optionally substituted with one or more R$^8$;

each dashed line and solid line together represent a double bond or a single bond;

$Y^1$ is

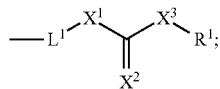

$X^1$ and $X^3$ are each independently selected from the group consisting of O, S, $NR^5$, and a bond, provided that $X^1$ and $X^3$ do not both represent a bond;

$X^2$ is selected from the group consisting of O, S, and $NR^5$;

$L^1$ is selected from the group consisting of $C_{1-6}$alkylene, $C_{3-6}$cycloalkylene, arylene, heteroarylene, heterocyclylene, $C_{1-6}$alkyl$C_{3-6}$cycloalkylene, $C_{1-6}$alkylarylene, $C_{1-6}$alkylheteroarylene, $C_{1-6}$alkylheterocyclylene, $C_{3-6}$cycloalkyl$C_{1-6}$alkylene, aryl$C_{1-6}$alkylene, heteroaryl$C_{1-6}$alkylene, heterocyclyl$C_{1-6}$alkylene, $C_{1-6}$alkoxy$C_{1-6}$alkylene, $C_{3-6}$cycloalkyloxy$C_{1-6}$alkylene, aryloxy$C_{1-6}$alkylene, heteroaryloxy$C_{1-6}$alkylene, heterocyclyloxy$C_{1-6}$alkylene, $C_{1-6}$alkoxy$C_{3-6}$cycloalkylene, $C_{1-6}$alkoxyarylene, $C_{1-6}$alkoxyheteroalkylene, $C_{1-6}$alkoxyheterocyclylalkylene, $C_{1-6}$alkylthio$C_{1-6}$alkylene, $C_{3-6}$cycloalkylthio$C_{1-6}$alkylene, arylthio$C_{1-6}$alkylene, heteroarylthio$C_{1-6}$alkylene, heterocyclylthio$C_{1-6}$alkylene, $C_{1-6}$alkylthio$C_{3-6}$cycloalkylene, $C_{1-6}$alkylthioarylene, $C_{1-6}$alkylthioheteroalkylene, $C_{1-6}$alkylthioheterocyclylalkylene, $C_{1-6}$alkylamino$C_{1-6}$alkylene, $C_{3-6}$cycloalkylamino$C_{1-6}$alkylene, arylamino$C_{1-6}$alkylene, heteroarylamino$C_{1-6}$alkylene, heterocyclylamino$C_{1-6}$alkylene, $C_{1-6}$alkylamino$C_{3-6}$cycloalkylene, $C_{1-6}$alkylaminoarylene, $C_{1-6}$alkylaminoheteroalkylene, and $C_{1-6}$alkylaminoheterocyclylalkylene each of which is optionally substituted with one or more $R^6$;

$R^1$ is selected from the group consisting of $C_{3-18}$alkyl, $C_{3-8}$cycloalkyl, aryl, heterocyclyl, heteroaryl, $C_{3-8}$cycloalkyl$C_{1-6}$alkyl, aryl$C_{1-6}$alkyl, heterocyclyl$C_{1-6}$alkyl, heteroaryl$C_{1-6}$alkyl, $C_{3-18}$alkyloxy$C_{1-6}$alkyl, $C_{3-8}$cycloalkyloxy$C_{1-6}$alkyl, aryloxy$C_{1-6}$alkyl, heterocyclyloxy$C_{1-6}$alkyl, heteroaryloxy$C_{1-6}$alkyl, $C_{3-18}$alkylcarbonyloxy$C_{1-6}$alkyl, $C_{3-8}$cycloalkylcarbonyloxy$C_{1-6}$alkyl, arylcarbonyloxy$C_{1-6}$alkyl, heterocyclylcarbonyloxy$C_{1-6}$alkyl, heteroarylcarbonyloxy$C_{1-6}$alkyl, $C_{3-18}$alkyloxycarbonyl$C_{1-6}$alkyl, $C_{3-8}$cycloalkyloxycarbonyl$C_{1-6}$alkyl, aryloxycarbonyl$C_{1-6}$alkyl, heterocyclyloxycarbonyl$C_{1-6}$alkyl, heteroaryloxycarbonyl $C_{1-6}$alkyl, $C_{1-6}$alkyl$C_{3-8}$cycloalkyl, $C_{1-6}$alkylaryl, $C_{1-6}$alkylheterocyclyl, $C_{1-6}$alkylheteroaryl, $C_{1-6}$alkyl$C_{3-8}$cycloalkyl$C_{1-6}$alkyl, $C_{1-6}$alkylheterocyclyl$C_{1-6}$alkyl, $C_{1-6}$alkylheteroaryl$C_{1-6}$alkyl, $C_{1-18}$alkylcarbonyloxy$C_{1-6}$alkyl, $C_{1-18}$alkyloxycarbonyl $C_{1-6}$alkyl, each of which is optionally substituted with one or more $R^7$; or $R^1$ is $C_{1-6}$alkylaryl$C_{1-6}$alkyl substituted with one or more $R^7$;

$R^5$ at each instance is independently selected from the group consisting of hydrogen, $C_{1-6}$alkyl, $C_{3-6}$cycloalkyl, aryl, heterocyclyl, and heteroaryl;

$R^6$ at each instance is independently selected from the group consisting of hydroxyl, thiol, amino, cyano, nitro, halo, $C_{1-6}$alkyl, $C_{1-6}$haloalkyl, $C_{1-6}$alkoxy, and $C_{1-6}$haloalkoxy;

$R^7$ at each instance is independently selected from the group consisting of hydroxyl, thiol, amino, amido, acylamino, cyano, nitro, nitroso, azide, halo, cyanate, thiocyanate, isocyanate, isothiocyanate, oxo, imino, acyl, $C_{1-6}$alkyl, $C_{1-6}$haloalkyl, $C_{3-6}$cycloalkyl, aryl, heterocyclyl, heteroaryl, $C_{1-6}$alkoxy, $C_{1-6}$haloalkoxy, $C_{3-6}$cycloalkoxy, aryloxy, heterocyclyloxy, heteroaryloxy, $C_{1-6}$alkylcarbonyloxy, $C_{3-6}$cycloalkylcarbonyloxy, arylcarbonyloxy, heterocyclylcarbonyloxy, heteroarylcarbonyloxy, $C_{1-6}$alkyloxycarbonyl, $C_{3-6}$cycloalkyloxycarbonyl, aryloxycarbonyl, heterocyclyloxycarbonyl, heteroaryloxycarbonyl, sulfenyl, sulfonyl, sulfoxide, sulfate, sulfonate, sulfonamide, phosphate, phosphonate, phosphinate, phosphine, phosphite, carbonate, carbamate, and urea;

$R^8$ at each instance is selected from the group consisting of hydroxyl, thiol, amino, cyano, nitro, halo, $C_{1-6}$alkyl, $C_{1-6}$haloalkyl, $C_{1-6}$alkoxyl, and $C_{1-6}$haloalkoxy;

$R^{11}$ is selected from the group consisting of hydrogen, $C_{1-6}$alkyl, and $C_{1-6}$haloalkyl;

R at each instance is selected from the group consisting of halo, $C_{1-6}$alkyl, carboxyl, carboxyl$C_{1-6}$alkyl, amido $C_{1-6}$alkyl, acyloxy, sulfenyl, sulfoxide, sulfonyl, and aryl, wherein each $C_{1-6}$alkyl and aryl is optionally substituted with one or more $R^8$; and n is an integer selected from 0 to 3; or a salt or solvate thereof.

2. The compound of claim 1, wherein $R^1$ is selected from the group consisting of $C_{3-18}$alkyl, $C_{3-8}$cycloalkyl, aryl, heterocyclyl, heteroaryl, $C_{3-8}$cycloalkyl$C_{1-6}$alkyl, aryl$C_{1-6}$alkyl, heterocyclyl$C_{1-6}$alkyl, heteroaryl$C_{1-6}$alkyl, $C_{3-18}$alkyloxy$C_{1-6}$alkyl, $C_{3-8}$cycloalkyloxy$C_{1-6}$alkyl, aryloxy$C_{1-6}$alkyl, heterocyclyloxy$C_{1-6}$alkyl, heteroaryloxy$C_{1-6}$alkyl, $C_{3-18}$alkylcarbonyloxy$C_{1-6}$alkyl, $C_{3-8}$cycloalkylcarbonyloxy$C_{1-6}$alkyl, arylcarbonyloxy$C_{1-6}$alkyl, heterocyclylcarbonyloxy$C_{1-6}$alkyl, heteroarylcarbonyloxy$C_{1-6}$alkyl, $C_{3-18}$alkyloxycarbonyl$C_{1-6}$alkyl, $C_{3-8}$cycloalkyloxycarbonyl$C_{1-6}$alkyl, aryloxycarbonyl$C_{1-6}$alkyl, heterocyclyloxycarbonyl$C_{1-6}$alkyl, heteroaryloxycarbonyl$C_{1-6}$alkyl.

3. The compound of claim 1, wherein $Ar^1$ and $Ar^2$ are each independently a phenyl ring optionally substituted with one or more $R^8$.

4. The compound of claim 1, wherein $Het^1$ and $Het^2$ are each independently pyridyl optionally substituted with one or more $R^8$.

5. The compound of claim 1, wherein the stereochemical configuration at the bridgehead of the dicarboximide ring is endo.

6. The compound of claim 1, wherein the compound is a compound of formula (II):

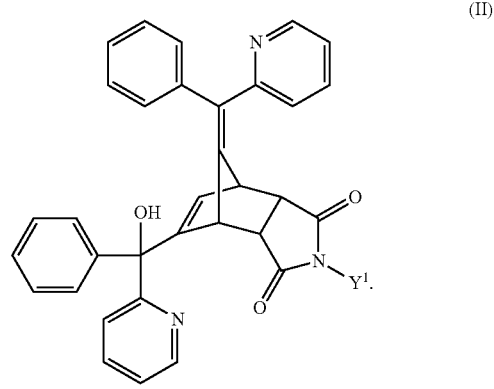

(II)

7. The compound of claim 1, wherein $L^1$ is selected from the group consisting of $C_{1-6}$alkylene, $C_{1-6}$alkyl$C_{3-6}$cycloalkylene, $C_{1-6}$alkylarylene, $C_{3-6}$cycloalkyl$C_{1-6}$alkylene, aryl$C_{1-6}$alkylene, $C_{1-6}$alkoxy$C_{1-6}$alkylene, each of which is optionally substituted with one or more $R^6$.

8. The compound of claim 7, wherein $L^1$ is $C_{1-6}$alkylene optionally substituted with one or more $R^6$.

9. The compound of claim 1, wherein $X^1$ is selected from the group consisting of O and $NR^5$, $X^2$ is O, and $X^3$ is a bond; or $X^1$ is a bond, $X^2$ is O, and $X^3$ is selected from the group consisting of O and $NR^5$.

10. The compound of claim 9, wherein $X^1$ and $X^2$ are each O and $X^3$ is a bond.

11. The compound of claim 1, wherein $R^1$ is selected from the group consisting of $C_{3-18}$alkyl, aryl, aryl$C_{1-6}$alkyl, aryloxy$C_{1-6}$alkyl, arylcarbonyloxy$C_{1-6}$alkyl, and aryloxycarbonyl$C_{1-6}$alkyl, each of which is optionally substituted with one or more $R^7$.

12. The compound of claim 11, wherein $R^1$ is selected from the group consisting of $C_{3-12}$alkyl, aryl, aryl$C_{1-6}$saturated alkyl, aryl$C_{1-6}$alkenyl, each of which is optionally substituted with one or more $R^7$.

13. A compound of formula (V):

(V)

wherein
$Ar^1$ and $Ar^e$ at each instance are independently a 6 to 10 membered monocyclic or bicyclic aryl ring, wherein the ring is optionally substituted with one or more $R^8$;
$Het^1$ and $Het^2$ at each instance are each independently a 5 to 10 membered monocyclic or bicyclic heteroaryl ring comprising 1 to 4 ring nitrogen atoms, wherein the ring is optionally substituted with one or more $R^8$;
each dashed line and solid line together represent a double bond or a single bond;
$Y^3$ is

—$L^1$—$X^1$—$X^2$;

$L^1$ is selected from the group consisting of $C_{1-6}$alkylene, $C_{3-6}$cycloalkylene, arylene, heteroarylene, heterocyclylene, $C_{1-6}$alkyl$C_{3-6}$cycloalkylene, $C_{1-6}$alkylarylene, $C_{1-6}$alkylheteroarylene, $C_{1-6}$alkylheterocyclylene, $C_{3-6}$cycloalkyl$C_{1-6}$alkylene, aryl$C_{1-6}$alkylene, heteroaryl$C_{1-6}$alkylene, and heterocyclyl$C_{1-6}$alkylene, each of which is optionally substituted with one or more $R^6$;

$X^1$ is selected from the group consisting of C(=O), C(=S), C(=$NR^5$), and a bond;
$X^2$ is selected from the group consisting of OH, SH, and $NHR^5$;
$R^5$ at each instance is independently selected from the group consisting of hydrogen, $C_{1-6}$alkyl, $C_{3-6}$cycloalkyl, aryl, heterocyclyl, and heteroaryl;
$R^6$ at each instance is independently selected from the group consisting of hydroxyl, thiol, amino, cyano, nitro, halo, $C_{1-6}$alkyl, $C_{1-6}$haloalkyl, $C_{1-6}$alkoxy, and $C_{1-6}$haloalkoxy;
$R^8$ at each instance is selected from the group consisting of hydroxyl, thiol, amino, cyano, nitro, halo, $C_{1-6}$alkyl, $C_{1-6}$haloalkyl, $C_{1-6}$alkoxy, and $C_{1-6}$haloalkoxy;
$R^{11}$ is selected from the group consisting of hydrogen, $C_{1-6}$alkyl, and $C_{1-6}$haloalkyl;
R at each instance is selected from the group consisting of halo, $C_{1-6}$alkyl, carboxyl, carboxyl$C_{1-6}$alkyl, amido $C_{1-6}$alkyl, acyloxy, sulfenyl, sulfoxide, sulfonyl, and aryl, wherein each $C_{1-6}$alkyl and aryl is optionally substituted with one or more $R^8$; and
n is an integer selected from 0 to 3; or
a salt or solvate thereof.

14. The compound of claim 13, wherein the stereochemical configuration at the bridgehead of the dicarboximide ring is endo.

15. The compound of claim 13, wherein the compound is a compound of formula (VI):

(VI)

16. The compound of claim 13, wherein $L^1$ is $C_{1-6}$alkylene optionally substituted with one or more $R^6$.

17. The compound of claim 13, wherein $X^1$ is selected from the group consisting of C(=O) and a bond.

18. The compound of claim 13, wherein $X^2$ is OH or $NH_2$.

19. A rodenticidal composition comprising an effective amount of a compound of claim 1; and one or more edible diluent or carrier materials.

20. A method of controlling rodents comprising making a rodenticidal composition of claim 19 available for consumption by the rodents.

* * * * *